(12) United States Patent
Pulici et al.

(10) Patent No.: US 9,114,137 B2
(45) Date of Patent: *Aug. 25, 2015

(54) DERIVATIVES OF PYRAZOLOPHENYL-BENZENESULFONAMIDE COMPOUNDS AND USE THEREOF AS ANTITUMOR AGENTS

(75) Inventors: Maurizio Pulici, Caponago (IT); Chiara Marchionni, Milan (IT); Gabriella Traquandi, Milan (IT); Alessandra Scolaro, Bresso (IT); Daniele Donati, Nerviano (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 111 days.

This patent is subject to a terminal disclaimer.

(21) Appl. No.: 13/752,807

(22) PCT Filed: Aug. 2, 2011

(86) PCT No.: PCT/EP2011/063325
§ 371 (c)(1),
(2), (4) Date: Mar. 7, 2013

(87) PCT Pub. No.: WO2012/016993
PCT Pub. Date: Feb. 9, 2012

(65) Prior Publication Data
US 2013/0217715 A1    Aug. 22, 2013

(30) Foreign Application Priority Data

Aug. 3, 2010  (EP) ..................... 10171759

(51) Int. Cl.
| | |
|---|---|
| C07D 401/04 | (2006.01) |
| C07D 401/14 | (2006.01) |
| C07D 403/14 | (2006.01) |
| C07D 405/14 | (2006.01) |
| C07D 471/04 | (2006.01) |
| A61K 31/4439 | (2006.01) |
| C07D 403/04 | (2006.01) |
| C07D 451/04 | (2006.01) |
| A61K 31/437 | (2006.01) |
| A61K 31/4545 | (2006.01) |
| A61K 31/506 | (2006.01) |
| A61K 45/06 | (2006.01) |

(52) U.S. Cl.
CPC ............ *A61K 31/4439* (2013.01); *A61K 31/437* (2013.01); *A61K 31/4545* (2013.01); *A61K 31/506* (2013.01); *A61K 45/06* (2013.01); *C07D 401/04* (2013.01); *C07D 401/14* (2013.01); *C07D 403/04* (2013.01); *C07D 403/14* (2013.01); *C07D 405/14* (2013.01); *C07D 451/04* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 8,541,575 B2 | 9/2013 | Pulici et al. | |
| 8,791,265 B2 * | 7/2014 | Pulici et al. | 546/268.4 |
| 2013/0053419 A1 | 2/2013 | Pulici et al. | |
| 2014/0005150 A1 | 1/2014 | Pulici et al. | |

FOREIGN PATENT DOCUMENTS

| | | |
|---|---|---|
| WO | WO 98/52940 | 11/1998 |
| WO | WO 00/31063 | 6/2000 |
| WO | WO 03/055860 A1 | 7/2003 |
| WO | WO 2007/024843 A2 | 3/2007 |
| WO | WO 2007/105058 A2 | 9/2007 |
| WO | WO 2010/010154 A1 | 1/2010 |
| WO | WO 2011/092088 A1 | 8/2011 |

OTHER PUBLICATIONS

International Search Report dated Aug. 31, 2011 for co-pending International Patent Application No. PCT/EP2011/063325.
Cohen, Y.; Xing, M.; Mambo, E.; Guo, Z.; Wu, G.; Trink, B.; Beller, U.; Westra, W.H.; Ladenson, P.W.; Sidransky, D. "BRAF Mutation in Papillary Thyroid Carcinoma," *J. Nat'l. Cancer Inst.*, 2003, 95, 625-627.

(Continued)

*Primary Examiner* — Kamal Saeed
(74) *Attorney, Agent, or Firm* — Fish & Richardson P.C.

(57) ABSTRACT

Substituted pyrazolophenyl-benzenesulfonamide compounds of formula (I) are described, wherein m, R1, R2, R3, and R4 are defined in the description, which modulate the activity of protein kinases, These compounds find utility in treating diseases caused by deregulated protein kinase activity, such as cancer and cell proliferative disorders.

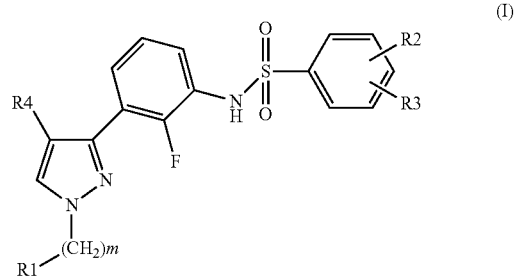

17 Claims, No Drawings

(56) References Cited

OTHER PUBLICATIONS

Davies, H.; Bignell, G.R.; Cox, C.; Stephens, P.; Edkins, S.; Clegg, S.; Teague, J.; Woffendin, H.; Garnett, M.J.; Bottomley, W.; Davis, N.; Dicks, E.; Ewing, R.; Floyd, Y.; Gray, K.; Hall, S.; Hawes, R.; Hughes, J.; Kosmidou V.; Menzies, A.; Mould, C.; Parker, A.; Stevens, C.; Watt, S.; Hooper, S.; Wilson, R.; Jayatilake, H.; Gusterson, B.A.; Cooper, C.; Shipley, J.; Hargrave, D.; Pritchard-Jones, K.; Maltland, N.; Chenevix-Trench, G.; Riggins, G.J.; Bigner, D.D.; Palmieri, G.; Cossu, A.; Flangan, A.; Nicholson, A.; Ho, J.W.C.; Leung, S.Y.; Yuen S.T.; Weber, B.L.; Seigler, H.F.; Darrow, T.L.; Paterson, H.; Marals, R.; Marshall, C.J.; Wooster, R.; Stratton, M.R.; Futreal, P.A. "Mutations of the BRAF Gene in Human Cancer," *Nature*, 2002, 417, 949-954.

Hagemann, C.; Rapp, U.R. "Isotype-Specific Functions of Raf Kinases," *Expt. Cell Res.*, 1999, 253, 34-46.

Hingorani, S.R.; Jacobetz, M.A.; Robertson, G.P.; Herlyn, M.; Tuveson, D.A. "Suppression of BRAF$^{V599E}$ in Human Melanoma Abrogates Transformation," *Cancer Res.*, 2003, 63, 5198-5202.

Hoshino, R.; Chatani, Y.; Yamori, T.; Tsuruo, T.; Oka, H.; Yoshida, O.; Shimada, Y.; Ari-i, S.; Wada, H.; Fujimoto, J.; Kohno, M. "Constitutive Activation of the 41-/43-kDa Mitogen-Activated Protein Kinase Signaling Pathway in Human Tumors," *Oncogene*, 1999, 18, 813-822.

Kolch, W.; Kotwaliwale, A.; Vass, K.; Janosch, P. "The Role of Raf Kinases in Malignant Transformation," *Exp. Rev. Mol. Med.*, 2002, 4, 1-18.

Mercer, K.E.; Pritchard, C.A. "RAF Proteins and Cancer: B-Raf is Identified as a Mutational Target," *Biochim. Biophys. Acta*, 2003, 1653, 25-40.

Peyssonnaux, C.; Eychene, A. "The Raf/MEK/ERK Pathway: New Concepts of Activation," *Biology of the Cell*, 2001, 93, 53-62.

Tannapfel, A.; Sommerer, F.; Benicke, M.; Katalinic, A.; Uhlmann, D.; Witzigmann, H.; Hauss, J.; Wittekind, C. *Gut*, 2003, 52, 706-712.

Wellbrock, C.; Ogilvie, L.; Hedley, D; Karasarides, M.; Martin, J.; Niculescu-Duvaz, D.; Springer, C.J.; Marais, R. "$^{V599E}$B-RAF is an Oncogene in Melanocytes," *Cancer Res.*, 2004, 64, 2338-2342.

Wojnowski, L.; Zimmer, A.M.; Beck, T.W.; Hahn, H.; Bernal, R.; Rapp, U.R.; Zimmer, A. "Endothelial Apoptosis in Braf-Deficient Mice," *Nature Genet.*, 1997, 16, 293-297.

\* cited by examiner

DERIVATIVES OF PYRAZOLOPHENYL-BENZENESULFONAMIDE COMPOUNDS AND USE THEREOF AS ANTITUMOR AGENTS

RELATED APPLICATIONS

This application is a §371 filing based on International Application No. PCT/EP2011/063325, filed Aug. 3, 2011, which claims the benefit of European Patent Application Serial Number 10171759.3 filed Aug. 3, 2010. The entire contents of these patent applications are hereby incorporated herein by reference.

TECHNICAL FIELD

The present invention relates to certain substituted pyrazolophenyl-benzenesulfonamide compounds, which modulate the activity of protein kinases. The compounds of this invention are therefore useful in treating diseases caused by deregulated protein kinase activity. The present invention also provides methods for preparing these compounds, pharmaceutical compositions comprising these compounds, and methods of treating diseases utilizing pharmaceutical compositions comprising these compounds.

BACKGROUND ART

The classical Ras, Raf, MEK (mitogen activated protein kinase/extracellular signal-regulated kinase), ERK (extracellular signal-regulated kinase) pathway plays a central role in the regulation of a variety of cellular functions dependent upon cellular context, including cellular proliferation, differentiation, survival, immortalization and angiogenesis (reviewed in Peyssonnaux and Eychene, Biology of the Cell, 2001, 93, 3-62).

In this pathway, Raf family members are recruited to the plasma membrane upon binding to guanosine triphosphate (GTP) loaded Ras resulting in the phosphorylation and activation of Raf proteins. Activated Rafs then phosphorylate and activate MEKs, which in turn phosphorylate and activate ERKs. Upon activation, ERKs translocate from the cytoplasm to the nucleus resulting in the phosphorylation and regulation of activity of transcription factors such as Elk-I and Myc. The Ras/Raf/MEK/ERK pathway has been reported to contribute to the tumorigenic phenotype by inducing immortalisation, growth factor-independent growth, insensitivity to growth-inhibitory signals, ability to invade and metastasize, by stimulating angiogenesis and by inhibiting apoptosis (reviewed in Kolch et al., Exp. Rev. Mol. Med., 2002, 25 Apr., http://www.expertreviews.org/02004386h.htm). In fact, ERK phosphorylation is enhanced in approximately 30% of all human tumours (Hoshino et al., Oncogene, 1999, 18, 813-822). This may be a result of overexpression and/or mutation of key members of the pathway.

Three Raf serine/threonine protein kinase isoforms have been reported Raf-1/c-Raf, [beta]-Raf and A-Raf (reviewed in Mercer and Pritchard, Biochim. Biophys. Acta, 2003, 1653, 25-40), the genes for which are thought to have arisen from gene duplication. All three Raf genes are expressed in most tissues but with differences: c-Raf is expressed ubiquitously at high levels, whereas [beta]-Raf high-level expression is found in neuronal tissue and A-Raf in urogenital tissue.

The highly homologous Raf family members have overlapping but distinct biochemical activities and biological functions (Hagemann and Rapp, Expt, Cell Res. 1999, 253, 34-46). Expression of all three Raf genes is required for normal murine development however both c-Raf and B-Raf are required to complete gestation. [beta]-Raf-/- mice die at E12.5 due to vascular haemorrhaging caused by increased apoptosis of endothelial cells (Wojnowski et al, Nature Genet., 1997, 16, 293-297), B-Raf is reportedly the major isoform involved in cell proliferation and the primary target of oncogenic Ras.

Activating 5 somatic missense mutations have been identified exclusively for [beta]-Raf, occurring with a frequency of 66% in malignant cutaneous melanomas (Davies et al., Nature, 2002, 417, 949-954) and also present in a wide range of human cancers, including but not limited to papillary thyroid tumours (Cohen et al., J. Natl. Cancer Inst., 2003, 95, 625-627), cholangiocarcinomas (Tannapfel et al., Gut, 2003, 52, 706-712), colon and ovarian cancers (Davies et al., Nature, 10 2002, 417, 949-954). The most frequent mutation in [beta]-Raf (80%) is a glutamic acid for valine substitution at position 600. These mutations increase the basal kinase activity of B-Raf and are thought to uncouple Raf/MEK/ERK signalling from upstream proliferation drives including Ras and growth factor receptor activation resulting in constitutive activation of ERK. Mutated B-Raf proteins are transforming in NIH3T3 cells (Davies et al., Nature, 2002, 15 417, 949-954) and melanocytes (Wellbrock et al., Cancer Res., 2004, 64, 2338-2342) and have also been shown to be essential for melanoma cell viability and transformation (Hingorani at al., Cancer Res., 2003, 63, 5198-5202). As a key driver of the Raf/MEK/ERK signalling cascade, [beta]-Raf represents a likely point of intervention in tumours dependent on this pathway.

Substituted pyrazole derivatives for the treatment of cytokine-mediated diseases such as inflammation and arthritis are disclosed in WO98/52940 and WO00/31063 in the name of G.D. Searle & Co. Hydroxyaryl-pyrazole derivatives for the treatment of cancer are disclosed in WO03/055860 in the name of Cancer Research Institute and in WO07/105,058 in the name of Pfizer Inc, Pyrimidinyl-pyrazole derivatives for the treatment of hyperproliferative disorders such as cancer are disclosed in WO07/24843 in the name of SmithKline Beecham Corporation. 3,4-Diarylpyrazole derivatives for the treatment of diseases associated by a disregulated protein activity such as cancer are disclosed in WO2010/010154. Despite these developments, there is still need for effective agents for said diseases.

SUMMARY

A new class of protein kinase inhibitors has now been identified endowed with a higher activity than previously achieved in the prior art. These compounds were found able to prevent the proliferation of human tumour cells at a remarkably low concentration, thereby maximizing the antitumour efficacy while simultaneously reducing risk of the side effects linked to the administration of higher amounts of drugs. The new compounds have the structure shown in formula (I)

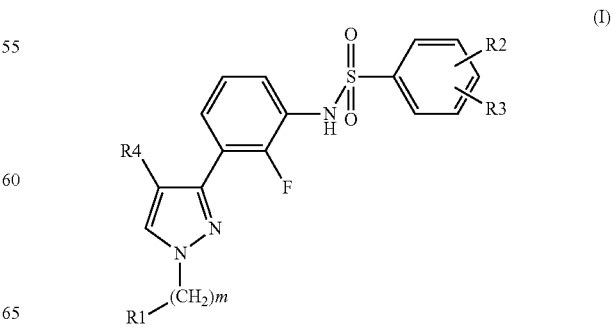

wherein:
m is an integer from 0 to 6;
R1 is hydrogen, trichloromethyl, trifluoromethyl, halogen, cyano, OH, OR5, NR6R7, NR8COR9, COOH, COOR10, CONR11R12, or an optionally substituted group selected from straight or branched $(C_1-C_8)$alkyl, $(C_2-C_8)$alkenyl or $(C_2-C_8)$alkynyl, $(C_3-C_8)$cycloalkyl, $(C_3-C_8)$cycloalkenyl, heterocyclyl, aryl and heteroaryl,
wherein:
R5 and R10 are each independently an optionally substituted group selected from straight or branched $(C_1-C_8)$ alkyl, $(C_3-C_8)$cycloalkyl, heterocyclyl, aryl and heteroaryl,
R6, R7, R8, R9, R11 and R12 are the same or different and are each independently hydrogen or an optionally substituted group selected from straight or branched $(C_1-C_8)$alkyl, $(C_3-C_8)$cycloalkyl,
heterocyclyl, aryl and heteroaryl, or taken together with the nitrogen atom to which they are bonded either R6 and R7 as well as R8 and R9, and R11 and R12 may form an optionally substituted heterocyclyl or heteroaryl, optionally containing one additional heteroatom or heteroatomic group selected from S, O, N or NH;
R2, and R3 are each independently hydrogen, halogen, trifluoromethyl, trichloromethyl, cyano, nitro, OR13 or a group optionally substituted selected from straight or branched $(C_1-C_8)$alkyl, and $(C_3-C_8)$cycloalkyl, wherein:
R13 is an optionally substituted group selected from straight or branched $(C_1-C_8)$alkyl and $(C_3-C_8)$cycloalkyl;
R4 is a heteroaryl group selected from

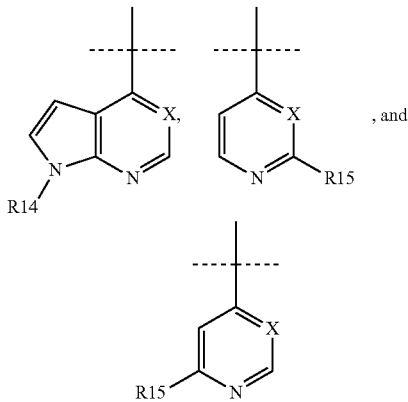

wherein R14 is hydrogen or an optionally substituted group selected from straight or branched $(C_1-C_8)$alkyl and $(C_3-C_8)$ cycloalkyl;
X is CH or N;
R15 is hydrogen, an optionally substituted group selected from straight or branched $(C_1-C_8)$alkyl and $(C_3-C_8)$cycloalkyl, halogen, cyano, NR16R17, CONR18R19, COOR20, OR20, SR20 or $SO_2$R20, wherein:
R16 and R17 are independently hydrogen or an optionally substituted group selected from straight or branched $(C_1-C_8)$ alkyl, $(C_3-C_8)$cycloalkyl, heterocyclyl, aryl and heteroaryl; or taken together with the nitrogen atom to which they are bonded R16 and R17 may form an optionally substituted 3 to 8 membered heterocyclyl or heteroaryl, optionally containing one additional heteroatom or heteroatomic group selected from S, O, N or NH; or R16 is hydrogen and R17 is COR21, wherein:

R21 is OR22, NR23R24 or an optionally substituted group selected from straight or branched $(C_1-C_8)$alkyl, $(C_2-C_8)$alkenyl or $(C_2-C_8)$alkynyl, $(C_3-C_8)$cycloalkyl, $(C_3-C_8)$ cylcoalkenyl, heterocyclyl, aryl and heteroaryl,
wherein:
R22 is an optionally substituted group selected from straight or branched $(C_1-C_8)$alkyl, $(C_3-C_8)$cycloalkyl, heterocyclyl, aryl and heteroaryl,
R23 and R24 are each independently an optionally substituted group selected from straight or branched $(C_1-C_8)$alkyl, $(C_3-C_8)$cycloalkyl, heterocyclyl, aryl and heteroaryl, or taken together with the nitrogen atom to which they are bonded R23 and R24 may form an optionally substituted 3 to 8 membered heterocyclyl or heteroaryl, optionally containing one additional heteroatom or heteroatomic group selected from S, O, N or NH;
R18 and R19 are independently hydrogen or a group optionally substituted selected from straight or branched $(C_1-C_8)$alkyl, $(C_3-C_8)$cycloalkyl, heterocyclyl, aryl and heteroaryl; or taken together with the nitrogen atom to which they are bonded R18 and R19 may form an optionally substituted 3 to 8 membered heterocyclyl or heteroaryl, optionally containing one additional heteroatom or heteroatomic group selected from S, O, N or NH.
R20 is a group optionally substituted selected from straight or branched $(C_1-C_8)$alkyl, $(C_3-C_8)$cycloalkyl, heterocyclyl, aryl and heteroaryl,
and pharmaceutically acceptable salts thereof,
with the exception of N-[3-(1-ethyl-4-pyridin-4-yl-1H-pyrazol-3-yl)-2-fluoro-phenyl]-2,5-difluoro-benzenesulfonamide.

In some embodiments, R1 is trichloromethyl, trifluoromethyl, halogen, cyano, OH, OR5, NR6R7, NR8COR9, COOH, COOR10, CONR11R12, or an optionally substituted group selected from straight or branched $(C_1-C_8)$alkyl, $(C_2-C_8)$alkenyl or $(C_2-C_8)$alkynyl, $(C_3-C_8)$cycloalkyl, $(C_3-C_8)$cycloalkenyl, heterocyclyl, aryl and heteroaryl, wherein:
R5 and R10 are each independently an optionally substituted group selected from straight or branched $(C_1-C_8)$ alkyl, $(C_3-C_8)$cycloalkyl, heterocyclyl, aryl and heteroaryl;
R6, R7, R8, R9, R11 and R12 are the same or different and are each independently hydrogen or an optionally substituted group selected from straight or branched $(C_1-C_8)$alkyl, $(C_3-C_8)$cycloalkyl, heterocyclyl, aryl and heteroaryl, or taken together with the nitrogen atom to which they are bonded either R6 and R7 as well as R8 and R9, and R11 and R12 may form an optionally substituted heterocyclyl or heteroaryl, optionally containing one additional heteroatom or heteroatomic group selected from S, O, N or NH.

In some embodiments, R4 is a heteroaryl group selected from

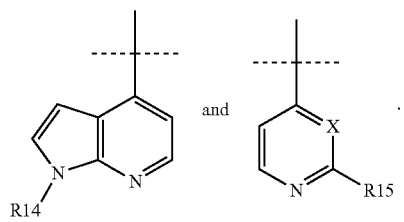

In some embodiments, R15 is hydrogen, an optionally substituted group selected from straight or branched ($C_1$-$C_8$) alkyl and ($C_3$-$C_8$)cycloalkyl, halogen, cyano, NR16R17, CONR18R19, OR20, SR20 or $SO_2$R20, wherein: R16 and R17 are independently hydrogen or an optionally substituted group selected from straight or branched ($C_1$-$C_8$)alkyl, ($C_3$-$C_8$)cycloalkyl, heterocyclyl, aryl and heteroaryl; or taken together with the nitrogen atom to which they are bonded R16 and R17 may form an optionally substituted 3 to 8 membered heterocyclyl or heteroaryl, optionally containing one additional heteroatom or heteroatomic group selected from S, O, N or NH; or R16 is hydrogen and R17 is COR21, wherein: R21 is OR22, NR23R24 or an optionally substituted group selected from straight or branched ($C_1$-$C_8$)alkyl, ($C_2$-$C_8$)alkenyl or ($C_2$-$C_8$)alkynyl, ($C_3$-$C_8$)cycloalkyl, ($C_3$-$C_8$) cylcoalkenyl, heterocyclyl, aryl and heteroaryl, wherein: R22 is an optionally substituted group selected from straight or branched ($C_1$-$C_8$)alkyl, ($C_3$-$C_8$)cycloalkyl, heterocyclyl, aryl and heteroaryl; R23 and R24 are each independently an optionally substituted group selected from straight or branched ($C_1$-$C_8$)alkyl, ($C_3$-$C_8$)cycloalkyl, heterocyclyl, aryl and heteroaryl, or taken together with the nitrogen atom to which they are bonded R23 and R24 may form an optionally substituted 3 to 8 membered heterocyclyl or heteroaryl, optionally containing one additional heteroatom or heteroatomic group selected from S, O, N or NH; R18 and R19 are independently hydrogen or a group optionally substituted selected from straight or branched ($C_1$-$C_8$)alkyl, ($C_3$-$C_8$)cycloalkyl, heterocyclyl, aryl and heteroaryl; or taken together with the nitrogen atom to which they are bonded R18 and R19 may form an optionally substituted 3 to 8 membered heterocyclyl or heteroaryl, optionally containing one additional heteroatom or heteroatomic group selected from S, O, N or NH; R20 is a group optionally substituted selected from straight or branched ($C_1$-$C_8$)alkyl, ($C_3$-$C_8$)cycloalkyl, heterocyclyl, aryl and heteroaryl; and pharmaceutically acceptable salts thereof,

DETAILED DESCRIPTION

Unless otherwise specified, the following definitions apply. When referring to the compounds of formula (I) per se as well as to any pharmaceutical composition thereof or to any therapeutic treatment comprising them, the present invention includes all of the isomers, tautomers, hydrates, solvates, complexes, metabolites, prodrugs, carriers, N-oxides and pharmaceutically acceptable salts of the compounds of this invention, A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I). N-oxides are compounds of formula (I) wherein nitrogen and oxygen are tethered through a dative bond. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases when compounds can exist in tautomeric forms, each form is contemplated as being included within this invention whether existing in equilibrium or predominantly in one form. In cases wherein compounds may exist in other tautomeric forms, such as keto-enol tautomers, each tautomeric form is contemplated as being included within this invention whether existing in equilibrium or predominantly in one form.

The term "straight or branched $C_1$-$C_8$ alkyl" refers to any of the groups including, but not limited to, methyl, ethyl, n-propyl, isopropyl, n-butyl, isobutyl, tert-butyl, sec-butyl, n-pentyl, n-hexyl, n-heptyl, n-octyl and the like.

The term "$C_3$-$C_8$ cycloalkyl" means, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentane, cyclohexane, cyclohexene and cyclohexadiene.

The term "heterocyclyl" refers to a 3- to 8-membered, saturated or partially unsaturated carbocyclic ring where one or more carbon atoms are replaced by heteroatoms such as nitrogen, oxygen and sulfur. The heterocyclyl ring can be optionally further fused or linked to aromatic and non-aromatic carbocyclic and heterocyclic rings. Examples of heterocyclyl include, but not limited to, pyrane, pyrrolidine, pyrroline, imidazoline, pyrazolidine, pyrazoline, thiazoline, thiazolidine, dihydrofuran, tetrahydrofuran, 1,3-dioxolane, piperidine, piperazine, morpholine, quinuclidine and the like.

The term "$C_2$-$C_8$ (or $C_3$-$C_8$)alkenyl" refers to an aliphatic $C_2$-$C_8$ (or $C_3$-$C_8$) hydrocarbon chain containing at least one carbon-carbon double bond and which can be straight or branched. Representative examples include, but are not limited to, ethenyl, 1-propenyl, 2-propenyl, 1- or 2-butenyl, and the like.

The term "$C_2$-$C_8$ (or $C_3$-$C_8$)alkynyl" refers to an aliphatic $C_2$-$C_8$ (or $C_3$-$C_8$) hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic," wherein the term "aromatic" refers to a completely conjugated π-electron bond system. Non-limiting examples of such aryl groups include phenyl, α- or β-naphthyl and biphenyl groups.

The term "heteroaryl" refers to aromatic heterocyclic rings, typically 5- to 8-membered heterocycles with from 1 to 3 heteroatoms selected among N, O or S. The heteroaryl ring can optionally be further fused or linked to aromatic and non-aromatic carbocyclic and heterocyclic rings. Non-limiting examples of such heteroaryl groups include, but not limited to, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

Unless otherwise provided, any of the above R1, R2, R3, R4, group may be optionally substituted, in any of their free positions, by one or more groups, for instance 1 to 6 groups, independently selected from: halogen, nitro, oxo groups (=O), cyano, $C_1$-$C_8$ alkyl, polyfluorinated alkyl, polyfluorinated alkoxy, $C_2$-$C_8$ alkenyl, $C_2$-$C_8$ alkynyl, hydroxyalkyl, aryl, arylalkyl, heteroaryl, heteroarylalkyl, heterocyclyl, heterocyclylalkyl, $C_3$-$C_8$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonyl-amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbanyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn and whenever appropriate, each of the above substituents may be further substituted by one or more of the aforementioned groups. In some embodiments, when R1, R2, R3 or R4 is substituted with one or more of the aforementioned groups, each of the aforementioned groups that is present is either unsubstituted, or is substituted with up to three groups selected from halo, $C_1$-$C_4$ alkyl, $C_1$-$C_4$-alkoxy, $C_1$-$C_4$ haloalkyl, $C_1$-$C_4$ haloalkoxy, CN, CONR'$_2$, COOR', OH, —NR'$_2$, and S(O)$_q$R', wherein q is 0-2 and each R' is independently H or $C_1$-$C_4$ alkyl.

The term halogen atom refers to a fluorine, chlorine, bromine or iodine atom. The term cyano refers to a —CN residue. The term nitro refers to a —NO$_2$ group. The term polyfluorinated alkyl or polyfluorinated alkoxy refers to any of the above straight or branched $C_1$-$C_8$ alkyl or alkoxy groups which are substituted by more than one fluorine atom including, but not limited to, trifluoromethyl, trifluoroethyl, 1,1,1, 3,3,3-hexafluoropropyl, trifluoromethoxy and the like. The term hydroxyalkyl refers to any of the above $C_1$-$C_8$ alkyl, bearing a hydroxyl group including, but not limited to, hydroxy methyl, 2-hydroxyethyl, 3-hydroxypropyl and the like.

As used herein, the term "therapeutically effective amount" of a compound of formula (I) refers to an amount which is effective in modulating the activity of protein kinases. The compounds of formula (I) are, therefore, useful in treating diseases caused by deregulated protein kinase activity.

As used herein, a "patient" refers to one in need of treatment for diseases and conditions affected by modulating protein kinase activity or is afflicted within one or more of the diseases or conditions described herein or is at a recognized risk of developing one or more of the diseases or conditions described herein as diagnosed by an attending physician or clinician. The identification of those patients who are in need of treatment for the conditions identified herein is well within the ability and knowledge of one skilled in the art. A clinician skilled in the art can readily identify, by the use of clinical tests, physical examination and medical/family history, those patients who are in need of such treatment. A patient includes a warm-blooded animal such as a mammal which is in need of modulated protein kinase activity. It is understood that guinea pigs, dogs, cats, rats, mice, horses, cattle, sheep, and humans are examples of animals within the scope of the meaning of the term. From all of the above, it is clear to the skilled person that any group which name is a composite name such as arylamino has to be intended as conventionally construed by the parts from which it derives, e.g. by an amino group which is further substituted by aryl, wherein aryl is as above defined. Likewise, any of the terms such as alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_8$cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid. Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

In some embodiments, m is an integer from 0 to 3. In some embodiments, m is 0, 1 or 2. In some embodiments, R1 is trifluoromethyl, halogen, cyano, OR5, NR6R7, COOR10, CONR11R12, or an optionally substituted group selected from ($C_1$-$C_8$)alkyl, ($C_3$-$C_8$)cycloalkyl and heterocyclyl. In some embodiments, R1 is an optionally substituted group selected from ($C_3$-$C_8$)cycloalkyl or heterocyclyl. In some embodiments, R2 and R3 are independently chosen from hydrogen and halogen. In some embodiments, when R4 is

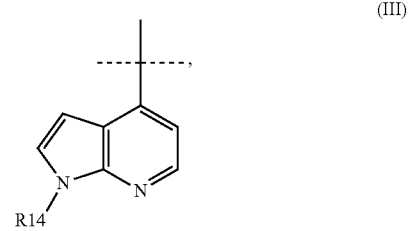

(III)

and R14 is hydrogen; or when R4 is

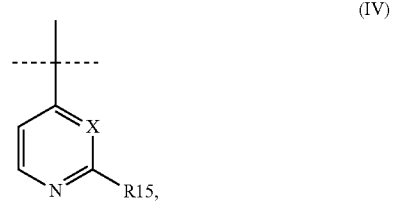

(IV)

and R15 is hydrogen, halogen or NH$_2$.

In some embodiments, compounds of formula (I) include any one or more of the following:
1) 2,5-difluoro-N-{2-fluoro-3-[1-(1-isopropyl-piperidin-4-yl)-4-pyridin-4-yl-1H-pyrazol-3-yl]-phenyl}-benzenesulfonamide
2) N-{3-[1-(1-cyclopropyl-piperidin-4-yl)-4-pyridin-4-yl-1H-pyrazol-3-yl]-2-fluoro-phenyl}-2,5-difluoro-benzenesulfonamide 3) N-{3-[4-(2-amino-pyrimidin-4-yl)-1-ethyl-1H-pyrazol-3-yl]-2-fluoro-phenyl}-2,5-difluoro-benzenesulfonamide
4) N-{3-[4-(2-amino-pyrimidin-4-yl)-1-ethyl-1H-pyrazol-3-yl}-2-fluoro-phenyl]-2,5-difluoro-benzenesulfonamide
5) 2,5-difluoro-N-{2-fluoro-3-[1-(1-methyl-piperidin-4-yl)-4-pyridin-4-yl-1H-pyrazol-3-yl]-phenyl}-benzenesulfonamide
6) N-{3-[4-(2-amino-pyrimidin-4-yl)-1-(1-methyl-piperidin-4-yl)-1H-pyrazol-3-yl]-2-fluoro-phenyl}-2,5-difluoro-benzenesulfonamide
7) 2,5-difluoro-N-{2-fluoro-3-[1-(2-fluoro-ethyl)-4-pyridin-4-yl-1H-pyrazol-3-yl]-phenyl}-benzenesulfonamide
8) 2,5-difluoro-N-{2-fluoro-3-[1-(1-methyl-piperidin-4-yl)-4-(1H-pyrrolo[2,3-b]pyridin-4-yl)-1H-pyrazol-3-yl]-phenyl}-benzenesulfonamide
9) 2,5-difluoro-N-[2-fluoro-3-(1-isopropyl-4-pyridin-4-yl-1H-pyrazol-3-yl)-phenyl]-benzenesulfonamide
10) N-{3-[4-(2-amino-pyrimidin-4-yl)-1-isopropyl-1H-pyrazol-3-yl]-2-fluoro-phenyl}-2,5-difluoro-benzenesulfonamide
11) N-{3-[4-(2-amino-pyrimidin-4-yl)-1-(2-fluoro-ethyl)-1H-pyrazol-3-yl]-2-fluoro-phenyl}-2,5-difluoro-benzenesulfonamide
12) N-{3-[4-(2-amino-pyridin-4-yl)-1-isopropyl-1H-pyrazol-3-yl]-2-fluoro-phenyl}-2,5-difluoro-benzenesulfonamide
13) N-{3-[4-(2-amino-pyridin-4-yl)-1-(2-fluoro-ethyl)-1H-pyrazol-3-yl]-2-fluoro-phenyl}-2,5-difluoro-benzenesulfonamide
14) N-{3-[4-(2-amino-pyridin-4-yl)-1-(tetrahydro-pyran-4-yl)-1H-pyrazol-3-yl]-2-fluoro-phenyl}-2,5-difluoro-benzenesulfonamide
15) N-{3-[4-(2-amino-pyrimidin-4-yl)-1-(tetrahydro-pyran-4-yl) 1H-pyrazol-3-yl]-2-fluoro-phenyl}-2,5-difluoro-benzenesulfonamide
16) 2,5-difluoro-N-{2-fluoro-3-[4-pyridin-4-yl-1-(tetrahydro-pyran-4-yl)-1H-pyrazol-3-yl]-phenyl}-benzenesulfonamide
17) N-{3-[4-(2-amino-pyridin-4-yl)-1-cyclopentyl-1H-pyrazol-3-yl]-2-fluoro-phenyl}-2,5-difluoro-benzenesulfonamide
18) N-{3-[4-(2-amino-pyrimidin-4-yl)-1-(1-cyclopropyl-piperidin-4-yl)-1H-pyrazol-3-yl]-2-fluoro-phenyl}-2,5-difluoro-benzenesulfonamide
19) N-{3-[4-(2-amino-pyrimidin-4-yl)-1-(1-isopropyl-piperidin-4-yl)-1H-pyrazol-3-yl]-2-fluoro-phenyl}-2,5-difluoro-benzenesulfonamide
20) N-{3-[4-(2-amino-pyridin-4-yl)-1-oxetan-3-yl-1H-pyrazol-3-yl]-2-fluoro-phenyl}2,5-difluoro-benzenesulfonamide
21) 2,5-difluoro-N-[2-fluoro-3-(1-oxetan-3-yl-4-pyridin-4-yl-1H-pyrazol-3-yl)-phenyl]-benzenesulfonamide
22) N-(3-{4-[2-(2-amino-pyrimidin-4-ylamino)-pyrimidin-4-yl]-1-ethyl-1H-pyrazol-3-yl}-2-fluoro-phenyl)-2,5-difluoro-benzenesulfonamide and
23) N-{3-[4-(2-amino-pyridin-4-yl)-1-(1-cyclopropyl-piperidin-4-yl)-1H-pyrazol-3-yl]-2-fluoro-phenyl}-2,5-difluoro-benzenesulfonamide
24) 2,5-difluoro-N-{2-fluoro-3-[4-(2-fluoropyridin-4-yl)-1-(1-methylpiperidin-4-yl)-1H-pyrazol-3-yl]phenyl}benzenesulfonamide
25) N-{3-[1-(4,4-difluorocyclohexyl)-4-(pyridin-4-yl)-1H-pyrazol-3-yl]-2-fluorophenyl}-2,5-difluorobenzenesulfonamide
26) N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}acetamide
27) 2,5-difluoro-N-{2-fluoro-3-[4-(2-fluoropyridin-4-yl)-1-(tetrahydro-2H-pyran-4-yl)-1H-pyrazol-3-yl]phenyl}benzenesulfonamide
28) 2,5-difluoro-N-{2-fluoro-3-[1-(1-methylpiperidin-4-yl)-4-(2-methylpyridin-4-yl)-1H-pyrazol-3-yl]phenyl}benzenesulfonamide
29) 2,5-difluoro-N-{2-fluoro-3-[4-(2-methylpyridin-4-yl)-1-(tetrahydro-2H-pyran-4-yl)-1H-pyrazol-3-yl]phenyl}benzenesulfonamide
30) N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}-2-methylpropanamide; and
31) N-{4-[3-(3-{[(2,5-difluorophenyl)sulfonyl]amino}-2-fluorophenyl)-1-(1-methylpiperidin-4-yl)-1H-pyrazol-4-yl]pyridin-2-yl}acetamide.

In some embodiments, compounds of formula (I) include any one or more of the following:

1) 2,5-difluoro-N-{2-fluoro-3-[1-(1-isopropyl-piperidin-4-yl)-4-pyridin-4-yl-1H-pyrazol-3-yl]-phenyl}-benzenesulfonamide
2) N-{3-[1-(1-cyclopropyl-piperidin-4-yl)-4-pyridin-4-yl-1H-pyrazol-3-yl]-2-fluoro-phenyl}-2,5-difluoro-benzenesulfonamide
3) N-{3-[4-(2-amino-pyrimidin-4-yl)-1-ethyl-1H-pyrazol-3-yl]-2-fluoro-phenyl}-2,5-difluoro-benzenesulfonamide
4) N-{3-[4-(2-amino-pyrimidin-4-yl)-1-ethyl-1H-pyrazol-3-yl]-2-fluoro-phenyl}-2,5-difluoro-benzenesulfonamide
5) 2,5-Difluoro-N-{2-fluoro-3-[1-(1-methyl-piperidin-4-yl)-4-pyridin-4-yl-1H-pyrazol-3-yl]-phenyl}-benzenesulfonamide
6) N-{3-[4-(2-amino-pyrimidin-4-yl)-1-(1-methyl-piperidin-4-yl)-1H-pyrazol-3-yl]-2-fluoro-phenyl}-2,5-difluoro-benzenesulfonamide
7) 2,5-difluoro-N-{2-fluoro-3-[1-(2-fluoro-ethyl)-4-pyridin-4-yl-1H-pyrazol-3-yl]-phenyl}-benzenesulfonamide
8) 2,5-difluoro-N-{2-fluoro-3-[1-(1-methyl-piperidin-4-yl)-4-(1H-pyrrolo[2,3-b]pyridin-4-yl)-1H-pyrazol-3-yl]-phenyl}-benzenesulfonamide
9) 2,5-difluoro-N-[2-fluoro-3-(1-isopropyl-4-pyridin-4-yl-1H-pyrazol-3-yl)-phenyl]-benzenesulfonamide
10) N-{3-[4-(2-amino-pyrimidin-4-yl)-1-isopropyl-1H-pyrazol-3-yl]-2-fluoro-phenyl}-2,5-difluoro-benzenesulfonamide
11) N-{3-[4-(2-amino-pyrimidin-4-yl)-1-(2-fluoro-ethyl)-1H-pyrazol-3-yl]-2-fluoro-phenyl}-2,5-difluoro-benzenesulfonamide
12) N-{3-[4-(2-amino-pyridin-4-yl)-1-isopropyl-1H-pyrazol-3-yl]-2-fluoro-phenyl}-2,5-difluoro-benzenesulfonamide
13) N-{3-[4-(2-amino-pyridin-4-yl)-1-(2-fluoro-ethyl)-1H-pyrazol-3-yl]-2-fluoro-phenyl}-2,5-difluorombenzenesulfonamide
14) N-{3-[4-(2-amino-pyridin-4-yl)-1-(tetrahydro-pyran-4-yl)-1H-pyrazol-3-yl]-2-fluoro-phenyl}-2,5-difluoro-benzenesulfonamide
15) N-{3-[4-(2-amino-pyrimidin-4-yl)-1-(tetrahydro-pyran-4-yl)-1H-pyrazol-3-yl]-2-fluoro-phenyl}-2,5-difluoro-benzenesulfonamide
16) 2,5-difluoro-N-{2-fluoro-3-[4-pyridin-4-yl-1-(tetrahydro-pyran-4-yl)-1H-pyrazol-3-yl]-phenyl}-benzenesulfonamide
17) N-{3-[4-(2-amino-pyridin-4-yl)-1-cyclopentyl-1H-pyrazol-3-yl]-2-fluoro-phenyl}-2,5-difluoro-benzenesulfonamide
18) N-{3-[4-(2-amino-pyrimidin-4-yl)-1-(1-isopropyl-piperidin-4-yl)-1H-pyrazol-3-yl]-2-fluoro-phenyl}-2,5-difluoro-benzenesulfonamide 19) 2,5-difluoro-N-[2-fluoro-3-(1-oxetan-3-yl-4-pyridin-4-yl-1H-pyrazol-3-yl)-phenyl]-benzenesulfonamide
20) N-(3-{4-[2-(2-amino-pyrimidin-4-ylamino)-pyrimidin-4-yl]-1-ethyl-1H-pyrazol-3-yl}-2-fluoro-phenyl)-2,5-difluoro-benzenesulfonamide and
21) N-{3-[4-(2-amino-pyridin-4-yl)-1-(1-cyclopropyl-piperidin-4-yl)-1H-pyrazol-3-yl]-2-fluoro-phenyl}-2,5-difluoro-benzenesulfonamide
22) 2,5-difluoro-N-{2-fluoro-3-[4-(2-fluoropyridin-4-yl)-1-(1-methylpiperidin-4-yl)-1H-pyrazol-3-yl]phenyl}benzenesulfonamide
23) N-{3-[1-(4,4-difluorocyclohexyl)-4-(pyridin-4-yl)-1H-pyrazol-3-yl]-2-fluorophenyl}-2,5-difluorobenzenesulfonamide
24) N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}acetamide
25) 2,5-difluoro-N-{2-fluoro-3-[4-(2-fluoropyridin-4-yl)-1-(tetrahydro-2H-pyran-4-yl)-1H-pyrazol-3-yl]phenyl}benzenesulfonamide
26) 2,5-difluoro-N-{2-fluoro-3-[1-(1-methylpiperidin-4-yl)-4-(2-methylpyridin-4-yl)-1H-pyrazol-3-yl]phenyl}benzenesulfonamide
27) 2,5-difluoro-N-{2-fluoro-3-[4-(2-methylpyridin-4-yl)-1-(tetrahydro-2H-pyran-4-yl)-1H-pyrazol-3-yl]phenyl}benzenesulfonamide
28) N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}-2-methylpropanamide
29) N-{4-[3-(3-{[(2,5-difluorophenyl)sulfonyl]amino}-2-fluorophenyl)-1-(1-methylpiperidin-4-yl)-1H-pyrazol-4-yl]pyridin-2-yl}acetamide.

In some embodiments, compounds of formula (I) include any one or more of the following:
1) 2,5-difluoro-N-{2-fluoro-3-[1-(1-isopropyl-piperidin-4-yl)-4-pyridin-4-yl-1H-pyrazol-3-yl]-phenyl}-benzenesulfonamide
2) N-{3-[1-(1-cyclopropyl-piperidin-4-yl)-4-pyridin-4-yl-1H-pyrazol-3-yl]-2-fluoro-phenyl}-2,5-difluoro-benzenesulfonamide
3) N-{3-[4-(2-amino-pyridin-4-yl)-1-ethyl-1H-pyrazol-3-yl]-2-fluoro-phenyl}-2,5-difluoro-benzenesulfonamide
4) N-{3-[4-(2-amino-pyridin-4-yl)-1-ethyl-1H-pyrazol-3-yl]-2-fluoro-phenyl}-2,5-difluoro-benzenesulfonamide
5) 2,5-difluoro-N-{2-fluoro-3-[1-(1-methyl-piperidin-4-yl)-4-pyridin-4-yl-1H-pyrazol-3-yl]-phenyl}-benzenesulfonamide
6) N-{3-[4-(2-amino-pyrimidin-4-yl)-1-(1-methyl-piperidin-4-yl)-1H-pyrazol-3-yl]-2-fluoro-phenyl}-2,5-difluoro-benzenesulfonamide
7) 2,5-difluoro-N-{2-fluoro-3-[1-(2-fluoro-ethyl)-4-pyridin-4-yl-1H-pyrazol-3-yl]-phenyl}-benzenesulfonamide
8) 2,5-difluoro-N-{2-fluoro-3-[1-(1-methyl-piperidin-4-yl)-4-(1H-pyrrolo[2,3-b]pyridin-4-yl)-1H-pyrazol-3-yl]-phenyl}-benzenesulfonamide
9) 2,5-difluoro-N-[2-fluoro-3-(1-isopropyl-4-pyridin-4-yl-1H-pyrazol-3-yl)-phenyl]-benzenesulfonamide
10) N-{3-[4-(2-amino-pyrimidin-4-yl)-1-isopropyl-1H-pyrazol-3-yl]-2-fluoro-phenyl}-2,5-difluoro-benzenesulfonamide
11) N-{3-[4-(2-amino-pyrimidin-4-yl)-1-(2-fluoro-ethyl)-1H-pyrazol-3-yl]-2-fluoro-phenyl}-2,5-difluoro-benzenesulfonamide
12) N-{3-[4-(2-amino-pyridin-4-yl)-1-isopropyl-1H-pyrazol-3-yl]-2-fluoro-phenyl}-2,5-difluoro-benzenesulfonamide
13) N-{3-[4-(2-amino-pyridin-4-yl)-1-(2-fluoro-ethyl)-1H-pyrazol-3-yl]-2-fluoro-phenyl}-2,5-difluoro-benzenesulfonamide
14) N-{3-[4-(2-amino-pyridin-4-yl)-1-(tetrahydro-pyran-4-yl)-1H-pyrazol-3-yl]-2-fluoro-phenyl}-2,5-difluoro-benzenesulfonamide
15) N-{3-[4-(2-amino-pyrimidin-4-yl)-1-(tetrahydro-pyran-4-yl)-1H-pyrazol-3-yl]-2-fluoro-phenyl}-2,5-difluoro-benzenesulfonamide
16) 2,5-difluoro-N-{2-fluoro-3-[4-pyridin-4-yl-1-(tetrahydro-pyran-4-yl)-1H-pyrazol-3-yl]-phenyl}-benzenesulfonamide
17) N-{3-[4-(2-amino-pyridin-4-yl)-1-cyclopentyl-1H-pyrazol-3-yl]-2-fluoro-phenyl}-2,5-difluoro-benzenesulfonamide
18) N-{3-[4-(2-amino-pyrimidin-4-yl)-1-(1-cyclopropyl-piperidin-4-yl)-1H-pyrazol-3-yl]-2-fluoro-phenyl}-2,5-difluoro-benzenesulfonamide
19) N-{3-[4-(2-amino-pyrimidin-4-yl)-1-(1-isopropyl-piperidin-4-yl)-1H-pyrazol-3-yl]-2-fluoro-phenyl}-2,5-difluoro-benzenesulfonamide
20) N-{3-[4-(2-amino-pyridin-4-yl)-1-oxetan-3-yl-1H-pyrazol-3-yl]-2-fluoro-phenyl}-2,5-difluoro-benzenesulfonamide
21) 2,5-difluoro-N-[2-fluoro-3-(1-oxetan-3-yl-4-pyridin-4-yl-1H-pyrazol-3-yl)-phenyl]-benzenesulfonamide
22) N-(3-{4-[2-(2-amino-pyrimidin-4-ylamino)-pyrimidin-4-yl]-1-ethyl-1H-pyrazol-3-yl}-2-fluoro-phenyl)-2,5-difluoro-benzenesulfonamide and
23) N-{3-[4-(2-amino-pyridin-4-yl)-1-(1-cyclopropyl-piperidin-4-yl)-1H-pyrazol-3-yl]-2-fluoro-phenyl}-2,5-difluoro-benzenesulfonamide.

In some embodiments, compounds of formula (I) include any one or more of the following:
1) 2,5-difluoro-N-{2-fluoro-3-[1-(1-isopropyl-piperidin-4-yl)-4-pyridin-4-yl-1H-pyrazol-3-yl]-phenyl}-benzenesulfonamide
2) N-{3-[1-(1-cyclopropyl-piperidin-4-yl)-4-pyridin-4-yl-1H-pyrazol-3-yl]-2-fluoro-phenyl}-2,5-difluoro-benzenesulfonamide
3) N-{3-[4-(2-amino-pyrimidin-4-yl)-1-ethyl-1H-pyrazol-3-yl]-2-fluoro-phenyl}-2,5-difluoro-benzenesulfonamide
4) N-{3-[4-(2-amino-pyridin-4-yl)-1-ethyl-1H-pyrazol-3-yl]-2-fluoro-phenyl}-2,5-difluoro-benzenesulfonamide
5) 2,5-difluoro-N-{2-fluoro-3-[1-(1-methyl-piperidin-4-yl)-4-pyridin-4-yl-1H-pyrazol-3-yl]-phenyl}-benzenesulfonamide
6) N-{3-[4-(2-amino-pyrimidin-4-yl)-1-(1-methyl-piperidin-4-yl)-1H-pyrazol-3-yl]-2-fluoro-phenyl}-2,5-difluoro-benzenesulfonamide
7) 2,5-difluoro-N-{2-fluoro-3-[1-(2-fluoro-ethyl)-4-pyridin-4-yl-1H-pyrazol-3-yl]-phenyl}-benzenesulfonamide
8) 2,5-difluoro-N-{2-fluoro-3-[1-(1-methyl-piperidin-4-yl)-4-(1H-pyrrolo[2,3-b]pyridin-4-yl)-1H-pyrazol-3-yl]-phenyl}-benzenesulfonamide
9) 2,5-difluoro-N-[2-fluoro-3-(1-isopropyl-4-pyridin-4-yl-1H-pyrazol-3-yl)-phenyl]-benzenesulfonamide
10) N-{3-[4-(2-amino-pyrimidin-4-yl)-1-isopropyl-1H-pyrazol-3-yl]-2-fluoro-phenyl}-2,5-difluoro-benzenesulfonamide
11) N-{3-[4-(2-amino-pyrimidin-4-yl)-1-(2-fluoro-ethyl)-1H-pyrazol-3-yl]-2-fluoro-phenyl}-2,5-difluoro-benzenesulfonamide
12) N-{3-[4-(2-amino-pyridin-4-yl)-1-isopropyl-1H-pyrazol-3-yl]-2-fluoro-phenyl}-2,5-difluoro-benzenesulfonamide 13) N-{3-[4-(2-amino-pyridin-4-yl)-1-(2-fluoro-ethyl)-1H-pyrazol-3-yl]-2-fluoro-phenyl}-2,5-difluoro-benzenesulfonamide
14) N-{3-[4-(2-amino-pyridin-4-yl)-1-(tetrahydro-pyran-4-yl)-1H-pyrazol-3-yl]-2-fluoro-phenyl}-2,5-difluoro-benzenesulfonamide
15) N-{3-[4-(2-amino-pyrimidin-4-yl)-1-(tetrahydro-pyran-4-yl)-1H-pyrazol-3-yl]-2-fluoro-phenyl}-2,5-difluoro-benzenesulfonamide
16) 2,5-difluoro-N-{2-fluoro-3-[4-pyridin-4-yl-1-(tetrahydro-pyran-4-yl)-1H-pyrazol-3-yl]-phenyl}-benzenesulfonamide
17) N-{3-[4-(2-amino-pyridin-4-yl-1-cyclopentyl-1H-pyrazol-3-yl]-2-fluoro-phenyl}-2,5-difluoro-benzenesulfonamide
18) N-{3-[4-(2-amino-pyrimidin-4-yl)-1-(1-isopropyl-piperidin-4-yl)-1H-pyrazol-3-yl]-2-fluoro-phenyl}-2,5-difluoro-benzenesulfonamide
19) 2,5-difluoro-N-[2-fluoro-3-(1-oxetan-3-yl-4-pyridin-4-yl-1H-pyrazol-3-yl)-phenyl]-benzenesulfonamide
20) N-(3-{4-[2-(2-amino-pyrimidin-4-ylamino)-pyrimidin-4-yl]-1-ethyl-1H-pyrazol-3-yl}-2-fluoro-phenyl)-2,5-difluoro-benzenesulfonamide and
21) N-{3-[4-(2-amino-pyridin-4-yl)-1-(1-cyclopropyl-piperidin-4-yl)-1H-pyrazol-3-yl]-2-fluoro-phenyl}-2,5-difluoro-benzenesulfonamide.

In some embodiments, compounds of formula I are disclosed wherein each substituted straight or branched $(C_1-C_8)$ alkyl, $(C_2-C_8)$alkenyl or $(C_2-C_8)$alkynyl, $(C_3-C_8)$cycloalkyl, $(C_3-C_8)$cycloalkenyl, heterocyclyl, aryl and heteroaryl is substituted with up to 4 substitutents selected from halogen, nitro, oxo groups (=O), cyano, $C_1-C_8$ straight or branched alkyl, polyfluorinated alkyl, polyfluorinated alkoxy, $C_2-C_8$ alkenyl, $C_2-C_8$ alkynyl, hydroxyalkyl, aryl, arylalkyl, heteroaryl, heteroarylalkyl, heterocyclyl, heterocyclylalkyl, $C_3-C_8$cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In some embodiments, compounds of formula I are disclosed wherein each substituted straight or branched $(C_1-C_8)$ alkyl, $(C_3-C_8)$cycloalkyl, heterocyclyl, aryl and heteroaryl is substituted with up to 4 substitutents selected from halogen, nitro, oxo groups (=O), cyano, $C_1-C_8$ straight or branched alkyl, polyfluorinated alkyl, polyfluorinated alkoxy, $C_2-C_8$ alkenyl, $C_2-C_8$ alkynyl, hydroxyalkyl, aryl, arylalkyl, heteroaryl, heteroarylalkyl, heterocyclyl, heterocyclylalkyl, $C_3-C_8$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In preferred embodiments, compounds of formula I are disclosed wherein each substituted straight or branched $(C_1-C_8)$alkyl, $(C_3-C_8)$cycloalkyl, heterocyclyl, aryl and heteroaryl is substituted with up to 4 substitutents selected from halogen, nitro, oxo groups (=O), cyano, $C_1-C_4$ straight or branched alkyl, $C_1-C_4$ straight or branched alkoxy, $C_1-C_4$ haloalkyl, $C_1-C_4$ haloalkoxy, hydroxy, CONR'$_2$, COOR', —NR'$_2$, and —S(O)$_q$R', wherein q is 0-2 and each R' is independently H or $C_1-C_4$ straight or branched alkyl.

In one aspect, methods of preparing the pyrazolophenyl-benzenesulfonamide compounds represented by formula (I), prepared through a process consisting of standard synthetic transformations are disclosed.

In another aspect, a method for treating diseases caused by and/or associated with deregulated protein kinase activity, particularly the RAF family, PLK family, protein kinase C in different isoforms, Met, PAK-4, PAK-5, ZC-1, STLK-2, DDR-2, Aurora A, Aurora B, Aurora C, Bub-1, Chk1, Chk2, HER2, MEK1, MAPK, EGF-R, PDGF-R, FGF-R, IGF-R, PI3K, wee1 kinase, Src, Abl, Akt, MAPK, ILK, MK-2, IKK-2, Cdc7, Nek, Cdk/cyclin kinase family, more particularly the RAF family, which comprises administering to a mammal, in need thereof, an effective amount of a pyrazolophenyl-benzenesulfonamide compounds represented by formula (I) as defined above is disclosed. In one embodiment, a method to treat a disease caused by and/or associated with deregulated protein kinase activity selected from the group consisting of cancer, cell proliferative disorders, viral infections, autoimmune and neurodegenerative disorders is disclosed.

In another aspect, a method to treat specific types of cancer including but not limited to: carcinoma such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia, tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma is disclosed.

In one embodiment, a method to treat specific cellular proliferation disorders including, but not limited to, benign prostate hyperplasia, familial adenomatosis polyposis, neurofibromatosis, psoriasis, vascular smooth cell proliferation associated with atherosclerosis, pulmonary fibrosis, arthritis, glomerulonephritis and postsurgical stenosis and restenosis is disclosed. In one embodiment, a method to treat viral infections, in particular the prevention of AIDS development in HIV-infected individuals is disclosed. In addition, a method also provides tumor angiogenesis and metastasis inhibition as well as the treatment of organ transplant rejection and host versus graft disease.

In one embodiment, a method further comprises subjecting a mammal in need of treatment to a radiation therapy or chemotherapy regimen in combination with at least one cytostatic or cytotoxic agent. Moreover, an in vitro method for inhibiting the RAF family protein activity which comprises contacting the said protein with an effective amount of a compound of formula (I) is disclosed.

In one aspect, a pharmaceutical composition comprising one or more compounds of formula (I) or a pharmaceutically acceptable salt thereof and a pharmaceutically acceptable excipient, carrier or diluents is disclosed. In one embodiment, a pharmaceutical composition comprising a compound of formula (I) in combination with known anticancer agents, e.g. cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like is disclosed. Additionally, a product or kit is disclosed comprising a compound of formula (I) or a pharmaceutically acceptable salt thereof, as defined above, or pharmaceutical compositions thereof and one or more anticancer agents, as a combined preparation for simultaneous, separate or sequential use in anticancer therapy.

In another aspect, a compound of formula (I) or a pharmaceutically acceptable salt thereof, as defined above, for use as a medicament is disclosed. Moreover, the use of a compound of formula (I) or a pharmaceutically acceptable salt thereof, as defined above, is disclosed in the manufacture of a medicament with antitumor activity. A compound of formula (I) or a pharmaceutically acceptable salt thereof, as defined above, is also disclosed for use in any of the methods described above.

In one aspect, a process for the preparation of a compound of formula (I) as defined above is disclosed, by using the reaction routes and synthetic schemes described below, employing the techniques available in the art and starting materials readily available. The preparation of certain embodiments is described in the examples that follow, but those of ordinary skill in the art will recognize that the preparations described may be readily adapted to prepare other embodiments. For example, the synthesis on non-exemplified compounds may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds.

In cases when the pyrazole ring bears a protective group such as PG2 as defined according to the examples below, the protective group can be attached to any of the nitrogen atoms of the pyrazole ring providing isomeric compounds of formula general IIa and IIb. Said isomeric compounds are contemplated as being included as, unless otherwise provided, the position of said protecting group is not relevant to the preparation of the compounds of formula (I).

Unless otherwise described, when compounds of general formula (II) are shown with only one of the following regioisomeric forms of formula (IIa) or (IIb), the remaining one is still intended as comprised within the meaning of the general formula.

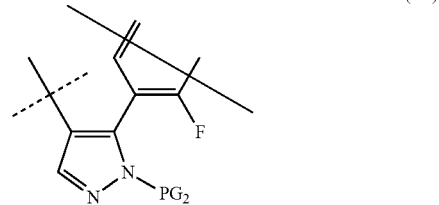

(IIa)

(IIb)

As a consequence, when R29 as defined according to the examples below has the meaning of PG2, the group can be attached to any of the nitrogen atoms of the pyrazole ring providing isomeric compounds of formula general IIc and IId. The isomeric compounds are contemplated as being included unless otherwise provided. The position of the protecting group is irrelevant to the preparation of the compounds of formula (I) provided.

Unless otherwise described, when compounds of general formula (II) show only one of the following regioisomeric forms of formula (IIc) or (IId), the remaining one is still intended as comprised within the meaning of the general formula.

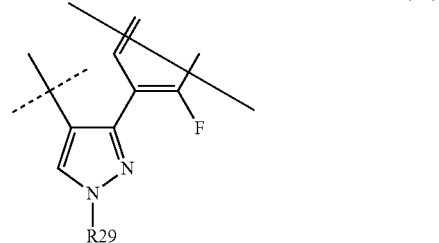

(IIc)

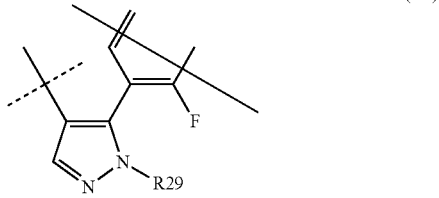

(IId)

A compound of formula (I) can be prepared according to the general synthetic processes described hereafter in method A and method B.

The intermediate compounds of general formulas 1 and 9 are prepared according to method C shown below, starting from a compound of formula 14.

The intermediate compounds of general formula 14A and 14B are prepared according to method D shown below, staring from a compound of formula 20.

The intermediate compound of general formula 2 prepared according to method A and method B, may be further transformed into another compound of formula 2, according to method D and method F below.

Persons with ordinary skill in the art will appreciate that any transformation performed according to these methods may require standard modifications such as protection of interfering groups, change to other suitable reagents known in the art, or routine modifications of reaction conditions.

Method A ethoxymethyl (MEM) or the like, acetyl, ethoxycarbonyl or the like, R30 is either hydrogen or a group $SO_2Ph(R2)(R3)$, wherein R2 and R3 are as defined above. M is $B(OH)_2$, $B(OAlk)_2$, $Sn(Alk)_3$, $Al(Alk)_2$, ZnHal, MgHal or $ZrCp_2Hal$ M' is $B(OAlk)_2$ or $Sn(Alk)_3L'$ is a group that may work as a leaving group, such as a halogen atom, a tosylate, mesylate or triflate, R4 is also defined above.

Referring to a synthetic process for the preparation of a compound of formula (I) which is described in method A, in step "a" a compound of formula 1 can be transformed into a compound of formula 2 by exploiting any of the cross-coupling reactions suitable for the formation of carbon-carbon bonds. Such reactions, which are well known in the art, imply

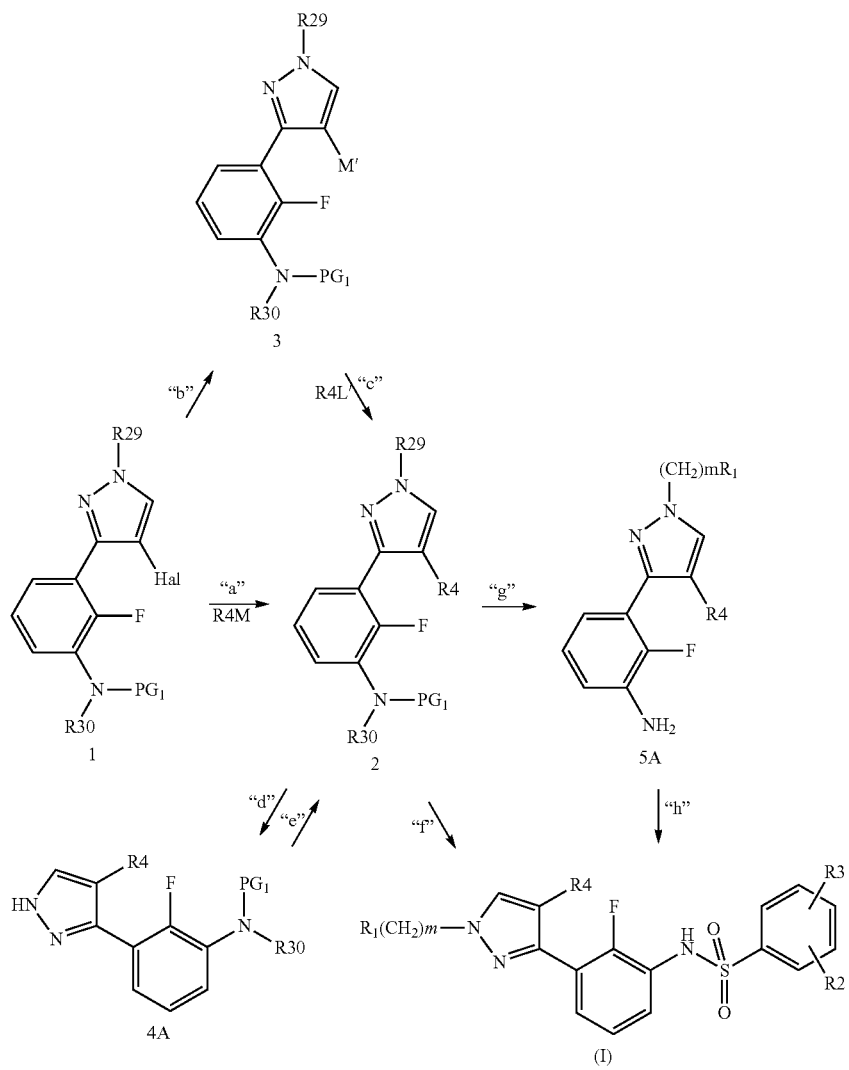

In the above scheme for method A, Hal is a halogen atom such as iodide or bromide, R29 is —$(CH_2)_m$R1 or $PG_2$, where m and R1 are as defined above, and $PG_2$ is a suitable protective group of the pyrazole ring, such as p-methoxybenzyl, tetrahydropyranyl, trityl or a silyl derivative such as trimethylsilylethoxymethyl (SEM) and 2-trimethylsilylethanesulfonyl (SES). In one embodiment, the protecting group is tetrahydropyranyl. $PG_1$ is a suitable protective group of the aniline or the sulfonamide, such as t-butoxycarbonyl (BOC), benzyloxycarbonyl, methoxymethyl (MOM), 2-methoxycoupling with a suitable organometallic reagent, such as an organoboron, organotin, organozinc, organoaluminum or organozirconium compound and the like. Alternatively, in step "b" a compound of formula 1 is transformed into an organometallic derivative of formula 3, such as a boronpyrazolo derivative, which, in turn in step"c" is cross-coupled to a suitable electrophile, according to the conditions of step "a" to form a compound of formula 2. When in a compound of formula 2 R29 is $PG_2$, such a protective group is removed according to step "d," to form a compound of formula 4A, and in step "e" such a compound of formula 4A is converted back to a compound of formula 2 where R29 is —(CH$_2$)mR1. The introduction of such a group is normally accomplished through N-alkylation with a suitable alkylating agent of formula L-(CH2)mR1, where L is OH or a group that may work as a leaving group, such as a halogen atom, a tosylate, mesylate or triflate, or L is a group —B(OH)$_2$. Such an alkylation could yield a mixture of regioisomers from which the desired isomer is purified by known methods such as silica gel chromatography or preparative HPLC. In step "f" a compound of formula 2 where R29 is —(CH$_2$)mR1 and R30 is SO$_2$Ph(R2)(R3) is transformed into a compound of formula (I) by removing the protective group PG$_1$. Alternatively, when in a compound of formula 2 R29 is —(CH$_2$)mR1 and R30 is hydrogen, removing the protective group according to step "g" leads to a compound of general formula 5A, which in step "h" is converted into a compound of general formula (I) by reaction with a suitable sulfonyl chloride.

According to step "a" of method A, a compound of formula 1 is cross-coupled to a suitable organometallic compound of general formula R4M, such as an organoboron compound (Suzuki reaction), an organotin compound (Stifle reaction), an organozinc, organoaluminium or organozirconium compound (Negishi reaction), and the like. Such reactions are well known among those with ordinary skill in the art. In one synthetic method, a Suzuki reaction uses an appropriate aryl or heteroaryl boronate is used in the presence of a palladium-based catalyst, such as palladium tetrakis triphenyl phosphine, and a suitable base, such as Cs$_2$CO$_3$, Na$_2$CO$_3$, K$_2$CO$_3$, Rb$_2$CO$_3$, NaOH, CsF, and the like. Such reactions can be carried out in a solvent such as N,N-dimethylformamide, dimethylsulfoxide, water, dimethoxyethane, 1,4-dioxane, tetrahydrofuran or the like, and mixture thereof, at a temperature ranging from about 20° C. to reflux and for a time ranging from about 30 minutes to about 24 hours.

According to step "b" of method A, a compound of formula 1 can be converted into a suitable organometallic derivative of formula 3, such as an organoboron, an organotin or the like. In one embodiment, organometal is used. The organo metal can be organoboron compounds obtained by reacting a compound of formula 1 with a suitable boron compound, such as bis(pinacolato)diboron, pinacolborane, or the like in the presence of a suitable palladium catalyst such as palladium acetate (Pd(OAc)$_2$), 1,1'-bis(diphenylphosphino)ferrocene-palladium(II)dichloride dichloromethane complex (Pd(dppf)Cl$_2$.CH$_2$Cl$_2$) or Pd(CH$_3$CN)$_2$Cl$_2$ and of a suitable base, such as KOAc, triethylamine and the like, in solvents such as N,N-dimethylformamide, dimethylsulfoxide, dimethoxyethane, 1,4-dioxane, tetrahydrofuran, toluene or the like, at a temperature ranging from about 20° C. to reflux and for a time ranging from about 30 minutes to about 24 hours.

According to step "c" of method A, the organometallic derivative of formula 3 is cross-coupled with an appropriate electrophile of formula R4L', such as an aryl halide or a trifluoromethanesulfonate (triflate), a methanesulfonate (mesylate) or a p-toluenesulfonate (tosylate) in the presence of a palladium or nickel-based catalyst, such as palladium(tetrakistriphenyl)phosphine, and a suitable base, such as Cs$_2$CO$_3$, K$_2$CO$_3$, Rb$_2$CO$_3$, NaOH, CsF, and the like to give a compound of formula 2 Such reactions can be carried out in a solvent such as N,N-dimethylformamide, dimethylsulfoxide, water, dimethoxyethane, 1,4-dioxane, tetrahydrofuran and the like, and mixture thereof, at temperature ranging from about 20° C. to reflux and for a time ranging from about 30 minutes to about 24 hours.

According to step "d" of method A, which applies when R29 is PG$_2$, the removal of the protective group PG$_2$ can be accomplished in a number of ways depending on the nature of the protective group. For instance, when PG$_2$ is a tetrahydropyranyl group, transformation of a compound of formula 2 to a compound of formula 4A can be accomplished using an acid, such as p-toluenesulfonic acid or hydrochloric acid in methanol or ethanol. When said protective group is p-methoxybenzyl or trityl, transformation of a compound of formula 2 into a compound of formula 4A can be accomplished using strong acids such as trifluoroacetic acid in a suitable cosolvent such as dichloromethane at a temperature ranging from 20° C. to reflux or above, provided that the reaction is carried out in a sealed vial and heated for instance with a microwave oven, for a time ranging from 30 minutes to about 24 hours.

According to step "e" of method A, the conversion of the N-unsubstituted pyrazole of formula 4A into a compound of formula 2 where R29 is —(CH$_2$)mR1 can be accomplished using a compound of formula L-(CH$_2$)$_m$R1. When L is OH, the well-known Mitsunobu conditions can be employed, in which case the reaction can be accomplished using a dialkyl azodicarboxylate, such as diethyl azodicarboxylate (DEAD), diisopropyl azodicarboxylate (DIAD) or the like, in the presence of a trialkyl or triaryl phosphine, preferably triphenyl phosphine in a suitable solvent such as tetrahydrofuran, 1,4-dioxane, 1,2-dimethoxyethane, or acetonitrile. When L is a group that, optionally upon activation, may work as a leaving group, such as a halogen atom, a tosylate, mesylate, triflate or the like, the conversion can be accomplished using a suitable base such as NaH, K$_2$CO$_3$, Cs$_2$CO$_3$, NaOH, 1,8-diazabicyclo[5.4.0]-undec-7-ene (DBU), lithium bis(trimethylsilyl)amide (LiHMDS) and the like, in a suitable solvent such as dichloromethane, tetrahydrofuran, 1,4-dioxane, 1,2-dimethoxyethane, methanol, ethanol, isopropanol, acetonitrile, acetic acid, N,N-dimethylformamide, N,N-dimethylacetamide, dimethylsulfoxide and the like. Said reactions can be carried out at temperatures ranging from about 0° C. to reflux and for a time ranging from about 30 minutes to about 48 hours. When L is a boronic acid group B(OH)$_2$, the reaction is normally carried out in the presence of a base such as Na$_2$CO$_3$, K$_2$CO$_3$, Cs$_2$CO$_3$ and the like, a copper salt, such as Cu(OAc)$_2$, and a further copper ligand, such as [2,2']bipyridinyl. That reaction is performed in a suitable solvent such as dichloroethane, dichloromethane, and the like and can be carried out at temperatures ranging from about 0° C. to reflux and for a time ranging from about 30 minutes to about 48 hours. If required, compounds of formula 2 so obtained can be separated and purified by silica gel chromatography or preparative HPLC.

According to step "f" of method A, which applies when R29 is —(CH$_2$)mR1 and R30 is SO$_2$Ph(R2)(R3), the removal of protective group PG$_1$ to afford a compound of formula (I) can be accomplished in a number of ways depending on the nature of the protective group. For instance, when PG$_1$ is an acetyl or ethoxycarbonyl, removal of the protective group can be accomplished under basic conditions, using for instance a base such as triethylamine or N,N-diisopropylethylamine (DIPEA) in methanol or ethanol, or using an aqueous solution of an inorganic base such as sodium or potassium carbonate, sodium or potassium hydroxide and the like. Such reactions can be carried out at temperatures ranging from about 0° C. to reflux and for a time ranging from about 30 minutes to about 48 hours. When PG$_1$ is a group such as BOC, MOM, MEM or the like, the deprotection reaction can be carried out under acidic conditions, using for instance hydrochloric acid in a solvent such as 1,4-dioxane, dimethoxyethane and the like, or using trifluoroacetic acid in solvents such as water, dichloromethane and the like. Said reactions can be carried out at temperatures ranging from about 0° C. to reflux and for a time ranging from about 30 minutes to about 48 hours. When such a group is benzyloxycarbonyl, the deprotection reaction can be carried out using $H_2$ in the presence of a suitable hydrogenation catalyst. The hydrogenation catalyst is usually a metal, most often palladium, which can be used as such or supported on carbon, in a suitable solvent such as tetrahydrofuran, 1,4-dioxane, N,N-dimethylformamide, methanol, ethyl acetate, and mixtures thereof.

According to step "g" of method A, which applies when R29 is —$(CH_2)mR1$ and R30 is hydrogen, the removal of the protective group $PG_1$ to afford a compound of formula 5A can be accomplished in a number of ways depending on the nature of the protective group as described under step "f" of method A.

According to step "h" of method A, a compound of formula 5A can be converted into a compound of formula (I) by reaction with an appropriate sulfonyl chloride in the presence of a suitable base, such as pyridine, N-methyl morpholine, or DIPEA, in an appropriate solvent such as pyridine, dichloromethane or tetrahydrofuran, at a temperature ranging from about 0° C. to reflux and for a time varying from about 1 hour to about 7 days.

Method B

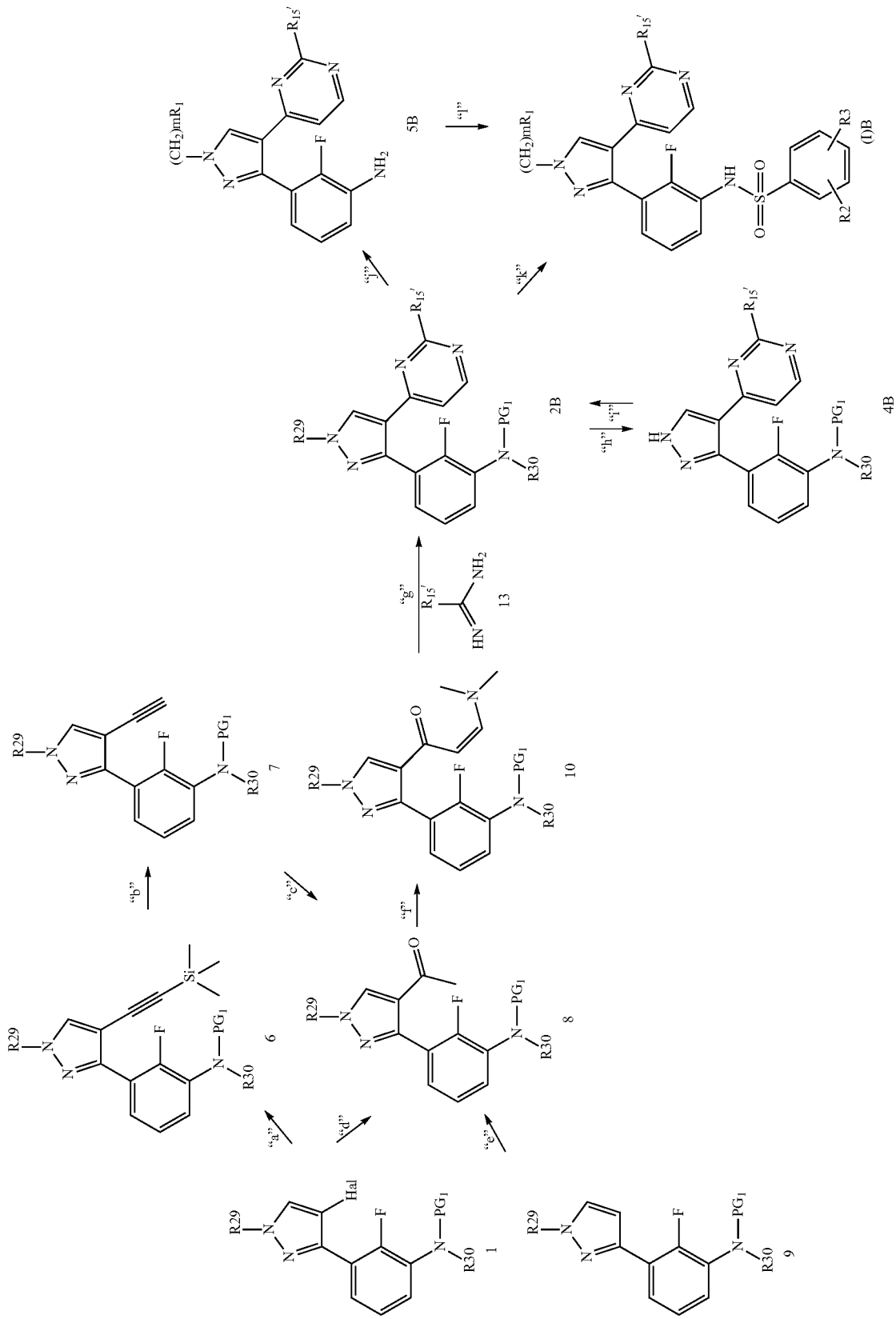

In the above scheme, m, R1, R2, R3, R4, R29, R30 and PG$_1$, are as defined above, and R15' is as R15 defined above but does not include halogen.

Referring to a synthetic process for the preparation of a compound of formula IB which is described in method B in step "a," a compound of formula 1 is subjected to a Sonogashira type reaction with trimethylsilylacetylene to form an intermediate of formula 6. In step "b," desilylation of the latter following hydration of the intermediate alkyne that is carried out in step "c," yields a compound of formula 8. Alternatively, in step "d" a compound of formula 1 is transformed into a compound of formula 8 by a two-step sequence involving cross-coupling with a suitable enol ether or enol ether organometallic derivative followed by hydrolysis of the enol ether intermediate.

Compound of formula 8 can be alternatively prepared according to step "e" by acylation under classical Friedel-Crafts conditions of a compound of formula 9. In step "f," the compound of formula 8 is transformed into an enaminone derivative of formula 10, which, in step "g" is condensed with an appropriate guanidine or amidine derivative or an S-alkyl isothiourea derivative to give a compound of formula 2B. When in a compound of formula 2B R29 is PG$_2$, the protective group is removed according to step "h," to form a compound of formula 4B, and in step "i" such a compound of formula 4B is converted back to a compound of formula 2B where R29 is —(CH$_2$)mR1. The introduction of such a group is normally accomplished through N-alkylation with a suitable alkylating agent L-(CH$_2$)mR1, where L is defined above. The latter reaction could yield a mixture of regioisomers from which the desired isomer is purified by known methods such as silica gel chromatography or preparative HPLC. In step "k" a compound of formula 2B where R29 is —(CH$_2$)mR1 and R30 is SO$_2$Ph(R2)(R3) is transformed into a compound of formula (I)B by removing the protective group PG$_1$. Alternatively, when in a compound of formula 2B R29 is —(CH$_2$)mR1 and R30 is hydrogen, removing the protective group according to step "j" leads to a compound of general formula 5B, which, in step "l" is converted into a compound of general formula (I)B by reaction with a suitable sulfonyl chloride.

According to step "a" of method B, a compound of formula 1 is reacted with trimethylsilylacetylene in the presence of a suitable palladium catalyst such as bis(triphenylphosphine)palladium(II) dichloride (PdCl$_2$(PPh$_3$)$_2$), tetrakis(triphenylphosphine)palladium (Pd(PPh$_3$)$_4$), and the like, and of a suitable copper catalyst, such as CuI. Said reaction is carried out in the presence of a suitable base, such as triethylamine, diethylamine, diisopropylamine and the like, optionally in the presence of a phosphine ligand, such as triphenylphosphine. The reaction is normally carried out at temperatures ranging from about −20° C. to reflux and for a time ranging from about 30 minutes to about 48 hours.

According to step "b" of method B, the trimethylsilyl group is removed using a base such as KOH, NaOH, K$_2$CO$_3$, in a solvent such as methanol, ethanol and the like or using a suitable fluoride salt, such as KF, n-Bu$_4$NF in solvents such as tetrahydrofuran, dimethoxyethane, N,N-dimethylformamide and the like.

According to step "c" of method B, the hydration of the alkyne of formula 7 to give a compound of formula 8 is accomplished using, for instance acetic acid, trifluoroacetic acid, trifluoromethansulfonic acid, mercuric triflate (Hg(OTf)$_2$), NaHSO$_3$, and the like in a suitable aqueous solvent such as acetonitrile, 1,4-dioxane, ethanol and the like.

According to step "d" of method B, a compound of formula 1 is cross-coupled with a suitable enol ether organometallic derivative, such as 1-ethoxyvinyltri-n-butyltin following hydrolysis of the enol ether intermediate. The cross-coupling is carried out in the presence of a suitable palladium catalyst such as tris(dibenzylideneacetone)dipalladium(0) (Pd$_2$(dba)$_3$), Pd(OAc)$_2$, PdCl$_2$(PPh$_3$)$_2$, Pd(PPh$_3$)$_4$, and the like, and of a suitable base, such as triethylamine, diethylamine, diisopropylamine or CsF, and the like, optionally in the presence of a phosphine ligand, such as triphenylphosphine, tritolylphosphine and the like. The hydrolysis of the resulting enol ether is normally carried out under acidic conditions, using for instance hydrochloric acid, acetic acid, trifluoroacetic acid, trifluoromethansulfonic acid, and the like in a suitable aqueous solvent such as acetonitrile, 1,4-dioxane, ethanol and the like.

According to step "e" of method B, a compound of formula 8 can be prepared starting from a compound of formula 9 by reaction with a suitable electrophile, such as acetyl chloride or acetic anhydride in the presence of a suitable Lewis acid, such as aluminium trichloride, tin chloride and the like. Such a reaction is normally carried out in solvents such as carbon disulfide, dichloromethane, dichloroethane, carbon tetrachloride and the like, at a temperature ranging from about −70° C. to reflux.

According to step "f" of method B, synthesis of the enaminone derivative of formula 10 is accomplished using a N,N-dimethylformamide dialkyl acetal, such as N,N-dimethylformamide dimethyl acetal, N,N-dimethylformamide ditertbutyl acetal and the like, in a suitable solvent such as tetrahydrofuran, 1,4-dioxane, 1,2-dimethoxyethane, acetonitrile, N,N-dimethylformamide, N,N-dimethylacetamide, and the like at a temperature ranging from about 0° C. to reflux and for a time ranging from about 30 minutes to about 24 hours.

According to step "g" of method B, the condensation of the compound of formula 10 with a compound of formula 13 to form a compound of formula 2B is accomplished using solvents such as N,N-dimethylformamide, N,N-dimethylacetamide, water, tetrahydrofuran, 1,4-dioxane, dimethoxyethane, acetonitrile, ethanol, isopropanol and mixtures thereof, optionally in the presence of a suitable base such as sodium ethoxide, sodium methoxide, K$_2$CO$_3$, NaOH, DBU, or the like at temperatures ranging from about 20° C. to reflux and for a time ranging from about 30 minutes to about 48 hours.

According to step "h" of method B, the conversion of a compound of formula 2B in a compound of formula 4B is accomplished as described under step "d" of method A.

According to step "i" of method B, the conversion of a compound of formula 4B into another compound of formula 2B is accomplished as described under step "e" of method A.

According to step "k" of method B, conversion of a compound of formula 2B into a compound of formula (I)B is accomplished as described under step "f" of method A.

According to step "j" of method B, the conversion of a compound of formula 2B in a compound of formula 5B is accomplished as described under step "g" of method A.

According to step "l" of method B, the conversion of a compound of formula 5B into a compound of formula (I)B is accomplished as described under step "h" of method A.

In a general synthetic process, the intermediate compounds of general formulas 1 and 9 are prepared starting from a compound of formula 14 according to method C shown below.

Method C

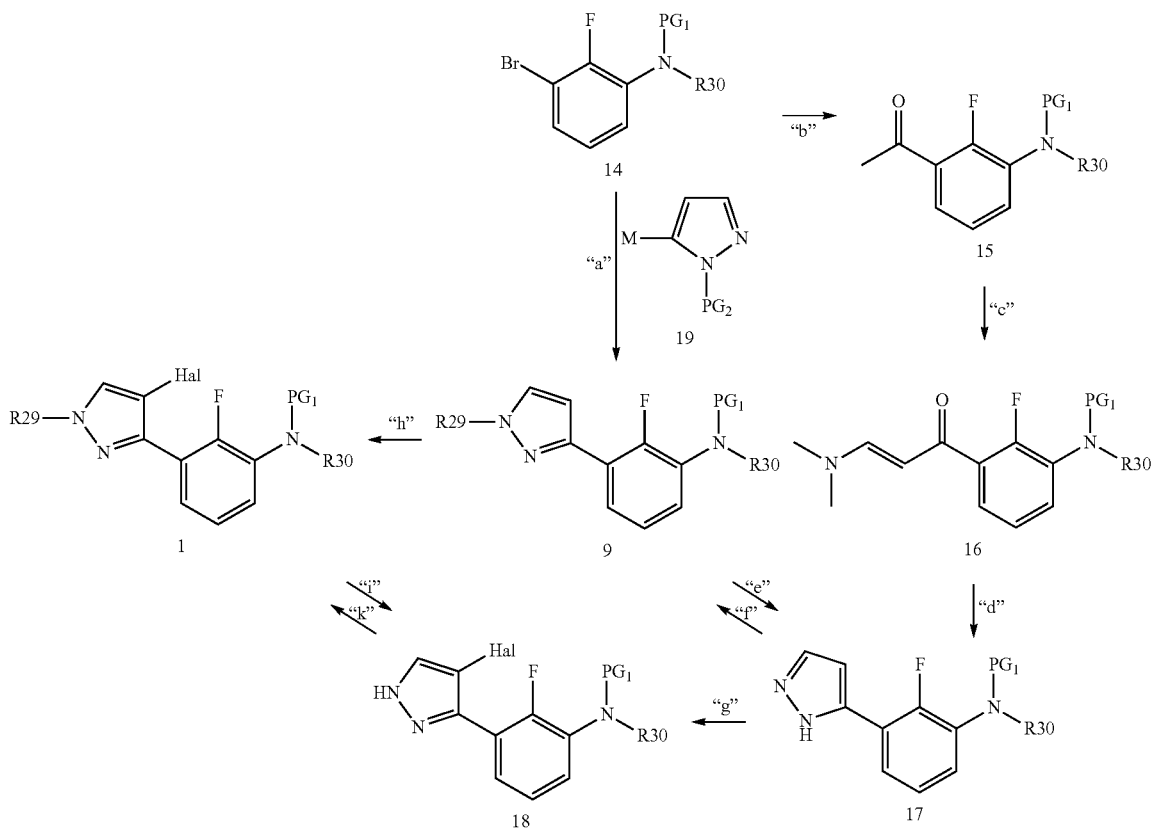

In the above scheme, m, R1, R29, R30, PG$_1$, PG$_2$, L and M, are as defined above.

Referring to a synthetic process for the preparation of compounds of general formula 1 and 9, which are described in method C, in step "a" a compound of formula 14 is converted in a compound of formula 9 by a cross-coupling reaction with a suitable organometallic derivative of general formula 19. According to step "h," the halogenation of compound 9 affords compounds of general formula 1. According to step "b" a compound of formula 14 is transformed into a compound of formula 15 by a two-step sequence involving cross-coupling with a suitable enol ether organometallic derivative followed by hydrolysis of the enol ether intermediate. In step "c," a compound of formula 15 is transformed into an enaminone derivative of formula 16, which, in step "d" is condensed with hydrazine to form a pyrazole of formula 17. The latter can be obtained also from a compound of formula 9, when R29 is PG$_2$, by removing the protective group PG$_2$ according to step "e". In step "f," a compound of general formula 17 is converted back to a compound of formula 9 where R29 is —(CH$_2$)mR1. The introduction of such a group is normally accomplished through N-alkylation with a suitable alkylating agent L-(CH$_2$)mR1, where L is defined above. The latter reaction could yield a mixture of regioisomers from which the desired isomer is purified by known methods such as silica gel chromatography or preparative HPLC. According to step "g" the halogenation of compound 17 affords compounds of general formula 18. The latter can be obtained also from a compound of formula 1, when R29 is PG$_2$, by removing the protective group PG$_2$ according to step "i". In step "k," a compound of general formula 18 is converted back to a compound of formula 1 where R29 is —(CH$_2$)mR1. The introduction of such a group is normally accomplished through N-alkylation with a suitable alkylating agent L-(CH$_2$)mR1, where L is defined above. The latter reaction could yield a mixture of regioisomers from which the desired isomer is purified by known methods such as silica gel chromatography or preparative HPLC.

According to step "a" of method C, a compound of formula 14 is cross-coupled with an organometallic derivative of general formula 19, such as an organoboron compound. Such reactions are well known among those with ordinary skill in the art. When an appropriate pyrazolyl boronate derivative is used, the reaction can be carried out in the presence of a palladium-based catalyst, such as Pd(PPh$_3$)$_4$, and a suitable base, such as Cs$_2$CO$_3$, K$_2$CO$_3$, Rb$_2$CO$_3$, NaOH, CsF, and the like. Such reactions can be carried out in a solvent such as N,N-dimethylformamide, dimethylsulfoxide, water, dimethoxyethane, 1,4-dioxane, tetrahydrofuran and the like, and mixture thereof, at a temperature ranging from about 20° C. to reflux and for a time ranging from about 30 minutes to about 24 hours.

According to step "b" of method C, a compound of formula 14 is cross-coupled with a suitable enol ether organometallic derivative, such as 1-ethoxyvinyltri-n-butyltin following hydrolysis of the enol ether intermediate. The cross-coupling is carried out in the presence of a suitable palladium catalyst such as Pd$_2$(dba)$_3$, Pd(OAc)$_2$, PdCl$_2$(PPh$_3$)$_2$, Pd(PPh$_3$)$_4$, and the like, and a suitable base, such as triethylamine, diethylamine, diisopropylamine or CsF, and the like, optionally in the presence of a phosphine ligand, such as triphenylphosphine, tritolylphosphine and the like. The hydrolysis of the resulting enol ether is normally carried out under acidic conditions, using for instance hydrochloric acid, acetic acid, trifluoroacetic acid, trifluoromethansulfonic acid, and the like in a suitable aqueous solvent such as acetonitrile, 1,4-dioxane, ethanol and the like.

According to step "c" of method C, the conversion of a compound of formula 15 into a compound of formula 16 is accomplished as described under step "f" of method B.

According to step "d" of method C, the conversion of a compound of formula 16 into a compound of formula 17 is accomplished by using a hydrazine in a suitable solvent such as tetrahydrofuran, 1,4-dioxane, 1,2-dimethoxyethane, methanol, ethanol, acetonitrile, acetic acid, N,N-dimethylformamide and mixtures thereof at a temperature ranging from about 0° C. to reflux and for a time ranging from about 30 minutes to about 24 hours.

According to step "e" of method C, the conversion of a compound of formula 9 into a compound of formula 17 is accomplished as described under step "d" of method A.

According to step "f" of method C, the conversion of a compound of formula 17 into another compound of formula 9 is accomplished as described under step "e" of method A.

According to step "g" of method C, transformation of a compound of formula 17 into a compound of formula 18 can be accomplished using a number of halogenating agents. In one embodiment, the compound of formula 17 is brominated using, for instance, N-bromosuccinamide in solvents such as acetonitrile, toluene, dichloromethane or water and the like, at temperatures ranging from about −20° C. to reflux and for a time ranging from about 30 minutes to about 48 hours.

According to step "h" of method C, transformation of a compound of formula 9 into a compound of formula 1 is accomplished as described under step "g" of method C.

According to step "i" of method C, the conversion of a compound of formula 1 into a compound of formula 18 is accomplished as described under step "d" of method A.

According to step "k" of method C, the conversion of a compound of formula 18 into another compound of formula 1 is accomplished as described under step "e" of method A.

In a general synthetic process, the intermediate compounds of general formulas 14A and 14B can be prepared according to method D shown below, staring from a compound of formula 20.

Method D

In the above scheme, $PG_1$, R2 and R3 are as defined above

Referring to a synthetic process for the preparation of compounds of general formula 14 which is described in method D, in step "a" a compound of formula 20 is protected to give a compound of formula 14A. In step "b" a compound of formula 20 is reacted with an appropriate sulfonyl chloride to give a compound of general formula 21, which in step "c" is protected with a suitable protective group to yield a compound of formula 14B.

According to step "a" of method D, protection of an aniline derivative of formula 20 can be accomplished in a number of ways that are well known to those skilled in the art, depending on the nature of the protective group. For instance, protection can be carried out using di tert-butyl dicarbonate or benzyloxycarbonyl chloride in solvents such as dichloromethane, tetrahydrofuran, pyridine and the like, optionally in the presence of a suitable base such as triethylamine, DIPEA and the like at temperatures ranging from about 20° C. to reflux and for a time ranging from about 30 minutes to about 24 hours.

According to step "b" of method D, the compound of formula 20 can be converted into a compound of formula 2I by reaction with an appropriate sulfonyl chloride in the presence of a suitable base, such as pyridine, N-methyl morpholine, DIPEA, or ethylamine, in an appropriate solvent such as pyridine, dichloromethane or tetrahydrofuran, at a temperature ranging from about 0° C. to reflux and for a time varying from about 1 hour to about 7 days. Such reactions can be performed using a variety of solvents such as dichloromethane, toluene, tetrahydrofuran, 1,4-dioxane, 1,2-dimethoxyethane, or acetonitrile at a temperature ranging from about 0° C. to reflux and for a time ranging from about 30 minutes to about 24 hours.

According to step "c" of method D, protection of a compound of general formula 2I can be accomplished in a number of ways that are well-known to those skilled in the art, depending on the nature of the protective group. For instance protection can be carried out using reagents such as MEM chloride or MOM chloride, which can be also prepared in situ. Such reactions are normally carried out in solvents such as tetrahydrofuran, dichloromethane and the like, in the presence of a proton scavenger such as DIPEA at a temperature ranging from about 0° C. to reflux and for a time varying from about 1 hour to about 7 days. Such a protection can be carried

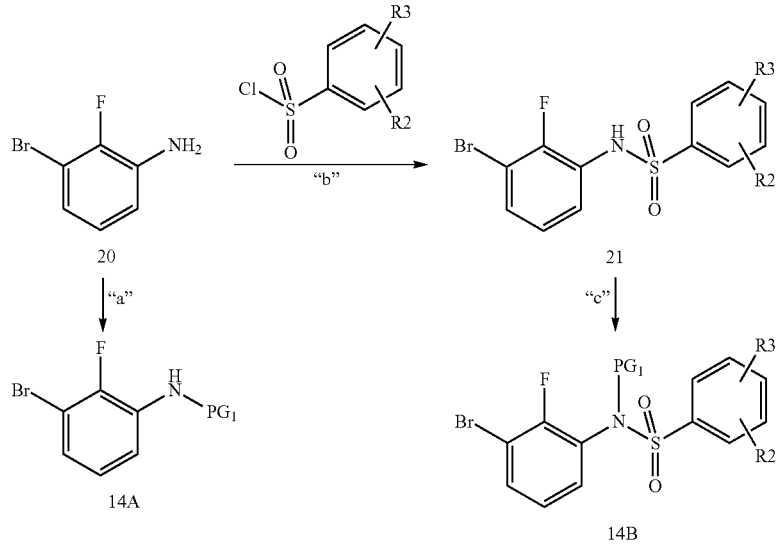

out using reagents such as acetyl chloride or ethoxycarbonyl chloride and the like. in solvents such as tetrahydrofuran, dichloromethane and the like, in the presence of a proton scavenger such as DIPEA at a temperature ranging from about 0° C. to reflux and for a time varying from about 1 hour to about 7 days.

A compound of general formula 2 prepared according to method A and method B, may be further transformed into another compound of formula 2 following procedures well known to those skilled in the art.

A compound of general formula 2 prepared according to method A wherein R30 is $SO_2Ph(R2)(R3)$ and R4 is group of formula IV wherein X is represented by a CH group and R15 is hydrogen (compound of formula 2A) or R15 is a halogen (compound of formula 2C), may be further transformed into another compound of general formula 2 following procedures well known to those skilled in the art. For instance, such compounds can further be transformed into another compound of formula 2D, 2E, 2F and 2G according to method E shown below.

Method E

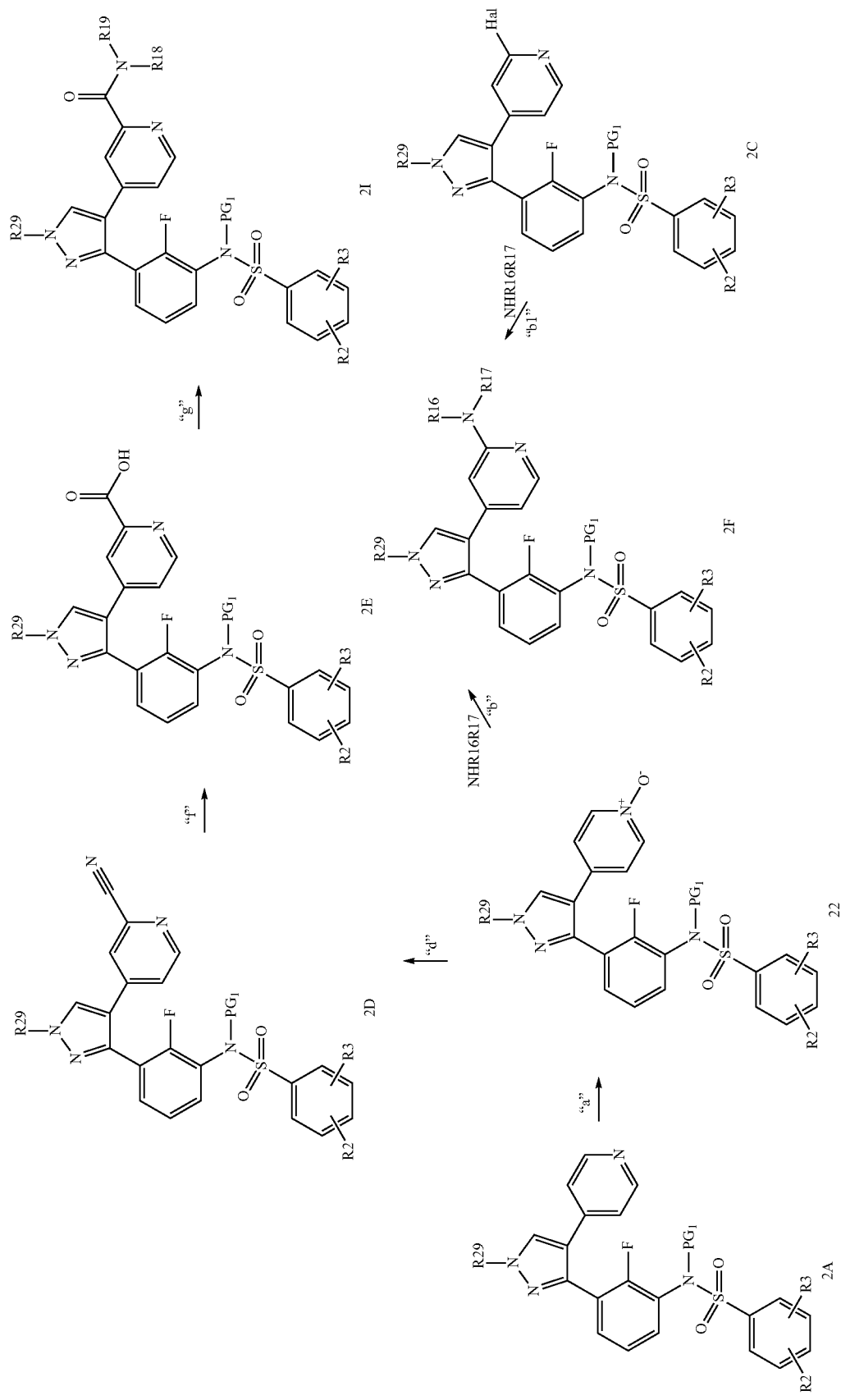

-continued
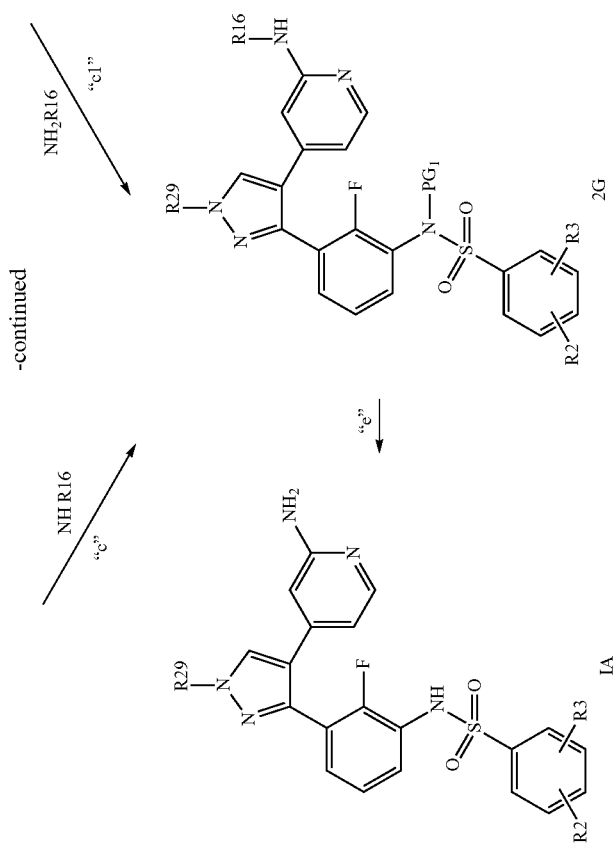

In the above scheme, R2, R3, R16, R17, R18, R19, R29, PG$_1$ and Hal are as defined above.

Referring to a synthetic process for the preparation of a compound of formula 2D, 2E, 2F, and 2G which is described in method E, in step "a" the pyridine nitrogen of a compound of formula 2A is oxidized to form a N-oxide derivative of formula 22. In step "b," "c," and "d" the reaction of the latter with a suitable electrophilic species such as tosyl anhydride in the presence or followed by treatment with a suitable nucleophile such as a secondary amine (NHR16R17), a primary amine (NH$_2$R16), or a source of cyanide (CN$^-$) yields a compound of formula 2F, 2G and 2D respectively. Alternatively, in step "b1" and "c1" respectively, a compound of formula 2C is reacted with a suitable nucleophile such as a secondary amine (NHR16R17) or a primary amine (NH$_2$R16) to yield a compound of formula 2F and 2G respectively. Optionally in step "e," when R16 is represented by a t-butyl group, a benzyl group and the like, the groups may be removed for instance by treatment with acid or under reductive conditions to yield a compound of formula (I)A. In step "f" a compound of formula 2D can be further hydrolyzed into another compound of general formula 2E. The latter, in step "g" is then condensed with a suitable amine to form a compound of formula 2I.

According to step "a" of method E, the oxidation of the pyridine nitrogen can be carried out using oxidizing agents well-known to those skilled in the art, such as hydrogen peroxide in a solvent such as acetic acid or m-chloroperbenzoic acid in solvents such as dichloromethane, acetone, tetrahydrofuran and the like at temperatures ranging from about 0° C. to reflux and for a time ranging from about 30 minutes to about 48 hours.

According to step "b" and "c" of method E, the transformation of a compound of formula 22 into a compound of formula 2F and 2G is accomplished by activating the pyridine N-oxide and reacting it with a secondary or primary amine. Activation is normally carried using a suitable electrophilic reagent, such as oxalyl chloride, trifluoromethanesulfonyl chloride, tosyl chloride, phosphoryl chloride (POCl$_3$), benzoyl chloride, acetic anhydride, tosyl anhydride and the like, in a solvent such as dichloromethane, tetrahydrofuran, acetonitrile, toluene, trifluoromethyl benzene and the like. In some embodiments, tosyl anhydride in trifluoromethyl benzene is used. The reaction is normally carried out in the presence of the secondary or primary amine, and may be carried out at temperatures ranging from about 20° C. to reflux and for a time ranging from about 30 minutes to about 48 hours.

According to step "d" of method E, the transformation of a compound of formula 22 into a compound of formula 2D is accomplished by activating the pyridine N-oxide and reacting it with a cyanating agent. The activation is normally carried using a suitable electrophilic reagent, such as oxalyl chloride, trifluoromethanesulfonyl chloride, tosyl chloride, phosphoryl chloride (POCl$_3$), benzoyl chloride, acetic anhydride, tosyl anhydride and the like, in a solvent such as dichloromethane, tetrahydrofuran, acetonitrile, toluene, trifluoromethyl benzene and the like. In some embodiments, tosyl anhydride in trifluoromethyl benzene is used. The reaction can be carried out in the presence of a cyanating agent, such as trimethylsilyl cyanide, and may be carried out at temperatures ranging from about 20° C. to reflux and for a time ranging from about 30 minutes to about 48 hours.

According to steps "b1" and "c1" of method E, the transformation of a compound of formula 2C into a compound of formula 2F and 2G is accomplished by reacting it with a secondary or primary amine in solvents such as N,N-dimethylformamide, N,N-dimethylacetamide, N-methyl pyrrolidone, dimethylsulfoxide, dichloromethane, tetrahydrofuran, 1,4-dioxane, ethanol and the like, optionally in the presence of a suitable base such as K$_2$CO$_3$, NaOH, or triethylamine at temperatures ranging from about 20° C. to reflux and for a time ranging from about 30 minutes to about 48 hours.

According to step "e" of method E, when a primary amine such as t-butylamine or benzylamine has been used in step "c" or in step "c1" of method E, the alkylic residue of such amine may be removed to yield a compound of general formula (I)A. The reaction, is normally carried out using strong acids, such as trifluoroacetic acid, optionally in the presence of suitable co-solvent, such as dichloromethane or water, at temperatures ranging from about 20° C. to reflux and for a time ranging from about 30 minutes to about 48 hours. Alternatively, the reaction is carried out using reductive conditions, such as H$_2$ in the presence of a suitable hydrogenation catalyst. The hydrogenation catalyst is usually a metal, such as palladium, which can be used as such or supported on carbon, in a suitable solvent such as tetrahydrofuran, 1,4-dioxane, N,N-dimethylformamide, methanol, ethyl acetate, and mixtures thereof.

According to step "f" of method E, compounds of formula 2D are converted to carboxylic acid derivatives of formula 2E. The reaction can be carried out under basic or acidic conditions, using for instance aqueous sodium hydroxide or aqueous hydrochloric acid or the like at a temperature ranging from about 0° C. to reflux and for a suitable time, for instance from about 30 minutes to about 96 hours.

According to step "g" of method E, a compound of formula 2E is transformed into an amide of formula 2I by the condensation with a suitable amine. It is clear to the skilled person that this reaction can be accomplished in a variety of ways and operative conditions, which are widely known in the art for the preparation of carboxamides. As an example, the reaction can be carried out in the presence of a coupling agent such as 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. Said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, isobutyl, or isopropyl chloroformate, in the presence of a tertiary base such as triethylamine, DIPEA or pyridine, in a suitable solvent such as toluene, dichloromethane, chloroform, tetrahydrofuran, acetonitrile, diethyl ether, 1,4-dioxane, or N,N-dimethylformamide, at a temperature ranging from about −30° C. to room temperature.

A compound of general formula 2 prepared according to method A and method B, may be further transformed in another compound of formula 2 following procedures well known to those skilled in the art.

For instance, when R4 is the group represented by formula IV, where X is represented by a nitrogen atom and R15 is thiomethyl (compound of formula 2J) or R15 is a halogen (compound of formula 2M), those compounds can be transformed into another compound of formulas 2K, 2L, 2N and 2P according to method F shown below.

Method F

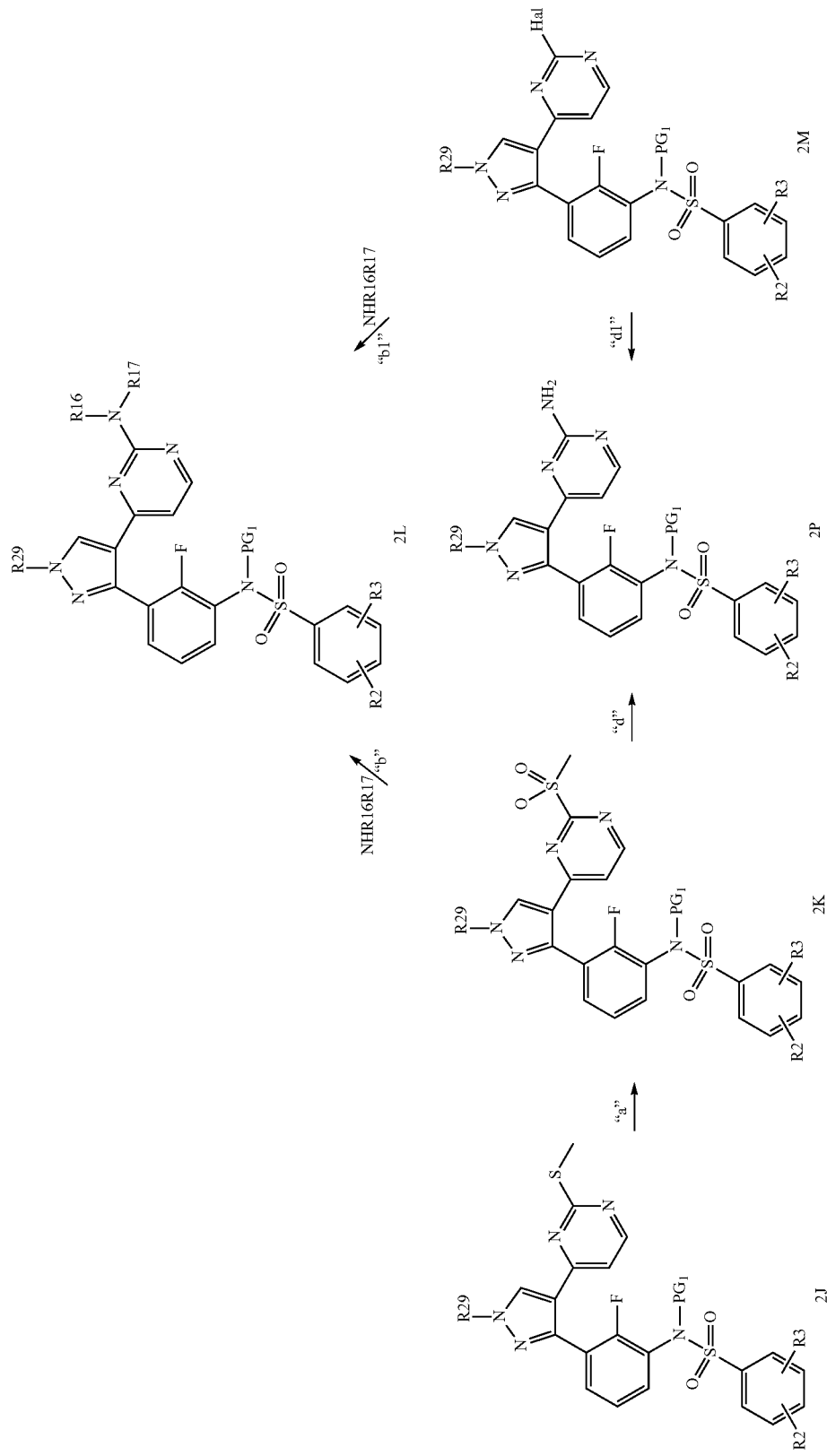

-continued
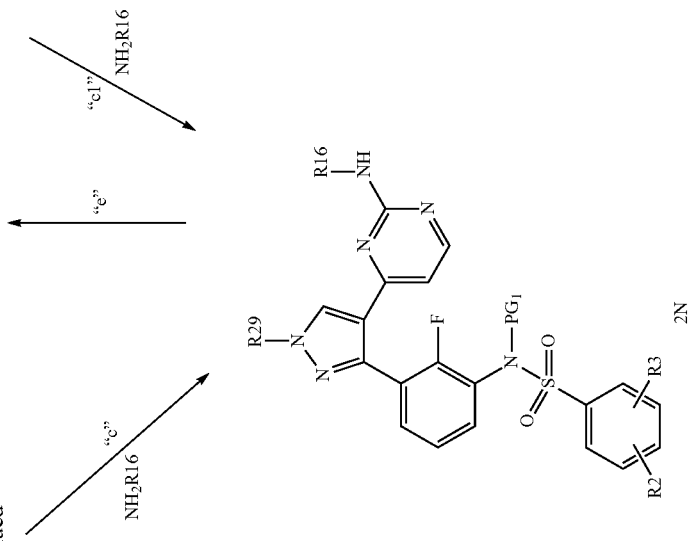

In the above scheme, R2, R3, R16, R17, R29, PG$_1$ and Hal are as defined above.

Referring to a synthetic process for the preparation of a compound of formula 2K, 2L, 2N and 2P which is described in method F, in step "a," the reaction of a compound of formula 2J with an oxidizing agent yields a sulfonyl derivative of formula 2K which is then treated with a suitable nucleophile. In step "b," such a nucleophile is a secondary amine, affording a compound of general formula 2L. In step "c," such a nucleophile is a primary amine, affording a compound of general formula 2N. In step "d" such a nucleophile is an ammonia equivalent such as ammonium acetate, affording a compound of general formula 2P. Alternatively, in steps "b1," "c1" and "d1," a compound of formula 2M is reacted with a suitable nucleophile such as a secondary amine, a primary amine or with an ammonia equivalent such as ammonium acetate to yield a compound of formula 2L, 2N or 2P respectively. Optionally in step "e," when R16 is represented by a t-butyl group, a benzyl group and the like, said groups may be removed for instance by treatment with acid or under reductive conditions to yield a compound of formula 2P.

According to step "a" of method F, the oxidation of the thiomethyl group is carried out using oxidizing agents well known to those skilled in the art, such as oxone in a suitable solvent such as tetrahydrofuran, 1,4-dioxane, acetone, optionally in the presence of water as a cosolvent, or m-chloroperbenzoic acid in solvents such as dichloromethane, acetone, tetrahydrofuran and the like at temperatures ranging from about 0° C. to reflux and for a time ranging from about 30 minutes to about 48 hours.

According to step "b" and "b1" of method F, the transformation of a compound of formula 2K or 2M into a compound of formula 2L is carried out using a secondary amine of formula R16R17NH in solvents such as N,N-dimethylformamide, N,N-dimethylacetamide, N-methyl pyrrolidone, dimethylsulfoxide, dichloromethane, tetrahydrofuran, 1,4-dioxane, ethanol and the like, optionally in the presence of a suitable base such as K$_2$CO$_3$, NaOH, triethylamine at temperatures ranging from about 20° C. to reflux and for a time ranging from about 30 minutes to about 48 hours.

According to step "c" and "c1" of method F, the transformation of a compound of formula 2K or 2M in a compound of formula 2N is carried out using a primary amine of formula R16NH$_2$ in solvents such as N,N-dimethylformamide, N,N-dimethylacetamide, N-methyl pyrrolidone, dimethylsulfoxide, dichloromethane, tetrahydrofuran, 1,4-dioxane, ethanol and the like, optionally in the presence of a suitable base such as K$_2$CO$_3$, NaOH, triethylamine at temperatures ranging from about 20° C. to reflux and for a time ranging from about 30 minutes to about 48 hours.

According to step "d" and "d1" of method F, the formation of a compound 2P from a compound of formula 2K or 2M is accomplished using a solution of ammonia in a suitable solvent, such as, dichloromethane, ethanol and the like, or ammonium salts, such as ammonium acetate in solvents such as N,N-dimethylformamide, N,N-dimethylacetamide, N-methyl pyrrolidone, dimethylsulfoxide and the like at temperatures ranging from about 20° C. to reflux and for a time ranging from about 30 minutes to about 48 hours.

According to step "e" of method F, when a primary amine such as t-butylamine or benzylamine has been used in step "c" or in step "c1" of method F, the alkylic residue of such amine may be removed to yield a compound of general formula 2P. The reaction can be carried out using strong acids, such as trifluoroacetic acid, optionally in the presence of suitable co-solvent, such as dichloromethane or water, at temperatures ranging from about 20° C. to reflux and for a time ranging from about 30 minutes to about 48 hours. Alternatively, the reaction is carried out using reductive conditions, such as H$_2$ in the presence of a suitable hydrogenation catalyst. The hydrogenation catalyst is usually a metal, most often palladium, which can be used as such or supported on carbon, in a suitable solvent such as tetrahydrofuran, 1,4-dioxane, N,N-dimethylformamide, methanol, ethyl acetate, and a mixtures thereof.

When preparing the compounds of formula (I) according to any variant of the process, optional functional groups within the starting materials, the reagents or the intermediates thereof, and which could give rise to unwanted side reactions, need to be properly protected according to conventional techniques.

The starting materials of these processes include comprehensive of any possible variant, as well as any reactant thereof, are known compounds and if not commercially available per se may be prepared according to well-known methods.

Pharmacology

Assays

In Vitro Cell Proliferation Assay

Exponentially growing human melanoma cells A375 (with a mutated B-RAF) and human melanoma cells Mewo (with wild-type B-Raf) were seeded and incubated at 37° C. in a humidified 5% CO2 atmosphere. After 24 hours, scalar doses of the compound were added to the medium and cells incubated for 72 hours. At the end of treatment, cells were washed and counted. Cell number was determined by a cellular adenosine triphosphate monitoring system. Cell proliferation was compared to control cells and the concentration inhibiting cell growth by 50% was calculated.

p-MAPK (T202/Y204) ArrayScan Assay

A375 human melanoma cells, having a mutated B—RAF, were seeded in 384-well poly-lysine coated plates (Matrix) at a density of 1000 cells/well with appropriate medium supplemented with 10% FCS and incubated for 16-24 hours. Cells were treated for 1.5 or 2 hours with increasing doses of compounds (starting dose 10 µM, dilution factor 2.5). At the end of the treatment cells were fixed with p-formaldehyde 3.7% for 15-30 min, then washed twice with D-PBS (80 µl/well) and permeabilized with D-PBS containing 0.1% Triton X-100 and 1% BSA (Sigma-Aldrich) for 15 minutes at room temperature (staining solution). Anti-phospho-MAPK (T202/Y204) monoclonal antibody E10 (Cell Signaling, cat. #9106) diluted 1:100 was added in staining solution and incubated for 1 hour at 37° C. After removal of the primary antibody solution, the anti-mouse Cy™2-conjugated (Green) secondary antibody (Amersham) diluted 1:500 in staining solution containing 2 µg/ml DAPI was added. The plate was incubated for 1 hour at 37° C., washed twice and then red with Cellomics' ArrayScan VTI (4 fields/well, CytoNucTrans algorithm).

The parameter "MEAN_RingAvgIntenCh2," which measures the mean cytoplasmatic fluorescence intensity associated to p-MAPK staining, is reported as the final result.

B-RAF mutations, that constitutively activate the kinase, have been identified in the majority of melanoma and a large fraction of colorectal and papillary thyroid carcinoma. The growth of cells with activated B-RAF strictly depends on B-RAF activity.

A number of compounds according to formula (I) were tested. The results are shown in the Table 1 below. As evident from these results, the compounds of formula (I) possess a remarkable activity in inhibiting cell proliferation, with IC$_{50}$ values lower than 0.030 μM on the cell line with mutated B-Raf (A375), more potent than on the cell line with wild-type B-Raf (Mewo).

In the same table, the data obtained with compounds of formula (I) in the ArrayScan assay are also reported and demonstrate the ability of the compounds of formula (I) to inhibit the signal transduction pathway controlled by B-RAF activation in A375 cell line with mutated B-RAF. The $IC_{50}$ values are always lower than 0.030 μM and are in agreement with the $IC_{50}$ values obtained in the proliferation assay on the same cell line, confirming that the antiproliferative activity of the compounds is due to the inhibition of B-RAF activity.

TABLE 1

Proliferation and Array Scan data

| | | Proliferation | | Array Scan |
|---|---|---|---|---|
| | | A375 | Mewo | A375 |
| Cmpd. No | Name | $IC_{50}$ (μM) | $IC_{50}$ (μM) | $IC_{50}$ (μM) |
| Ref. cpd | N-{3-[1-ethyl-4-(pyridin-4-yl)-1H-pyrazol-3-yl]-2-fluorophenyl}-2,5-difluorobenzenesulfonamide | 0.048 | >10 | <0.016 |
| 9 | 2,5-Difluoro-N-[2-fluoro-3-(1-isopropyl-4-pyridin-4-yl-1H-pyrazol-3-yl)-phenyl]-benzenesulfonamide | 0.005 | >10 | <0.016 |
| 5 | 2,5-Difluoro-N-{2-fluoro-3-[1-(1-methyl-piperidin-4-y]}-4-pyridin-4-yl-1H-pyrazol-3-yl]-phenyl}-benzenesulfonamide | 0.008 | >10 | <0.016 |
| 10 | N-{3-[4-(2-Amino-pyrimidin-4-yl)-1-isopropyl-1H-pyrazol-3-yl]-2-fluoro-phenyl}-2,5-difluoro-benzenesulfonamide | 0.003 | >10 | <0.016 |
| 2 | N-{3-[1-(1-Cyclopropyl-piperidin-4-yl)-4-pyridin-4-yl-1H-pyrazol-3-yl]-2-fluoro-phenyl}-2,5-difluoro-benzenesulfonamide | 0.012 | >10 | <0.016 |
| 7 | 2,5-Difluoro-N-{2-fluoro-3-[1-(2-fluoro-ethyl)-4-pyridin-4-yl-1H-pyrazol-3-yl]-phenyl}-benzenesulfonamide | <0.016 | >10 | <0.016 |
| 11 | N-{3-[4-{2-Amino-pyrimidin-4-yl)-1-(2-fluoro-ethyl)-1H-pyrazol-3-yl]-2-fluoro-phenyl}-2,5-difluoro-benzenesulfonamide | 0.017 | >10 | <0.016 |
| 12 | N-{3-[4-(2-Amino-pyridin-4-yl}-1-isopropyl-1H-pyrazol-3-yl]-2-fluoro-phenyl}-2,5-difluoro-benzenesulfonamide | 0.017 | >10 | <0.016 |
| 13 | N-{3-[4-(2-Amino-pyridin-4-yl}-1-(2-fluoro-ethyl)-1H-pyrazol-3-yl]-2-fluoro-phenyl}-2,5-difluoro-benzenesulfonamide | <0.016 | >10 | <0.016 |
| 17 | N-{3-[4-(2-Amino-pyridin-4-yl)-1-cyclopentyl-1H-pyrazol-3-yl]-2-fluoro-phenyl}-2,5-difluoro-benzenesulfonamide | 0.028 | >10 | <0.016 |
| 14 | N-{3-[4-(2-Amino-pyridin-4-yl)-1-(tetrahydro-pyran-4-yl)-1H-pyrazol-3-yl]-2-fluoro-phenyl}-2,5-difluoro-benzenesulfonamide | 0.034 | >10 | <0.016 |
| 25 | N-{3-[1-(4,4-difluorocyclohexyl)-4-(pyridin-4-yl)-1H-pyrazol-3-yl]-2-fluorophenyl}-2,5-difluorobenzenesulfonamide | <0.016 | >10 | <0.016 |
| 26 | N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}acetamide | 0.007 | >10 | <0.016 |
| 30 | N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}-2-methylpropanamide | <0.016 | >10 | <0.016 |
| 31 | N-{4-[3-(3-{[(2,5-difluorophenyl)sulfonyl]amino}-2-fluorophenyl)-1-(1-methylpiperidin-4-yl)-1H-pyrazol-4-yl]pyridin-2-yl}acetamide | <0.016 | >10 | <0.016 |

It is noted that the reference compound (i.e. the disclaimed compound that corresponds to compound no. 60 of WO2010/010154), compared to the present compounds, showed at least a four fold lower (0.084) antiproliferative activity.

From all of the above, the novel compounds of formula (I) appear to be particularly advantageous in the therapy of diseases caused by deregulated protein kinase activity such as cancer.

The compounds disclosed herein can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds disclosed herein within the dosage range described below and the other pharmaceutically active agent within the approved dosage range.

Compounds of formula (I) may be used sequentially with known anticancer agents when a combination formulation is inappropriate.

The compounds of formula (I) disclosed herein can be suitable for administration to a mammal, e.g., to humans, can be administered by the usual routes, e.g. oral, intravenous, topical, transmucosal, etc., and the dosage level depends upon the age, weight, and conditions of the patient and administration route.

For example, suitable dosages adopted for oral administration of a compound of formula (I) are comprised between 1 and 500 mg/Kg. In some embodiments, the dosage is between 5 and 100 mg/Kg.

The compounds disclosed herein can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

Pharmaceutical compositions are also disclosed comprising a compound of formula (I) or a pharmaceutically acceptable salt thereof in association with a pharmaceutically acceptable excipient, which may be a carrier or a diluent.

The pharmaceutical compositions containing the compounds disclosed herein are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate, effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

The terms "treatment," "treating" and "treat," as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present methods include both medical therapeutic and/or prophylactic treatment, as appropriate.

EXPERIMENTAL SECTION

For a reference to any specific compound of formula (I) disclosed herein, optionally in the form of a pharmaceutically acceptable salt, see the experimental section and claims. Referring to the examples that follow, compounds were synthesized using the methods described herein, or other methods, which are well known in the art.

The short forms and abbreviations used herein have the following meaning:

| | |
|---|---|
| g (grams) | mg (milligrams) |
| ml (milliliters) | mM (millimolar) |
| μM (micromolar) | mmol (millimoles) |
| h (hours) | MHz (Mega-Hertz) |
| mm (millimetres) | Hz (Hertz) |
| M (molar) | min (minutes) |
| mol (moles) | TLC (thin layer chromatography) |
| r.t. (room temperature) | TEA (triethylamine) |
| TFA (trifluoroacetic acid) | DMF (N,N-dimethyl formamide) |

| | |
|---|---|
| DIPEA (N,N-diisopropyl-N-ethylamine) | DCM (dichloromethane) |
| THF (tetrahydrofuran) | Hex (hexane) |
| MeOH (Methanol) | DMSO (dimethylsulfoxide) |
| TIPS (triisopropylsilyl) | bs (broad singlet) |
| TBDMS (dimethyl-tert-butylsilyl) | BOC (tert-butyloxycarbonyl) |
| NaH = sodium hydride, 60% in mineral oil | Ac$_2$O acetic anhydride |
| Dppf (1,1'-bis(diphenylphosphino)ferrocene) | ESI = electrospray ionization |
| mCPBA (m-chloroperbenzoic acid) | Ac (acetyl) |
| TBTU (2-(1H-benzotriazol-1-yl)-1,1,3,3-tetramethyluronium tetrafluoroborate | |
| RP-HPLC (reverse phase high performance liquid chromatography) | |

With the aim to better illustrate this disclosure, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, CH$_2$Cl$_2$ and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 minutes, hold 90% B 2 minutes. UV detection at 220 nm and 254 nm. Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water—0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% NH$_3$, and mobile phase B was acetonitrile. Gradient from 10 to 100% B in 8 min, hold 100% B 2 min. Flow rate 20 mL/min.

1H-NMR spectrometry was performed on a Mercury VX 400 operating at 400.45 MHz equipped with a 5 mm double resonance probe [1H (15N-31P) ID_PFG Varian].

EXPERIMENTAL SECTION

Preparation 1

N-[3-(4-Bromo-1H-pyrazol-3-yl)-2-fluoro-phenyl]-2,5-difluoro-N-methoxymethyl-benzenesulfonamide Formula 18, where Hal=Br; PG$_1$=methoxymethyl; R30=2,5-difluoro-benzenesulfonyl Method D, Step b N-(3-Bromo-2-fluoro-phenyl)-2,5-difluoro-benzenesulfonamide Formula 21, where R2,R3=F)

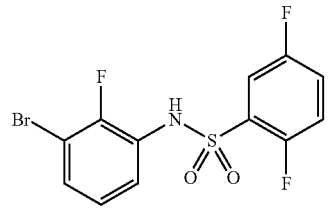 [SMILES: O=S(=O)(Nc1cccc(Br)c1F)c1cc(F)ccc1F]

3-Bromo-2-fluoroaniline (10 g, 52.63 mmol) was dissolved in DCM (100 mL) under nitrogen atmosphere. Dry pyridine was added (6 mL, 73.68 mmol, 1.4 eq), followed by 2,5-difluorobenzenesulfonyl chloride (7.08 mL, 52.63 mmol, 1 eq) and the mixture was stirred at r.t. for 2 h. It was then diluted with DCM and washed with aqueous 0.5 N HCl (3×80 mL) and brine. The organic layer was dried over Na$_2$SO$_4$ and evaporated to dryness. The solid was taken up with ethyl ether and stirred for 30 minutes. It was then filtered and dried at 40° C. under reduced pressure to give 17.8 g of N-(3-bromo-2-fluoro-phenyl)-2,5-difluoro-benzenesulfonamide as a pale yellow solid (92%). HPLC (254 nm): R$_t$: 6.28 min; $^1$H NMR (DMSO-d6) Shift: 10.86 (s, 1H), 7.50-7.73 (m, 4H), 7.23-7.31 (m, 1H), 7.12 (dt, J=1.3, 8.1 Hz, 1H).

Method D, Step c

N-(3-Bromo-2-fluoro-phenyl)-2,5-difluoro-N-methoxymethyl-benzenesulfonamide

Formula 14B, where PG$_1$=methoxymethyl; R2,R3=F

To a solution of N-(3-bromo-2-fluoro-phenyl)-2,5-difluoro-benzenesulfonamide (17.8 g, 48.61 mmol) in anhydrous DCM (160 mL) at 0° C., DIPEA (12.5 mL, 73 mmol 1.5 eq) was added followed by MOMCl (5/mL, 73 mmol, 1.5 eq). The reaction mixture was stirred at 0° C. for 10 minutes and then allowed to warm to r.t. After 2 h a saturated solution of ammonium chloride was added and the mixture was stirred at r.t. for 10 minutes. It was then diluted with DCM and washed with water and brine, dried over Na$_2$SO$_4$ and evaporated to dryness. The residue was treated with Hex and stirred for 30 minutes. The solid was filtered and dried to give 18.52 g (93%) of the title compound as a white powder. HPLC (254 nm): R$_t$: 6.88 min; $^1$H NMR (DMSO-d6) Shift: 7.78 (ddd, J=1.7, 6.4, 8.1 Hz, 1H), 7.67-7.73 (m, 1H), 7.61 (dt, J=4.3, 9.6, 1H), 7.49-7.55 (m, 1H), 7.28-7.34 (m, 1H), 7.17-7.23 (m, 1H), 5.06 (s, 2H), 3.35 (s, 3H).

Method C, Step a 2,5-Difluoro-N-{2-fluoro-3-[2-(tetrahydro-pyran-2-yl)-2H-pyrazol-3-yl]-phenyl}-N-methoxymethyl-benzenesulfonamide Formula 9, where PG$_1$=methoxymethyl; R30=2,5-difluoro-benzenesulfonyl; R29=tetrahydro-pyran-2-yl

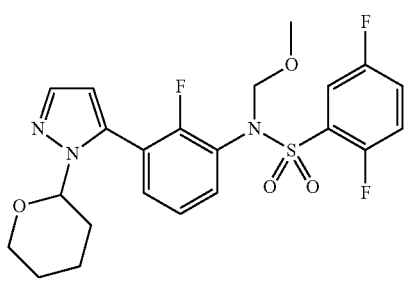 [SMILES: COCN(c1cccc(-c2ccnn2C2CCCCO2)c1F)S(=O)(=O)c1cc(F)ccc1F]

N-(3-Bromo-2-fluoro-phenyl)-2,5-difluoro-N-methoxymethyl-benzenesulfonamide (12 g, 29.25 mmol) was dissolved in 1,4-dioxane (156 mL) and argon was bubbled through the solution for 10 minutes. 1-(tetrahydro-2H-pyran-2-yl)-5-(4,4,5,5-tetramethyl-1,3,2-dioxaborolan-2-yl)-1H-pyrazole (prepared as described in WO2010/010154) (10.6 g, 38.03 mmol, 1.3 eq) was then added, followed by cesium carbonate (9.5 g, 29.25 mmol, 2 eq), 1,1'-bis(diphenylphosphino)ferrocene-palladium(II)dichloride dichloromethane complex (Pd(dppf)Cl$_2$.CH$_2$Cl$_2$) (1.2 g, 1.46 mmol, 0.05 eq) and water (0.9 mL) and the reaction mixture was heated to 100° C. and stirred at this temperature for 2 h. A further addition of 1-(tetrahydro-2H-pyran-2-yl)-5-(4,4,5,5-tetramethyl-1,3,2-dioxaborolan-2-yl)-1H-pyrazole (4 g, 0.5 eq) was made and heating was continued for 2 h. The mixture was then concentrated under reduced pressure, taken up with AcOEt (200 mL) and filtered over a Celite pad. The filtrate was washed with water and brine, dried over Na$_2$SO$_4$ and evaporated to dryness. The crude was purified by chromatography on silica gel (cyclohexane/AcOEt 7:3) to give 18 g of 2,5-difluoro-N-{2-fluoro-3-[2-(tetrahydro-pyran-2-yl)-2H-pyrazol-3-yl]-phenyl}-N-methoxymethyl-benzene-sulfonamide contaminated by N-tetrahydropyranylpyrazole.

Method C, Step e 2,5-Difluoro-N-[2-fluoro-3-(2H-pyrazol-3-yl)-phenyl]-N-methoxymethyl-benzene-sulfonamide Formula 17, where PG$_1$=methoxymethyl; R30=2,5-difluoro-benzenesulfonyl

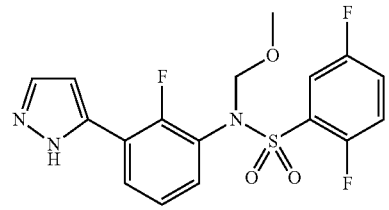 [SMILES: COCN(c1cccc(-c2ccn[nH]2)c1F)S(=O)(=O)c1cc(F)ccc1F]

To a solution of crude 2,5-difluoro-N-{2-fluoro-3-[2-(tetrahydro-pyran-2-yl)-2H-pyrazol-3-yl]-phenyl}-N-methoxymethyl-benzene-sulfonamide (1.39 g) in MeOH (20 mL), p-toluenesulfonic acid (100 mg) was added and the solution was stirred at r.t. for 1 h. The reaction mixture was then concentrated under reduced pressure, taken up with AcOEt (100 mL) and washed with sat, aq. NaHCO$_3$ (2×50 mL) and brine (50 mL). the organic phase was dried over Na$_2$SO$_4$ and evaporated to dryness. The crude product was purified by chromatography on silica gel (gradient cyclohexane/AcOEt 6:4 to 1:1) to give 630 mg of 2,5-difluoro-N-[2-fluoro-3-(2H-pyrazol-3-yl)-phenyl]-N-methoxymethyl-benzene-sulfonamide as a white powder (80% yield over two steps). HPLC (254 nm): R$_t$: 5.86 min; $^1$H NMR (DMSO-d6) Shift: 13.13 (br. s., 1H), 7.93-8.02 (m, 1H), 7.83 (br. s., 1H), 7.55-7.73 (m, 2H), 7.46-7.53 (m, 1H), 7.18-7.33 (m, 2H), 6.49 (br. s., 1H), 5.10 (s, 2H), 3.36-3.42 (m, 3H); HRMS (ESI) calcd for C17H15F3N3O3S [M+H]$^+$ 3980781. found 398.0779.

Method C, Step g

N-[3-(4-Bromo-2H-pyrazol-3-yl)-2-fluoro-phenyl]-2,5-difluoro-N-methoxymethyl-benzenesulfonamide Formula 18, where Hal=Br; PG$_1$=methoxymethyl; R30=2,5-difluoro-benzenesulfonyl

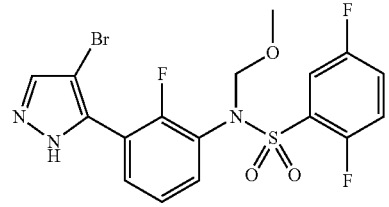 [SMILES: COCN(c1cccc(-c2[nH]ncc2Br)c1F)S(=O)(=O)c1cc(F)ccc1F]

To a stirred solution of 2,5-difluoro-N-[2-fluoro-3-(2H-pyrazol-3-yl)-phenyl]-N-methoxymethyl-benzene-sulfonamide (620 mg, 1.56 mmol) in DCM (15 mL) N-bromosuccinimide (277 mg, 1.56 mmol, 1 eq) was added and the solution was stirred at r.t. for 1.5 hrs. The mixture was then diluted with DCM (100 mL) and washed with 10% aqueous NaHSO$_3$ (2×30 mL) and brine. The organic layer was dried over Na$_2$SO$_4$ and evaporated to dryness to give 714 mg (96%) of the title product as white foam. HPLC (254 nm): R$_t$: 6.22 min; $^1$H NMR (DMSO-d6) Shift: 13.49 (br. s., 1H), 8.08 (br. s., 1H), 7.57-7.70 (m, 2H), 7.47-7.57 (m, 2H), 7.39-7.47 (m, 1H), 7.30-7.38 (m, 1H), 5.10 (s, 2H), 3.38 (s, 3H).

Example 1

2,5-Difluoro-N-[2-fluoro-3-(1-isopropyl-4-pyridin-4-yl-1H-pyrazol-3-yl)-phenyl]-benzenesulfonamide (Compound 9 in Table 1)

Formula I, where m=0; $R_1$=isopropyl; R2, R3=F; R4=4-pyridinyl
Method C, Step k

N-[3-(4-Bromo-1-isopropyl-3H-pyrazol-3-yl)-2-fluoro-phenyl]-2,5-difluoro-N-methoxymethyl-benzenesulfonamide Formula (I), where Hal=Br; $PG_1$=methoxymethyl; R29=isopropyl; R30=2,5-difluoro-benzene-sulfonyl

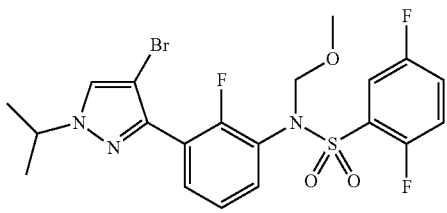 [SMILES: COCN(c1cccc(-c2nn(C(C)C)cc2Br)c1F)S(=O)(=O)c1cc(F)ccc1F]

Cesium carbonate (164 mg, 0.504 mmol) and isopropyl iodide (50 μL, 0.504 mmol) were added to a solution of N-[3-(4-bromo-1H-pyrazol-3-yl)-2-fluoro-phenyl]-2,5-difluoro-N-methoxymethyl-benzenesulfonamide (prepared as described in Preparation 1) (160 mg, 0.336 mmol) in DMF (1 mL) and the suspension was stirred at 50° C. for 3 h. The mixture was treated with water and AcOEt. The organic layer was washed once again with water and brine, then it was dried over $Na_2SO_4$ and concentrated under reduced pressure. The residue was purified by flash chromatography on silica gel (Hex:AcOEt 7:3) affording 120 mg of the title compound (68% yield). HPLC (254 nm): $R_t$: 7.23 min; $^1$H NMR (DMSO-d6) Shift: 8.13 (s, 1H), 7.57-7.70 (m, 2H), 7.46-7.55 (m, 2H), 7.37-7.45 (m, 1H), 7.32 (t, J=7.8 Hz, 1H), 5.09 (s, 2H), 4.41-4.62 (m, 1H), 3.38 (s, 3H), 1.43 (d, J=6.6 Hz, 6H); HRMS (ESI) calcd for C20H20BrF3N3O3S [M+H]$^+$ 518.0356. found 518.0344.

According to this same methodology, but employing suitable alkylating agents, the following intermediates were prepared:

N-[3-(4-Bromo-1-ethyl-1H-pyrazol-3-yl)-2-fluoro-phenyl]-2,5-difluoro-N-methoxy-methyl-benzenesulfonamide Formula 1, where Hal=Br; $PG_1$=methoxymethyl; R29=ethyl; R30=2,5-difluoro-benzene-sulfonyl

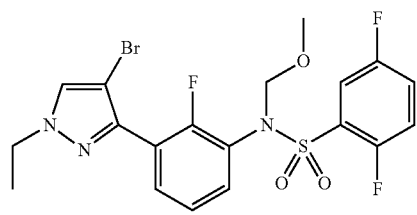 [SMILES: CCn1cc(Br)c(-c2cccc(N(COC)S(=O)(=O)c3cc(F)ccc3F)c2F)n1]

HPLC (254 nm): $R_t$: 6.92 min; $^1$H NMR (DMSO-d6) Shift: 8.10 (s, 1H), 7.56-7.70 (m, 2H), 7.47-7.54 (m, 2H), 7.41 (dt, J=18, 7.5 Hz, 1H), 7.32 (t, J=8.2 Hz, 1H), 5.09 (s, 2H), 4.16 (q, J=7.2 Hz, 2H), 3.38 (s, 3H), 1.38 (t, 3H); HRMS (ESI) calcd for C19H18BrF3N3O3S [M+H]$^+$ 504.0199. found 504.0177.

N-{3-[4-Bromo-1-(2-methoxy-ethyl)-1H-pyrazol-3-yl]-2-fluoro-phenyl}-2,5-difluoro-N-methoxymethyl-benzenesulfonamide Formula 1, where Hal=Br; $PG_1$=methoxymethyl; R29=2-methoxy-ethyl; R30=2,5-difluoro-benzene-sulfonyl

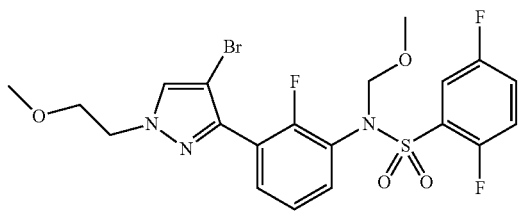 [SMILES: COCCn1cc(Br)c(-c2cccc(N(COC)S(=O)(=O)c3cc(F)ccc3F)c2F)n1]

HPLC (254 nm): $R_t$: 6.74 min; $^1$H NMR (DMSO-d6) Shift: 8.05 (s, 1H), 7.55-7.70 (m, 2H), 7.46-7.56 (m, 2H), 7.38-7.46 (m, 1H), 7.32 (t, J=7.9 Hz, 1H), 5.09 (s, 2H), 4.29 (t, J=5.2 Hz, 2H), 3.70 (t, J=5.2 Hz, 2H), 3.38 (s, 3H), 3.24 (s, 3H); HRMS (ESI) calcd for C20H20BrF3N3O4S [M+H]$^+$ 534.0305. found 534.031.

N-[3-(4-Bromo-1-cyanomethyl-1H-pyrazol-3-yl)-2-fluoro-phenyl]-2,5-difluoro-N-methoxymethyl-benzenesulfonamide Formula (I), where Hal=Br; $PG_1$=methoxymethyl; R29=cyanomethyl; R30=2,5-difluoro-benzene-sulfonyl

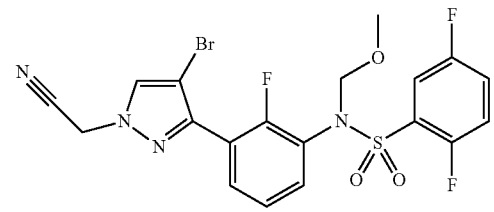 [SMILES: COCN(c1cccc(-c2nn(CC#N)cc2Br)c1F)S(=O)(=O)c1cc(F)ccc1F]

HPLC (254 nm): $R_t$: 6.55 min; $^1$H NMR (DMSO-d6) Shift: 8.21 (s, 1H), 7.57-7.73 (m, 2H), 7.42-7.57 (m, 3H), 7.35 (t, J=7.9 Hz, 1H), 5.55 (s, 2H), 5.10 (s, 2H), 3.38 (s, 3H); HRMS (ESI) calcd for C19H14BrF3N4O3SNa [M+Na]$^+$ 536.9814. found 536.9793.

N-{3-[4-Bromo-1-(2,2,2-trifluoro-ethyl)-1H-pyrazol-3-yl]-2-fluoro-phenyl}-2,5-difluoro-N-methoxymethyl-benzenesulfonamide Formula 1, where Hal=Br; $PG_1$=methoxymethyl; R29=2,2,2-trifluoro-ethyl; R30=2,5-difluoro-benzene-sulfonyl

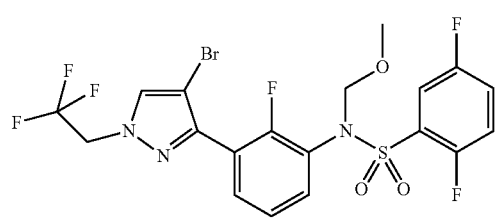 [SMILES: COCN(c1cccc(-c2nn(CC(F)(F)F)cc2Br)c1F)S(=O)(=O)c1cc(F)ccc1F]

HPLC (254 nm): R$_t$: 7.08 min; $^1$H NMR (DMSO-d6) Shift: 8.23 (s, 1H), 7.56-7.72 (m, 2H), 7.39-7.56 (m, 3H), 7.35 (t, J=7.8 Hz, 1H), 5.21 (q, J=9.0 Hz, 2H), 5.10 (s, 2H), 3.38 (s, 3H); HRMS (ESI) calcd for C19H15BrF6N3O3S [M+H]$^+$ 557.9916. found 557.9925.

(4-Bromo-3-{3-[(2,5-difluoro-benzenesulfonyl)-methoxymethyl-amino]-2-fluoro-phenyl}-pyrazol-1-yl)-acetic acid ethyl ester Formula 1, where Hal=Br; PG$_1$=methoxymethyl; R29=2-ethoxycarbonyl-methyl; R30=2,5-difluoro-benzene-sulfonyl

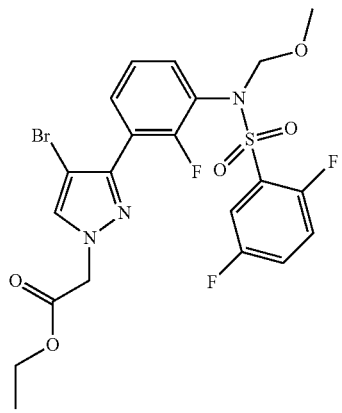 [SMILES: CCOC(=O)Cn1cc(Br)c(-c2cccc(N(COC)S(=O)(=O)c3cc(F)ccc3F)c2F)n1]

HPLC (254 nm): R$_t$: 6.90 min; $^1$H NMR (DMSO-d$_6$) Shift: 8.09 (s, 1H), 7.56-7.70 (m, 2H), 7.46-7.54 (m, 2H), 7.42 (td, J=7.5, 1.8 Hz, 1H), 7.29-7.38 (m, 1H), 4.95-5.24 (m, 4H), 4.17 (q, J=7.1 Hz, 2H), 3.38 (s, 3H), 1.21 (t, J=7.1 Hz, 3H); HRMS (ESI) calcd for C21H20BrF3N3O5S [M+H]$^+$ 562.0254. found 562.0239.

2-(4-Bromo-3-{3-[(2,5-difluoro-benzenesulfonyl)-methoxymethyl-amino]-2-fluoro-phenyl}-pyrazol-1-yl)-acetamide Formula 1, where Hal=Br; PG$_1$=methoxymethyl; R29=2-acetamidyl; R30=2,5-difluoro-benzene-sulfonyl

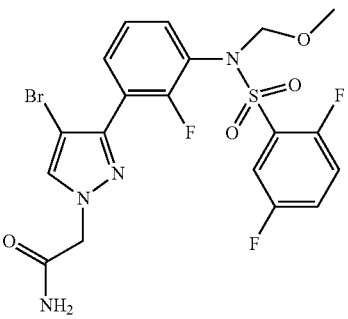 [SMILES: COCN(c1cccc(-c2nn(CC(N)=O)cc2Br)c1F)S(=O)(=O)c1cc(F)ccc1F]

HPLC (254 nm): R$_t$: 5.74 min; $^1$H NMR (DMSO-d$_6$) Shift: 8.02 (s, 1H), 7.55-7.71 (m, 3H), 7.47-7.54 (m, 2H), 7.41 (td, J=7.5, 1.9 Hz, 1H), 7.32 (t, J=7.6 Hz, 2H), 5.09 (s, 2H), 4.81 (s, 2H), 3.38 (s, 3H); HRMS (ESI) calcd for C19H17BrF3N4O4S [M+H]$^+$ 533.0101. found 533.0090.

N-{3-[4-Bromo-1-(tetrahydro-pyran-4-yl)-1H-pyrazol-3-yl]-2-fluoro-phenyl}-2,5-difluoro-N-methoxymethyl-benzenesulfonamide Formula 1, where Hal=Br; PG$_1$=methoxymethyl; R29=tetrahydro-pyran-4-yl; R30=2,5-difluoro-benzene-sulfonyl

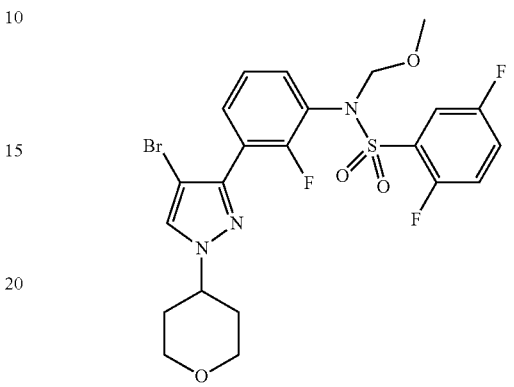

HPLC (254 nm): R$_t$: 7.02 min; $^1$H NMR (DMSO-d$_6$) Shift: 8.18 (s, 1H), 7.70-7.58 (m, 2H), 7.55-7.45 (m, 2H), 7.44-7.38 (m, 1H), 7.35-7.28 (m, 1H), 5.09 (s, 2H), 4.50-4.38 (m, 1H), 4.04-3.84 (m, 2H), 3.45 (dt, J=2.1, 11.6 Hz, 2H), 3.38 (s, 3H), 2.06-1.86 (m, 4H); HRMS (ESI) calcd for C22H22BrF3N3O4S [M+H]$^+$ 560.0461. found 560.0488.

N-{3-[4-Bromo-1-(4,4-difluoro-cyclohexyl)-1H-pyrazol-3-yl]-2-fluoro-phenyl}-2,5-difluoro-N-methoxymethyl-benzenesulfonamide Formula 1, where Hal=Br; PG$_1$=methoxymethyl; R29=4,4-difluoro-cyclohex-1-yl; R30=2,5-difluoro-benzene-sulfonyl

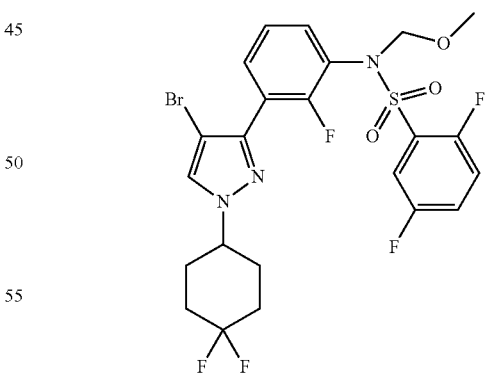

HPLC (254 nm): Rt: 7.68 min; $^1$H NMR (DMSO-d$_6$) Shift: 8.19 (s, 1H), 7.70-7.56 (m, 2H), 7.55-7.45 (m, 2H), 7.44-7.36 (m, 1H), 7.32 (t, J=8.1 Hz, 1H), 5.09 (s, 2H), 4.47-4.36 (m, 1H), 3.38 (s, 3H), 2.21-1.76 (m, 8H); HRMS (ESI) calcd for C23H22BrF5N3O3S [M+H]+ 594.0480. found 594.0486.

Method A, Step a 2,5-Difluoro-N-[2-fluoro-3-(1-isopropyl-4-pyridin-4-yl-1H-pyrazol-3-yl)-phenyl]-N-methoxymethyl-benzenesulfonamide Formula 2, where R4=4-pyridinyl; PG$_1$=methoxymethyl; R29=isopropyl; R30=2,5-difluoro-benzene-sulfonyl

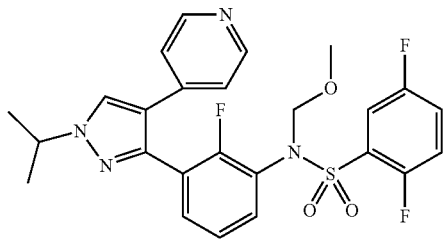 [SMILES: COCN(c1cccc(-c2nn(C(C)C)cc2-c2ccncc2)c1F)S(=O)(=O)c1cc(F)ccc1F]

To an argon degassed solution of N-[3-(4-bromo-1-isopropyl-3H-pyrazol-3-yl)-2-fluoro-phenyl]-2,5-difluoro-N-methoxymethyl-benzenesulfonamide (100 mg, 0.193 mmol) in 1,2-dimethoxyethane:water 9:1 (2 mL) in a microwave vial, 4-(4,4,5,5-tetramethyl-[1,3,2]dioxaborolan-2-yl)-pyridine (59 mg, 0.289 mmol), cesium carbonate (126 mg, 0.386 mmol) and Pd(dppf)Cl$_2$.CH$_2$Cl$_2$, (16 mg, 0.0193 mmol) were added, under argon atmosphere. The mixture was heated in the microwave oven at 100° C. for 30 minutes, then it was filtered through a Celite pad. The solution was taken up with AcOEt and washed with saturated aqueous NaHCO$_3$ and brine. The organic layer was dried over Na$_2$SO$_4$ and concentrated to dryness. The residue was purified by flash chromatography on silica gel (DCM:MeOH:7N NH$_3$ in MeOH 97:2:1) affording 80 mg of the title compound (80% yield).

HPLC (254 nm): R$_t$: 6.97 min; $^1$H NMR (DMSO-d6) Shift: 8.42 (s, 1H), 8.38 (d, J=5.7 Hz, 2H), 7.57-7.65 (m, 1H), 7.44-7.57 (m, 3H), 7.28-7.38 (m, 2H), 7.08 (d, J=6.0 Hz, 2H), 5.01 (s, 2H), 4.57 (dt, J=13.4, 6.7 Hz, 1H), 3.27 (s, 3H), 1.50 (d, J=6.6 Hz, 6H); HRMS (ESI) calcd for C25H24F3N4O3S [M+H]$^+$ 517.1516. found 517.1508.

According to this same methodology, but employing suitably substituted starting material, the following intermediates were prepared:

2,5-Difluoro-N-{2-fluoro-3-[1-(2-methoxy-ethyl)-4-pyridin-4-yl-1H-pyrazol-3-yl]-phenyl}-N-methoxymethyl-benzenesulfonamide Formula 2, where R4=4-pyridinyl; PG$_1$=methoxymethyl; R29=2-methoxy-ethyl; R30=2,5-difluoro-benzene-sulfonyl

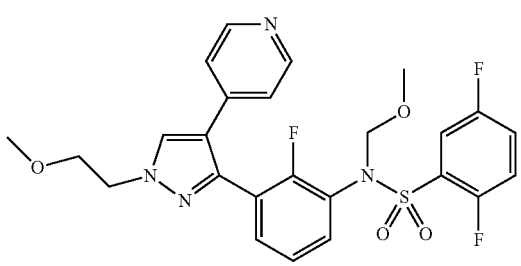 [SMILES: COCCn1cc(-c2ccncc2)c(-c2cccc(N(COC)S(=O)(=O)c3cc(F)ccc3F)c2F)n1]

HPLC (254 nm): R$_t$: 5.92 min; $^1$H NMR (DMSO-d6) Shift: 8.36-8.42 (m, 2H), 8.35 (s, 1H), 7.57-7.65 (m, 1H), 7.43-7.57 (m, 3H), 7.27-7.38 (m, 2H), 7.05-7.10 (m, 2H), 5.01 (s, 2H), 4.35 (t, J=5.3 Hz, 2H), 3.77 (t, J=5.3 Hz, 2H), 3.31 (s, 3H), 3.28 (s, 3H); HRMS (ESI) calcd for C25H24F3N4O4S [M+H]$^+$ 533.1465. found 533.144.

N-[3-(1-Cyanomethyl-4-pyridin-4-yl-1H-pyrazol-3-yl)-2-fluoro-phenyl]-2,5-difluoro-N-methoxymethyl-benzenesulfonamide Formula 2, R4=4-pyridinyl; PG$_1$=methoxymethyl; R29=cyanomethyl; R30=2,5-difluoro-benzene-sulfonyl

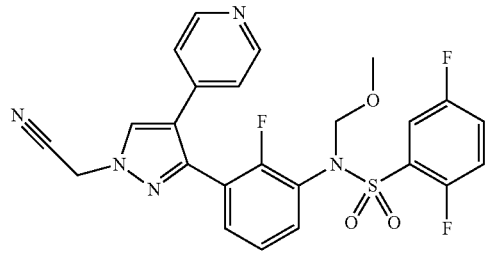 [SMILES: COCN(c1cccc(-c2nn(CC#N)cc2-c2ccncc2)c1F)S(=O)(=O)c1cc(F)ccc1F]

HPLC (254 nm): R$_t$: 5.85 min; $^1$H NMR (DMSO-d6) Shift: 8.46 (s, 1H), 8.39-8.44 (m, 2H), 7.58-7.65 (m, 1H), 7.44-7.58 (m, 3H), 7.34 (t, J=7.7 Hz, 1H), 7.31-7.43 (m, 1H), 7.04-7.11 (m, 2H), 5.62 (s, 2H), 5.00 (s, 2H), 3.27 (s, 3H); HRMS (ESI) calcd for C24H19F3N5O3S [M+H]$^+$ 514.1155. found 514.1136.

2,5-Difluoro-N-{2-fluoro-3-[4-pyridin-4-yl-1-(2,2,2-trifluoro-ethyl)-1H-pyrazol-3-yl]-phenyl}-N-methoxymethyl-benzenesulfonamide Formula 2, where R4=4-pyridinyl; PG$_1$=methoxymethyl; R29=2,2,2-trifluoro-ethyl; R30=2,5-difluoro-benzene-sulfonyl

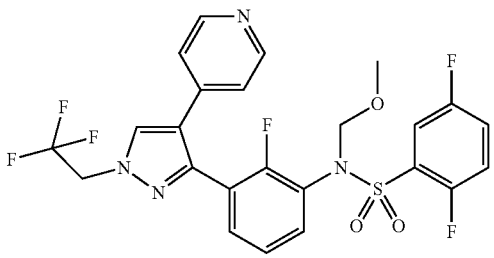 [SMILES: COCN(c1cccc(-c2nn(CC(F)(F)F)cc2-c2ccncc2)c1F)S(=O)(=O)c1cc(F)ccc1F]

HPLC (254 nm): R$_t$: 6.39 min; $^1$H NMR (DMSO-d6) Shift: 8.47 (s, 1H), 8.39-8.45 (m, 2H), 7.57-7.67 (m, J=8.9, 7.6, 3.7, 3.7 Hz, 1H), 7.43-7.57 (m, 3H), 7.36-7.41 (m, 1H), 7.33 (t, J=7.7 Hz, 1H), 7.06-7.12 (m, 2H), 5.27 (q, J=9.0 Hz, 2H), 5.00 (s, 2H), 3.26 (s, 3H); HRMS (ESI) calcd for C24H19F6N4O3S [M+H]$^+$ 557.1077. found 557.1056.

2,5-Difluoro-N-{2-fluoro-3-[4-(2-fluoro-pyridin-4-yl)-1-isopropyl-1H-pyrazol-3-yl]-phenyl}-N-methoxymethyl-benzenesulfonamide Formula 2, where R4=2-fluoro-4-pyridinyl; PG$_1$=methoxymethyl; R29=isopropyl; R30=2,5-difluoro-benzene-sulfonyl

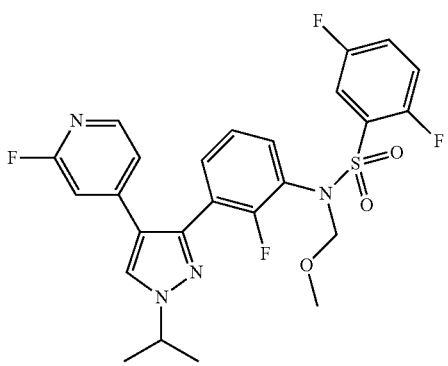 [SMILES: COCN(c1cccc(-c2nn(C(C)C)cc2-c2ccnc(F)c2)c1F)S(=O)(=O)c1cc(F)ccc1F]

HPLC (254 nm): R$_t$: 6.94 min; $^1$H NMR (DMSO-d6) Shift: 8.52 (s, 1H), 8.05 (d, J=5.2 Hz, 1H), 7.59-7.68 (m, 1H), 7.51-7.59 (m, 2H), 7.43-7.49 (m, 1H), 7.30-7.39 (m, 2H), 7.04 (dt, J=5.3, 1.7 Hz, 1H), 6.82 (s, 1H), 5.02 (s, 2H), 4.59 (sot, J=6.6 Hz, 1H), 3.28 (s, 3H), 1.50 (d, J=6.7 Hz, 6H); HRMS (ESI) calcd for C25H23F4N4O3S [M+H]$^+$ 535.1422. found 535.1412.

2,5-Difluoro-N-{2-fluoro-3-[4-(2-fluoro-pyridin-4-yl)-1-(tetrahydro-pyran-4-yl)-1H-pyrazol-3-yl]-phenyl}-N-methoxymethyl-benzenesulfonamide Formula 2, where R4=2-fluoro-4-pyridinyl; PG$_1$=methoxymethyl; R29=tetrahydro-pyran-4-yl; R30=2,5-difluoro-benzene-sulfonyl

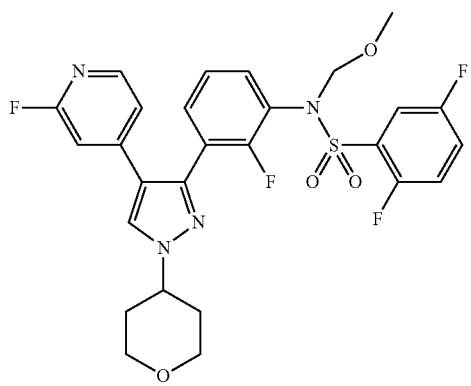 [SMILES: COCN(c1cccc(-c2nn(C3CCOCC3)cc2-c2ccnc(F)c2)c1F)S(=O)(=O)c1cc(F)ccc1F]

HPLC (254 nm): R$_t$: 6.76 min; $^1$H NMR (DMSO-d6) Shift: 8.56 (s, 1H), 8.06 (d, J=5.1 Hz, 1H), 7.68-7.41 (m, 4H), 7.39-7.29 (m, 2H), 7.04 (d, J=5.4 Hz, 1H), 6.82 (s, 1H), 5.02 (s, 2H), 4.58-4.39 (m, 1H), 3.95-4.02 (m, 2H), 3.50 (t, J=11.1 Hz, 2H), 3.27 (s, 3H), 2.23-1.85 (m, 4H); HRMS (ESI) calcd for C27H25F4N4O4S [M+H]+ 577.1527. found 577.1511.

Method A, Step f 2,5-Difluoro-N-[2-fluoro-3-(1-isopropyl-4-pyridin-4-yl-1H-pyrazol-3-yl)-phenyl]-benzenesulfonamide (Compound 9 in Table 1)

Formula 1, where m=0; R$_1$=isopropyl; R2, R3=F; R4=4-pyridinyl

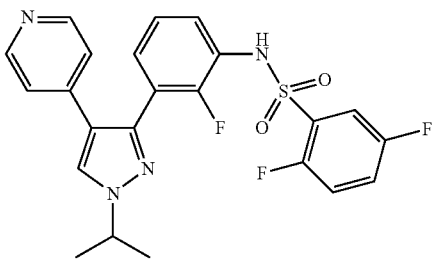 [SMILES: CC(C)n1cc(-c2ccncc2)c(-c2cccc(NS(=O)(=O)c3cc(F)ccc3F)c2F)n1]

2,5-Difluoro-N-[2-fluoro-3-(1-isopropyl-4-pyridin-4-yl-1H-pyrazol-3-yl)-phenyl]-N-methoxymethyl-benzenesulfonamide (80 mg, 0.155 mmol) was dissolved in a mixture of TFA:water 9:1 (1.7 mL) and stirred for 1.5 h at 60° C. The reaction mixture was concentrated under reduced pressure, then taken up with a saturated solution of NaHCO$_3$ and extracted with AcOEt. The organic layer was dried over Na$_2$SO$_4$ and concentrated to dryness. The residue was purified by flash chromatography on silica gel (Hex:AcOEt 2:8) affording 44 mg of the title compound (60% yield). HPLC (254 nm): R$_t$: 6.03 min; $^1$H NMR (DMSO-d6) Shift: 10.66 (br. s., 1H), 8.56 (s, 1H), 8.50 (d, J=6.5 Hz, 2H), 7.51-7.61 (m, 1H), 7.41-7.51 (m, 2H), 7.33-7.40 (m, 2H), 7.22-7.33 (m, 3H), 4.53-4.64 (m, 1H), 1.49 (d, J=6.7 Hz, 6H); HRMS (ESI) calcd for C23H20F3N4O2S [M+H]$^+$ 473.1254. found 473.1231.

According to this same methodology, but employing suitably substituted starting material, the following compounds were prepared:

2,5-Difluoro-N-{2-fluoro-3-[1-(2-methoxy-ethyl)-4-pyridin-4-yl-1H-pyrazol-3-yl]-phenyl}-benzenesulfonamide Formula I, where m=2; R$_1$=methoxy; R2, R3=F; R4=4-pyridinyl

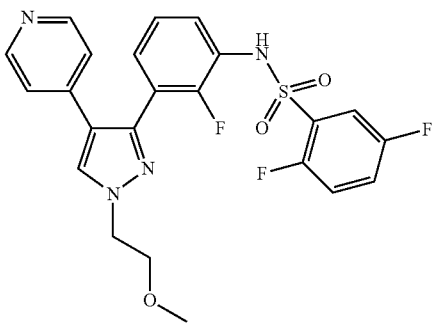 [SMILES: COCCn1cc(-c2ccncc2)c(-c2cccc(NS(=O)(=O)c3cc(F)ccc3F)c2F)n1]

HPLC (254 nm): R$_t$: 5.5 min; $^1$H NMR (DMSO-d6) Shift: 10.66 (br. s., 1H), 8.35-8.40 (m, 2H), 8.32 (s, 1H), 7.51-7.60 (m, 1H), 7.41-7.49 (m, 2H), 7.36 (td, J=7.6, 2.0 Hz, 1H), 7.27-7.33 (m, 1H), 7.24 (t, J=7.8 Hz, 1H), 7.01-7.06 (m, 2H), 4.33 (t, J=5.3 Hz, 2H), 3.76 (t, J=5.3 Hz, 2H), 3.26 (s, 3H); HRMS (ESI) calcd for C23H20F3N4O3S [M+H]+ 489.1203. found 489.1187.

N-[3-(1-Cyanomethyl-4-pyridin-4-yl-1H-pyrazol-3-yl)-2-fluoro-phenyl]-2,5-difluoro-benzenesulfonamide Formula I, where m=1; R₁=cyano; R2, R3=F; R4=4-pyridinyl

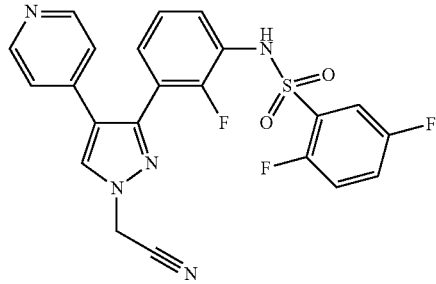 [SMILES: N#CCn1cc(-c2ccncc2)c(-c2cccc(NS(=O)(=O)c3cc(F)ccc3F)c2F)n1]

HPLC (254 nm): R$_t$: 5.44 min; ¹H NMR (DMSO-d6) Shift: 10.69 (br. s., 1H), 8.51 (s, 1H), 8.49 (d, J=6.2 Hz, 2H), 7.51-7.60 (m, 1H), 7.40-7.51 (m, 2H), 7.32-7.40 (m, 2H), 7.28 (t, J=7.8 Hz, 1H), 7.19 (d, J=5.9 Hz, 2H), 5.62 (s, 2H); HRMS (ESI) calcd for C22H15F3N5O2S [M+H]+ 470.0893. found 470.0876.

2,5-Difluoro-N-{2-fluoro-3-[4-pyridin-4-yl-1-(2,2,2-trifluoro-ethyl)-1H-pyrazol-3-yl]-phenyl}-benzenesulfonamide Formula 1, where m=1; R₁=trifluoromethyl; R2, R3=F; R4=4-pyridinyl

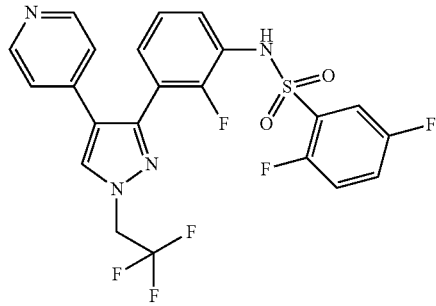 [SMILES: O=S(=O)(Nc1cccc(-c2nn(CC(F)(F)F)cc2-c2ccncc2)c1F)c1cc(F)ccc1F]

HPLC (254 nm): R$_t$: 6.03 min; ¹H NMR (DMSO-d6) Shift: 10.69 (br. s., 1H), 8.62 (s, 1H), 8.57 (d, J=6.5 Hz, 2H), 7.52-7.62 (m, 1H), 7.42-7.52 (m, 2H), 7.33-7.42 (m, 4H), 7.29 (t, J=7.8 Hz, 1H), 5.30 (q, J=9.1 Hz, 2H); HRMS (ESI) calcd for C22H15F6N4O2S [M+H]+ 513.0815. found 513.0798.

2-{3-[3-(2,5-Difluoro-benzenesulfonylamino)-2-fluoro-phenyl]-4-pyridin-4-yl-pyrazol-1-yl}-acetamide Formula 1, where m=1; R₁=carboxamido; R2, R3=F; R4=4-pyridinyl

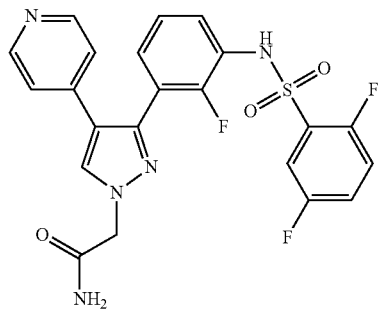 [SMILES: NC(=O)Cn1cc(-c2ccncc2)c(-c2cccc(NS(=O)(=O)c3cc(F)ccc3F)c2F)n1]

HPLC (254 nm): R$_t$: 4.69 min; ¹H NMR (DMSO-d6) Shift: 10.67 (br. s., 1H), 8.35-8.40 (m, 2H), 8.29 (s, 1H), 7.40-7.69 (3 m, 3H), 7.20-7.40 (3 m, 3H), 6.99-7.05 (m, 2H), 4.84 (s, 2H); HRMS (ESI) calcd for C22H17F3N5O3S [M+H]+ 488.0999. found 488.0997.

2-{3-[3-(2,5-Difluoro-benzenesulfonylamino)-2-fluoro-phenyl]-4-pyridin-4-yl-pyrazol-1-yl}-N-methyl-acetamide Formula I, where m=1; R₁=N-methyl-carboxamido; R2, R3=F; R4=4-pyridinyl

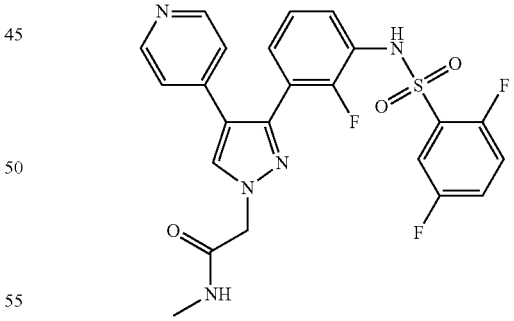

HPLC (254 nm); R$_t$: 4.88 min; ¹H NMR (DMSO-d6) Shift: 10.67 (br. s., 1H), 8.34-8.42 (m, 2H), 8.30 (s, 1H), 8.12 (q, J=4.4 Hz, 1H), 7.51-7.58 (m, 1H), 7.40-7.50 (m, 2H), 7.36 (td, J=2.0, 7.6 Hz, 1H), 7.20-7.31 (m, 2H), 7.00-7.05 (m, 2H), 4.84 (s, 2H), 2.64 (d, J=4.5 Hz, 3H); HRMS (ESI) calcd for C23H19F3N5O3S [M+H]+ 502.1155. found 502.1132.

63

2-{3-[3-(2,5-Difluoro-benzenesulfonylamino)-2-fluoro-phenyl]-4-pyridin-4-yl-pyrazol-1-yl}-N,N-dimethyl-acetamide Formula I, where m=1; $R_1$=N,N-dimethyl-carboxamido; R2, R3=F; R4=4-pyridinyl

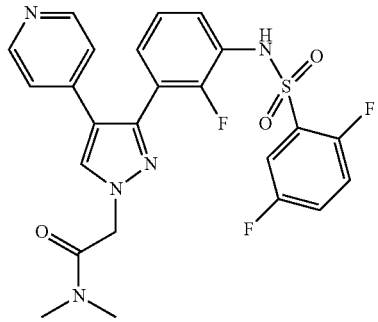 [SMILES: CN(C)C(=O)Cn1cc(-c2ccncc2)c(-c2cccc(NS(=O)(=O)c3cc(F)ccc3F)c2F)n1]

HPLC (254 nm): $R_t$: 5.07 min; $^1$H NMR (DMSO-d6) Shift: 10.68 (br. s., 1H), 8.48 (d, J=6.0 Hz, 2H), 8.37 (s, 1H), 7.52-7.59 (m, 1H), 7.42-7.51 (m, 2H), 7.29-7.39 (m, 2H), 7.20-7.29 (m, 3H), 5.23 (s, 2H), 3.05 (s, 3H), 2.88 (s, 3H); HRMS (ESI) calcd for C24H21F3N5O3S [M+H]$^+$ 516.1312. found 516.1304.

2,5-Difluoro-N-{2-fluoro-3-[4-(2-fluoro-pyridin-4-yl)-1-isopropyl-1H-pyrazol-3-yl]-phenyl}-benzene-sulfonamide Formula I, where m=0; $R_1$=isopropyl; R2, R3=F; R4=2-fluoro-pyridin-4-yl

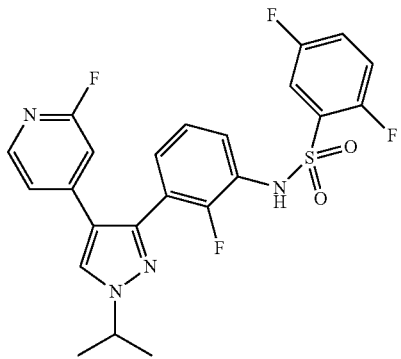 [SMILES: CC(C)n1cc(-c2ccnc(F)c2)c(-c2cccc(NS(=O)(=O)c3cc(F)ccc3F)c2F)n1]

HPLC (254 nm): $R_t$: 6.56 min; $^1$H NMR (DMSO-d6) Shift: 10.67 (s, 1H), 8.49 (s, 1H), 8.03 (d, J=5.4 Hz, 1H), 7.50-7.59 (m, 1H), 7.31-7.48 (m, 4H), 7.26 (t, J=7.8 Hz, 1H), 6.97 (dt, J=5.2, 1.8 Hz, 1H), 6.80 (s, 1H), 4.55 (spt, 1H), 4.56 (spt, J=6.7 Hz, 1H), 1.48 (d, J=6.7 Hz, 6H); HRMS (ESI) calcd for C23H19F4N4O2S [M+H]$^+$ 491.116. found 491.1151.

64

N-{3-[1-(4,4-Difluoro-cyclohexyl)-4-pyridin-4-yl-1H-pyrazol-3-yl]-2-fluoro-phenyl}-2,5-difluoro-benzenesulfonamide Formula I, where m=0; $R_1$=4,4-difluorocyclohex-1-yl; R2, R3=F; R4=4-pyridinyl

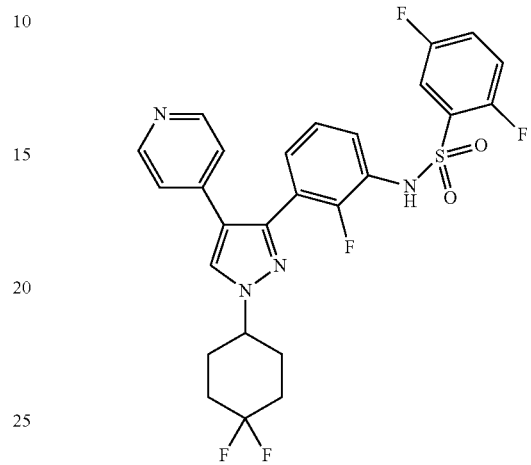

HPLC (254 nm): $R_t$: 6.12 min; $^1$H NMR (DMSO-d6) Shift: 10.66 (br. s., 1H), 8.44 (s, 1H), 8.37 (d, J=5.9 Hz, 1H), 7.60-7.51 (m, 1H), 7.49-7.39 (m, 2H), 7.36 (dt, J=2.0, 7.6 Hz, 1H), 7.33-7.26 (m, 1H), 7.26-7.19 (m, 1H), 7.07-7.03 (m, 2H), 4.53-4.43 (m, 1H), 2.21-1.99 (m, 8H); HRMS (ESI) calcd for C26H22F5N4O2S [M+H]$^+$ 549.1378. found 549.1373.

2,5-difluoro-N-{2-fluoro-3-[4-(2-fluoropyridin-4-yl)-1-(tetrahydro-2H-pyran-4-yl)-1H-pyrazol-3-yl]phenyl}benzenesulfonamide Formula I, where m=0; $R_1$=tetrahydro-2H-pyran-4-yl; R2, R3=F; R4=2-F-pyridin-4-yl

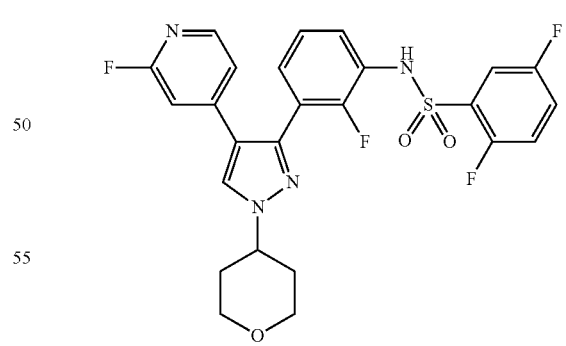

HPLC (254 nm): $R_t$: 6.31 min; $^1$H NMR (DMSO-d6) Shift: 10.67 (s, 1H), 8.53 (s, 1H), 8.04 (d, J=5.4 Hz, 1H), 7.59-7.51 (m, 1H), 7.50-7.30 (m, 4H), 7.29-7.20 (m, 1H), 7.00-6.87 (m, J=5.2 Hz, 1H), 6.80 (s, 1H), 4.56-4.40 (m, 1H), 4.01-3.92 (m, 2H), 3.49 (dt, J=2.1, 11.7 Hz, 2H), 2.14-1.83 (m, 4H); HRMS (ESI) calcd for C25H21F4N4O3S [M+H]$^+$ 533.1265. found 533.1243.

Example 2

2,5-Difluoro-N-{2-fluoro-3-[1-(1-methyl-piperidin-4-yl)-4-pyridin-4-yl-1H-pyrazol-3-yl]-phenyl}-benzenesulfonamide (Compound 5 in Table 1)

Formula I, where m=0; R1=1-methyl-piperidin-4-yl; R2, R3=F; R4=4-pyridinyl
Method C, Step k

4-(4-Bromo-3-{3-[(2,5-difluoro-benzenesulfonyl)-methoxymethyl-amino]-2-fluoro-phenyl}-pyrazol-1-yl)-piperidine-1-carboxylic acid tert-butyl ester Formula 1, where Hal=Br; PG$_1$=methoxymethyl; R29=N-Boc-piperidin-4-yl; R30=2,5-difluoro-benzene-sulfonyl

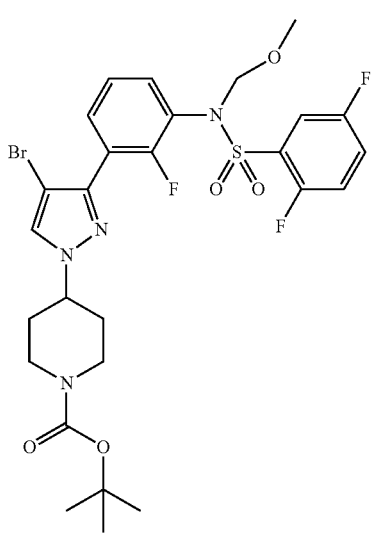 [SMILES: COCN(c1cccc(-c2nn(C3CCN(C(=O)OC(C)(C)C)CC3)cc2Br)c1F)S(=O)(=O)c1cc(F)ccc1F]

Cesium carbonate (10.07 g, 30.91 mmol, 2.2 eq) and 4-Methanesulfonyloxy-piperidine-1-carboxylic acid tert-butyl ester (7.95 g, 28.46 mmol, 2 eq) were added to a solution of N-[3-(4-bromo-1H-pyrazol-3-yl)-2-fluoro-phenyl]-2,5-difluoro-N-methoxymethyl-benzene-sulfonamide (6.69 g, 14.05 mmol) (prepared as described in Preparation 1) in anhydrous DMF (100 mL) and the suspension was stirred at 60° C. for 16 h. The solvent was then concentrated under reduced pressure and the residue was taken up with AcOEt and washed with sat. aq. NaHCO$_3$ and brine, dried over Na$_2$SO$_4$ and evaporated to dryness. The crude two regioisomers were separated by chromatography on silica gel (n-Hex/AcOEt 8:2 to 7:3) 7.63 g of the desired N1-alkylated regioisomer in mixture with excess 4-Methanesulfonyloxy-piperidine-1-carboxylic acid tert-butyl ester. Analytical data for 4-(4-Bromo-3-{3-[(2,5-difluoro-benzenesulfonyl)-methoxy-methyl-amino]-2-fluoro-phenyl}-pyrazol-1-yl)-piperidine-1-carboxylic acid tert-butyl ester induces, HPLC (254 nm): R$_t$: 7.68 min; $^1$H NMR (DMSO-d6) Shift: 8.17 (s, 1H), 7.57-7.70 (m, 2H), 7.46-7.54 (m, 2H), 7.37-7.44 (m, 1H), 7.27-7.34 (m, 1H), 5.09 (s, 2H), 4.34-4.46 (m, 1H), 3.97-4.08 (m, 2H), 3.38 (s, 3H), 2.90 (br. s., 2H), 1.97-2.06 (m, 2H), 1.77 (qd, J=4.9, 12.3 Hz, 2H), 1.41 (s, 9H); HRMS (ESI) calcd for C27H31BrF3N4O5S [M+H]$^+$ 681.0965. found 681.0945.

According to this same methodology, but employing the 3-Iodo-8-aza-bicyclo[3.2.1]octane-8-carboxylic acid benzyl ester as alkylating agent, the following intermediate was prepared.

3-(4-Bromo-3-{3-[(2,5-difluoro-benzenesulfonyl)-methoxymethyl-amino]-2-fluoro-phenyl}-pyrazol-1-yl)-8-aza-bicyclo[3.2.1]octane-8-carboxylic acid benzyl ester Formula 1, where Hal=Br; PG$_1$=methoxymethyl; R29=N-benzyloxycarbonyl-8-aza-bicyclo[3.2.1]octane-3-yl; R30=2,5-difluoro-benzene-sulfonyl

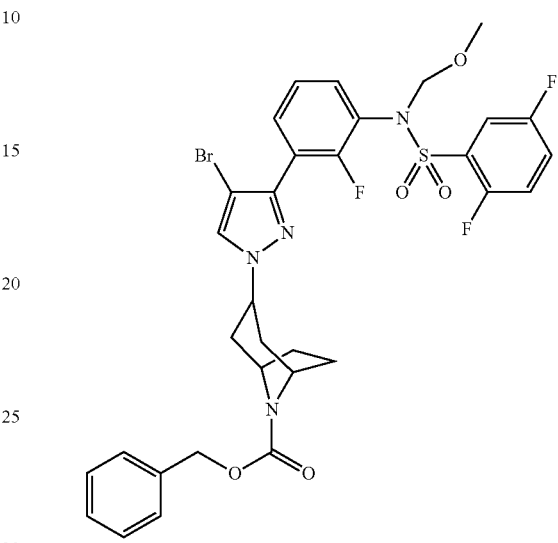

HPLC (254 nm): R$_t$: 8.14 min; $^1$H NMR (DMSO-d$_6$) Shift: 8.36 (s, 1H), 7.71-7.15 (m, 11H), 5.12 (s, 2H), 5.09 (s, 2H), 4.51-4.38 (m, 1H), 4.29-4.07 (m, 2H), 3.38 (s, 3H), 2.57 (d, J=15.3 Hz, 2H), 2.28 (br. s., 2H), 1.76 (br. s., 2H), 1.47 (d, J=7.7 Hz, 2H); HRMS (ESI) calcd for C32H31BrF3N4O5S [M+H]$^+$ 719.1145. found 7191159.

Method A, Step a

4-(3-{3-[(2,5-Difluoro-benzenesulfonyl)-methoxymethyl-amino]-2-fluoro-phenyl}-4-pyridin-4-yl-pyrazol-1-yl)-piperidine-1-carboxylic acid tert-butyl ester Formula 2, where R4=4-pyridinyl; PG$_1$=methoxymethyl; R29=N-Boc-piperidin-4-yl; R30=2,5-difluoro-benzene-sulfonyl

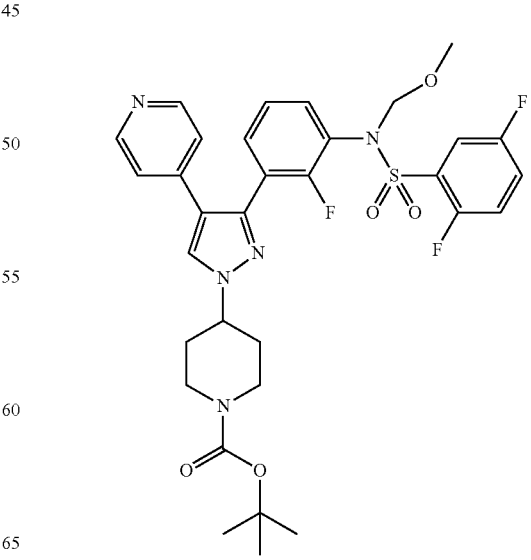

A solution of 4-(4-bromo-3-{3-[(2,5-difluoro-benzene-sulfonyl)-methoxymethyl-amino]-2-fluoro-phenyl}-pyrazol-1-yl)-piperidine-1-carboxylic acid tert-butyl ester (6.71 mmol) in a 10:1 dioxane/water mixture (66 mL) was degassed by bubbling argon for 5 minutes, 4-pyridinyl boronic acid pinacol ester (2.06 mg, 10.07 mmol, 1.5 eq) was then added, followed by cesium carbonate (4.37 g, 13.42 mmol, 2 eq) and Pd(dppf)Cl$_2$·CH$_2$Cl$_2$ (547 mg, 0.670 mmol, 0.1 eq) and the mixture was stirred at 100° C. for 2 h. The solvent was concentrated under reduced pressure and the residue was taken up with AcOEt and filtered over a Celite pad. The filtrate was washed with saturated aqueous NaHCO$_3$ and brine. The organic layer was dried over Na$_2$SO$_4$ and evaporated to dryness. The crude product was purified by chromatography on silica gel (AcOEt/Hex 7.3 to 8:2) affording 4.0 g of the title compound (43% over the last two steps). HPLC (254 nm): R$_t$: 7.03 min; $^1$H NMR (DMSO-d6) Shift: 8.48 (s, 1H), 8.36-8.41 (m, 2H), 7.56-7.66 (m, 1H), 7.45-7.57 (m, 3H), 7.25-7.38 (m, 2H), 7.11 (d, J=6.1 Hz, 2H), 5.01 (s, 2H), 4.40-4.50 (m, 1H), 3.99-4.12 (m, 2H), 3.27 (s, 3H), 2.94 (br. s., 2H), 2.04-2.17 (m, J=1.8 Hz, 2H), 1.84 (qd, J=4.5, 12.2 Hz, 2H), 1.42 (s, 9H); HRMS (ESI) calcd for C32H35F3N5O5S [M+H]$^+$ 6582306. found 6582314.

According to this same methodology, but employing suitable starting materials, the following intermediates were prepared:

4-[3-{3-[(2,5-Difluoro-benzenesulfonyl)-methoxymethyl-amino]-2-fluoro-phenyl}-4-(2-fluoro-pyridin-4-yl)-pyrazol-1-yl]-piperidine-1-carboxylic acid tert-butyl ester Formula 2, where R4=2-fluoro-pyridin-4-yl; PG$_1$=methoxymethyl; R29=N-Boc-piperidin-4-yl; R30=2,5-difluoro-benzenesulfonyl

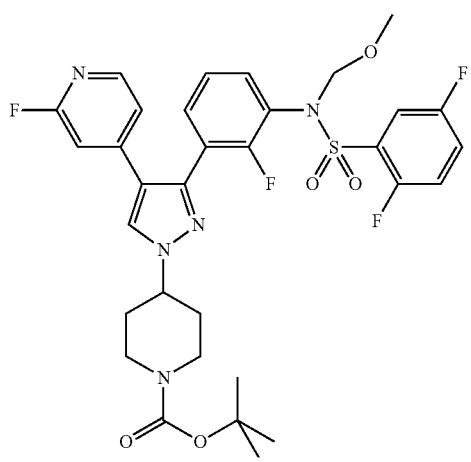 [SMILES: COCN(c1cccc(-c2nn(C3CCN(C(=O)OC(C)(C)C)CC3)cc2-c2ccnc(F)c2)c1F)S(=O)(=O)c1cc(F)ccc1F]

HPLC (254 nm): R$_t$: 7.69 min; $^1$H NMR (DMSO-d6) Shift: 8.56 (s, 1H), 8.03-8.09 (m, 1H), 7.58-7.66 (m, 1H), 7.51-7.58 (m, 2H), 7.41-7.49 (m, 1H), 7.29-7.40 (m, 2H), 6.99-7.08 (m, 1H), 6.82 (s, 1H), 5.02 (s, 2H), 4.36-4.52 (m, 1H), 3.96-4.16 (m, 2H), 3.27 (s, 3H), 2.95 (br. s., 2H), 2.07-2.16 (m, 2H), 1.84 (qd, J=12.2, 4.5 Hz, 2H), 1.42 (s, 9H); HRMS (ESI) calcd for C32H34F4N5O5S [M+H]$^+$ 676.2212. found 676.2185.

2,5-Difluoro-N-[2-fluoro-3-(1-piperidin-4-yl-4-pyridin-4-yl-1H-pyrazol-3-yl)-phenyl]-N-methoxymethyl-benzenesulfonamide Formula 2, where R4=4-pyridinyl; PG$_1$=methoxymethyl; R29=piperidin-4-yl; R30=2,5-difluoro-benzene-sulfonyl

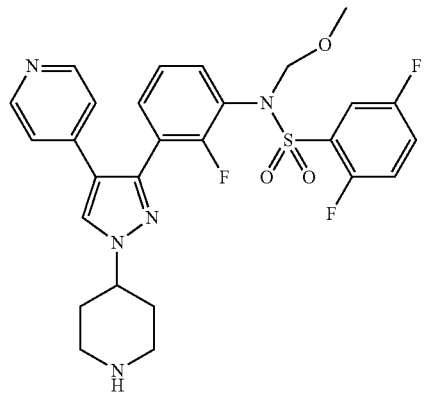 [SMILES: COCN(c1cccc(-c2nn(C3CCNCC3)cc2-c2ccncc2)c1F)S(=O)(=O)c1cc(F)ccc1F]

To a solution of 4-(3-{3-[(2,5-difluoro-benzenesulfonyl)-methoxymethyl-amino]-2-fluoro-phenyl}-4-pyridin-4-yl-pyrazol-1-yl)-piperidine-1-carboxylic acid tert-butyl ester (2.2 g, 3.35 mmol) in anhydrous 1,4-dioxane (17 mL) under nitrogen at r.t., a 4N solution of HCl in 1,4-dioxane (17 mL, 67 mmol, 20 eq) was added dropwise and the mixture was stirred at r.t. for 30 minutes. The solvent was concentrated under reduced pressure and the residue was diluted with DCM and washed with saturated aqueous NaHCO$_3$, water and brine. The organic layer was dried over Na$_2$SO$_4$ and evaporated to dryness. 1.8 g of the title compound (96%) were obtained and used without purification in the following step. HPLC (254 nm): R$_t$: 5.23 min; $^1$H NMR (DMSO-d6) Shift: 8.43 (s, 1H), 8.38-8.40 (m, 2H), 7.57-7.66 (m, 1H), 7.44-7.57 (m, 2H), 7.28-7.39 (m, 2H), 7.06-7.11 (m, 3H), 5.01 (s, 2H), 4.35-4.46 (m, 1H), 3.28 (s, 3H), 3.19-3.30 (m, 2H), 2.79-2.89 (m, 2H), 1.92-2.24 (m, 4H); HRMS (ESI) calcd for C27H27F3N5O3S [M+H]$^+$ 558.1781. found 558.1782.

2,5-Difluoro-N-{2-fluoro-3-[1-(1-methyl-piperidin-4-yl)-4-pyridin-4-yl-1H-pyrazol-3-yl]-phenyl}-N-methoxymethyl-benzenesulfonamide Formula 2, where R4=4-pyridinyl; PG$_1$=methoxymethyl; R29=N-methyl-piperidin-4-yl; R30=2,5-difluoro-benzene-sulfonyl

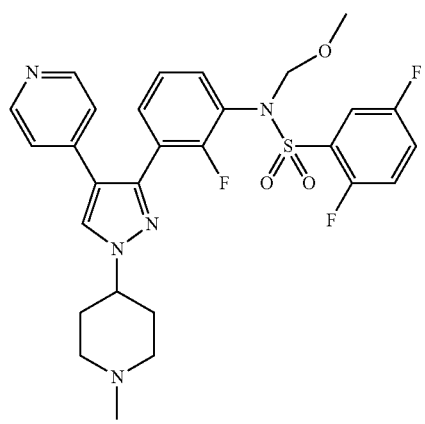 [SMILES: COCN(c1cccc(-c2nn(C3CCN(C)CC3)cc2-c2ccncc2)c1F)S(=O)(=O)c1cc(F)ccc1F]

To a solution of 2,5-difluoro-N-[2-fluoro-3-(1-piperidin-4-yl-4-pyridin-4-yl-1H-pyrazol-3-yl)-phenyl]-N-methoxymethyl-benzenesulfonamide (1.8 g, 3.23 mmol) in MeOH (20 mL) 37% aqueous formaldehyde (0.36 mL, 4.85 mmol, 1.5 eq) was added, followed by acetic acid (0.554 mL, 9.69 mmol, 3 eq) and sodium cyanoborohydride (325 mg, 5.17 mmol, 1.6 eq) and the mixture was stirred at r.t. for 1 h. The solvent was then evaporated under reduced pressure and the residue was taken up with AcOEt and washed with saturated aqueous NaHCO$_3$ and brine. The organic layer was dried over Na$_2$SO$_4$ and evaporated to dryness affording 1.62 g (88%) of the title compound, which was used without any further purification in the following step. HPLC (254 nm): R$_t$: 5.46 min; $^1$H NMR (DMSO-d6) Shift (selected signals): 8.44 (s, 1H), 8.36-8.40 (m, 2H), 7.57-7.66 (m, 1H), 7.44-7.57 (m, 3H), 7.25-7.39 (m, 2H), 7.04-7.10 (m, 2H), 5.01 (s, 2H), 4.12-4.26 (m, 1H), 3.27 (s, 3H), 2.85-2.92 (m, 2H), 2.22 (s, 3H), 1.87-2.15 (m, 4H); HRMS (ESI) calcd for C28H29F3N5O3S [M+H]$^+$ 572.1938. found 572.1933. Method A, Step f 2,5-Difluoro-N-{2-fluoro-3-[1-(1-methyl-piperidin-4-yl)-4-pyridin-4-yl-1H-pyrazol-3-yl]-phenyl}-benzenesulfonamide (Compound 5 of Table 1)

Formula 1, where m=0; R1=1-methyl-piperidin-4-yl; R2, R3=F; R4=4-pyridinyl

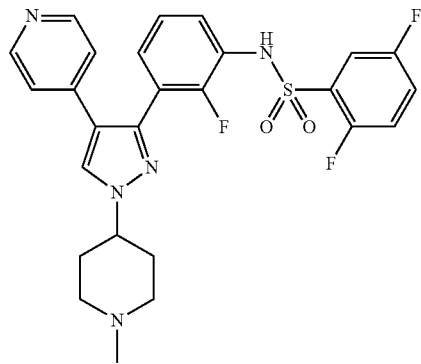 [SMILES: CN1CCC(n2cc(-c3ccncc3)c(-c3cccc(NS(=O)(=O)c4cc(F)ccc4F)c3F)n2)CC1]

2,5-Difluoro-N-{2-fluoro-3-[1-(1-methyl-piperidin-4-yl)-4-pyridin-4-yl-1H-pyrazol-3-yl]-phenyl}-N-methoxymethyl-benzenesulfonamide (1.62 g, 2.83 mmol) was dissolved in a 9:1 TFA/water mixture and stirred at 60° C. for 2 h. The reaction mixture was concentrated under reduced pressure, then taken up with AcOEt and washed with a saturated solution of NaHCO$_3$ and brine. The organic layer was dried over Na$_2$SO$_4$ and concentrated to dryness. The residue was purified by flash chromatography on silica gel (DCM/MeOH/NH$_3$ 7M in MeOH 85:10:5). The pure fractions were treated with ethyl ether, filtered and dried, affording 780 mg (52%) of the title compound as a white solid. HPLC (254 nm): R$_t$: 4.59 min. $^1$H NMR (DMSO-d6) Shift (selected signals): 8.41 (s, 1H), 8.34-8.39 (m, 2H), 7.26-7.53 (m, 4H), 7.09-7.18 (m, 2H), 7.04-7.10 (m, 2H), 4.16-4.35 (m, 1H), 3.00-3.14 (m, J=5.7 Hz, 2H), 2.41 (s, 3H), 1.98-2.21 (m, 4H); HRMS (ESI) calcd for C26H25F3N5O2S [M+H]$^+$ 528.1676. found 528.1670.

According to this same methodology, but employing suitable reagents in the reductive amination step or in the Suzuki coupling, the following compounds were prepared:

2,5-Difluoro-N-{2-fluoro-3-[4-(2-fluoro-pyridin-4-yl)-1-(1-methyl-piperidin-4-yl)-1H-pyrazol-3-yl]-phenyl}-benzenesulfonamide Formula I, where m=0; R1=1-methyl-piperidin-4-yl; R2, R3=F; R4=2-fluoro-pyridin-4-yl

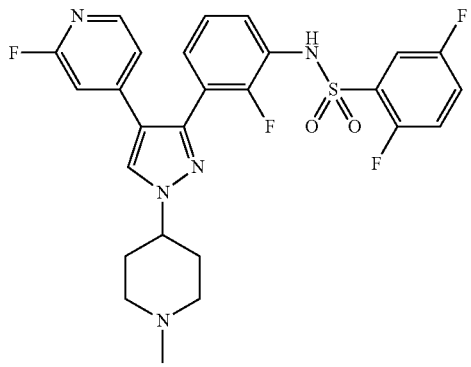 [SMILES: CN1CCC(n2cc(-c3ccnc(F)c3)c(-c3cccc(NS(=O)(=O)c4cc(F)ccc4F)c3F)n2)CC1]

HPLC (254 nm): R$_t$: 4.87 min; $^1$H NMR (DMSO-d6) Shift: 8.51 (s, 1H), 8.04 (d, J=5.2 Hz, 1H), 7.27-7.52 (m, 4H), 7.07-7.19 (m, 2H), 6.93-7.04 (m, 1H), 6.83 (s, 1H), 4.20-4.36 (m, 1H), 2.95-3.14 (m, 2H), 2.36-2.45 (m, 5H), 2.13-2.22 (m, 2H), 2.00-2.11 (m, 2H); HRMS (ESI) calcd for C26H24F4N5O2S [M+H]$^+$ 546.1582. found 546.1573.

N-{3-[1-(1-cyclopropylpiperidin-4-yl)-4-(2-fluoro-pyridin-4-yl)-1H-pyrazol-3-yl]-2-fluorophenyl}-2,5-difluorobenzenesulfonamide Formula I, where m=0; R1=1-cyclopropyl-piperidin-4-yl; R2, R3=R4=2-fluoro-pyridin-4-yl

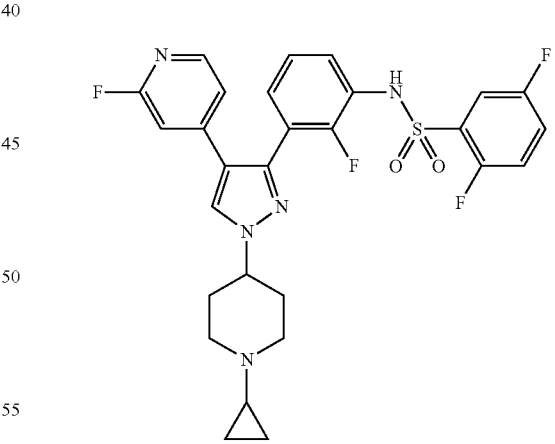

HPLC (254 nm): R$_t$: 6.49 min; $^1$H NMR (DMSO-d6) Shift: 10.61 (br. s., 1H), 8.50 (s, 1H), 8.03 (d, J=5.2 Hz, 1H), 7.58-7.50 (m, 1H), 7.48-7.38 (m, 2H), 7.35 (dt, J=2.0, 7.6 Hz, 1H), 7.32-7.27 (m, 1H), 7.27-7.15 (m, 1H), 6.97 (d, J=5.4 Hz, 1H), 6.79 (s, 1H), 4.31-4.16 (m, 1H), 3.05 (d, J=11.6 Hz, 2H), 2.39 (t, J=11.2 Hz, 2H), 2.14-2.03 (m, 2H), 1.98-1.85 (m, 2H), 1.71 (br. s., 1H), 0.51-0.43 (m, 2H), 0.34 (d, J=2.9 Hz, 2H); HRMS (ESI) calcd for C28H26F4N5O2S [M+H]$^+$ 572.1738. found 572.1739.

71

2,5-difluoro-N-{2-fluoro-3-[1-(1-methylpiperidin-4-yl)-4-(2-methylpyridin-4-yl)-1H-pyrazol-3-yl]phenyl}benzenesulfonamide Formula I, where m=0; R1=1-methyl-piperidin-4-yl; R2, R3=F; R4=2-methyl-pyridin-4-yl

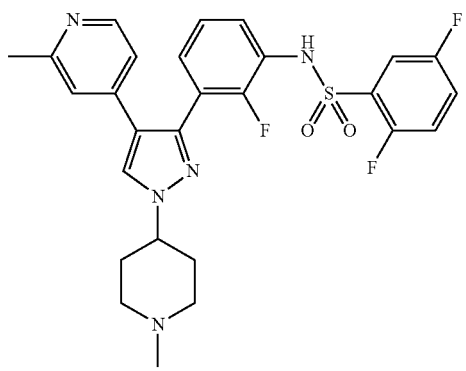 [SMILES: Cc1cc(-c2cn(C3CCN(C)CC3)nc2-c2cccc(NS(=O)(=O)c3cc(F)ccc3F)c2F)ccn1]

HPLC (254 nm): R$_t$: 3.72 min; $^1H$ NMR (DMSO-d6) Shift: 10.46-9.91 (br. s., 1H), 8.37 (s, 1H), 8.21 (d, J=5.2 Hz, 1H), 7.52-7.44 (m, 1H), 7.44-7.34 (m, 2H), 7.30 (dt, J=2.5, 7.5 Hz, 1H), 7.17-7.06 (m, 2H), 7.03 (s, 1H), 6.80 (dd, J=1.5, 5.2 Hz, 1H), 4.34-4.13 (m, 1H), 3.11-2.93 (m, 2H), 2.38 (s, 3H), 2.35 (s, 3H), 2.43-2.31 (m, 2H), 2.21-1.88 (m, 4H); HRMS (ESI) calcd for C27H27F3N5O2S [M+H]+ 542.1832. found 542.1832.

N-{3-[4-(2-chloropyridin-4-yl)-1-(1-methylpiperidin-4-yl)-1H-pyrazol-3-yl]-2-fluorophenyl}-2,5-difluorobenzenesulfonamide Formula I, where m=0; R1=1-methyl-piperidin-4-yl; R2, R3=F; R4=2-chloro-pyridin-4-yl

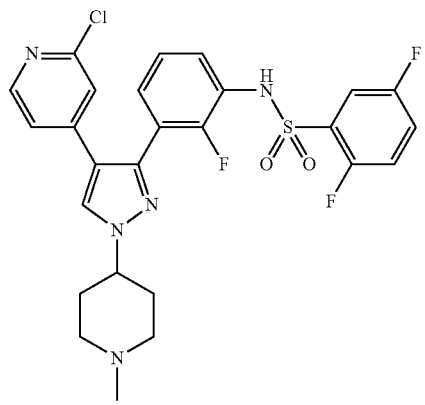 [SMILES: CN1CCC(n2cc(-c3ccnc(Cl)c3)c(-c3cccc(NS(=O)(=O)c4cc(F)ccc4F)c3F)n2)CC1]

HPLC (254 nm): R$_t$: 4.06 min; $^1$H NMR (DMSO-d6) Shift: 8.53 (s, 1H), 8.18 (d, J=5.2 Hz, 1H), 7.49-7.30 (m, 4H), 7.28 (d, J=1.1 Hz, 1H), 7.19-7.07 (m, 2H), 7.00 (dd, J=1.5, 5.2 Hz, 1H), 4.36-4.20 (m, 1H), 3.12-2.95 (m, J=11.8 Hz, 2H), 2.42 (s, 3H), 2.47-2.35 (m, 2H), 2.22-2.13 (m, 2H), 2.12-2.00 (m, 2H); HRMS (ESI) calcd for C26H24ClF3N5O2S [M+H]$^+$ 562.1286. found 562.1293.

72

2,5-difluoro-N-{2-fluoro-3-[4-(2-methoxypyridin-4-yl)-1-(1-methylpiperidin-4-yl)-1H-pyrazol-3-yl]phenyl}benzenesulfonamide Formula I, where m=0; R1=1-methyl-piperidin-4-yl; R2, R3=F; R4=2-methoxy-pyridin-4-yl

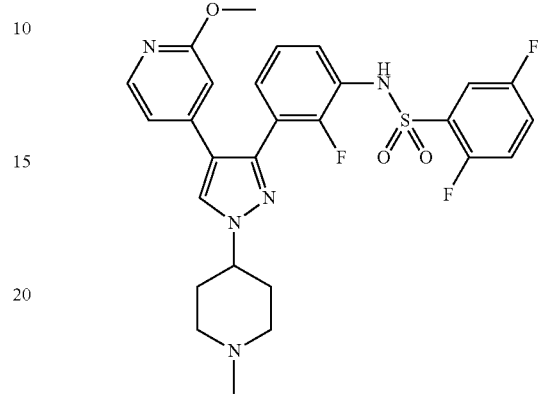

HPLC (254 nm): R$_t$: 4.04 min; $^1$H NMR (DMSO-d6) Shift: 10.42 (br. s., 1H), 8.39 (s, 1H), 7.96 (d, J=5.4 Hz, 1H), 7.55-7.35 (m, 3H), 7.31 (dt, J=2.4, 7.5 Hz, 1H), 7.18-7.02 (m, 2H), 6.67 (dd, J=1.3, 5.4 Hz, 1H), 6.50 (d, J=0.6 Hz, 1H), 4.38-4.15 (m, 1H), 3.79 (s, 3H), 3.16-3.00 (m, 2H), 2.45-2.38 (m, 2H), 2.22-1.99 (m, 4H); HRMS (ESI) calcd for C27H27F3N5O3S [M+H]$^+$ 558.1781. found 5581780.

2,5-difluoro-N-{2-fluoro-3-[1-(8-methyl-8-azabicyclo[3.2.1]oct-3-yl)-4-(pyridin-4-yl)-1H-pyrazol-3-yl]phenyl}benzenesulfonamide Formula I, where m=0, R1=8-methyl-8-azabicyclo[3.2.1]oct-3-yl, R2, R3=F, R4=4-pyridinyl

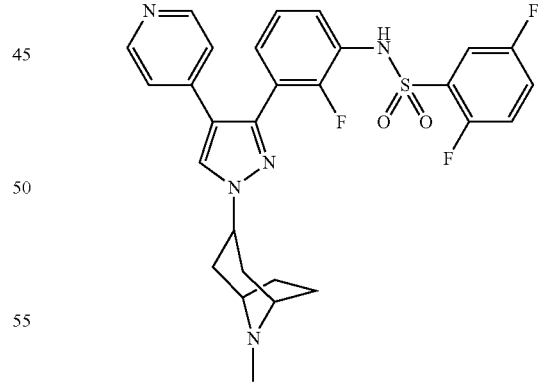

HPLC (254 nm): R$_t$: 4.72 min; $^1$H NMR (DMSO-d6) Shift (selected signals): 8.67 (s, 1H), 8.38 (d, J=6.0 Hz, 2H), 7.42 (ddd, J=3.3, 5.2, 8.1 Hz, 1H), 7.38-7.21 (m, 3H), 7.16 (d, J=6.1 Hz, 2H), 6.97 (t, J=7.8 Hz, 1H), 6.79 (br. s., 1H), 4.58-4.50 (m, 1H), 3.68 (br. s., 2H), 2.91-2.76 (m, 2H), 2.55 (s, 3H), 2.45 (d, J=4.3 Hz, 2H), 2.05-1.93 (m, 2H), 1.66 (d, J=8.3 Hz, 2H); HRMS (ESI) calcd for C28H27F3N5O2S [M+H]$^+$ 554.1832. found 554.1843.

73

2,5-Difluoro-N-{2-fluoro-3-[1-(1-isopropyl-piperidin-4-yl)-4-pyridin-4-yl-1H-pyrazol-3-yl]-phenyl}-benzenesulfonamide (Compound 1)

Formula 1, where m=0; R1=1-isopropyl-piperidin-4-yl; R2, R3=F; R4=pyridin-4-yl]

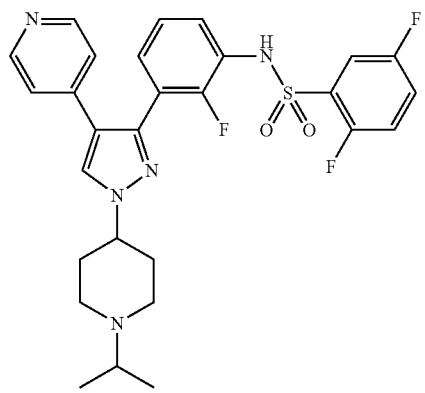 [SMILES: CC(C)N1CCC(n2cc(-c3ccncc3)c(-c3cccc(NS(=O)(=O)c4cc(F)ccc4F)c3F)n2)CC1]

HPLC (254 nm): $R_t$: 4.81 min; $^1$H NMR (DMSO-d6) Shift: 9.93 (s, 1H), 8.40 (s, 1H), 8.36-8.39 (m, 2H), 7.46-7.53 (m, 1H), 7.39-7.45 (m, 2H), 7.30-7.36 (m, 1H), 7.12-7.20 (m, 2H), 7.02-7.11 (m, 2H), 4.37-4.46 (m, 1H), 3.15-3.40 (m, 4H), 2.85 (br. s., 1H), 2.07-2.32 (m, 4H), 1.16 (d, J=6.5 Hz, 6H); HRMS (ESI) calcd for C28H29F3N5O2S [M+H]$^+$ 556.1989. found 556.1964.

2,5-Difluoro-N-{2-fluoro-3-[4-(2-fluoro-pyridin-4-yl)-1-(1-isopropyl-piperidin-4-yl)-1H-pyrazol-3-yl]-phenyl}-benzenesulfonamide Formula I, where m=0; R1=1-isopropyl-piperidin-4-yl; R2, R3=F; R4=2-fluoro-pyridin-4-yl

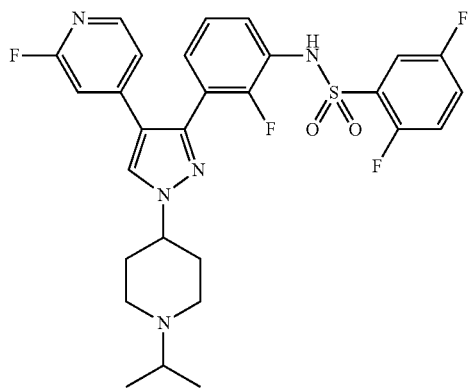 [SMILES: CC(C)N1CCC(n2cc(-c3ccnc(F)c3)c(-c3cccc(NS(=O)(=O)c4cc(F)ccc4F)c3F)n2)CC1]

HPLC (254 nm): $R_t$: 4.98 min; $^1$H NMR (DMSO-d6) Shift: 8.50 (s, 1H), 8.04 (d, J=5.2 Hz, 1H), 7.23-7.47 (m, 4H), 7.06-7.17 (m, J=7.1 Hz, 2H), 6.98-7.04 (m, J=5.2 Hz, 1H), 6.84 (s, 1H), 4.22-4.40 (m, 1H), 3.11 (br. s., 4H), 2.56-2.71 (m, 1H), 2.14-2.25 (m, J=10.4 Hz, 2H), 2.00-2.11 (m, 2H), 1.09 (d, J=6.5 Hz, 6H); HRMS (ESI) calcd for C28H28F4N5O2S [M+H]$^+$ 574.1895. found 574.1908.

74

N-{3-[1-(1-Cyclopropyl-piperidin-4-yl)-4-pyridin-4-yl-1H-pyrazol-3-yl]-2-fluoro-phenyl}-2,5-difluoro-benzenesulfonamide (Compound 2)

Formula I, where m=0, R1=1-cyclopropyl-piperidin-4-yl, R2, R3=F, R4=4-pyridinyl

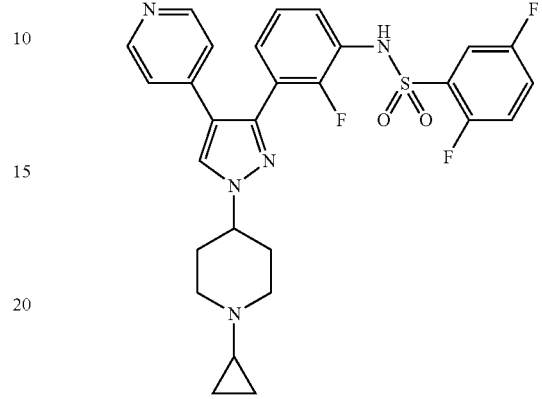

HPLC (254 nm): $R_t$: 5.67 min; $^1$H NMR (DMSO-d6) Shift: 10.59 (br. s., 1H), 8.39-8.42 (m, 1H), 8.34-8.38 (m, 2H), 7.51-7.57 (m, 1H), 7.40-7.48 (m, 2H), 7.35 (td, J=2.0, 7.6 Hz, 1H), 7.25-7.30 (m, 1H), 7.18-7.24 (m, 1H), 7.00-7.07 (m, 2H), 4.18-4.28 (m, 1H), 3.06 (d, J=16.4 Hz, 2H), 2.38 (br. s., 2H), 2.03-2.14 (m, 2H), 1.85-2.00 (m, 2H), 1.71 (br. s., 1H), 0.41-0.50 (m, 2H), 0.29-0.38 (m, 2H); HRMS (ESI) calcd for C28H27F3N5O2S [M+H]$^+$ 554.1832. found 554.1808.

3-(4-{3-[3-(2,5-Difluoro-benzenesulfonylamino)-2-fluoro-phenyl]-4-pyridin-4-yl-pyrazol-1-yl}-piperidin-1-yl)-propionic acid ethyl ester Formula I, where m=0, R1=1-(2-ethoxycarbonyl-ethyl)piperidin-4-yl, R2, R3=F, R4=4-pyridinyl

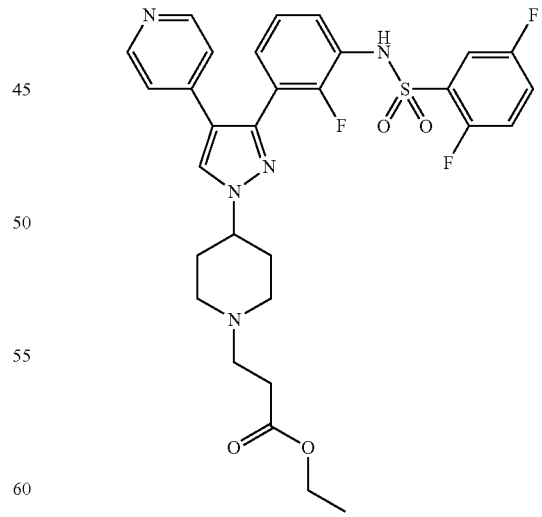

HPLC (254 nm): $R_t$: 5.54 min; $^1$H NMR (DMSO-d6) Shift (selected signals): 10.55 (br. s., 1H), 8.41 (s, 1H), 8.34-8.38 (m, 2H), 7.47-7.57 (m, 1H), 7.38-7.47 (m, 2H), 7.34 (td, J=2.1, 7.5 Hz, 1H), 7.15-7.31 (m, 2H), 7.02-7.07 (m, 2H), 4.14-4.27 (m, 1H), 4.07 (q, J=7.1 Hz, 2H), 2.98 (m, 2H), 2.64-2.73 (m, 2H), 2.16-2.28 (m, 2H), 2.04-2.16 (m, 2H), 1.91-2.02 (m, 2H), 1.19 (t, J=7.1 Hz, 3H); HRMS (ESI) calcd for C30H31F3N5O4S [M+H]+ 614.2044. found 614.2028.

3-(4-{3-[3-(2,5-Difluoro-benzenesulfonylamino)-2-fluoro-phenyl]-4-pyridin-4-yl-pyrazol-1-yl}-piperidin-1-yl)-propionic acid methyl ester Formula I, where m=0, R1=1-(2-methoxycarbonyl-ethyl)-piperidin-4-yl, R2, R3=F, R4=4-pyridinyl

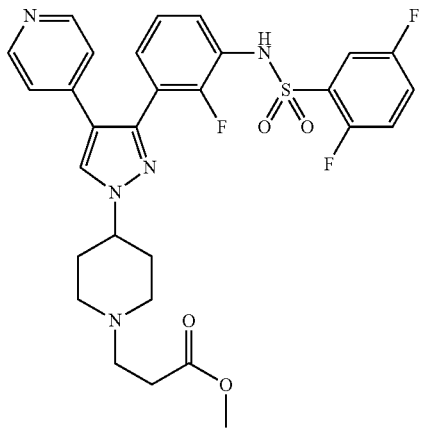 [SMILES: COC(=O)CCN1CCC(n2cc(-c3ccncc3)c(-c3cccc(NS(=O)(=O)c4cc(F)ccc4F)c3F)n2)CC1]

HPLC (254 nm): R$_t$: 5.20 min; $^1$H NMR (DMSO-d6) Shift: 10.51 (br. s., 1H), 8.41 (s, 1H), 8.34-8.38 (m, 2H), 7.48-7.58 (m, 1H), 7.39-7.47 (m, 2H), 7.34 (td, J=2.1, 7.5 Hz, 1H), 7.15-7.28 (m, 2H), 7.02-7.06 (m, 2H), 4.16-4.27 (m, 1H), 3.61 (s, 3H), 2.96-3.04 (m, 2H), 2.65-2.72 (m, 2H), 2.51-2.55 (m, 2H), 2.16-2.27 (m, 2H), 2.04-2.12 (m, 2H), 1.92-2.03 (m, 2H); HRMS (ESI) calcd for C29H29F3N5O4S [M+H]+ 600.1887. found 600.1876.

2,5-Difluoro-N-[2-fluoro-3-(1-piperidin-4-yl-4-pyridin-4-yl-1H-pyrazol-3-yl)-phenyl]-benzenesulfonamide Formula I, where m=0, R$_1$=piperidin-4-yl, R2, R3=F, R4=4-pyridinyl

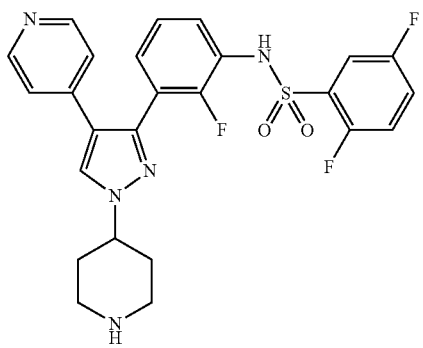 [SMILES: O=S(=O)(Nc1cccc(-c2nn(C3CCNCC3)cc2-c2ccncc2)c1F)c1cc(F)ccc1F]

4-(3-{3-[(2,5-Difluoro-benzenesulfonyl)-methoxymethyl-amino]-2-fluoro-phenyl}-4-pyridin-4-yl-pyrazol-1-yl)-piperidine-1-carboxylic acid tert-butyl ester, (47 mg, 0.072 mmol) was dissolved in a 9:1 TFA/water mixture (2 mL) and stirred at 70° C. for 2 h. The reaction mixture was then concentrated under reduced pressure, taken up with AcOEt and washed with a saturated solution of NaHCO$_3$ and brine. The organic layer was dried over Na$_2$SO$_4$ and concentrated to dryness. The crude was eluted on a small silica gel column eluting with methanol. 12 mg of the title compound were obtained as a white solid. HPLC (254 nm): R$_t$: 4.52 min; $^1$H NMR (DMSO-d6) Shift (selected signals): 8.27-8.53 (m, 3H), 7.40 (ddd, J=2.9, 5.3, 8.2 Hz, 1H), 7.19-7.30 (m, 2H), 7.14-7.18 (m, 2H), 6.85 (t, J=7.8 Hz, 1H), 6.61 (t, J=7.8 Hz, 1H), 4.40-4.56 (m, 1H), 3.14-3.46 (m, 2H), 3.00 (t, J=11.2 Hz, 2H), 2.19-2.29 (m, 2H), 1.99-2.17 (m, 2H); HRMS (ESI) calcd for C25H23F3N5O2S [M+H]+ 514.1519. found 514.1505.

Example 3

N-{3-[1-(1-Acetyl-piperidin-4-yl)-4-pyridin-4-yl-1H-pyrazol-3-yl]-2-fluoro-phenyl}-2,5-difluoro-benzenesulfonamide Formula I, where m=0, R1=1-acetyl-piperidin-4-yl; R2, R3=F; R4=4-pyridinyl

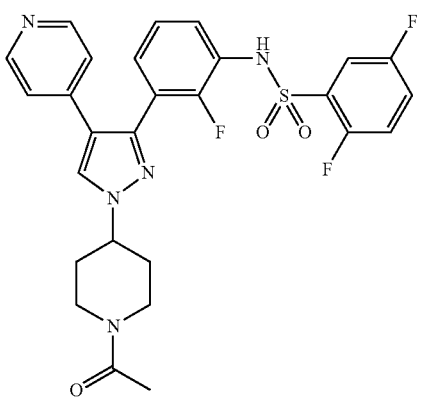 [SMILES: CC(=O)N1CCC(n2cc(-c3ccncc3)c(-c3cccc(NS(=O)(=O)c4cc(F)ccc4F)c3F)n2)CC1]

To a solution of 2,5-difluoro-N-[2-fluoro-3-(1-piperidin-4-yl-4-pyridin-4-yl-1H-pyrazol-3-yl)-phenyl]-N-methoxymethyl-benzenesulfonamide (135 mg, 0.242 mmol) (prepared as described in Example 2) in DCM (2 mL) triethylamine (0.040 mL, 0.290 mmol, 1.2 eq) was added, followed by acetylchloride (0.019 mL, 0.266 mmol, 1.1 eq) and the solution was stirred at r.t. for 2 h. The reaction mixture was then diluted with DCM and washed with saturated aqueous NaHCO$_3$ and brine, dried over Na$_2$SO$_4$ and evaporated to dryness. The crude product was purified by flash chromatography (DCM/MeOH 97:3) affording 81 mg (56%) of N-{3-[1-(1-Acetyl-piperidin-4-yl)-4-pyridin-4-yl-1H-pyrazol-3-yl]-2-fluoro-phenyl}-2,5-difluoro-N-methoxymethyl-benzene-sulfonamide. This intermediate was then treated with a 9:1 TFA/water mixture (1 mL) and stirred at 60° C. for 1.5 h. The reaction mixture was concentrated under reduced pressure, then taken up with AcOEt and washed with a saturated solution of NaHCO$_3$ and brine. The organic layer was dried over Na$_2$SO$_4$ and concentrated to dryness. The residue was purified by flash chromatography on silica gel (DCM/MeOH 95:5) affording 9 mg of the title compound. HPLC (254 nm): R$_t$: 5.22 min; $^1$H NMR (DMSO-d6) Shift: 10.66 (br. s., 1H), 8.48 (s, 1H), 8.38-8.43 (m, 2H), 7.51-7.60 (m, 1H), 7.40-7.49 (m, 2H), 7.29-7.38 (m, 2H), 7.21-7.27 (m, 1H), 7.11 (d, J=6.0 Hz, 2H), 4.44-4.55 (m, 2H), 3.90-3.96 (m, 1H), 3.17-3.28 (m, 1H), 2.69-2.78 (m, 1H), 2.07-2.18 (m, 2H), 2.04 (s, 3H), 1.91-1.99 (m, 1H), 1.74-1.84 (m, 1H); HRMS (ESI) calcd for C27H25F3N5O3S [M+H]+ 556.1625. found 556.1620.

Example 4

N-{3-[4-(2-Amino-pyrimidin-4-yl)-1-isopropyl-1H-pyrazol-3-yl]-2-fluoro-phenyl}-2,5-difluoro-benzenesulfonamide (Compound 10 in Table 1)

Formula 1, where m=0; $R_1$=i-Pr; R2, R3=F; R4=2-Amino-pyrimidin-4-yl

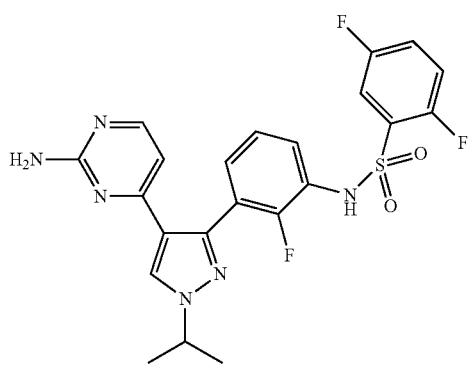 [SMILES: CC(C)n1cc(-c2ccnc(N)n2)c(-c2cccc(NS(=O)(=O)c3cc(F)ccc3F)c2F)n1]

Method A, Step b 2,5-Difluoro-N-{2-fluoro-3-[1-isopropyl-4-(4,4,5,5-tetramethyl-[1,3,2]dioxaborolan-2-yl)-1H-pyrazol-3-yl]-phenyl}-N-methoxymethyl-benzenesulfonamide Formula 3, where M'=4,4,5,5-tetramethyl-[1,3,2]dioxaborolan-2-yl; $PG_1$=methoxymethyl; R29=isopropyl; R30=2,5-difluoro-benzene-sulfonyl

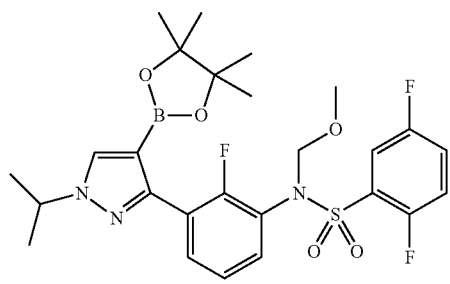 [SMILES: COCN(c1cccc(-c2nn(C(C)C)cc2B2OC(C)(C)C(C)(C)O2)c1F)S(=O)(=O)c1cc(F)ccc1F]

To an argon degassed solution of N-[3-(4-bromo-1-isopropyl-3H-pyrazol-3-yl)-2-fluoro-phenyl]-2,5-difluoro-N-methoxymethyl-benzenesulfonamide (see Example 1, Method C, Step k) (295 mg, 0.569 mmol) in toluene (4 mL) in a microwave vial, 4,4,5,5-tetramethyl-[1,3,2]dioxaborolane (728 mg, 5.69 mmol), TEA (0.2 mL, 1.42 mmol), 2-dicyclohexylphosphino-2',6'-dimethoxy-1,1'-biphenyl (35 mg, 0.085 mmol) and bis(acetonitrile)dichloropalladium(II) (PdCl$_2$° (CH$_3$CN)$_2$) (8 mg, 0.028 mmol) were added, under argon atmosphere. The mixture was heated in the microwave oven at 90° C. for 1 hour, then it was filtered through a Celite pad. The solution was concentrated to dryness and the residue was purified by flash chromatography on silica gel (Hex: AcOEt 7.3) affording 330 mg of the title compound (quantitative yield). HPLC (254 nm): R$_t$: 7.59 min; $^1$H NMR (DMSO-d6) Shift: 8.00 (s, 1H), 7.55-7.69 (m, 2H), 7.43-7.55 (m, 2H), 725-7.31 (m, 1H), 7.22 (t, J=7.8 Hz, 1H), 5.11 (s, 2H), 4.54 (quin, J=6.6 Hz, 1H), 3.37 (s, 3H), 1.43 (d, J=6.7 Hz, 6H), 1.18 (s, 12H); HRMS (ESI) calcd for C26H32BF3N3O5S [M+H]+ 565.2139. found 565.2124.

According to this same methodology, but employing suitable starting materials, the following intermediate was prepared:

N-{3-[1-Ethyl-4-(4,4,5,5-tetramethyl-[1,3,2]dioxaborolan-2-yl)-1H-pyrazol-3-yl]-2-fluoro-phenyl}-2,5-difluoro-N-methoxymethyl-benzenesulfonamide Formula 3, M'=4,4,5,5-tetramethyl-[1,3,2]dioxaborolan-2-yl; $PG_1$=methoxymethyl; R29=ethyl; R30=2,5-difluoro-benzene-sulfonyl

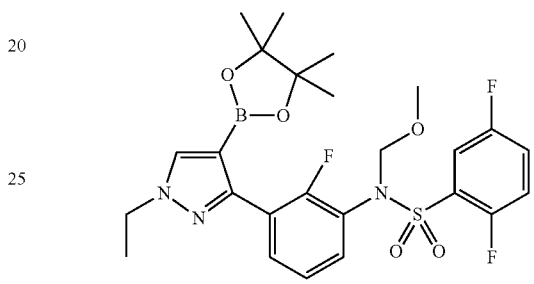

HPLC (254 nm): R$_t$: 6.37 min; $^1$H NMR (DMSO-d6) Shift: 7.99 (s, 1H), 7.45-7.69 (m, 4H), 7.19-7.31 (m, 2H), 5.11 (s, 2H), 4.16 (q, J=7.2 Hz, 2H), 3.37 (s, 3H), 1.39 (t, J=7.3 Hz, 3H), 1.12-1.20 (m, 12H); HRMS (ESI) calcd for C25H30BF3N3O5S [M+H]+ 551.1982. found 551.1965.

Method A, Step c

N-{3-[4-(2-Amino-pyrimidin-4-yl)-1-isopropyl-1H-pyrazol-3-yl]-2-fluoro-phenyl}-2,5-difluoro-N-methoxymethyl-benzenesulfonamide Formula 2, where R4=2-Amino-pyrimidin-4-yl; $PG_1$=methoxymethyl; R29=isopropyl; R30=2,5-difluoro-benzene-sulfonyl

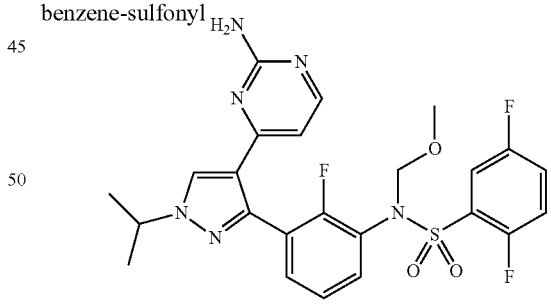

To an argon degassed solution of 2,5-Difluoro-N-{2-fluoro-3-[1-isopropyl-4-(4,4,5,5-tetramethyl-[1,3,2]dioxaborolan-2-yl)-1H-pyrazol-3-yl]-phenyl}-N-methoxymethyl-benzenesulfonamide (330 mg, 0.569 mmol) in 1,2-dimethoxyethane:water 9:1 (6 mL) in a microwave vial, 4-chloro-pyrimidin-2-ylamine (110 mg, 0.853 mmol), cesium carbonate (371 mg, 1.138 mmol) and Pd(dppf)Cl$_2$.CH$_2$Cl$_2$ (46 mg, 0.057 mmol) were added, under argon atmosphere. The mixture was heated in the microwave oven at 100° C. for 90 minutes, and then filtered through a Celite pad. The solution was taken up with AcOEt and washed with saturated aqueous NaHCO$_3$ and brine. The organic layer was dried over Na$_2$SO$_4$ and concentrated to dryness. The residue was purified by flash chromatography on silica gel (DCM: MeOH 97:3) affording 100 mg of the title compound (33% yield). HPLC (254 nm): $R_t$: 6.1 min; $^1$H NMR (DMSO-d6) Shift: 8.34 (s, 1H), 8.00 (d, J=5.2 Hz, 1H), 7.59-7.67 (m, 1H), 7.54-7.59 (m, 1H), 7.45-7.54 (m, 2H), 7.30-7.35 (m, 1H), 7.28 (d, J=15.3 Hz, 1H), 6.23 (d, J=5.2 Hz, 3H), 5.05 (s, 2H), 4.58 (quin, J=6.6 Hz, 1H), 3.33 (s, 3H), 1.48 (d, J=6.7 Hz, 6H); HRMS (ESI) calcd for C24H24F3N6O3S [M+H]$^+$ 533.1577. found 533.1567.

According to this same methodology, but employing suitable starting materials and arylhalides, the following compounds were prepared:

2,5-Difluoro-N-{2-fluoro-3-[4-(2-methyl-pyridin-4-yl)-1-(tetrahydro-pyran-4-yl)-1H-pyrazol-3-yl]-phenyl}-N-methoxymethyl-benzenesulfonamide Formula 2, where R4=2-Methyl-pyridin-4-yl; PG$_1$=methoxymethyl; R29=tetrahydro-pyran-4-yl; R30=2,5-difluoro-benzene-sulfonyl

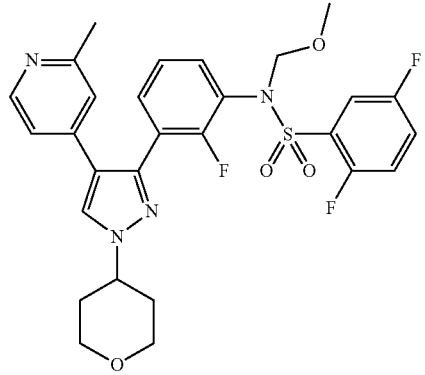 [SMILES: COCN(c1cccc(-c2nn(C3CCOCC3)cc2-c2ccnc(C)c2)c1F)S(=O)(=O)c1cc(F)ccc1F]

HPLC (254 nm): $R_t$: 6.27 min; $^1$H NMR (DMSO-d6) Shift: 8.43 (s, 1H), 8.24 (d, J=5.2 Hz, 1H), 7.67-7.57 (m, 1H), 7.57-7.41 (m, 3H), 7.37-7.29 (m, 2H), 7.00 (s, 1H), 6.87 (d, J=6.2 Hz, 1H), 5.01 (s, 2H), 4.54-4.42 (m, 1H), 4.03-3.94 (m, 2H), 3.57-3.42 (m, 2H), 3.29 (s, 3H), 2.35 (s, 3H), 2.19-1.90 (m, 4H); HRMS (ESI) calcd for C28H28F3N4O4S [M+H]+ 573.1778. found 573.1754.

2,5-Difluoro-N-{2-fluoro-3-[4-(2-chloro-pyridin-4-yl)-1-(tetrahydro-pyran-4-yl)-1H-pyrazol-3-yl]-phenyl}-N-methoxymethyl-benzenesulfonamide]

Formula 2, where R4=2-Chloro-pyridin-4-yl; PG$_1$=methoxymethyl; R29=tetrahydro-pyran-4-yl; R30=2,5-difluoro-benzene-sulfonyl]

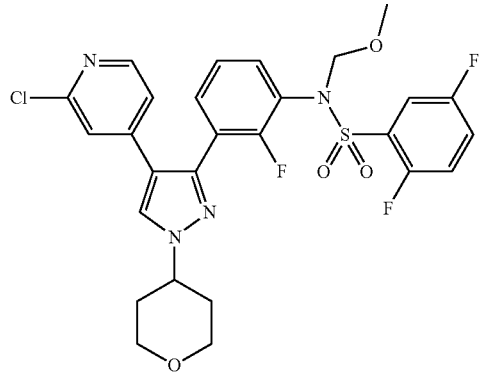 [SMILES: COCN(c1cccc(-c2nn(C3CCOCC3)cc2-c2ccnc(Cl)c2)c1F)S(=O)(=O)c1cc(F)ccc1F]

HPLC (254 nm): $R_t$: 6.87 min; $^1$H NMR (DMSO-d6) Shift: 8.58 (s, 1H), 8.21 (d, J=5.4 Hz, 1H), 7.67-7.59 (m, 1H), 7.59-7.51 (m, 2H), 7.51-7.44 (m, 1H), 7.39-7.30 (m, 2H), 7.28 (d, J=1.1 Hz, 1H), 7.04 (dd, J=1.5, 5.3 Hz, 1H), 5.02 (s, 2H), 4.62-4.35 (m, 1H), 4.05-3.92 (m, 2H), 3.50 (dt, J=2.1, 11.7 Hz, 2H), 3.28 (s, 3H), 2.14-2.05 (m, 2H), 2.05-1.86 (m, 2H); HRMS (ESI) calcd for C27H25ClF3N4O4S [M+H]$^+$ 593.1232. found 593.1250.

N-{3-[4-(2-Amino-pyridin-4-yl)-1-(tetrahydro-pyran-4-yl)-1H-pyrazol-3-yl]-2-fluoro-phenyl}-2,5-difluoro-N-methoxymethyl-benzenesulfonamide Formula 2, where R4=2-amino-pyridin-4-yl; PG$_1$=methoxymethyl; R29=tetrahydro-pyran-4-yl; R30=2,5-difluoro-benzene-sulfonyl

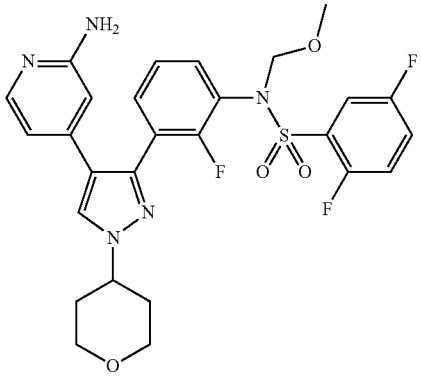 [SMILES: COCN(c1cccc(-c2nn(C3CCOCC3)cc2-c2ccnc(N)c2)c1F)S(=O)(=O)c1cc(F)ccc1F]

HPLC (254 nm): $R_t$: 4.70 min; $^1$H NMR (DMSO-d6) Shift: 8.22 (s, 1H), 7.70 (d, J=5.2 Hz, 1H), 7.67-7.57 (m, 1H), 7.57-7.42 (m, 3H), 7.36-7.22 (m, 2H), 6.27 (s, 1H), 6.14 (d, J=5.4 Hz, 1H), 5.70 (s, 2H), 5.00 (s, 2H), 4.60-4.39 (m, 1H), 4.02-3.94 (m, 2H), 3.91 (s, 3H), 3.55-3.42 (m, 2H), 2.14-1.86 (m, 4H); HRMS (ESI) calcd for C27H27F3N5O4S [M+H]$^+$ 574.1731. found 574.1740.

2,5-Difluoro-N-{2-fluoro-3-[4-(7H-pyrrolo[2,3-d]pyrimidin-4-yl)-1-(tetrahydro-pyran-4-yl)-1H-pyrazol-3-yl]-phenyl}-N-methoxymethyl-benzenesulfonamide Formula 2, where R4=7H-pyrrolo[2,3-d]pyrimidin-4-yl, PG$_1$=methoxymethyl, R29=ethyl, R30=2,5-difluoro-benzene-sulfonyl

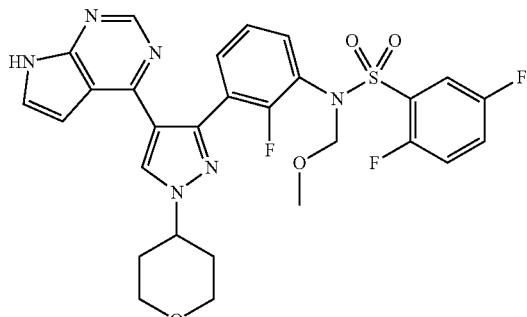

HPLC (254 nm): $R_t$: 5.77 min; $^1$H NMR (DMSO-d6) Shift: 12.02 (br. s., 1H), 8.58 (s, 1H), 8.41 (s, 1H), 7.61-7.53 (m, 2H), 7.52-7.45 (m, 2H), 7.43 (dt, J=2.6, 5.2 Hz, 1H), 7.29-7.22 (m, 2H), 6.51 (dd, J=1.5, 3.5 Hz, 1H), 4.90 (s, 2H), 4.64-4.53 (m, 1H), 4.06-3.92 (m, 2H), 3.59-3.43 (m, 2H), 3.29 (s, 3H), 2.21-1.94 (m, 4H); HRMS (ESI) calcd for C28H26F3N6O4S [M+H]$^+$ 599.1683. found 599.1687.

Method A, Step f

N-{3-[4-(2-Amino-pyrimidin-4-yl)-1-isopropyl-1H-pyrazol-3-yl]-2-fluoro-phenyl}-2,5-difluoro-benzenesulfonamide (Compound 10 in Table 1)

Formula I, where m=0; $R_1$=i-Pr; R2, R3=F; R4=2-Amino-pyrimidin-4-yl

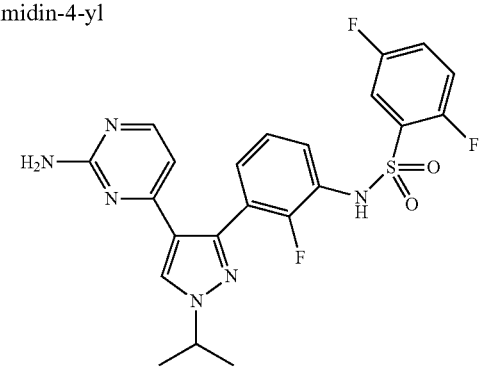

N-{3-[4-(2-Amino-pyrimidin-4-yl)-1-isopropyl-1H-pyrazol-3-yl]-2-fluoro-phenyl}-2,5-difluoro-N-methoxymethyl-benzenesulfonamide (100 mg, 0.188 mmol) was dissolved in a mixture of TFA:water 9:1 (1 mL) and stirred for 5 h at 60° C. The reaction mixture was concentrated under reduced pressure, then taken up with a saturated solution of NaHCO₃ and extracted with AcOEt. The organic layer was dried over Na₂SO₄ and concentrated to dryness. The residue was purified by flash chromatography on silica gel (DCM:MeOH:acetone 94:3:3) affording 26 mg of the title compound (28% yield), HPLC (254 nm): $R_t$: 5.68 min; ¹H NMR (DMSO-d6) Shift: 10.65 (s, 1H), 8.28 (s, 1H), 7.95 (d, J=5.1 Hz, 1H), 7.53-7.62 (m, 1H), 7.43-7.53 (m, 2H), 7.25-7.37 (m, 2H), 7.21 (t, J=7.9 Hz, 1H), 6.30 (br. s., 2H), 6.03 (d, J=5.2 Hz, 1H), 4.52-4.66 (q, J=6.7 Hz, 1H), 1.47 (d, J=6.7 Hz, 6H); HRMS (ESI) calcd for C22H20F3N6O2S [M+H]⁺ 489.1315. found 489.1306.

According to this same methodology, but employing suitable starting materials, the following compounds were prepared:

2,5-difluoro-N-{2-fluoro-3-[4-(2-methylpyridin-4-yl)-1-(tetrahydro-2H-pyran-4-yl)-1H-pyrazol-3-yl]phenyl}benzenesulfonamide Formula I, where m=0; R1=tetrahydro-2H-pyran-4-yl; R2, R3=F; R4=2-methyl-pyridin-4-yl

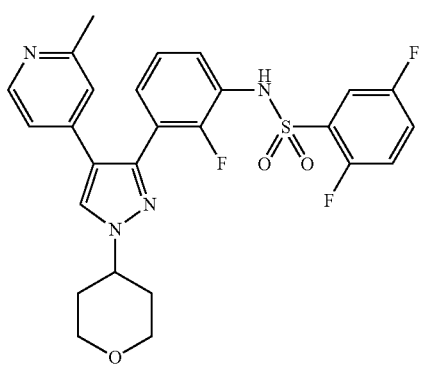 [SMILES: Cc1cc(-c2cn(C3CCOCC3)nc2-c2cccc(NS(=O)(=O)c3cc(F)ccc3F)c2F)ccn1]

HPLC (254 nm): $R_t$: 5.84 min; ¹H NMR (DMSO-d6) Shift: 10.66 (br. s., 1H), 8.40 (s, 1H), 8.21 (d, J=5.2 Hz, 1H), 7.60-7.50 (m, 1H), 7.51-7.37 (m, 2H), 7.36-7.26 (m, 2H), 7.25-7.17 (m, 1H), 7.02 (s, 1H), 6.77 (d, J=5.0 Hz, 1H), 4.56-4.36 (m, 1H), 4.02-3.94 (m, 2H), 3.48 (dt, J=2.0, 11.6 Hz, 2H), 2.36 (s, 3H), 2.13-1.82 (m, 4H); HRMS (ESI) calcd for C26H24F3N4O3S [M+H]⁺ 529.1516. found 529.1504.

N-{3-[4-(2-chloropyridin-4-yl)-1-(tetrahydro-2H-pyran-4-yl)-1H-pyrazol-3-yl]-2-fluorophenyl}-2,5-difluorobenzenesulfonamide Formula 1, where m=0; $R_1$=tetrahydro-2H-pyran-4-yl; R2, R3=F; R4=2-chloro-pyridin-4-yl

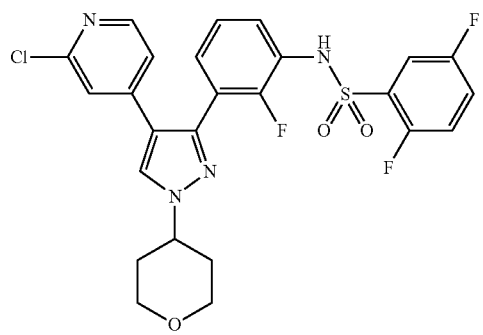 [SMILES: O=S(=O)(Nc1cccc(-c2nn(C3CCOCC3)cc2-c2ccnc(Cl)c2)c1F)c1cc(F)ccc1F]

HPLC (254 nm): $R_t$: 6.46 min; ¹H NMR (DMSO-d6) Shift: 10.68 (s, 1H), 8.55 (s, 1H), 8.18 (d, J=5.2 Hz, 1H), 7.59-7.52 (m, 1H), 7.50-7.41 (m, 2H), 7.40-7.29 (m, 2H), 7.29-7.19 (m, 2H), 6.96 (dd, J=1.5, 5.2 Hz, 1H), 4.54-4.36 (m, 1H), 4.05-3.93 (m, 2H), 3.53-3.42 (m, 2H), 2.13-2.04 (m, 2H), 2.03-1.89 (m, 2H); HRMS (ESI) calcd for C25H21ClF3N4O3S [M+H]⁺ 549.0970. found 549.0977.

N-{3-[4-(6-aminopyrimidin-4-yl)-1-(tetrahydro-2H-pyran-4-yl)-1H-pyrazol-3-yl]-2-fluorophenyl}-2,5-difluorobenzenesulfonamide Formula 1, where m=0; R1=tetrahydro-2H-pyran-4-yl; R2, R3=F; R4=6-amino-pyrimidin-4-yl

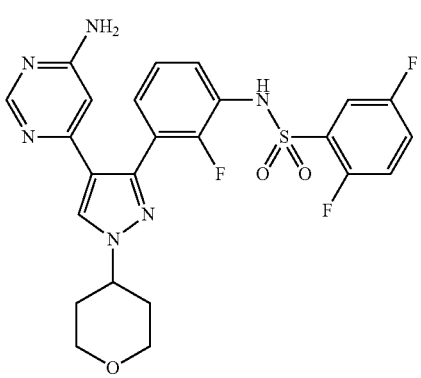 [SMILES: Nc1cc(-c2cn(C3CCOCC3)nc2-c2cccc(NS(=O)(=O)c3cc(F)ccc3F)c2F)ncn1]

HPLC (254 nm): $R_t$: 5.13 min; ¹H NMR (DMSO-d6) Shift: 10.69 (br. s., 1H), 8.49 (br. s., 1H), 8.42 (s, 1H), 7.61-7.53 (m, 2H), 7.52-7.45 (m, 4H), 7.41 (t, J=7.0 Hz, 1H), 7.35-7.28 (m, 1H), 7.28-7.18 (m, 1H), 6.22 (s, 1H), 4.61-4.46 (m, 1H), 3.98 (dd, J=3.4, 11.2 Hz, 2H), 3.49 (dt, J=2.3, 11.7 Hz, 2H), 2.12-1.87 (m, 4H); HRMS (ESI) calcd for C24H22F3N6O3S [M+H]⁺ 531.1421. found 531.1431.

2,5-difluoro-N-{2-fluoro-3-[4-(7H-pyrrolo[2,3-d]pyrimidin-4-yl)-1-(tetrahydro-2H-pyran-4-yl)-1H-pyrazol-3-yl]phenyl}benzenesulfonamide Formula 1, where m=0; R1=tetrahydro-2H-pyran-4-yl; R2, R3=F; R4=7H-pyrrolo[2,3-d]pyrimidin-4-yl]

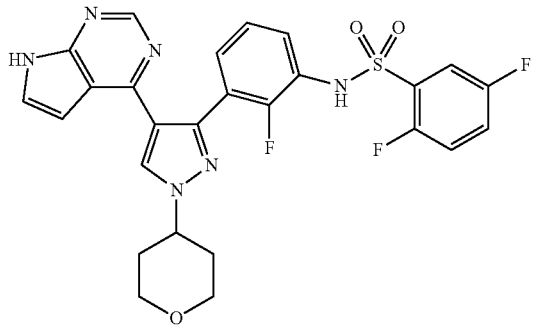 [SMILES: O=S(=O)(Nc1cccc(-c2nn(C3CCOCC3)cc2-c2ncnc3[nH]ccc23)c1F)c1cc(F)ccc1F]

HPLC (254 nm): R$_t$: 5.44 min; $^1$H NMR (DMSO-d6) Shift: 11.99 (s, 1H), 10.50 (s, 1H), 8.52 (s, 1H), 8.39 (s, 1H), 7.57-7.48 (m, 1H), 7.48-7.36 (m, 3H), 7.34 (t, J=6.4 Hz, 1H), 7.30-7.22 (m, 1H), 7.21-7.08 (m, 1H), 6.39 (dd, J=1.6, 3.3 Hz, 1H), 4.69-4.50 (m, 1H), 4.11-3.87 (m, 2H), 3.57-3.44 (m, 2H), 2.18-1.93 (m, 4H); HRMS (ESI) calcd for C26H22F3N6O3S [M+H]$^+$ 555.1421. found 555.1433.

N-{3-[4-(2-Amino-pyrimidin-4-yl)-1-ethyl-1H-pyrazol-3-yl]-2-fluoro-phenyl}-2,5-difluoro-benzenesulfonamide (Compound 3)

Formula I, where m=1; R1=methyl; R2, R3=F; R4=2-amino-pyrimidin-4-yl]

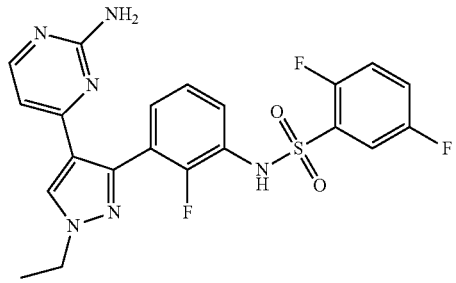 [SMILES: CCn1cc(-c2ccnc(N)n2)c(-c2cccc(NS(=O)(=O)c3cc(F)ccc3F)c2F)n1]

HPLC (254 nm): R$_t$: 5.33 min; $^1$H NMR (DMSO-d6) Shift: 10.66 (s, 1H), 8.27 (s, 1H), 7.95 (d, J=5.2 Hz, 1H), 7.44-7.61 (m, 3H), 7.26-7.36 (m, 2H), 7.17-7.24 (m, 1H), 6.32 (br. s., 2H), 6.02 (d, J=5.2 Hz, 1H), 4.15-4.25 (m, 2H), 1.38-1.44 (m, 3H); HRMS (ESI) calcd for C21H18F3N6O2S [M+H]$^+$ 475.1159. found 475.1138.

During this synthesis the following side product was obtained:

N-(3-{4-[2-(2-Amino-pyrimidin-4-ylamino)-pyrimidin-4-yl]-1-ethyl-1H-pyrazol-3-yl}-2-fluoro-phenyl)-2,5-difluoro-benzenesulfonamide (Compound 22)

Formula I, where m=1; R1=methyl; R2, R3=F; R4=2-Amino-pyrimidin-4-ylamino)-pyrimidin-4-yl

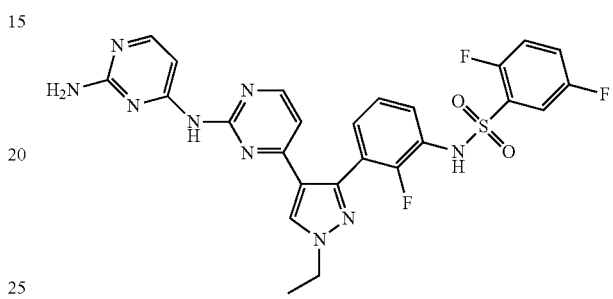

HPLC (254 nm): R$_t$: 4.83 min; $^1$H NMR (DMSO-d6) Shift: 10.66 (s, 1H), 9.02 (s, 1H), 8.43 (s, 1H), 8.38 (br. s., 1H), 7.80 (br. s., 1H), 7.45-7.69 (m, 4H), 7.37-7.43 (m, 1H), 7.24-7.35 (m, 1H), 7.11 (br. s., 1H), 6.72 (br. s., 1H), 6.11 (br. s., 2H), 4.24 (q, J=7.2 Hz, 2H), 1.45 (t, J=7.2 Hz, 3H); HRMS (ESI) calcd for C25H21F3N9O2S [M+H]$^+$ 568.1486. found 568.1468.

Example 5

N-{3-[4-(2-Amino-pyrimidin-4-yl)-1-(2-fluoro-ethyl)-1H-pyrazol-3-yl]-2-fluoro-phenyl}-2,5-difluoro-benzenesulfonamide (Compound 11)

Formula 1, where m=2; R$_1$, R2, R3=F; R4=2-Amino-pyrimidin-4-yl

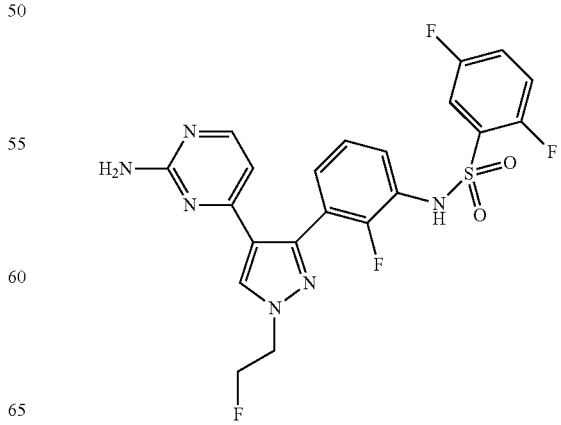

Method C, Step h

N-{3-[4-Bromo-1-(tetrahydro-pyran-2-yl)-1H-pyrazol-3-yl]-2-fluoro-phenyl}-2,5-difluoro-N-methoxymethyl-benzenesulfonamide Formula 1, where Hal=Br; PG₁=methoxymethyl; R29=tetrahydro-pyran-2-yl; R30=2,5-difluoro-benzene-sulfonyl

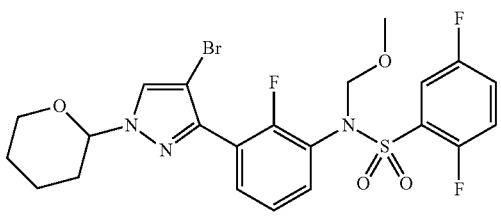 [SMILES: COCN(c1cccc(-c2nn(C3CCCCO3)cc2Br)c1F)S(=O)(=O)c1cc(F)ccc1F]

To a solution of 2,5-Difluoro-N-{2-fluoro-3-[2-(tetrahydro-pyran-2-yl)-2H-pyrazol-3-yl]-phenyl}-N-methoxymethyl-benzene-sulfonamide (4 g, 8.3 mmol)(obtained as described in Preparation 1) in DCM (30 mL), N-bromosuccinimide (2.2 g, 12.46 mmol, 1.5 eq) was added and the solution was stirred at r.t. for 4 h. The mixture was then diluted with DCM and washed with 10% aqueous NaHSO₃ and brine. The organic layer was dried over Na₂SO₄ and evaporated to dryness to give 4.1 g (88%) of N-{3-[4-Bromo-1-(tetrahydro-pyran-2-yl)-1H-pyrazol-3-yl]-2-fluoro-phenyl}-2,5-difluoro-N-methoxy-methyl-benzenesulfonamide as yellow wax (mixture of two regioisomers). HPLC (254 nm): R$_t$: 7.27 min; ¹H NMR (DMSO-d6) Shift (N1-THP regioisomer): 8.27 (s, 1H), 7.56-7.71 (m, 2H), 7.47-7.56 (m, 2H), 7.41-7.47 (m, 1H), 7.33 (t, J=7.7 Hz, 1H), 5.43 (dd, J=21, 9.7 Hz, 1H), 5.09 (s, 2H), 3.92 (dt, J=3.6, 11.9 Hz, 1H), 3.55-3.69 (m, 1H), 3.38 (s, 3H), 2.00-2.14 (m, 1H), 1.88-1.98 (m, 2H), 1.60-1.72 (m, 1H), 1.48-1.58 (m, 2H); HRMS (ESI) calcd for C22H22BrF3N3O4S [M+H]⁺ 560.0461. found 560.0447.

Method A, Step b 2,5-Difluoro-N-{2-fluoro-3-[1-(tetrahydro-pyran-2-yl)-4-(4,4,5,5-tetramethyl-[1,3,2]dioxaborolan-2-yl)-1H-pyrazol-3-yl]-phenyl}-N-methoxymethyl-benzene-sulfonamide Formula 3, where M'=4,4,5,5-tetramethyl-[1,3,2]dioxaborolan-2-yl; PG₁=methoxymethyl; R29=tetrahydropyran-2-yl; R30=2,5-difluoro-benzene-sulfonyl

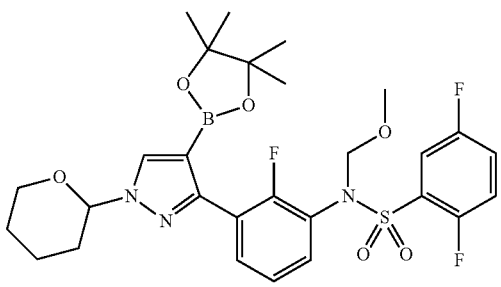 [SMILES: COCN(c1cccc(-c2nn(C3CCCCO3)cc2B2OC(C)(C)C(C)(C)O2)c1F)S(=O)(=O)c1cc(F)ccc1F]

In a microwave tube N-{3-[4-Bromo-1-(tetrahydro-pyran-2-yl)-1H-pyrazol-3-yl]-2-fluoro-phenyl}-2,5-difluoro-N-methoxy-methyl-benzenesulfonamide (2 g, 3.569 mmol) was dissolved in dry toluene (34 mL) and the solution was degassed by bubbling argon through it for 10 minutes. Triethylamine (1.24 mL, 8.92 mmol, 2.5 eq) was then added, followed by S-Phos (146 mg, 0.1 eq), PdCl₂(CH₃CN)₂ (46 mg, 0.05 eq) and pinacolborane (5.2 mL, 35.69 mmol, 10 eq). The tube was sealed and the mixture was irradiated in the microwave oven at 90° C. for 30 minutes. The reaction mixture was filtered over a Celite pad, which was washed thoroughly with AcOEt. The filtrate was washed with aq. sat. NaHCO₃ and brine, dried over Na₂SO₄ and evaporated to dryness. The crude product was purified by chromatography on silica gel Hex/AcOEt 7:3) to give 1.9 mg of the desired pyrazole boronate contaminated by de-brominated side product.

Method A, Step c

N-{3-[4-(2-Amino-pyrimidin-4-yl)-1-(tetrahydro-pyran-2-yl)-1H-pyrazol-3-yl]-2-fluoro-phenyl}-2,5-difluoro-N-methoxymethyl-benzenesulfonamide Formula 2, where R4=2-Amino-pyrimidin-4-yl; PG₁ methoxymethyl; R29=tetrahydropyran-2-yl; R30=2,5-difluoro-benzene-sulfonyl

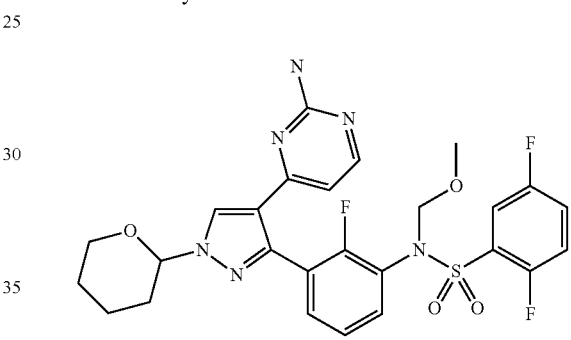

To an argon degassed solution of 2,5-difluoro-N-{2-fluoro-3-[1-(tetrahydro-pyran-2-yl)-4-(4,4,5,5-tetramethyl-[1,3,2]dioxaborolan-2-yl)-1H-pyrazol-3-yl]-phenyl}-N-methoxymethyl-benzenesulfonamide (383 mg, 0.63 mmol) in 1,2-dimethoxyethane:water 9:1 (4 mL) in a microwave vial, 4-Chloro-pyrimidin-2-ylamine (122 mg, 0.94 mmol), cesium carbonate (410 mg, 1.26 mmol) and Pd(dppf)Cl₂.CH₂Cl₂ (51 mg, 0.063 mmol) were added, under argon atmosphere. The mixture was heated in the microwave oven at 100° C. for 3 h, then it was filtered through a Celite pad. The solution was taken up with DCM and washed with saturated aqueous NaHCO₃ and brine. The organic layer was dried over Na₂SO₄ and concentrated to dryness. The residue was purified by flash chromatography on silica gel (DCM:MeOH:acetone 96:2:2) affording 135 mg of the title compound (37% yield). HPLC (254 nm): R$_t$: 6.19 min; ¹H NMR (DMSO-d6) Shift: 8.47 (s, 1H), 8.03 (d, J=5.2 Hz, 1H), 7.43-7.74 (m, 4H), 7.32-7.38 (m, 1H), 7.29 (t, J=7.8 Hz, 1H), 6.29 (d, J=5.1 Hz, 1H), 6.23 (br. s., 2H), 5.50 (dd, J=9.8, 2.3 Hz, 1H), 5.05 (s, 2H), 3.92-4.02 (m, J=11.8 Hz, 1H), 3.57-3.72 (m, 1H), 3.31 (s, 3H), 1.83-2.18 (m, 3H), 1.60-1.76 (m, 1H), 1.51-1.61 (m, 2H); HRMS (ESI) calcd for C26H26F3N6O4S [M+H]⁺ 575.1683. found 575.168.

Method A, Step d

N-{3-[4-(2-Amino-pyrimidin-4-yl)-1H-pyrazol-3-yl]-2-fluoro-phenyl}-2,5-difluoro-N-methoxymethyl-benzenesulfonamide Formula 4A, where R4=2-Amino-pyrimidin-4-yl; PG₁=methoxymethyl; R30=2,5-difluoro-benzene-sulfonyl

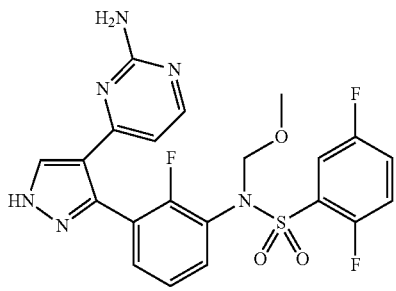 [SMILES: COCN(c1cccc(-c2n[nH]cc2-c2ccnc(N)n2)c1F)S(=O)(=O)c1cc(F)ccc1F]

To a solution of N-{3-[4-(2-Amino-pyrimidin-4-yl)-1-(tetrahydro-pyran-2-yl)-1H-pyrazol-3-yl]-2-fluoro-phenyl}-2,5-difluoro-N-methoxymethyl-benzenesulfonamide (135 mg, 0.23 mmol), p-toluenesulfonic acid monohydrate (90 mg, 0.47 mmol) was added and the reaction mixture was stirred at 60° C. for 2 h. The reaction mixture was concentrated under reduced pressure and taken up with AcOEt and washed with saturated aqueous NaHCO₃ and brine. The residue didn't need any further purification (45 mg, 40% yield). HPLC (254 nm): R$_t$: 5.11 min; ¹H NMR (DMSO-d6) Shift: 13.43 (br. s., 1H), 8.33 (s, 1H), 7.98-8.05 (m, 1H), 7.47-7.69 (m, 4H), 7.23-7.40 (m, 2H), 6.28 (dd, J=4.9, 3.0 Hz, 1H), 6.21 (d, J=16.6 Hz, 2H), 5.05 (s, 2H), 3.31-3.37 (m, 3H); HRMS (ESI) calcd for C21H18F3N6O3S [M+H]⁺ 491.1108. found 491.1095.

Method A, Step e

N-{3-[4-(2-Amino-pyrimidin-4-yl)-1-(2-fluoro-ethyl)-1H-pyrazol-3-yl]-2-fluoro-phenyl}-2,5-difluoro-N-methoxymethyl-benzenesulfonamide Formula 2, where R4=2-Amino-pyrimidin-4-yl; PG₁=methoxymethyl; R29=2-fluoroethyl; R30=2,5-difluoro-benzene-sulfonyl

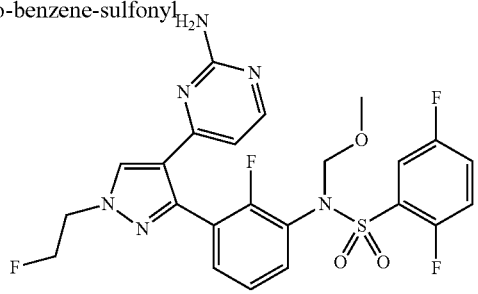

Cesium carbonate (100 mg, 0.306 mmol) and 1-fluoro-2-iodo-ethane (54 mg, 0.306 mmol) were added to a solution of N-{3-[4-(2-Amino-pyrimidin-4-yl)-1H-pyrazol-3-yl]-2-fluoro-phenyl}-2,5-difluoro-N-methoxymethyl-benzenesulfonamide (45 mg, 0.091 mmol) in DMF (2 mL) and the suspension was stirred at 50° C. for 1 hour. The mixture was treated with water and DCM. The organic layer was washed once again with water and brine, then it was dried over Na₂SO₄ and concentrated under reduced pressure. The residue was purified by flash chromatography on silica gel (DCM:MeOH:acetone 94:3:3) affording 36 mg of the title compound (73% yield). HPLC (254 nm): R$_t$: 5.64 min; ¹H NMR (DMSO-d6) Shift: 8.37 (s, 1H), 8.01 (d, J=5.1 Hz, 1H), 7.59-7.65 (m, 1H), 7.47-7.59 (m, 3H), 732-7.38 (m, 1H), 7.26-7.32 (m, 1H), 6.27 (br. s., 2H), 6.18 (d, J=5.2 Hz, 1H), 5.05 (s, 2H), 4.83 (dt, J=47.2, 4.6 Hz, 2H), 4.53 (dt, J=27.9, 4.6 Hz, 2H), 3.33 (s, 3H); HRMS (ESI) calcd for C23H21F4N6O3S [M+H]⁺ 537.1327. found 537.131.

According to this same methodology but employing the suitable starting material, the following compound was prepared:

2,5-Difluoro-N-{2-fluoro-3-[1-(2-fluoro-ethyl)-4-(1-methoxymethyl-1H-pyrrolo[2,3-b]pyridin-4-yl)-1H-pyrazol-3-yl]-phenyl}-N-methoxymethyl-benzenesulfonamide Formula 2, where R4=1-methoxymethyl-1H-pyrrolo[2,3-b]pyridin-4-yl; PG₁=methoxymethyl; R29=2-fluoro-ethyl; R30=2,5-difluoro-benzene-sulfonyl

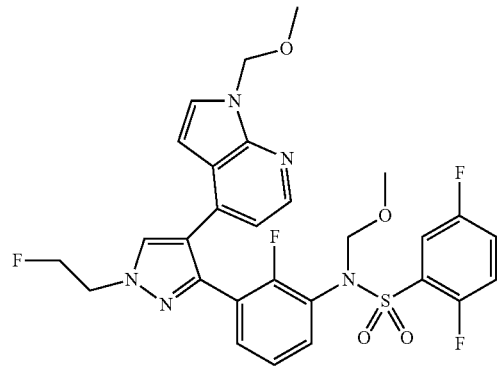 [SMILES: COCN(c1cccc(-c2nn(CCF)cc2-c2ccnc3c2ccn3COC)c1F)S(=O)(=O)c1cc(F)ccc1F]

HPLC (254 nm): R$_t$: 6.41 min; ¹H NMR (DMSO-d6) Shift: 8.12 (s, 1H), 8.05 (d, J=5.00 Hz, 1H), 7.54-7.64 (m, 2H), 7.36-7.42 (m, 1H), 7.29-7.35 (m, 1H), 6.54 (d, J=5.00 Hz, 1H), 6.37 (d, J=3.66 Hz, 1H), 5.56 (s, 2H), 4.93-5.13 (m, 2H), 4.61-4.79 (m, 2H), 4.06-4.36 (m, 2H), 3.32 (s, 3H), 3.18-3.23 (m, 3H); HRMS (ESI) calcd for C28H26F4N5O4S [M+H]⁺ 604.1636. found 604.1641.

Method A, Step f

N-{3-[4-(2-Amino-pyrimidin-4-yl)-1-(2-fluoro-ethyl)-1H-pyrazol-3-yl]-2-fluoro-phenyl}-2,5-difluoro-benzenesulfonamide (Compound 11)

Formula I, where m=0; R₁=2-fluoro-ethyl; R2, R3=F; R4=2-Amino-pyrimidin-4-yl

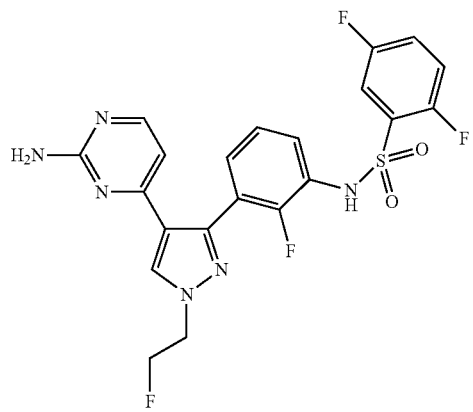 [SMILES: Nc1nccc(-c2cn(CCF)nc2-c2cccc(NS(=O)(=O)c3cc(F)ccc3F)c2F)n1]

N-{3-[4-(2-Amino-pyrimidin-4-yl)-1-(2-fluoro-ethyl)-1H-pyrazol-3-yl]-2-fluoro-phenyl}-2,5-difluoro-N-methoxymethyl-benzenesulfonamide (36 mg, 0.067 mmol) was dissolved in a mixture of TFA:water 9:1 (1 mL) and stirred for 16 h at 100° C. The reaction mixture was concentrated under reduced pressure, then taken up with a saturated solution of NaHCO₃ and extracted with AcOEt. The organic layer was dried over Na₂SO₄ and concentrated to dryness. The residue was purified by flash chromatography on silica gel (Hex:AcOEt:EtOH 4:4:2) affording 16 mg of the title compound (50% yield), HPLC (254 nm): $R_t$: 5.23 min; ¹H NMR (DMSO-d6) Shift: 10.67 (s, 1H), 8.31 (s, 1H), 7.89-7.99 (m, 1H), 7.53-7.61 (m, 1H), 7.44-7.53 (m, 2H), 7.26-7.39 (m, 2H), 7.23 (t, J=7.8 Hz, 1H), 6.35 (br. s., 2H), 6.01 (d, J=5.1 Hz, 1H), 4.81 (dt, J=47.2 Hz, J=4.3 Hz, 2H), 4.43-4.59 (m, 2H); HRMS (ESI) calcd for C21H17F4N6O2S [M+H]⁺ 493.1065. found 493.1049.

According to this same methodology, but employing suitable alkylating agents and standard functional group interconversions, the following compounds were prepared:

N-{3-[4-(2-Amino-pyrimidin-4-yl)-1-piperidin-4-yl-1H-pyrazol-3-yl]-2-fluoro-phenyl}-2,5-difluoro-benzenesulfonamide Formula 1, where m=0; R₁=piperidin-4-yl; R2, R3=F; R4=2-amino-pyrimidin-4-yl HPLC (254 nm): $R_t$: 4.31 min; ¹H NMR (DMSO-d6) Shift (selected signals): 10.64 (s, 1H), 8.62-8.66 (m, 1H), 8.33 (s, 1H), 7.99 (d, J=5.5 Hz, 1H), 7.51-7.59 (m, 1H), 7.43-7.51 (m, 2H), 7.25-7.32 (m, 2H), 7.17-7.23 (m, 1H), 6.60 (br. s., 2H), 6.14 (d, J=5.4 Hz, 1H), 4.52-4.63 (m, 1H), 3.00-3.13 (m, 2H), 2.03-2.29 (m, 4H); HRMS (ESI) calcd for C24H23F3N7O2S [M+H]⁺ 530.1581. found 530.1568.

N-{3-[4-(2-Amino-pyrimidin-4-yl)-1-(1-methyl-piperidin-4-yl)-1H-pyrazol-3-yl]-2-fluoro-phenyl}-2,5-difluoro-benzenesulfonamide (Compound 6)

Formula I, where m=0; R₁=1-methyl-piperidin-4-yl; R2, R3=F; R4=2-amino-pyrimidin-4-yl

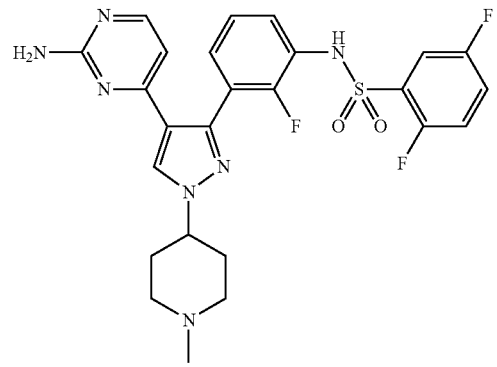 [SMILES: CN1CCC(n2cc(-c3ccnc(N)n3)c(-c3cccc(NS(=O)(=O)c4cc(F)ccc4F)c3F)n2)CC1]

HPLC (254 nm): $R_t$: 4.37 min; ¹H NMR (DMSO-d6) Shift: 8.27 (s, 1H), 7.95 (d, J=5.1 Hz, 1H), 7.44-7.55 (m, 2H), 7.36-7.44 (m, 1H), 7.26-7.33 (m, 1H), 7.06-7.17 (m, 2H), 6.31 (s, 2H), 6.06 (d, J=5.2 Hz, 1H), 4.22-4.35 (m, 1H), 3.01-3.06 (m, 2H), 2.37 (s, 3H), 2.25-2.42 (m, 2H), 1.88-2.20 (m, 4H); HRMS (ESI) calcd for C25H25F3N7O2S [M+H]⁺ 544.1737. found 544.1722.

N-{3-[4-(2-Amino-pyrimidin-4-yl)-1-(1-isopropyl-piperidin-4-yl)-1H-pyrazol-3-yl]-2-fluoro-phenyl}-2,5-difluoro-benzenesulfonamide (Compound 19)

Formula I, where m=0; R₁=1-Isopropyl-piperidin-4-yl; R2, R3=F; R4=2-amino-pyrimidin-4-yl

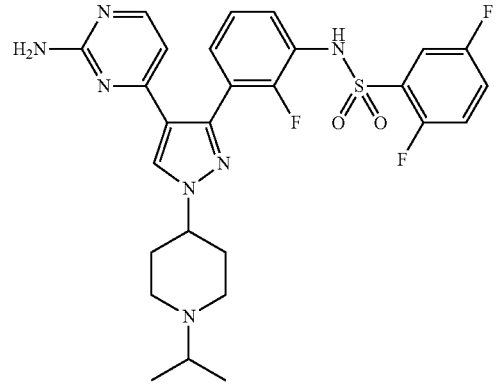 [SMILES: CC(C)N1CCC(n2cc(-c3ccnc(N)n3)c(-c3cccc(NS(=O)(=O)c4cc(F)ccc4F)c3F)n2)CC1]

HPLC (254 nm): $R_t$: 6.30 min; ¹H NMR (DMSO-d6) Shift: 10.67 (s, 1H), 8.32 (s, 1H), 7.99 (d, J=5.3 Hz, 1H), 7.42-7.62 (m, 4H), 7.27-7.39 (m, 2H), 6.44 (br. s., 2H), 6.10 (d, J=5.3 Hz, 1H), 4.53-4.66 (m, 1H), 3.48-3.58 (m, 2H), 3.12-3.23 (m, 2H), 2.17-2.44 (m, 4H), 1.28 (d, J=6.6 Hz, 1H); HRMS (ESI) calcd for C27H29F3N7O2S [M+H]⁺ 572.2050. found 572.2027.

N-{3-[4-(2-Amino-pyrimidin-4-yl)-1-(tetrahydro-pyran-4-yl-1H-pyrazol-3-yl]-2-fluoro-phenyl}-2,5-difluoro-benzenesulfonamide (Compound 15)

Formula I, where m=0; R$_1$=tetrahydro-pyran-4-yl; R2, R3=F; R4=2-amino-pyrimidin-4-yl

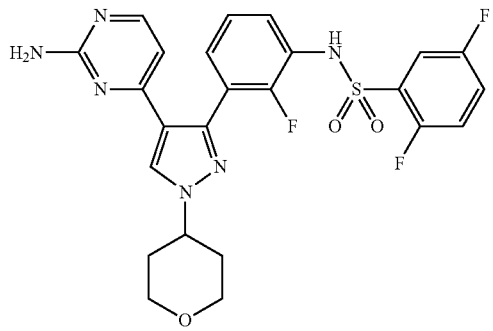 [SMILES: Nc1nccc(-c2cn(C3CCOCC3)nc2-c2cccc(NS(=O)(=O)c3cc(F)ccc3F)c2F)n1]

HPLC (254 nm): R$_t$: 5.3 min; $^1$H NMR (DMSO-d6) Shift: 10.65 (s, 1H), 8.31 (s, 1H), 7.96 (d, J=5.1 Hz, 1H), 7.53-7.61 (m, 1H), 7.41-7.53 (m, 2H), 7.25-7.37 (m, 2H), 7.21 (t, J=7.9 Hz, 1H), 6.31 (br. s., 2H), 6.06 (d, J=5.2 Hz, 1H), 4.41-4.55 (m, 1H), 3.92-4.01 (m, 2H), 3.42-3.52 (m, 2H), 1.87-2.13 (m, 4H); HRMS (ESI) calcd for C24H22F3N6O3S [M+H]$^+$ 531.1421. found 531.1412.

2,5-Difluoro-N-{2-fluoro-3-[1-(2-fluoro-ethyl)-4-(1H-pyrrolo[2,3-b]pyridin-4-yl)-1H-pyrazol-3-yl]phenyl}-benzenesulfonamide Formula 1, where m=2; R$_1$=2-fluoro-ethyl; R2, R3=F; R4=1H-pyrrolo[2,3-b]pyridin-4-yl

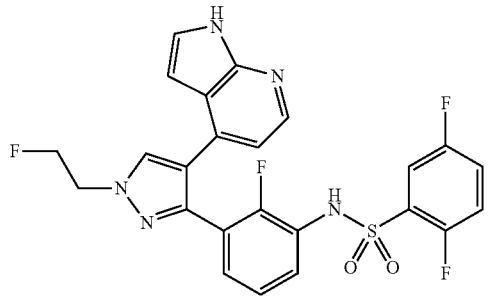 [SMILES: O=S(=O)(Nc1cccc(-c2nn(CCF)cc2-c2ccnc3[nH]ccc23)c1F)c1cc(F)ccc1F]

HPLC (254 nm): R$_t$: 5.631 min; $^1$H NMR (DMSO-d6) Shift: 11.60 (br. s., 1H), 10.57 (s, 1H), 8.34 (s, 1H), 7.97 (d, J=5.00 Hz, 1H), 7.51-7.59 (m, 1H), 7.38-7.48 (m, 2H), 7.36 (dd, J=2.69, 3.30 Hz, 1H), 7.30 (td, J=1.77, 7.60 Hz, 1H), 7.20-7.27 (m, 1H), 7.10-7.20 (m, 1H), 6.49 (d, J=5.00 Hz, 1H), 6.24 (dd, J=1.89, 3.31 Hz, 1H), 4.94 (t, J=4.70 Hz, 1H), 4.82 (t, J=4.70 Hz, 1H), 4.60 (t, J=4.82 Hz, 1H), 4.53 (t, J=4.82 Hz, 1H); HRMS (ESI) calcd for C24H18F4N5O4S [M+H]$^+$ 604.1636. found 604.1641.

Example 6

N-{3-[1-Ethyl-4-(1H-pyrrolo[2,3-b]pyridin-4-yl)-1H-pyrazol-3-yl]-2-fluoro-phenyl}-2,5-difluoro-benzenesulfonamide Formula 1, where m=1; R1=methyl; R2, R3=F; R4=1H-pyrrolo[2,3-b]-pyridin-4-yl Method A, Step c

N-{3-[1-Ethyl-4-(1H-pyrrolo[2,3-b]pyridin-4-yl)-1H-pyrazol-3-yl]-2-fluoro-phenyl}-2,5-difluoro-N-methoxymethyl-benzenesulfonamide Formula 2, where R4=1H-pyrrolo[2,3-b]pyridin-4-yl, PG$_1$=methoxymethyl, R29=ethyl, R30=2,5-difluoro-benzene-sulfonyl

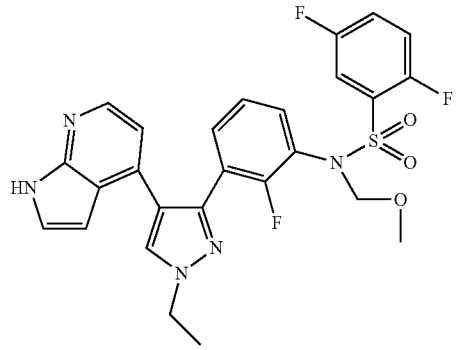 [SMILES: CCn1cc(-c2ccnc3[nH]ccc23)c(-c2cccc(N(COC)S(=O)(=O)c3cc(F)ccc3F)c2F)n1]

In a microwave tube a solution of N-{3-[1-Ethyl-4-(4,4,5,5-tetramethyl-[1,3,2]dioxaborolan-2-yl)-1H-pyrazol-3-yl]-2-fluoro-phenyl}-2,5-difluoro-N-methoxy-methyl-benzenesulfonamide (prepared as described in Example 4) (273 mg, 0.496 mmol) in DME/H$_2$O 9:1 (5 mL) was degassed by bubbling argon for 5 minutes. 4-Iodo-7-azaindole (121 mg, 0.496 mmol, 1 eq) was then added, followed by cesium carbonate (242 mg, 0.744 mmol, 1.5 eq) and Pd(dppf)Cl$_2$.CH$_2$Cl$_2$ (30 mg, 0.037 mmol, 0.075 eq). The mixture was irradiated in the microwave oven at 100° C. for 1 hr and then diluted with AcOEt and washed with saturated aqueous NaHCO$_3$ and brine. The organic layer was dried over Na$_2$SO$_4$ and evaporated to dryness, the crude product was purified by chromatography on silica gel (DCM/MeOH 96:4) to give 220 mg of product. After recrystallization from AcOEt/Hex mixture 122 mg (45%) of pure N-{3-[1-Ethyl-4-(1H-pyrrolo[2,3-b]pyridin-4-yl)-1H-pyrazol-3-yl]-2-fluoro-phenyl}-2,5-difluoro-N-methoxymethyl-benzenesulfonamide were obtained as a white solid. HPLC (254 nm): R$_t$: 6.12 min; $^1$H NMR (DMSO-d6) Shift: 11.59 (br. s., 1H), 8.32 (s, 1H), 7.99 (d, J=5.0 Hz, 1H), 7.52-7.66 (m, 1H), 7.40-7.55 (m, 3H), 7.36 (dd, J=2.6, 3.4 Hz, 1H), 7.16-7.33 (m, 2H), 6.55 (d, J=4.9 Hz, 1H), 6.22 (dd, J=1.9, 3.5 Hz, 1H), 4.88 (s, 2H), 4.27 (q, J=7.3 Hz, 2H), 3.21 (s, 3H), 1.49 (t, J=7.3 Hz, 3H); HRMS (ESI) calcd for C26H23F3N5O3S [M+H]$^+$ 542.1468. found 5421465.

Method A, Step f

N-{3-[1-Ethyl-4-(1H-pyrrolo[2,3-b]pyridin-4-yl)-1H-pyrazol-3-yl]-2-fluoro-phenyl}-2,5-difluoro-benzenesulfonamide Formula I, where m==methyl; R2, R3=F; R4=1H-pyrrolo[2,3-b]pyridin-4-yl

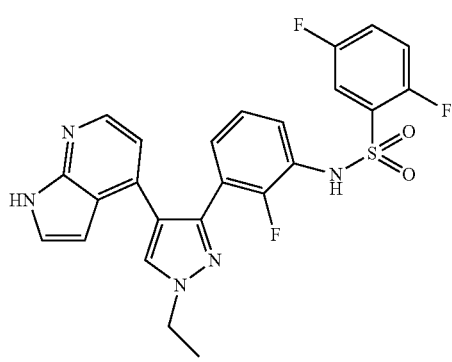 [SMILES: CCn1cc(-c2ccnc3[nH]ccc23)c(-c2cccc(NS(=O)(=O)c3cc(F)ccc3F)c2F)n1]

N-{3-[1-Ethyl-4-(1H-pyrrolo[2,3-b]pyridin-4-yl)-1H-pyrazol-3-yl]-2-fluoro-phenyl}-2,5-difluoro-N-methoxymethyl-benzenesulfonamide (116 mg, 0.214 mmol) was treated with TFA/H$_2$O 9:1 (2 mL) at 55° C. for 1 h. The reaction mixture was then evaporated to dryness, taken up with AcOEt and washed with sat, aq. NaHCO$_3$ and brine. The organic layer was dried over Na$_2$SO$_4$ and concentrated under reduced pressure. The residue was taken up with Hex/MTBE 5:1 mixture (2 mL) and stirred for 30 minutes, filtered and dried to give 93 mg (87%) of the title compound as white solid. HPLC (254 nm): R$_t$: 5.79 min; $^1$H NMR (DMSO-d6) Shift: 11.58 (s, 1H), 10.56 (s, 1H), 8.29 (s, 1H), 7.96 (d, J=5.0 Hz, 1H), 7.51-7.61 (m, 1H), 7.37-7.47 (m, 2H), 7.35 (dd, J=2.6, 3.4 Hz, 1H), 7.29 (td, J=18, 7.6 Hz, 1H), 7.18-7.25 (m, 1H), 7.05-7.18 (m, 1H), 6.49 (d, J=5.0 Hz, 1H), 6.25 (dd, J=1.8, 3.5 Hz, 1H), 4.26 (q, J=7.3 Hz, 2H), 1.47 (t, J=7.3 Hz, 3H); HRMS (ESI) calcd for C24H19F3N5O2S [M+H]$^+$ 498.1206. found 498.1195.

Example 7

N-{3-[4-(2-Amino-pyridin-4-yl)-1H-pyrazol-3-yl]-2-fluoro-phenyl}-2,5-difluoro-benzenesulfonamide
(Compound 4)

Formula 1, where m=1; R1=methyl; R2, R3=F; R4=2-Amino-pyridin-4-yl

Method A, Step a

N-[3-(1-Ethyl-4-pyridin-4-yl-1H-pyrazol-3-yl)-2-fluoro-phenyl]-2,5-difluoro-N-methoxymethyl-benzenesulfonamide Formula 2, where R4=4-pyridinyl, PG$_1$=methoxymethyl, R29=ethyl, R30=2,5-difluoro-benzenesulfonyl

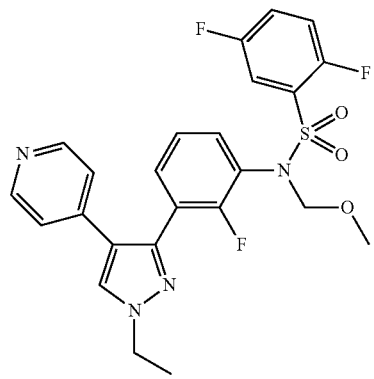 [SMILES: CCn1cc(-c2ccncc2)c(-c2cccc(N(COC)S(=O)(=O)c3cc(F)ccc3F)c2F)n1]

In a microwave tube a solution of N-[3-(4-Bromo-1-ethyl-1H-pyrazol-3-yl)-2-fluoro-phenyl]-2,5-difluoro-N-methoxy-methyl-benzenesulfonamide (prepared as described in Example 1) (420 mg, 0.833 mmol) in DME/H$_2$O 9:1 (10 mL) was degassed by bubbling argon for 5 minutes, 4-pyridinyl boronic acid pinacol ester (256 mg, 1.249 mmol, 1.5 eq) was then added, followed by cesium carbonate (543 mg, 1.666 mmol, 2 eq) and Pd(dppf)Cl$_2$.CH$_2$Cl$_2$ (68 mg, 0.083 mmol, 0.1 eq). The mixture was irradiated in the microwave oven at 100° C. for 30 minutes. It was then filtered over a Celite pad, which was washed thoroughly with AcOEt. The filtrate was washed with saturated aqueous NaHCO$_3$ and brine. The organic layer was dried over Na$_2$SO$_4$ and evaporated to dryness. The crude product was purified by chromatography on silica gel (DCM/MeOH 97:3) and 370 mg (88%) of N-[3-(1-Ethyl-4-pyridin-4-yl-1H-pyrazol-3-yl)-2-fluoro-phenyl]-2,5-difluoro-N-methoxymethyl-benzenesulfonamide were obtained as a white solid. HPLC (254 nm): R$_t$: 6.10 min; $^1$H NMR (DMSO-d6) Shift: 8.39 (s, 1H), 8.35-8.41 (m, 2H), 7.57-7.65 (m, 1H), 7.45-7.56 (m, 3H), 728-7.39 (m, 2H), 7.04-7.08 (m, 2H), 5.01 (s, 2H), 4.22 (q, J=7.2 Hz, 2H), 3.28 (s, 3H), 1.46 (t, J=7.3 Hz, 3H); HRMS (ESI) calcd for C24H22F3N4O3S [M+H]$^+$ 503.1359. found 503.1342.

Method E, Step a

N-{3-[1-Ethyl-4-(1-oxy-pyridin-4-yl)-1H-pyrazol-3-yl]-2-fluoro-phenyl}-2,5-difluoro-N-methoxymethyl-benzenesulfonamide Formula 22, where PG$_1$=methoxymethyl; R29=ethyl; R2,R3=F

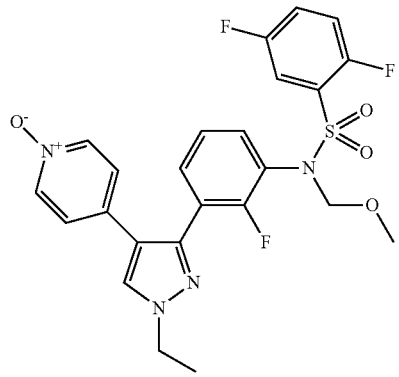 [SMILES: CCn1cc(-c2cc[n+]([O-])cc2)c(-c2cccc(N(COC)S(=O)(=O)c3cc(F)ccc3F)c2F)n1]

To a solution of N-[3-(1-Ethyl-4-pyridin-4-yl-1H-pyrazol-3-yl)-2-fluoro-phenyl]-2,5-difluoro-N-methoxymethyl-benzenesulfonamide (370 mg, 0.736 mmol) in DCM (5 mL) m-chloroperbenzoic acid (380 mg, 2.209 mmol, 3 eq) was added and the solution was stirred at r.t. for 16 h. A further addition of m-chloroperbenzoic acid (190 mg, 1.1 mmol, 1.5 eq) was made and stirring was continued for 1 h. The reaction mixture was then diluted with DCM and washed with saturated aqueous NaHCO$_3$ and brine. The organic layer was dried over Na$_2$SO$_4$ and evaporated to dryness to give 413 mg of crude N-{3-[1-Ethyl-4-(1-oxy-pyridin-4-yl)-1H-pyrazol-3-yl]-2-fluoro-phenyl}-2,5-difluoro-N-methoxymethyl-benzenesulfonamide, which was used without purification in the following step. HPLC (254 nm): R$_t$: 5.21 min; $^1$H NMR (DMSO-d6) Shift: 8.34 (s, 1H), 8.03-8.07 (m, 2H), 7.59-7.67 (m, 1H), 7.51-7.59 (m, 3H), 7.29-7.37 (m, 2H), 7.08 (d, J=7.2 Hz, 2H), 5.02 (s, 2H), 4.21 (q, J=7.2 Hz, 2H), 3.29 (s, 3H), 1.45 (t, J=7.3 Hz, 3H); HRMS (ESI) calcd for C24H22F3N4O4S [M+H]$^+$ 519.1309. found 519.1287.

Method E, Step c

N-{3-[4-(2-tert-Butylamino-pyridin-4-yl)-1-ethyl-1H-pyrazol-3-yl]-2-fluoro-phenyl}-2,5-difluoro-N-methoxymethyl-benzenesulfonamide Formula 2G, where PG$_1$=methoxymethyl; R2,R3=F; R16=tert-butyl; R29=ethyl

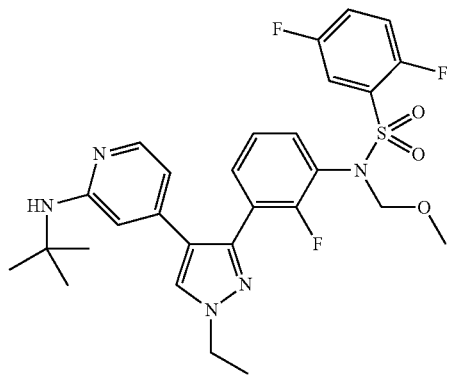 [SMILES: CCn1cc(-c2ccnc(NC(C)(C)C)c2)c(-c2cccc(N(COC)S(=O)(=O)c3cc(F)ccc3F)c2F)n1]

Crude N-{3-[1-Ethyl-4-(1-oxy-pyridin-4-yl)-1H-pyrazol-3-yl]-2-fluoro-phenyl}-2,5-difluoro-N-methoxymethyl-benzenesulfonamide (0.736 mmol) was dissolved in a trifluoromethylbenzene/DCM 2:1 mixture (9 mL) and cooled to 0° C. Tert-butylamine (0.387 mL, 3.68 mmol, 5 eq) was added, followed by tosylanhydride (480 mg, 1.472 mmol, 2 eq) in portions and the mixture was stirred at 0° C. After many additions of both tert-butylamine and tosylanhydride the reaction mixture was diluted with DCM and washed with saturated aqueous NaHCO$_3$ and brine. The organic layer was dried over Na$_2$SO$_4$ and evaporated to dryness. After chromatography on silica gel (DCM/MeOH 98:2 to 95:5) 256 mg of N-{3-[4-(2-tert-butylamino-pyridin-4-yl)-1-ethyl-1H-pyrazol-3-yl]-2-fluoro-phenyl}-2,5-difluoro-N-methoxymethyl-benzenesulfonamide were obtained (61% yield over 2 steps), HPLC (254 nm): R$_t$: 7.23 min; $^1$H NMR (DMSO-d6) Shift: 8.12 (s, 1H), 7.76 (d, J=5.3 Hz, 1H), 7.59-7.66 (m, 1H), 7.45-7.58 (m, 3H), 7.24-7.34 (m, 2H), 6.67 (br. s., 1H), 610-6.14 (m, 1H), 5.78 (br. s., 1H), 5.01 (s, 2H), 4.20 (q, J=7.3 Hz, 2H), 3.30 (s, 3H), 1.44 (t, J=7.3 Hz, 3H), 1.31 (s, 9H); HRMS (ESI) calcd for C28H31F3N5O3S [M+H]$^+$ 574.2094. found 574.2089.

Method E, Step e

N-{3-[4-(2-Amino-pyridin-4-yl)-1-ethyl-1H-pyrazol-3-yl]-2-fluoro-phenyl}-2,5-difluoro-benzenesulfonamide (Compound 4)

Formula I, where m=1; R1=methyl; R2, R3=F; R4=2-Amino-pyridin-4-yl

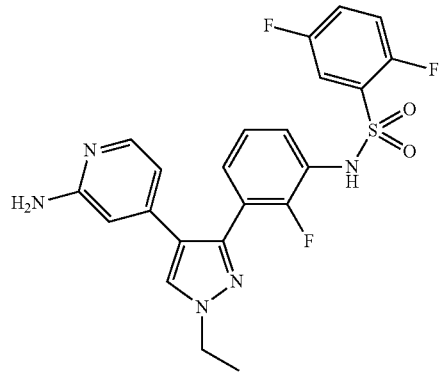 [SMILES: CCn1cc(-c2ccnc(N)c2)c(-c2cccc(NS(=O)(=O)c3cc(F)ccc3F)c2F)n1]

N-{3-[4-(2-tert-Butylamino-pyridin-4-yl)-1-ethyl-1H-pyrazol-3-yl]-2-fluoro-phenyl}-2,5-difluoro-N-methoxymethyl-benzenesulfonamide (250 mg, 0.436 mmol) was treated with TFA/H$_2$O 9:1 (3 mL) at 70° C. for 4.5 h. The reaction mixture was then evaporated to dryness, taken up with AcOEt and washed with sat. aq. NaHCO$_3$ and brine. The organic layer was dried over Na$_2$SO$_4$ and concentrated under reduced pressure. The crude product was purified by chromatography on silica gel (DCM/MeOH/NH$_3$ 7M in MeOH 90:8:2) and then treated with ethyl ether, filtered and dried to give 78 mg of N-{3-[4-(2-Amino-pyridin-4-yl)-1-ethyl-1H-pyrazol-3-yl]-2-fluoro-phenyl}-2,5-difluoro-benzene-sulfonamide as a white solid. HPLC (254 nm): R$_t$: 5.13 min; $^1$H NMR (DMSO-d6) Shift: 10.75 (br. s., 1H), 8.13 (s, 1H), 7.67 (dd, J=0.5, 5.4 Hz, 1H), 7.50-7.59 (m, 1H), 7.41-7.50 (m, 2H), 7.30 (td, J=24, 7.4 Hz, 1H), 7.12-7.26 (m, 2H), 6.27 (d, J=0.7 Hz, 1H), 6.08 (dd, J=14, 5.4 Hz, 1H), 5.82 (br. s., 2H), 4.18 (q, J=7.2 Hz, 2H), 1.42 (t, J=7.3 Hz, 3H); HRMS (ESI) calcd for C22H19F3N5O2S [M+H]$^+$ 474.1206. found 474.1184.

According to this same methodology, but employing suitable starting materials, the following compounds were prepared:

N-{3-[4-(2-Amino-pyridin-4-yl)-1-isopropyl-1H-pyrazol-3-yl]-2-fluoro-phenyl}-2,5-difluoro-benzenesulfonamide (Compound 12)

Formula 1, where m=0; R1=isopropyl; R2, R3=F; R4=2-Amino-pyridin-4-yl

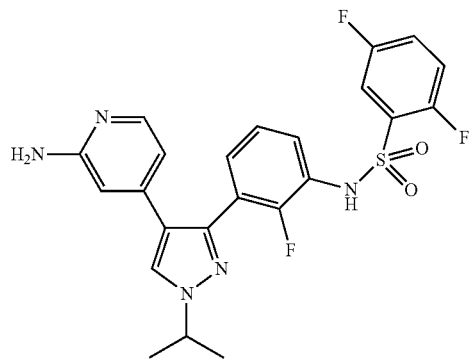 [SMILES: CC(C)n1cc(-c2ccnc(N)c2)c(-c2cccc(NS(=O)(=O)c3cc(F)ccc3F)c2F)n1]

HPLC (254 nm): R$_t$: 5.48 min; $^1$H NMR (DMSO-d6) Shift: 12.99 (s, 1H), 10.71 (br. s., 1H), 8.46 (s, 1H), 7.76-7.81 (m, 1H), 7.70 (br. s., 1H), 7.53-7.59 (m, 1H), 7.43-7.53 (m, 2H), 7.31-7.41 (m, 2H), 7.27 (t, J=7.9 Hz, 1H), 6.45-6.67 (m, 2H), 4.58 (spt, J=6.6 Hz, 1H), 1.48 (d, J=6.7 Hz, 6H); HRMS (ESI) calcd for C23H21F3N5O2S [M+H]$^+$ 488.1363. found 488.1357.

N-{3-[4-(2-Butylamino-pyridin-4-yl)-1-isopropyl-1H-pyrazol-3-yl]-2-fluoro-phenyl}-2,5-difluoro-benzenesulfonamide Formula I, where m=0; R1=isopropyl; R2, R3=F; R4=2-Butylamino-pyridin-4-yl

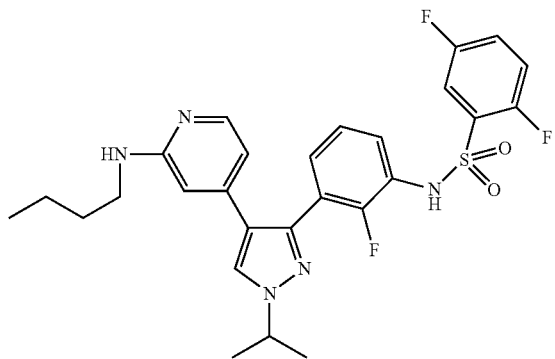 [SMILES: CCCCNc1cc(-c2cn(C(C)C)nc2-c2cccc(NS(=O)(=O)c3cc(F)ccc3F)c2F)ccn1]

HPLC (254 nm): R$_t$: 6.73 min; $^1$H NMR (DMSO-d6) Shift: 10.70 (br s., 1H), 8.43 (s, 1H), 7.77 (d, J=6.8 Hz, 1H), 7.56 (d, J=17.0 Hz, 1H), 7.41-7.53 (m, 2H), 7.30-7.39 (m, 2H), 7.25 (t, J=7.8 Hz, 1H), 6.51 (br. s., 2H), 4.58 (spt, J=6.6 Hz, 1H), 3.05-3.16 (m, J=5.9 Hz, 2H), 1.48 (d, J=6.7 Hz, 6H), 1.21-1.37 (m, J=15.1, 6.8 Hz, 4H), 0.88 (t, J=7.4 Hz, 3H); HRMS (ESI) calcd for C27H28F3N5O2S [M+H]$^+$ 544.1989. found 544.1978.

N-{3-[4-(2-Amino-pyridin-4-yl)-1-cyclopropyl-1H-pyrazol-3-yl]-2-fluoro-phenyl}-2,5-difluoro-benzenesulfonamide Formula I, where m=0; R1=cyclopropyl; R2, R3=F; R4=2-Amino-pyridin-4-yl

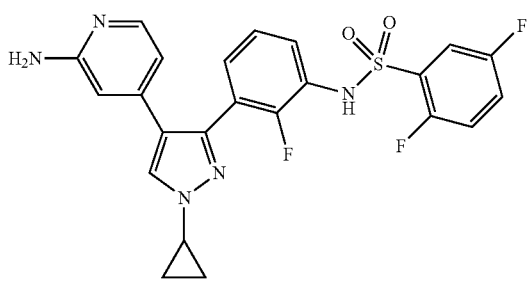 [SMILES: Nc1cc(-c2cn(C3CC3)nc2-c2cccc(NS(=O)(=O)c3cc(F)ccc3F)c2F)ccn1]

HPLC (254 nm): R$_t$: 5.31 min; $^1$H NMR (DMSO-d6) Shift: 10.75 (s, 1H), 8.17 (s, 1H), 7.67 (d, J=5.49 Hz, 1H), 7.51-7.59 (m, 1H), 7.39-7.51 (m, 2H), 7.30 (td, J=2.50, 7.29 Hz, 1H), 7.11-7.25 (m, 2H), 6.26 (s, 1H), 6.09 (dd, J=1.46, 5.9 Hz, 1H), 5.83 (br. s., 2H), 3.79 (tt, J=3.78, 7.38 Hz, 1H), 1.08-1.16 (m, 2H), 0.92-1.04 (m, 2H); HRMS (ESI) calcd for C23H19F3N5O2S [M+H]$^+$ 486.1206. found 486.1193.

Example 8

N-{3-[4-(2-Amino-pyridin-4-yl)-1-(2-fluoro-ethyl)-1H-pyrazol-3-yl]-2-fluoro-phenyl}-2,5-difluoro-benzenesulfonamide (Compound 13)

Formula I, where m=2; R1, R2, R3=F; R4=2-Amino-pyridin-4-yl

Method A, Step a 2,5-Difluoro-N-{2-fluoro-3-[4-pyridin-4-yl-1-(tetrahydro-pyran-2-yl)-1H-pyrazol-3-yl]-phenyl}-N-methoxymethyl-benzenesulfonamide Formula 2, where R4=4-pyridinyl, PG$_1$=methoxymethyl, R29=tetrahydro-pyran-2-yl, R30=2,5-difluoro-benzenesulfonyl

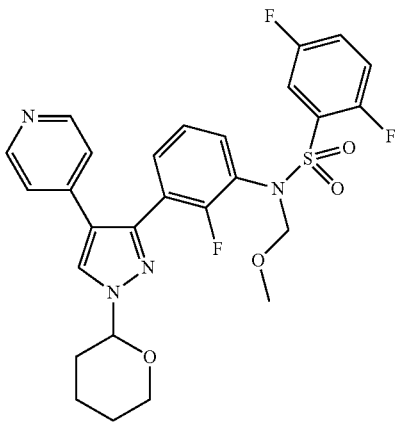 [SMILES: COCN(c1cccc(-c2nn(C3CCCCO3)cc2-c2ccncc2)c1F)S(=O)(=O)c1cc(F)ccc1F]

To an argon degassed solution of N-{3-[4-Bromo-1-(tetrahydro-pyran-2-yl-2H-pyrazol-3-yl]-2-fluoro-phenyl}-2,5-difluoro-N-methoxymethyl-benzenesulfonamide (900 mg, 1.607 mmol) (prepared as described in Example 5) in 1,2-dimethoxyethane:water 9:1 (11 mL) in a microwave vial, 4-(4,4,5,5-tetramethyl-[1,3,2]dioxaborolan-2-yl)-pyridine (494 mg, 2.41 mmol), cesium carbonate (1.048 g, 3.214 mmol) and Pd(dppf)Cl$_2$.CH$_2$Cl$_2$ (131 mg, 0.16 mmol) were added, under argon atmosphere. The mixture was heated in the microwave oven at 100° C. for 45 minutes, then it was filtered through a Celite pad. The solution was taken up with AcOEt and washed with saturated aqueous NaHCO$_3$ and brine. The organic layer was dried over Na$_2$SO$_4$ and concentrated to dryness. The residue was purified by flash chromatography on silica gel (AcOEt:Hex 9:1) affording 770 mg of the title compound (85% yield). HPLC (254 nm), R$_t$: 6.51 min; $^1$H NMR (DMSO-d6) Shift: 8.56 (s, 1H), 8.35-8.47 (m, 2H), 7.58-7.66 (m, 1H), 7.45-7.58 (m, 3H), 7.26-7.42 (m, 2H), 7.10-7.19 (m, 2H), 5.49 (dd, J=9.8, 2.4 Hz, 1H), 5.01 (s, 2H), 3.92-4.01 (m, 1H), 3.59-3.74 (m, 1H), 3.27 (s, 3H), 2.08-2.22 (m, 1H), 1.90-2.05 (m, 2H), 1.64-1.80 (m, J=11.8 Hz, 1H), 1.46-1.62 (m, J=3.4 Hz, 2H); HRMS (ESI) calcd for C27H26F3N4O4S [M+H]$^+$ 559.1622. found 559.1629.

Method E, Step a 2,5-Difluoro-N-{2-fluoro-3-[4-(1-oxy-pyridin-4-yl)-1-(tetrahydro-pyran-2-yl)-1H-pyrazol-3-yl]-phenyl}-N-methoxymethyl-benzenesulfonamide Formula 22, where PG$_1$=methoxymethyl; R29=tetrahydro-pyran-2-yl; R2,R3=F

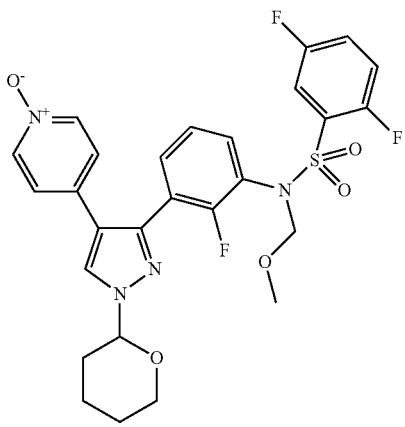 [SMILES: COCN(c1cccc(-c2nn(C3CCCCO3)cc2-c2cc[n+]([O-])cc2)c1F)S(=O)(=O)c1cc(F)ccc1F]

To a solution of 2,5-Difluoro-N-{2-fluoro-3-[4-pyridin-4-yl-1-(tetrahydro-pyran-2-yl)-1H-pyrazol-3-yl]-phenyl}-N-methoxymethyl-benzenesulfonamide (770 mg, 1.38 mmol) in DCM (10 mL) 3-chloro-perbenzoic acid (715 mg, 4.14 mmol) was added and the reaction was stirred at r.t. overnight. After the addition of 1 eq, more of the oxidizing agent and further 30 minutes, the reaction mixture was concentrated under reduced pressure and taken up with AcOEt and washed with saturated aqueous NaHCO$_3$ and brine. The intermediate was used without any further purification for the next step.

Method E, Step c

N-{3-[4-(2-tert-Butylamino-pyridin-4-yl)-1-(tetrahydro-pyran-2-yl)-1H-pyrazol-3-yl]-2-fluoro-phenyl}-2,5-difluoro-N-methoxymethyl-benzenesulfonamide Formula 2G, where PG$_1$=methoxymethyl; R2,R3=F; R16=tert-butyl; R29=tetrahydro-pyran-2-yl

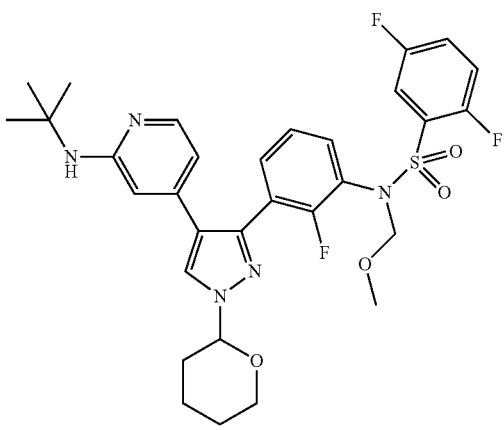 [SMILES: COCN(c1cccc(-c2nn(C3CCCCO3)cc2-c2ccnc(NC(C)(C)C)c2)c1F)S(=O)(=O)c1cc(F)ccc1F]

To a suspension of 2,5-Difluoro-N-{2-fluoro-3-[4-(1-oxy-pyridin-4-yl)-1-(tetrahydro-pyran-2-yl)-1H-pyrazol-3-yl]-phenyl}-N-methoxymethyl-benzenesulfonamide (1.38 mmol) in trifluorotoluene (20 mL), tert-butylamine (728 mL, 6.9 mmol) was added and the mixture was cooled down to 0° C. Tosyl anhydride (900 mg, 2.76 mmol) was added in portions and the reaction was stirred at 0° C. After 30 minutes another portion of reagents was added (tert-butylamine, 1.46 μL, tosyl anhydride, 225 mg) and the reaction was left stirring overnight at r.t. The reaction mixture was concentrated under reduced pressure and taken up with AcOEt and washed with saturated aqueous NaHCO$_3$ and brine. The residue was purified by flash chromatography on silica gel (Hex:AcOEt:EtOH 70:25:5) affording 572 mg of the title compound (66% yield, 2 steps). HPLC (254 nm): R$_t$: 7.57 min; $^1$H NMR (DMSO-d6) Shift: 8.26 (s, 1H), 7.78 (d, J=5.4 Hz, 1H), 7.58-7.67 (m, 1H), 7.45-7.58 (m, 3H), 7.25-7.36 (m, 2H), 6.28 (s, 1H), 6.16 (d, J=4.4 Hz, 1H), 5.78 (br. s., 1H), 5.47 (dd, J=9.9, 2.3 Hz, 1H), 5.00 (s, 2H), 3.96 (dt, J=11.7, 3.5 Hz, 1H), 3.59-3.71 (m, J=2.2 Hz, 1H), 3.30 (s, 3H), 2.08-2.20 (m, 1H), 1.89-2.03 (m, 2H), 1.62-1.77 (m, J=6.2 Hz, 1H), 1.50-1.61 (m, 2H), 1.27-1.36 (m, 9H); HRMS (ESI) calcd for C31H35F3N5O4S [M+H]$^+$ 630.2357. found 630.2368.

Method A, Step d

N-{3-[4-(2-tert-Butylamino-pyridin-4-yl)-1H-pyrazol-3-yl]-2-fluoro-phenyl}-2,5-difluoro-N-methoxymethyl-benzenesulfonamide Formula 4A, where R4=2-tert-butylamino-pyridin-4-yl; PG$_1$=methoxymethyl; R2,R3=F; R30=2,5-difluoro-benzenesulfonyl

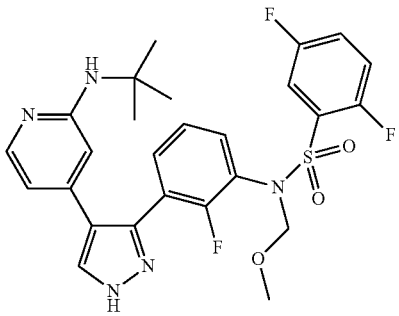 [SMILES: COCN(c1cccc(-c2n[nH]cc2-c2ccnc(NC(C)(C)C)c2)c1F)S(=O)(=O)c1cc(F)ccc1F]

To a solution of N-{3-[4-(2-tert-butylamino-pyridin-4-yl)-2-(tetrahydro-pyran-2-yl)-2H-pyrazol-3-yl]-2-fluoro-phenyl}-2,5-difluoro-N-methoxymethyl-benzenesulfonamide (572 mg, 0.91 mmol), p-toluenesulfonic acid monohydrate (346 g, 1.818 mmol) was added and the reaction mixture was stirred at 60° C. for 3 h. The reaction mixture was concentrated under reduced pressure and taken up with AcOEt and washed with saturated aqueous NaHCO$_3$ and brine. The residue didn't need any further purification (420 mg, 85% yield). HPLC (254 nm): R$_t$: 6.51 min; $^1$H NMR (DMSO-d6) Shift: 13.35 (br. s., 1H), 8.14 (br. s., 1H), 7.77 (d, J=5.5 Hz, 1H), 7.58-7.67 (m, 1H), 7.44-7.58 (m, 3H), 7.18-7.42 (m, 2H), 5.89-6.47 (m, 3H), 4.94-5.09 (m, 2H), 3.31 (s, 3H), 1.32 (s, 9H); HRMS (ESI) calcd for C26H27F3N5O3S [M+H]$^+$ 546.1781. found 546.1791.

Method A, Step e

N-{3-[4-(2-tert-Butylamino-pyridin-4-yl)-1-(2-fluoro-ethyl)-1H-pyrazol-3-yl]-2-fluoro-phenyl}-2,5-difluoro-N-methoxymethyl-benzenesulfonamide Formula 2, where R4=2-tert-butylamino-pyridin-4-yl; PG$_1$=methoxymethyl; R29=2-fluoroethyl; R30=2,5-difluoro-benzenesulfonyl

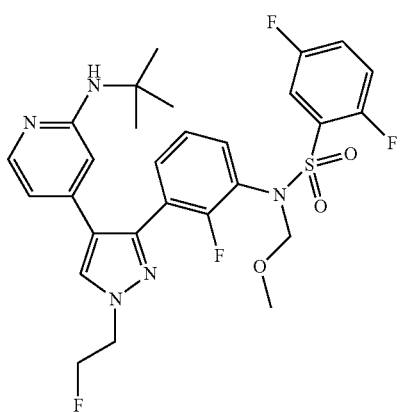 [SMILES: COCN(c1cccc(-c2nn(CCF)cc2-c2ccnc(NC(C)(C)C)c2)c1F)S(=O)(=O)c1cc(F)ccc1F]

Cesium carbonate (90 mg, 0.275 mmol) and 1-fluoro-2-iodo-ethane (48 mg, 0.275 mmol) were added to a solution of N-{3-[4-(2-tert-Butylamino-pyridin-4-yl)-1H-pyrazol-3-yl]-2-fluoro-phenyl}-2,5-difluoro-N-methoxymethyl-benzenesulfonamide (100 mg, 0.183 mmol) in DMF (2 mL) and the suspension was stirred at 50° C. for 1 hour. The mixture was treated with water and AcOEt. The organic layer was washed once again with water and brine, then it was dried over $Na_2SO_4$ and concentrated under reduced pressure. The residue was purified by flash chromatography on silica gel (Hex:EtOH 8:2) affording 49 mg of the title compound (45% yield). HPLC (254 nm): $R_t$: 7.04 min; $^1$H NMR (DMSO-d6) Shift: 8.16 (s, 1H), 7.77 (d, J=5.4 Hz, 1H), 7.59-7.68 (m, 1H), 7.43-7.58 (m, 3H), 7.24-7:35 (m, 2H), 6.31 (br. s., 1H), 6:12 (br. s., 1H), 5.84 (br. s., 1H), 5.01 (s, 2H), 4.84 (dt, J=47.1, 4.7 Hz, 2H), 4.50 (d, J=4.9 Hz, 2H), 3.31 (s, 3H), 1.32 (s, 9H); HRMS (ESI) calcd for C28H30F4N5O3S [M+H]$^+$ 592.2. found 592.2001.

According to this same methodology, but employing suitable starting materials, the following intermediate was prepared:

N-{3-[4-(2-tert-Butylamino-pyridin-4-yl)-1-(tetrahydro-pyran-4-yl)-1H-pyrazol-3-yl]-2-fluoro-phenyl}-2,5-difluoro-N-methoxymethyl-benzenesulfonamide Formula 2, where R4=2-tert-butylamino-pyridin-4-yl; PG$_1$=methoxymethyl; R29=tetrahydro-pyran-4-yl; R30=2,5-difluoro-benzenesulfonyl

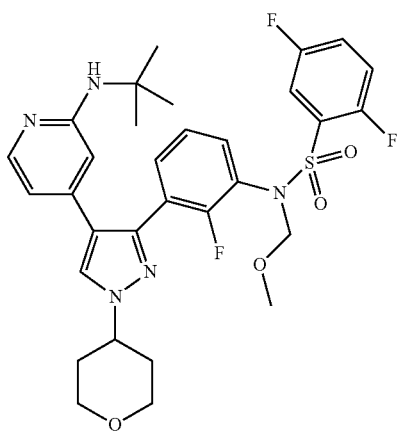 [SMILES: COCN(c1cccc(-c2nn(C3CCOCC3)cc2-c2ccnc(NC(C)(C)C)c2)c1F)S(=O)(=O)c1cc(F)ccc1F]

HPLC (254 nm), $R_t$: 759 min; $^1$H NMR (DMSO-d6) Shift: 8.18 (s, 1H), 7.77 (d, J=5.4 Hz, 1H), 7.58-7.66 (m, 1H), 7.42-7.58 (m, 3H), 7.21-7.35 (m, 2H), 6.27 (s, 1H), 6.15 (dd, J=5.2, 1.2 Hz, 1H), 5.77 (s, 1H), 5.01 (s, 2H), 4.38-4.54 (m, 1H), 3.98 (dd, J=10.4, 4.0 Hz, 2H), 3.43-3.53 (m, 2H), 3.29 (s, 3H), 1.87-2.18 (m, 4H), 1.31 (s, 9H); HRMS (ESI) calcd for C31H35F3N5O4S [M+H]$^+$ 630.2357. found 630.2372.

Method E, Step e

N-{3-[4-(2-Amino-pyridin-4-yl)-1-(2-fluoro-ethyl)-1H-pyrazol-3-yl]-2-fluoro-phenyl}-2,5-difluoro-benzenesulfonamide (Compound 13)

Formula I, where m=2; R1, R2, R3=F; R4=2-Amino-pyridin-4-yl

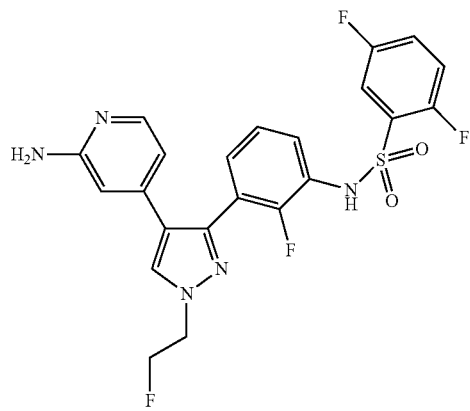 [SMILES: Nc1cc(-c2cn(CCF)nc2-c2cccc(NS(=O)(=O)c3cc(F)ccc3F)c2F)ccn1]

N-{3-[4-(2-tert-Butylamino-pyridin-4-yl)-1-(2-fluoro-ethyl)-1H-pyrazol-3-yl]-2-fluoro-phenyl}-2,5-difluoro-N-methoxymethyl-benzenesulfonamide (49 mg, 0.082 mmol) was dissolved in a mixture of TFA:water 9:1 (1.4 mL) and stirred for 3.5 h at 70° C. The reaction mixture was concentrated under reduced pressure, then taken up with a saturated solution of NaHCO$_3$ and extracted with AcOEt. The organic layer was dried over $Na_2SO_4$ and concentrated to dryness. The residue was purified by flash chromatography on silica gel (Hex:AcOEt:EtOH 4:4:2) affording 26 mg of the title compound (63% yield). HPLC (254 nm): $R_t$: 5.01 min; $^1$H NMR (DMSO-d6) Shift: 10.79 (br. s., 1H), 8.17 (s, 1H), 7.68 (d, J=5.5 Hz, 1H), 7.51-7.61 (m, 1H), 7.41-7.51 (m, 2H), 7.32 (td, J=7.5, 2.1 Hz, 1H), 7.12-7.28 (m, 2H), 6.29 (s, 1H), 6.03-6.14 (m, 1H), 5.90 (br. s., 2H), 4.82 (dt, J=47.1, 4.7 Hz, 2H), 4.48 (dt, J=282, 5.0 Hz, 2H); HRMS (ESI) calcd for C22H18F4N5O2S [M+H]$^+$ 492.1112. found 492.1125.

According to this same methodology, but employing suitable starting materials, the following compounds were prepared:

103

N-{3-[4-(2-Amino-pyridin-4-yl)-1-cyclopentyl-1H-pyrazol-3-yl]-2-fluoro-phenyl}-2,5-difluoro-benzenesulfonamide (Compound 17)

Formula I, where m=0; R1=cyclopentyl; R2, R3=F; R4=2-amino-pyridin-4-yl

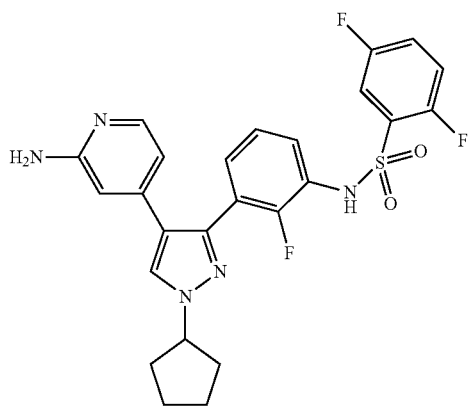 [SMILES: Nc1cc(-c2cn(C3CCCC3)nc2-c2cccc(NS(=O)(=O)c3cc(F)ccc3F)c2F)ccn1]

HPLC (254 nm): R$_t$: 6.05 min; $^1$H NMR (DMSO-d6) Shift: 10.68 (br. s., 1H), 8.15 (s, 1H), 7.67 (d, J=5.4 Hz, 1H), 7.50-7.58 (m, 1H), 7.39-7.50 (m, 2H), 7.29 (td, J=7.1, 2.8 Hz, 1H), 7.07-7.22 (m, J=7.3 Hz, 2H), 6.28 (s, 1H), 6.09 (dd, J=5.4, 1.4 Hz, 1H), 5.67-5.84 (m, 2H), 4.73 (quip, J=7.0 Hz, 1H), 2.06-2.18 (m, 2H), 1.91-2.05 (m, J=133, 8.6, 6.6, 6.6 Hz, 2H), 1.72-1.89 (m, 2H), 1.50-1.73 (m, 2H); HRMS (ESI) calcd for C25H22F3N5O2S [M+H]$^+$ 514.1519. found 514.1531.

N-{3-[4-(2-Amino-pyridin-4-yl)-1-cyclohexyl-1H-pyrazol-3-yl]-2-fluoro-phenyl}-2,5-difluoro-benzenesulfonamide Formula I, where m=0; R1=cyclohexyl; R2, R3=F; R4=2-amino-pyridin-4-yl]

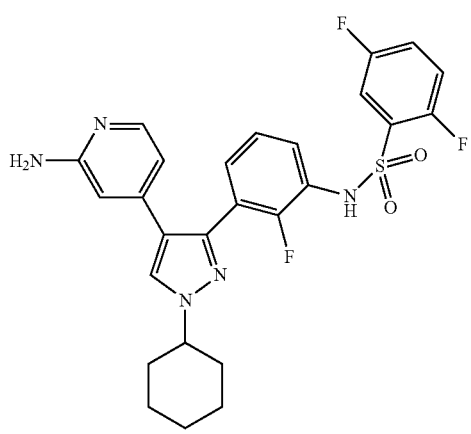 [SMILES: Nc1cc(-c2cn(C3CCCCC3)nc2-c2cccc(NS(=O)(=O)c3cc(F)ccc3F)c2F)ccn1]

HPLC (254 nm): R$_t$: 6.32 min; $^1$H NMR (DMSO-d6) Shift: 10.81 (s, 1H), 8.16 (s, 1H), 7.68 (d, J=5.5 Hz, 1H), 7.51-7.59 (m, 1H), 7.41-7.51 (m, 2H), 7.30 (td, J=7.5, 2.0 Hz, 1H), 7.12-7.25 (m, 2H), 6.29 (S, 1H), 6.11 (dd, J=5.4, 1.1 Hz, 1H), 5.87 (br. s., 2H), 4.18 (tt, J=11.4, 3.8 Hz, 1H), 2.02-2.14 (m, J=7.3 Hz, 2H), 1.77-1.87 (m, J=2.8 Hz, 2H), 1.59-1.78 (m, 3H), 1.31-1.48 (m, J=12.8, 3.4, 3.4 Hz, 2H), 1.13-1.30 (m, J=12.6 Hz, 1H); HRMS (ESI) calcd for C26H25F3N5O2S [M+H]$^+$ 528.1676. found 528.168.

104

N-{3-[4-(2-Amino-pyridin-4-yl)-1-(tetrahydro-pyran-4-yl)-1H-pyrazol-3-yl]-2-fluoro-phenyl}-2,5-difluoro-benzenesulfonamide (Compound 14)

Formula 1, where m=0; R1=tetrahydro-pyran-4-yl; R2, R3=F; R4=2-amino-pyridin-4-yl

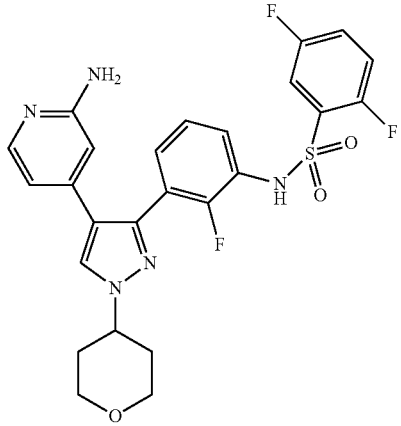 [SMILES: Nc1cc(-c2cn(C3CCOCC3)nc2-c2cccc(NS(=O)(=O)c3cc(F)ccc3F)c2F)ccn1]

HPLC (254 nm): R$_t$: 5.09 min; $^1$H NMR (DMSO-d6) Shift: 10.79 (s, 1H), 8.21 (s, 1H), 7.68 (d, J=5.5 Hz, 1H), 7.51-7.59 (m, 1H), 7.41-7.51 (m, 2H), 7.31 (td, J=7.5, 2.1 Hz, 1H), 7.10-7.26 (m, 2H), 6.29 (s, 1H), 6.11 (dd, J=5.4, 1.3 Hz, 1H), 5.86 (br. s., 2H), 4.35-4.55 (m, 1H), 3.86-4.03 (m, J=4.0, 1.6 Hz, 2H), 3.47 (td, J=11.5, 2.4 Hz, 2H), 1.86-2.13 (m, 4H); HRMS (ESI) calcd for C25H23F3N5O3S [M+H]$^+$ 530.1468. found 530.1471.

Example 9

N-{3-[4-(2-Amino-pyridin-4-yl)-1-(1-methyl-piperidin-4-yl)-1H-pyrazol-3-yl]-2-fluoro-phenyl}-2,5-difluoro-benzenesulfonamide Formula I, where m=0; R1=1-methyl-piperidin-4-yl; R2, R3=F; R4=2-amino-pyridin-4-yl Method E, Step a 4-[3-{3-[(2,5-Difluoro-benzenesulfonyl)-methoxymethyl-amino]-2-fluoro-phenyl}-4-(1-oxy-pyridin-4-yl)-pyrazol-1-yl]-piperidine-1-carboxylic acid tert-butyl ester Formula 22, where PG$_1$=methoxymethyl; R2,R3=F; R29=1-tert-butoxycarbonyl-piperidin-4-yl

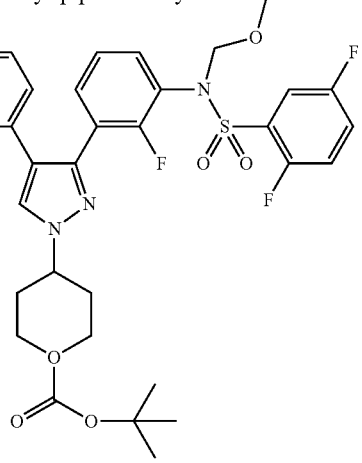

To a solution of 4-(3-{3-[(2,5-difluoro-benzenesulfonyl)-methoxymethyl-amino]-2-fluoro-phenyl}-4-pyridin-4-yl-pyrazol-1-yl)-piperidine-1-carboxylic acid tert-butyl ester (1.8 g, 2.737 mmol) (prepared as described in Example 2) benzoic acid (1.42 g, 8.210 mmol, 3 eq) was added and the solution was stirred at r.t. for 5 h. A further addition of m-chloroperbenzoic acid (350 mg, 0.75 eq) was made and stirring was continued overnight. The reaction mixture was then diluted with DCM and washed with saturated aqueous NaHCO$_3$ and brine. The organic layer was dried over Na$_2$SO$_4$ and evaporated to dryness. The crude product was purified by flash chromatography on silica gel (DCM/MeOH 95:5) affording 1.23 g (67%) of 4-[3-{3-[(2,5-Difluoro-benzene-sulfonyl)-methoxymethyl-amino]-2-fluoro-phenyl}-4-(1-oxy-pyridin-4-yl)-pyrazol-1-yl]-piperidine-1-carboxylic acid tert-butyl ester as a white foam, HPLC (254 nm): R$_t$: 6.22 min; $^1$H NMR (DMSO-d6) Shift: 8.43 (s, 1H), 8.00-8.09 (m, 2H), 7.60-7.68 (m, 1H), 7.50-7.60 (m, 3H), 7.30-7.34 (m, 2H), 7.08-7.12 (m, 2H), 5.02 (s, 2H), 4.36-4.49 (m, 1H), 4.01-4.11 (m, 2H), 3.29 (s, 3H), 2.95 (br. s., 2H), 2.05-2.14 (m, 2H), 1.76-1.89 (m, 2H), 1.42 (s, 9H); HRMS (ESI) calcd for C32H35F3N5O6S [M+H]$^+$ 674.2255. found 674.2268.
Method E, Step c 4-(4-(2-tert-Butylamino-pyridin-4-yl)-3-{3-[(2,5-difluoro-benzenesulfonyl)-methoxymethyl-amino]-2-fluoro-phenyl}-pyrazol-1-yl)-piperidine-1-carboxylic acid tert-butyl ester Formula 2G, where PG$_1$=methoxymethyl; R2,R3=F; R16=tert-butyl; R29=1-tert-butoxycarbonyl-piperidin-4-yl

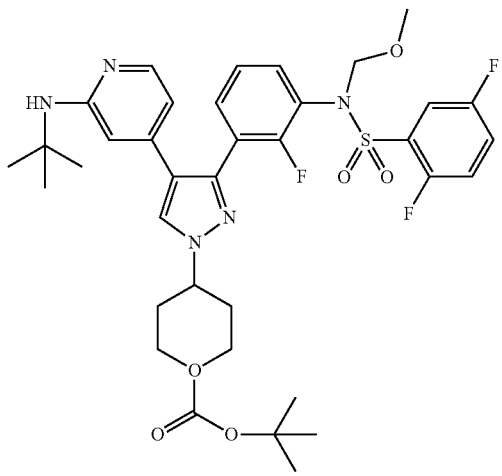

4-[3-{3-[(2,5-Difluoro-benzenesulfonyl)-methoxymethyl-amino]-2-fluoro-phenyl}-4-(1-oxy-pyridin-4-yl)-pyrazol-1-yl]-piperidine-1-carboxylic acid tert-butyl ester (0.727 mg, 1.079 mmol) was dissolved in trifluoromethyl-benzene (5 mL) and cooled to 0° C. Tert-butylamine (0.567 mL, 5.395 mmol, 5 eq) was added, followed by tosylanhydride (704 mg, 2.158 mmol, 2 eq) in portions and the mixture was stirred at 0° C. After two more additions of both tert-butylamine (5 eq) and tosylanhydride (2 eq) the reaction mixture was diluted with DCM and washed with saturated aqueous NaHCO$_3$ and brine. The organic layer was dried over Na$_2$SO$_4$ and evaporated to dryness. After flash chromatography on silica gel (DCM/MeOH 95:5 to 9:1) 574 mg of 4-(4-(2-tert-butylamino-pyridin-4-yl)-3-{3-[(2,5-difluoro-benzenesulfonyl)-methoxymethyl-amino]-2-fluoro-phenyl}-pyrazol-1-yl)-piperidine-1-carboxylic acid tert-butyl ester were obtained (73%). HPLC (254 nm): R$_t$: 7.97 min; $^1$H NMR (DMSO-d6) Shift: 8.19 (s, 1H), 7.77 (d, J=5.4 Hz, 1H), 7.58-7.66 (m, 1H), 7.45-7.58 (m, 3H), 7.24-7.32 (m, 2H), 6.26 (s, 1H), 6.13-6.17 (m, 1H), 5.75 (s, 1H), 5.00 (s, 2H), 4.37-4.48 (m, 1H), 4.01-4.11 (m, 2H), 3.29 (s, 3H), 2.86-3.03 (m, 2H), 2.04-2.12 (m, 2H), 1.76-1.90 (m, 2H), 1.42 (s, 9H), 1.31 (s, 9H); HRMS (ESI) calcd for C36H44F3N6O5S [M+H]$^+$ 729.3041. found 729.3051.

N-{3-[4-(2-tert-Butylamino-pyridin-4-yl)-1-piperidin-4-yl-1H-pyrazol-3-yl]-2-fluoro-phenyl}-2,5-difluoro-N-methoxymethyl-benzenesulfonamide Formula 2G, where PG$_1$=methoxymethyl; R2,R3=F; R16=tert-butyl; R29=piperidin-4-yl

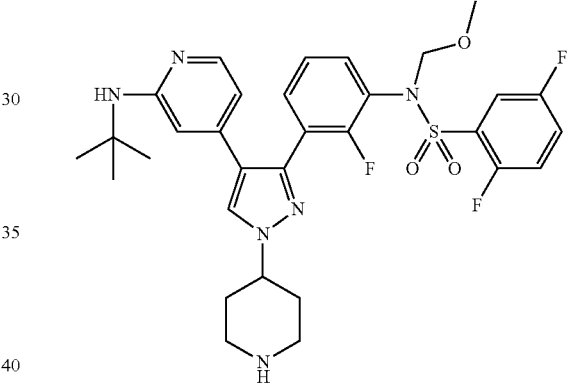

To a solution of 4-(4-(2-tert-butylamino-pyridin-4-yl)-3-{3-[(2,5-difluoro-benzene-sulfonyl)-methoxymethyl-amino]-2-fluoro-phenyl}-pyrazol-1-yl)-piperidine-1-carboxylic acid tert-butyl ester (235 mg, 0.322 mmol) in anhydrous dioxane (1 mL) under nitrogen at r.t., a 4N solution of HCl in dioxane (1 mL, 4 mmol, 12 eq) was added dropwise and the mixture was stirred at r.t. for 30 minutes. The solvent was concentrated under reduced pressure and the residue was diluted with AcOEt and washed with saturated aqueous NaHCO$_3$ and brine. The organic layer was dried over Na$_2$SO$_4$ and evaporated to dryness giving 220 mg of crude product which was used without purification in the following step. HPLC (254 nm): R$_t$: 5.89 min; $^1$H NMR (DMSO-d6) Shift: 8.13 (s, 1H), 7.77 (d, J=5.2 Hz, 1H), 7.59-7.68 (m, 1H), 7.44-7.59 (m, 3H), 7.23-7.34 (m, 2H), 6.27 (s, 1H), 6.14 (dd, J=1.2, 5.3 Hz, 1H), 5.75 (s, 1H), 5.01 (s, 2H), 4.22-4.32 (m, 1H), 3.29 (s, 3H), 3.03-3.12 (m, 2H), 2.57-2.69 (m, 2H), 1.98-2.08 (m, 2H), 1.84 (qd, J=4.0, 12.0 Hz, 2H), 1.31 (s, 9H); HRMS (ESI) calcd for C31H36F3N6O3S [M+H]$^+$ 629.2516. found 629.2536.

N-{3-[4-(2-tert-Butylamino-pyridin-4-yl)-1-(1-methyl-piperidin-4-yl)-1H-pyrazol-3-yl]-2-fluoro-phenyl}-2,5-difluoro-N-methoxymethyl-benzenesulfonamide Formula 2G, where PG$_1$=methoxymethyl; R2,R3=F; R16=tert-butyl; R29=1-methyl-piperidin-4-yl

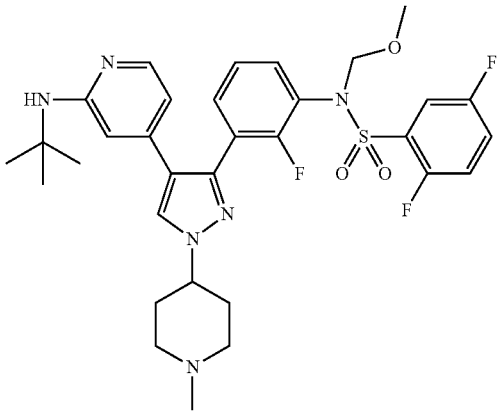 [SMILES: COCN(c1cccc(-c2nn(C3CCN(C)CC3)cc2-c2ccnc(NC(C)(C)C)c2)c1F)S(=O)(=O)c1cc(F)ccc1F]

To a solution of N-{3-[4-(2-tert-Butylamino-pyridin-4-yl)-1-piperidin-4-yl-1H-pyrazol-3-yl]-2-fluoro-phenyl}-2,5-difluoro-N-methoxymethyl-benzenesulfonamide (69 mg, 0.11 mmol) in MeOH (1 mL) 37% aqueous formaldehyde (0.013 mL, 0.165 mmol, 1.5 eq) was added, followed by acetic acid (0.019 mL, 0.33 mmol, 3 eq) and sodiumcyanoboro-hydride (13 mg, 0.176 mmol, 1.6 eq) and the mixture was stirred at r.t. for 1 h. The solvent was then evaporated under reduced pressure and the residue was taken up with AcOEt and saturated aqueous NaHCO$_3$ and the two phases were separated. The aqueous phase was basified to pH 10 by addition of ammonium hydroxide and extracted with AcOEt. The combined organic layers were washed with brine, dried over Na$_2$SO$_4$ and evaporated to dryness affording 66 mg of crude product (mixture of MOM-protected and deprotected product), which was used without purification in the following step. [M+H]$^+$ 643.
Method E, Step e

N-{3-[4-(2-Amino-pyridin-4-yl)-1-(1-methyl-piperidin-4-yl)-1H-pyrazol-3-yl]-2-fluoro-phenyl}-2,5-difluoro-benzenesulfonamide Formula I, where m=0; R1=1-methyl-piperidin-4-yl; R2, R3=F; R4=2-amino-pyridin-4-yl

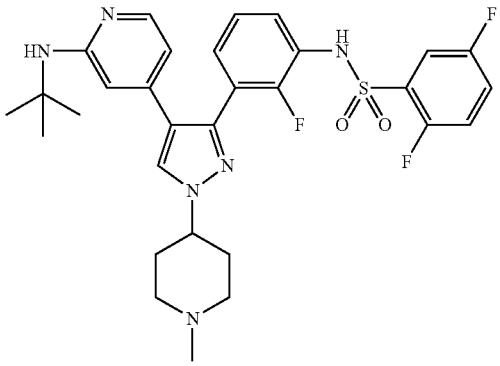 [SMILES: CN1CCC(n2cc(-c3ccnc(NC(C)(C)C)c3)c(-c3cccc(NS(=O)(=O)c4cc(F)ccc4F)c3F)n2)CC1]

Crude N-{3-[4-(2-tert-Butylamino-pyridin-4-yl)-1-(1-methyl-piperidin-4-yl)-1H-pyrazol-3-yl]-2-fluoro-phenyl}-2,5-difluoro-N-methoxymethyl-benzenesulfonamide (66 mg, 0.103 mmol) was dissolved in a 9:1 TFA/water mixture (1 mL) and stirred at 60° C. for 8 h. The reaction mixture was concentrated under reduced pressure, then taken up with AcOEt and washed with a saturated solution of NaHCO$_3$ and brine. The organic layer was dried over Na$_2$SO$_4$ and concentrated to dryness. The residue was purified by flash chromatography on silica gel (DCM/MeOH/NH$_3$ 7M in MeOH 80.15:5) affording 57 mg of the title compound as a white solid. HPLC (254 nm): R$_t$: 4.15 min; $^1$H NMR (DMSO-d6) Shift: 8.15 (s, 1H), 7.67 (d, J=5.4 Hz, 1H), 7.42-7.50 (m, 2H), 7.33-7.42 (m, 1H), 7.26 (td, J=2.0, 7.6 Hz, 1H), 6.97-7.11 (m, 2H), 6.27 (s, 1H), 6.10 (dd, J=1.3, 5.4 Hz, 1H), 5.72 (br. s., 2H), 4.17-7.28 (m, 1H), 2.95-3.06 (m, 2H), 2.35 (s, 3H), 2.25-2.33 (m, 2H), 1.95-2.15 (m, 4H); HRMS (ESI) calcd for C26H26F3N6O2S [M+H]$^+$ 543.1785. found 543.1778.

According to this same methodology, but employing suitable reagents in the reductive amination step, the following compounds were prepared:

N-{3-[4-(2-Amino-pyridin-4-yl)-1-(1-isopropyl-piperidin-4-yl)-1H-pyrazol-3-yl]-2-fluoro-phenyl}-2,5-difluoro-benzenesulfonamide Formula I, where m=0; R1=1-isopropyl-piperidin-4-yl; R2, R3=F; R4=2-amino-pyridin-4-yl

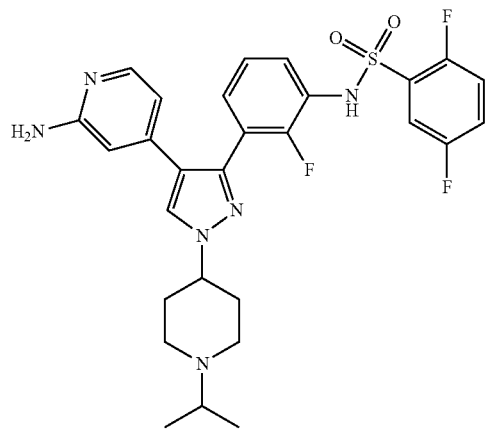 [SMILES: CC(C)N1CCC(n2cc(-c3ccnc(N)c3)c(-c3cccc(NS(=O)(=O)c4cc(F)ccc4F)c3F)n2)CC1]

HPLC (254 nm): R$_t$: 4.36 min; $^1$H NMR (DMSO-d6) Shift: 8.15 (s, 1H), 7.68 (d, J=5.4 Hz, 1H), 7.42-7.52 (m, 2H), 7.34-7.41 (m, 1H), 7.21-7.29 (m, 1H), 7.03-7.12 (m, 2H), 6.28 (s, 1H), 6.11-6.15 (m, 1H), 5.72 (br. s., 2H), 4.22-4.34 (m, 1H), 2.91-3.17 (m, 4H), 2.59 (br. s., 1H), 2.12-2.22 (m, 2H), 1.91-2.11 (m, 4H), 0.98-1.15 (m, 6H); HRMS (ESI) calcd for C28H30F3N6O2S [M+H]$^+$ 571.2098. found 571.2090.

N-{3-[4-(2-Amino-pyridin-4-yl)-1-(1-ethyl-piperidin-4-yl)-1H-pyrazol-3-yl]-2-fluoro-phenyl}-2,5-difluoro-benzenesulfonamide Formula I, where m=0; R1=1-ethyl-piperidin-4-yl; R2, R3=F; R4=2-amino-pyridin-4-yl]

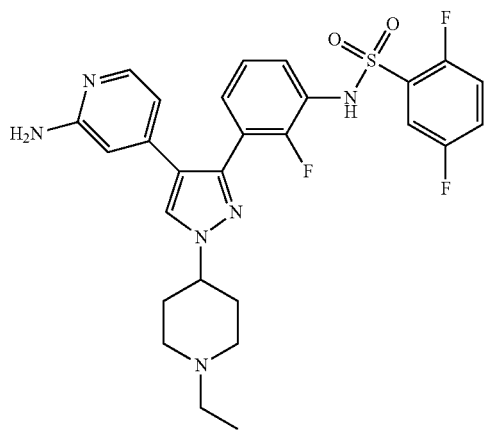 [SMILES: CCN1CCC(n2cc(-c3ccnc(N)c3)c(-c3cccc(NS(=O)(=O)c4cc(F)ccc4F)c3F)n2)CC1]

HPLC (254 nm): $R_t$: 4.25 min; $^1$H NMR (DMSO-d6) Shift: 8.17 (s, 1H), 7.68 (d, J=5.4 Hz, 1H), 7.37-7.53 (m, 3H), 7.27 (td, J=2.8, 7.3 Hz, 1H), 6.98-7.18 (m, 2H), 6.28 (s, 1H), 6.11 (dd, J=1.2, 5.2 Hz, 1H), 5.75 (s, 2H), 4.07-4.38 (m, 1H), 3.12-3.30 (m, 2H), 2.58-2.73 (m, 2H), 2.35-2.48 (m, 2H), 1.95-2.21 (m, 4H), 1.10 (t, J=7.2, 3H); HRMS (ESI) calcd for C27H28F3N6O2S [M+H]$^+$ 557.1941. found 557.1942.

N-{3-[4-(2-Amino-pyridin-4-yl)-1-(1-cyclopropyl-piperidin-4-yl)-1H-pyrazol-3-yl]-2-fluoro-phenyl}-2,5-difluoro-benzenesulfonamide (Compound 23)

Formula I, where m=0; R1=1-cyclopropyl-piperidin-4-yl; R2, R3=F; R4=2-amino-pyridin-4-yl

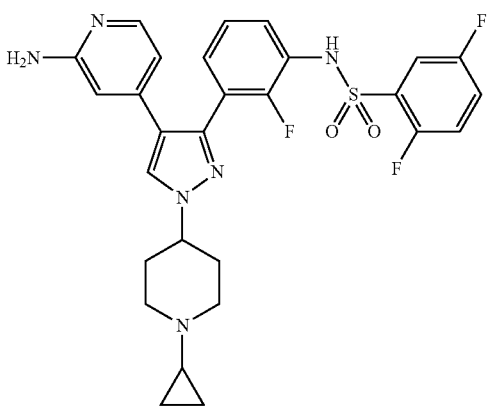 [SMILES: Nc1cc(-c2cn(C3CCN(C4CC4)CC3)nc2-c2cccc(NS(=O)(=O)c3cc(F)ccc3F)c2F)ccn1]

HPLC (254 nm): $R_t$: 5.12 min; $^1$H NMR (DMSO-d6) Shift: 8.22 (s, 1H), 7.69 (d, J=5.6 Hz, 1H), 7.51-7.59 (m, 1H), 7.42-7.51 (m, 2H), 7.31 (td, J=2.0, 7.5 Hz, 1H), 7.21-7.27 (m, 1H), 7.13-7.21 (m, 1H), 6.31 (s, 1H), 6.16 (d, J=5.4 Hz, 1H), 6.06 (br. s, 2H), 4.18-4.29 (m, 1H), 3.02-3.11 (m, 2H), 2.35-2.47 (m, 2H), 2.02-2.10 (m, 2H), 1.85-1.99 (m, 2H), 1.74 (br. s., 1H), 0.43-0.50 (m, 2H), 0.36 (br. s., 2H); HRMS (ESI) calcd for C28H28F3N6O2S [M+H]$^+$ 569.1941. found 569.1926.

In some cases, the following partially deprotected products were also isolated:

N-{3-[4-(2-tert-Butylamino-pyridin-4-yl)-1-piperidin-4-yl)-1H-pyrazol-3-yl]-2-fluoro-phenyl}-2,5-difluoro-benzenesulfonamide Formula I, where m=0; R1=piperidin-4-yl; R2, R3=F; R4=2-tert-butylamino-pyridin-4-yl

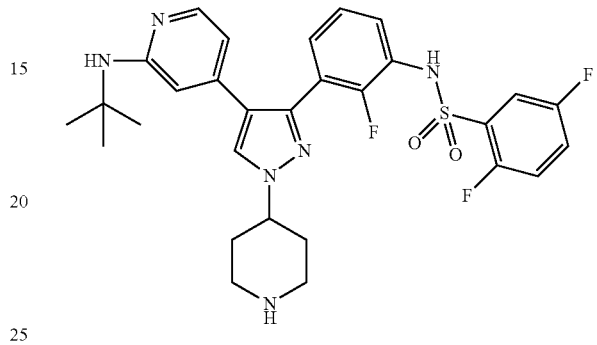

HPLC (254 nm): $R_t$: 5.27 min; $^1$H NMR (DMSO-d6) Shift (selected signals): 8.07 (s, 1H), 7.76 (d, J=5.4 Hz, 1H), 7.43 (ddd, J=3.1, 5.2, 8.1 Hz, 1H), 7.19-7.31 (m, 2H), 7.14 (td, J=1.7, 8.1 Hz, 1H), 6.82 (t, J=7.8 Hz, 1H), 6.55-6.62 (m, 1H), 6.35 (s, 1H), 6.22 (dd, J=1.3, 5.4 Hz, 1H), 5.81 (s, 1H), 4.33-4.57 (m, 1H), 2.99 (td, J=2.7, 12.3 Hz, 2H), 2.16-2.29 (m, 2H), 1.97-2.16 (m, 2H), 1.26 (s, 9H); HRMS (ESI) calcd for C29H31F3N6O2S [M+H]$^+$ 585.2254. found 585.2267.

N-{3-[4-(2-tert-Butylamino-pyridin-4-yl)-1-(1-methyl-piperidin-4-yl)-1H-pyrazol-3-yl]-2-fluoro-phenyl}-2,5-difluoro-benzenesulfonamide Formula I, where m=0; R1=1-methyl-piperidin-4-yl; R2, R3=F; R4=2-tert-butylamino-pyridin-4-yl

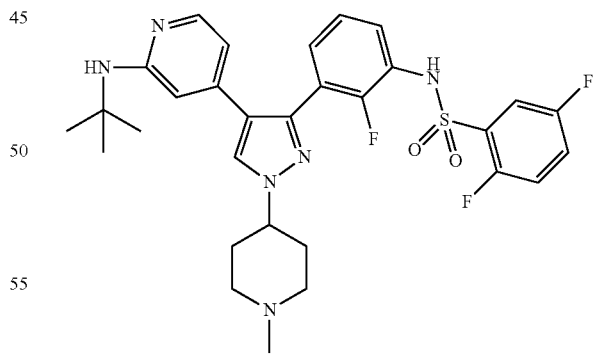

HPLC (254 nm) $R_t$: 5.45 min; $^1$H NMR (DMSO-d6) Shift: 8.12 (s, 1H), 7.74 (d, J=5.5 Hz, 1H), 7.44-7.52 (m, 2H), 7.35-7.42 (m, 1H), 7.24 (td, J=2.0, 7.6 Hz, 1H), 6.98-7.14 (m, 1H), 6.33 (s, 1H), 6.09 (dd, J=1.3, 5.4 Hz, 1H), 5.83 (s, 1H), 4.18-4.30 (m, 1H), 2.97-3.08 (m, 2H), 2.29-2.43 (m, 2H), 2.36 (s, 3H), 1.96-2.17 (m, 4H), 1.29 (s, 9H); HRMS (ESI) calcd for C30H34F3N6O2S [M+H]$^+$ 599.2411. found 599.2419.

Example 10

N-{3-[1-(1-Acetyl-piperidin-4-yl)-4-(2-amino-pyridin-4-yl)-1H-pyrazol-3-yl]-2-fluoro-phenyl}-2,5-difluoro-benzenesulfonamide Formula I, where m=0; R1=1-acetyl-piperidin-4-yl; R2, R3=F; R4=2-amino-pyridin-4-yl

N-{3-[1-(1-Acetyl-piperidin-4-yl)-4-(2-tert-butylamino-pyridin-4-yl)-1H-pyrazol-3-yl]-2-fluoro-phenyl}-2,5-difluoro-N-methoxymethyl-benzenesulfonamide Formula 2G, where PG$_1$=methoxymethyl; R2, R3=F; R16=tert-butyl; R29=1-acetyl-piperidin-4-yl

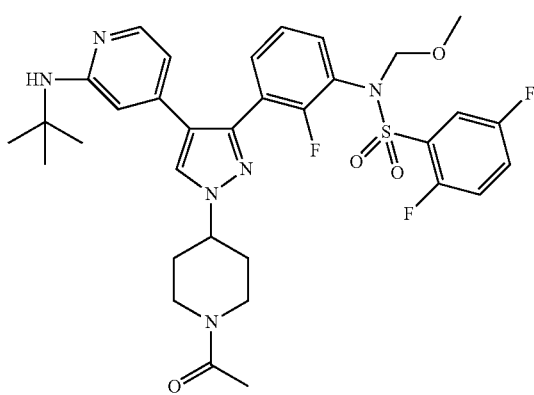 [SMILES: COCN(c1cccc(-c2nn(C3CCN(C(C)=O)CC3)cc2-c2ccnc(NC(C)(C)C)c2)c1F)S(=O)(=O)c1cc(F)ccc1F]

To a solution of N-{3-[4-(2-tert-Butylamino-pyridin-4-yl)-1-piperidin-4-yl-1H-pyrazol-3-yl]-2-fluoro-phenyl}-2,5-difluoro-N-methoxymethyl-benzenesulfonamide (100 mg, 0.159 mmol) (prepared as described in example 8) in DCM (1.5 mL) triethylamine (0.024 mL, 0.175 mmol, 1.1 eq) was added, followed by acetylchloride (0.011 mL, 0.159 mmol, 1 eq) and the solution was stirred at r.t. for 1 h. The reaction mixture was then diluted with DCM and washed with water. The aqueous phase was back extracted with DCM. The combined organic layers were washed with brine, dried over Na$_2$SO$_4$ and evaporated to dryness. The crude product was purified by flash chromatography (DCM/MeOH/NH$_3$ 7N in MeOH 94.5:1) affording 93 mg (87%) of N-{3-[1-(1-Acetyl-piperidin-4-yl)-4-(2-tert-butylamino-pyridin-4-yl)-1H-pyrazol-3-yl]-2-fluoro-phenyl}-2,5-difluoro-N-methoxymethyl-benzenesulfonamide, HPLC (254 nm): R$_t$: 6.59 min; $^1$H NMR (DMSO-d6) Shift: 8.18 (s, 1H), 7.77 (d, J=5.2 Hz, 1H), 7.58-7.66 (m, 1H), 7.45-7.58 (m, 3H), 7.23-7.35 (m, 2H), 6.26 (s, 1H), 6.15 (dd, J=1.1, 5.4 Hz, 1H), 5.76 (br. s., 1H), 5.01 (s, 2H), 4.43-4.56 (m, 2H), 3.89-3.97 (m, 1H), 3.30 (s, 3H), 3.17-3.25 (m, 1H), 2.69-2.78 (m, 1H), 2.02-2.16 (m, 2H), 2.05 (s, 3H), 1.94 (qd, J=4.6, 12.1 Hz, 1H), 1.79 (qd, J=4.5, 12.1 Hz, 1H), 1.31 (s, 9H); HRMS (ESI) calcd for C33H38F3N6O4S [M+H]$^+$ 671.2622. found 671.2623.

Method E, Step e

N-{3-[1-(1-Acetyl-piperidin-4-yl)-4-(2-amino-pyridin-4-yl)-1H-pyrazol-3-yl]-2-fluoro-phenyl}-2,5-difluoro-benzenesulfonamide Formula 1, where m=0; R1=1-acetyl-piperidin-4-yl; R2, R3=F; R4=2-amino-pyridin-4-yl

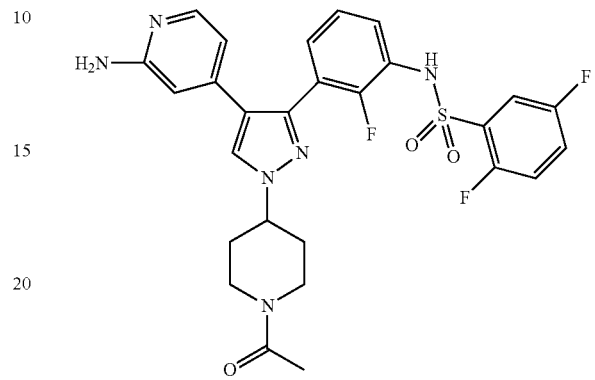

N-{3-[1-(1-Acetyl-piperidin-4-yl)-4-(2-tert-butylamino-pyridin-4-yl)-1H-pyrazol-3-yl]-2-fluoro-phenyl}-2,5-difluoro-N-methoxymethyl-benzenesulfonamide (85 mg, 0.127 mmol) was dissolved in a 9:1 TFA/water mixture (2 mL) and stirred at 60° C. for 8 h. The reaction mixture was concentrated under reduced pressure, then taken up with DCM and washed with a saturated solution of NaHCO$_3$ and brine. The organic layer was dried over Na$_2$SO$_4$ and concentrated to dryness. The residue was purified by flash chromatography on silica gel (DCM/MeOH 9:1) affording 63 mg (87%) of the title compound as a white solid, HPLC (254 nm): R$_t$: 4.75 min; $^1$H NMR (DMSO-d6) Shift: 10.74 (s, 1H), 8.20 (s, 1H), 7.68 (d, J=5.4 Hz, 1H), 7.51-7.57 (m, 1H), 7.40-7.50 (m, 2H), 7.30 (td, J=2.3, 7.4 Hz, 1H), 7.09-7.25 (m, 2H), 6.27 (s, 1H), 6.10 (dd, J=1.3, 5.4 Hz, 1H), 5.82 (br. s., 2H), 4.37-4.56 (2 m, 2H), 3.81-3.98 (m, 1H), 3.14-3.25 (m, 1H), 2.68-2.79 (m, 1H), 2.05-2.16 (m, 2H), 2.04 (s, 3H), 1.93 (qd, J=3.7, 12.0 Hz, 1H), 1.77 (qd, J=4.5, 12.2 Hz, 1H); HRMS (ESI) calcd for C27H26F3N6O3S [M+H]$^+$ 571.1734. found 571.1711.

Example 11

2,5-Difluoro-N-{2-fluoro-3-[4-pyridin-4-yl-1-(tetrahydro-pyran-4-yl)-1H-pyrazol-3-yl]-phenyl}-benzenesulfonamide (Compound 16)

Formula I, where m=0; R$_1$=tetrahydro-pyran-4-yl; R2, R3=F; R4=4-pyridinyl

Method A, Step d

2,5-Difluoro-N-[2-fluoro-3-(4-pyridin-4-yl-2H-pyrazol-3-yl)-phenyl]-N-methoxymethyl-benzenesulfonamide Formula 4A, where R4=4-pyridinyl; PG$_1$=methoxymethyl; R30=2,5-difluoro-benzene-sulfonyl

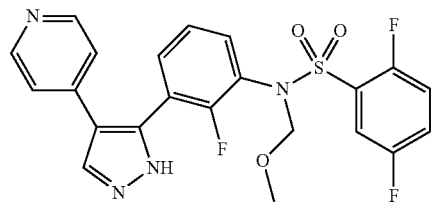 [SMILES: COCN(c1cccc(-c2[nH]ncc2-c2ccncc2)c1F)S(=O)(=O)c1cc(F)ccc1F]

2,5-Difluoro-N-{2-fluoro-3-[4-pyridin-4-yl-1-(tetrahydro-pyran-2-yl)-1H-pyrazol-3-yl]-phenyl}-N-methoxymethyl-benzenesulfonamide (950 mg, 1.61 mmol) (prepared as described in Example 8) was dissolved in MeOH (10 mL) and p-toluenesulfonic acid monohydrate (700 mg, 3.68 mmol) was added. The solution was heated at reflux for 2 h, it was concentrated under reduced pressure, then taken up with DCM and washed with a saturated solution of NaHCO$_3$ and brine. The organic layer was dried over Na$_2$SO$_4$ and concentrated to dryness. The residue was purified by flash chromatography on silica gel (cyclohexane/AcOEt from 4/6 to 2/8) affording 550 mg (72%) of the title compound as a colorless solid. HPLC (254 nm): R$_t$: 5.00 min; $^1$H NMR (DMSO-d6) Shift; 13.48 (s, 1H), 8.30-8.45 (m, 3H), 7.59 (m, 1H), 7.43-7.57 (m, 4H), 7.26-7.43 (m, 2H), 7.09 (d, J=5.98 Hz, 2H), 5.01 (s, 2H), 3.28 (s, 3H); HRMS (ESI) calcd for C20H14F3N4O2S [M+H]$^+$ 431.0784. found 431.0782.

Method A, Step e

2,5-Difluoro-N-{2-fluoro-3-[4-pyridin-4-yl-1-(tetrahydro-pyran-4-yl)-1H-pyrazol-3-yl]-phenyl}-N-methoxymethyl-benzenesulfonamide Formula 2, where R4=4-pyridyl; PG$_1$=methoxymethyl; R29=tetrahydro-pyran-4-yl; R30=2,5-difluoro-benzene-sulfonyl

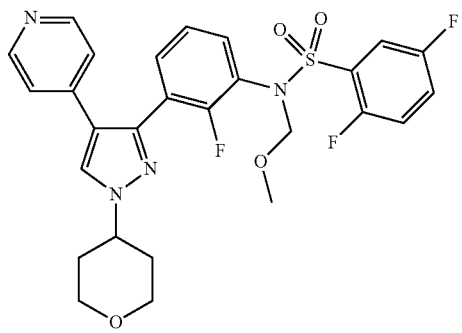 [SMILES: COCN(c1cccc(-c2nn(C3CCOCC3)cc2-c2ccncc2)c1F)S(=O)(=O)c1cc(F)ccc1F]

Cesium carbonate (260 mg, 0.8 mmol) and methanesulfonic acid tetrahydro-pyran-4-yl ester (108 mg, 0.6 mmol) were added to a solution of 2,5-difluoro-N-[2-fluoro-3-(4-pyridin-4-yl-2H-pyrazol-3-yl)-phenyl]-N-methoxymethyl-benzenesulfonamide (190 mg, 0.4 mmol) in DMF (3 mL) and the suspension was stirred at 70° C. overnight. The mixture was treated with water and AcOEt. The organic layer was washed once again with water and brine, then it was dried over Na$_2$SO$_4$ and concentrated under reduced pressure. The residue was purified by flash chromatography on silica gel (AcOEt:Hex 95:5) affording 60 mg of the title compound (27% yield). [M+H]$^+$ 559.

Method A, Step f

2,5-Difluoro-N-{2-fluoro-3-[4-pyridin-4-yl-1-(tetrahydro-pyran-4-yl)-1H-pyrazol-3-yl]-phenyl}-benzenesulfonamide Formula I, where m=0; R$_1$=tetrahydro-pyran-4-yl; R2, R3=F; R4=4-pyridinyl

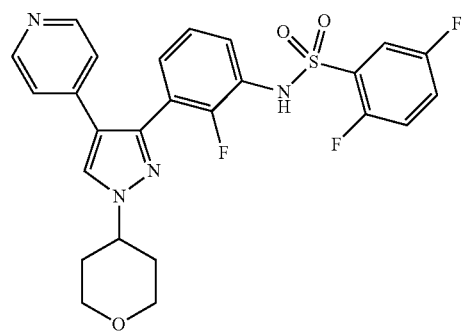 [SMILES: O=S(=O)(Nc1cccc(-c2nn(C3CCOCC3)cc2-c2ccncc2)c1F)c1cc(F)ccc1F]

2,5-Difluoro-N-{2-fluoro-3-[4-pyridin-4-yl-1-(tetrahydro-pyran-4-yl)-1H-pyrazol-3-yl]-phenyl}-N-methoxymethyl-benzenesulfonamide (60 mg, 0.107 mmol) was dissolved in a mixture of TFA:water 9:1 (1 mL) and stirred for 2 h at 70° C. The reaction mixture was concentrated under reduced pressure, then taken up with a saturated solution of NaHCO$_3$ and extracted with AcOEt. The organic layer was dried over Na$_2$SO$_4$ and concentrated to dryness. The residue was purified by flash chromatography on silica gel (AcOEt) affording 47 mg of the title compound (85% yield). HPLC (254 nm): R$_t$: 5.63 min; $^1$H NMR (DMSO-d6) Shift: 10.67 (br. s., 1H), 8.65 (s, 1H), 8.55 (d, J=6.6 Hz, 2H), 7.51-7.61 (m, 1H), 7.42-7.51 (m, 2H), 7.32-7.42 (m, 4H), 7.28 (t, J=7.9 Hz, 1H), 4.46-4.57 (m, 1H), 3.96-4.03 (m, 2H), 3.49 (td, J=11.7, 2.0 Hz, 2H), 2.05-2.16 (m, 2H), 1.93-2.06 (m, 2H); HRMS (ESI) calcd for C25H22F3N4O3S [M+H]$^+$ 515.1359. found 515.1356.

According to this same methodology but employing the suitable starting material, the following compound was prepared:

2,5-Difluoro-N-{2-fluoro-3-[1-(2-fluoro-ethyl)-4-pyridin-4-yl-1H-pyrazol-3-yl]-phenyl}-benzenesulfonamide (Compound 7)

Formula 1, where m=2; R$_1$; R2, R3=F; R4=4-pyridinyl

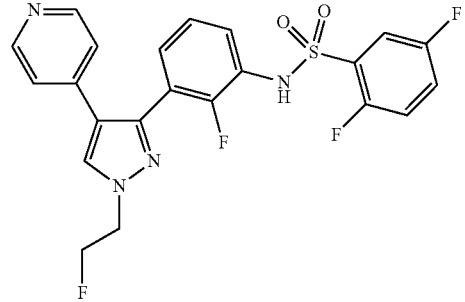 [SMILES: O=S(=O)(Nc1cccc(-c2nn(CCF)cc2-c2ccncc2)c1F)c1cc(F)ccc1F]

HPLC (254 nm): R$_t$: 5.54 min; $^1$H NMR (DMSO-d6) Shift: 10.67 (br. s., 1H), 8.36-8.39 (m, 3H), 7.51-7.60 (m, 1H), 7.40-7.51 (m, 2H), 7.37 (td, J=1.77, 7.60 Hz, 1H), 727-7.33

(m, 1H), 7.20-7.26 (m, 1H), 7.01-7.05 (m, 2H), 4.87-4.93 (m, 1H), 4.76-4.80 (m, 1H), 4.52-4.58 (m, 1H), 4.45-4.50 (m, 2H); HRMS (ESI) calcd for C22H17F4N4O2S [M+H]+ 477.1003. found 477.0981.

Example 12

2,5-Difluoro-N-(2-fluoro-3-{1-[2-(4-methyl-piperazin-1-yl)-ethyl]-4-pyridin-4-yl-1H-pyrazol-3-yl}-phenyl)-benzenesulfonamide Formula I, where m=2; R$_1$=4-methyl-piperazin-1-yl; R2, R3=F; R4=4-pyridinyl Method C, Step k

N-(3-{4-Bromo-[2-(tetrahydro-pyran-2-yloxy)-ethyl]-1H-pyrazol-3-yl}-2-fluoro-phenyl)-2,5-difluoro-N-methoxymethyl-benzenesulfonamide Formula 1, where Hal=Br; PG$_1$=methoxymethyl; R29=2-(tetrahydro-pyran-2-yloxy)-ethyl; R30=2,5-difluoro-benzene-sulfonyl

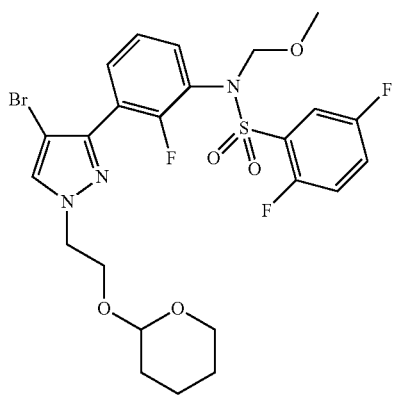 [SMILES: COCN(c1cccc(-c2nn(CCOC3CCCCO3)cc2Br)c1F)S(=O)(=O)c1cc(F)ccc1F]

A solution of N-[3-(4-Bromo-1H-pyrazol-3-yl)-2-fluoro-phenyl]-2,5-difluoro-N-methoxymethyl-benzenesulfonamide (346 mg, 0.726 mmol)(prepared as described in Preparation 1) in anhydrous DMF (4 mL) was cooled to 0° C. under an argon atmosphere and sodium hydride (60% in mineral oil, 87 mg, 2.179 mmol, 3 eq) was added. The mixture was stirred at 0° C. for 30 minutes, then 2-(2-bromo-ethoxy)-tetrahydro-pyran (0.165 mL, 1.089 mmol, 1.5 eq) was added dropwise and the mixture was stirred at 0° C. for 1 hour. The reaction mixture was then diluted with AcOEt and washed with water and brine. The organic layer was dried over Na$_2$SO$_4$ and evaporated to dryness. The crude product was purified by flash chromatography on silica gel (cyclohexane/AcOEt 55:45) affording 243 mg (55%) of the desired regioisomer N-(3-{4-Bromo-1-[2-(tetrahydro-pyran-2-yloxy)-ethyl]-1H-pyrazol-3-yl}-2-fluoro-phenyl)-2,5-difluoro-N-methoxymethyl-benzenesulfonamide. HPLC (254 nm): R$_t$: 7.21 min; $^1$H NMR (DMSO-d6) Shift (selected signals): 8.07 (s, 1H), 7.55-7.69 (m, 2H), 7.47-7.53 (m, 2H), 7.39-7.45 (m, 1H), 7.30-7.35 (m, 1H), 5.09 (s, 2H), 4.51-4.57 (m, 1H), 4.29-4.35 (m, 2H), 3.89-3.97 (m, 1H), 3.70-3.78 (m, 1H), 3.42-3.51 (m, 1H), 3.38 (s, 3H), 1.29-1.69 (3 m, 6H); HRMS (ESI) calcd for C24H26BrF3N3O5S [M+H]+ 604.0723. found 604.0693.

Method A, Step a

2,5-Difluoro-N-(2-fluoro-3-{4-pyridin-4-yl-1-[2-(tetrahydro-pyran-2-yloxy)-ethyl]-1H-pyrazol-3-yl}-phenyl)-N-methoxymethyl-benzenesulfonamide Formula 2, where R4=4-pyridinyl; PG$_1$=methoxymethyl; R29=2-(tetrahydro-pyran-2-yloxy)-ethyl; R30=2,5-difluoro-benzene-sulfonyl

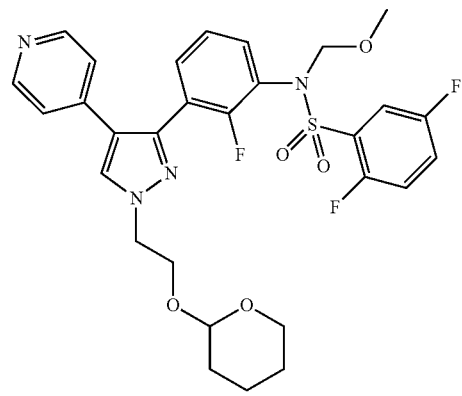 [SMILES: COCN(c1cccc(-c2nn(CCOC3CCCCO3)cc2-c2ccncc2)c1F)S(=O)(=O)c1cc(F)ccc1F]

To an argon degassed solution of N-(3-{4-Bromo-1-[2-(tetrahydro-pyran-2-yloxy)-ethyl]-1H-pyrazol-3-yl}-2-fluoro-phenyl)-2,5-difluoro-N-methoxymethyl-benzenesulfonamide (233 mg, 0.385 mmol) in 1,2-dimethoxyethane: water 9.1 (4.5 mL) in a microwave vial, 4-(4,4,5,5-tetramethyl-[1,3,2]dioxaborolan-2-yl)-pyridine (118 mg, 0.578 mmol, 1.5 eq), cesium carbonate (251 mg, 0.770 mmol, 2 eq) and Pd(dppf)Cl$_2$.CH$_2$Cl$_2$ (31 mg, 0.038 mmol, 0.1 eq) were added, under an argon atmosphere. The mixture was heated in the microwave oven at 100° C. for 30 minutes, then it was filtered through a Celite pad, which was washed thoroughly with AcOEt. The filtrate was washed with saturated aqueous NaHCO$_3$ and brine. The organic layer was dried over Na$_2$SO$_4$ and concentrated to dryness. The residue was purified by flash chromatography on silica gel (DCM/MeOH 97.3) affording 210 mg (90%) of the title compound. HPLC (254 nm): R$_t$: 6.38 min; $^1$H NMR (DMSO-d6) Shift: 8.37-8.40 (m, 2H), 8.37 (s, 1H), 7.56-7.65 (m, 1H), 7.45-7.56 (m, 3H), 7.29-7.41 (m, 2H), 7.03-7.08 (m, 2H), 5.00 (s, 2H), 4.57 (t, J=3.1 Hz, 1H), 4.34-4.41 (m, 2H), 3.95-4.03 (m, 1H), 3.76-3.84 (m, 1H), 3.41-3.50 (m, 1H), 3.27-3.34 (m, 1H), 3.29 (s, 1H), 1.25-1.70 (m, 6H); HRMS (ESI) calcd for C29H30F3N4O5S [M+]+ 603.1884. found 603.1870.

2,5-Difluoro-N-{2-fluoro-3-[1-(2-hydroxy-ethyl)-4-pyridin-4-yl-1H-pyrazol-3-yl]-phenyl}-N-methoxymethyl-benzenesulfonamide Formula 2, where R4=4-pyridinyl, PG$_1$=methoxymethyl, R29=2-hydroxy-ethyl, R30=2,5-difluoro-benzene-sulfonyl

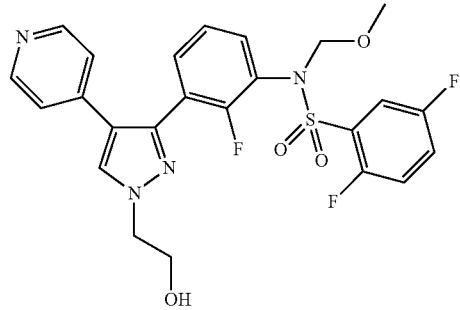 [SMILES: COCN(c1cccc(-c2nn(CCO)cc2-c2ccncc2)c1F)S(=O)(=O)c1cc(F)ccc1F]

To a solution of 2,5-difluoro-N-(2-fluoro-3-{4-pyridin-4-yl-1-[2-(tetrahydro-pyran-2-yloxy)-ethyl]-1H-pyrazol-3-yl}-phenyl)-N-methoxymethyl-benzenesulfonamide (205 mg, 0.340 mmol) in MeOH (2 mL) p-toluenesulfonic acid monohydrate (78 mg, 0.408 mmol, 1.2 eq) was added and the reaction mixture was stirred at r.t. for 2 h. It was then diluted with DCM and washed with saturated aqueous NaHCO₃ and brine. The organic layer was dried over Na₂SO₄ and concentrated to dryness. The crude product (181 mg) was used without further purification in the following step HPLC (254 nm): $R_t$: 5.27 min; ¹H NMR (DMSO-d6) Shift: 8.37-8.40 (m, 2H), 8.33 (s, 1H), 7.57-7.65 (m, 1H), 7.45-7.57 (m, 3H), 7.28-7.38 (m, 2H), 7.05-7.08 (m, 2H), 5.01 (s, 2H), 5.00 (t, J=5.25, 1H), 4.23 (t, J=5.4 Hz, 2H), 3.82 (q, J=5.4 Hz, 2H), 3.29 (s, 3H); HRMS (ESI) calcd for C24H22F3N4O4S [M+H]⁺ 519.1309. found 519.1285.

2,5-Difluoro-N-(2-fluoro-3-{1-[2-(4-methyl-piperazin-1-yl)-ethyl]-4-pyridin-4-yl-1H-pyrazol-3-yl}-phenyl)-N-methoxymethyl-benzenesulfonamide Formula 2, where R4=4-pyridinyl, PG₁=methoxymethyl, R29=2-(4-methyl-piperazin-1-yl)-ethyl, R30=2,5-difluoro-benzene-sulfonyl

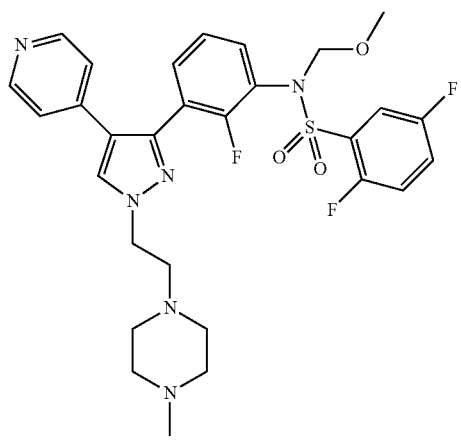 [SMILES: COCN(c1cccc(-c2nn(CCN3CCN(C)CC3)cc2-c2ccncc2)c1F)S(=O)(=O)c1cc(F)ccc1F]

To a solution of 2,5-difluoro-N-{2-fluoro-3-[1-(2-hydroxy-ethyl)-4-pyridin-4-yl-1H-pyrazol-3-yl]-phenyl}-N-methoxymethyl-benzenesulfonamide (177 mg, 0.341 mmol) in anhydrous DCM (2 mL) triethylamine (0.047 mL, 0.341 mmol, 1 eq) was added followed by mesylchloride (0.034 mL, 0.341 mmol, 1 eq) and the mixture was stirred at r.t. for 1 h. N-methyl piperazine (0.040 mL, 1 eq) was then added and the reaction mixture was stirred at r.t. for 1 h. A solvent switch to acetonitrile was then made and the reaction was heated to 80° C. After 1 hour, 2 more equivalents of N-methylpiperazine were added and heating was continued. After addition of 2 more equivalents of N-methylpiperazine and heating for 3 more h, the reaction was diluted with AcOEt and washed with saturated aqueous NaHCO₃. The aqueous phase was basified to pH11 and extracted with AcOEt. The combined organic layers were washed with brine, dried over Na₂SO₄ and concentrated to dryness. The crude product was purified by flash chromatography on silica gel (DCM/EtOH/NH₃ 7N in MeOH 90:8:2) affording 114 mg of the title compound.

2,5-Difluoro-N-(2-fluoro-3-{1-[2-(4-methyl-piperazin-1-yl)-ethyl]-4-pyridin-4-yl-1H-pyrazol-3-yl}-phenyl)-benzenesulfonamide Formula I, where m=2; $R_1$=4-methyl-piperazin-1-yl; R2, R3=F; R4=4-pyridinyl]

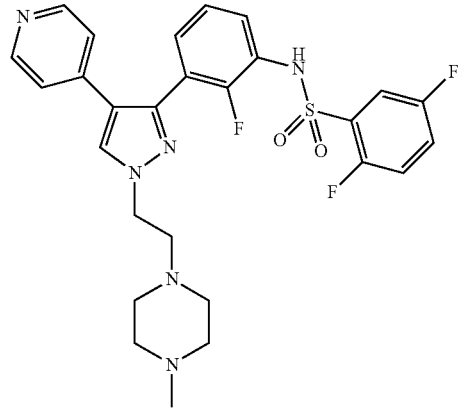 [SMILES: CN1CCN(CCn2cc(-c3ccncc3)c(-c3cccc(NS(=O)(=O)c4cc(F)ccc4F)c3F)n2)CC1]

2,5-Difluoro-N-{2-fluoro-3-[4-pyridin-4-yl-1-(tetrahydro-pyran-4-yl)-1H-pyrazol-3-yl]-phenyl}-N-methoxymethyl-benzenesulfonamide (57 mg, 0.095 mmol) was dissolved in a mixture of TFA:water 9:1 (2 mL) and stirred for 1 h at 60° C. The reaction mixture was concentrated under reduced pressure, then taken up with a saturated solution of NaHCO₃ and extracted with AcOEt. The organic layer was dried over Na₂SO₄ and concentrated to dryness. The residue was purified by flash chromatography on silica gel (DCM/EtOH/NH₃ 7N in MeOH 80:15:5) affording 44 mg of the title compound, impure of the minor regioisomer. After crystallization form AcOEt 33 mg of pure 2,5-difluoro-N-(2-fluoro-3-{1-[2-(4-methyl-piperazin-1-yl)-ethyl]-4-pyridin-4-yl-1H-pyrazol-3-yl}-phenyl)-benzenesulfonamide were obtained as white solid. HPLC (254 nm): $R_t$: 4.59 min; ¹H NMR (DMSO-d6) Shift: 10.20 (br. s, 1H), 8.35-8.40 (m, 2H), 8.33 (s, 1H), 7.34-7.48 (m, 3H), 7.31 (dt, J=1.95, 7.57, 1H), 7.07-7.16 (m, 1H), 7.02-7.07 (m, 2H), 4.28 (t, J=6.6 Hz, 2H), 2.81 (t, J=6.5 Hz, 2H), 2.53-2.62 (m, 8H), 2.29-2.38 (m, 3H); HRMS (ESI) calcd for C27H28F3N6O2S [M+H]⁺ 557.1941. found 557.1917.

According to this same methodology but employing the suitable nucleophile in the nucleophilic substitution, the following compound was prepared:

2,5-Difluoro-N-{2-fluoro-3-[1-(2-piperidin-1-yl-ethyl)-4-pyridin-4-yl-1H-pyrazol-3-yl]-phenyl}-benzenesulfonamide Formula I, where m=2; $R_1$=piperidin-1-yl; R2, R3=F; R4=4-pyridinyl

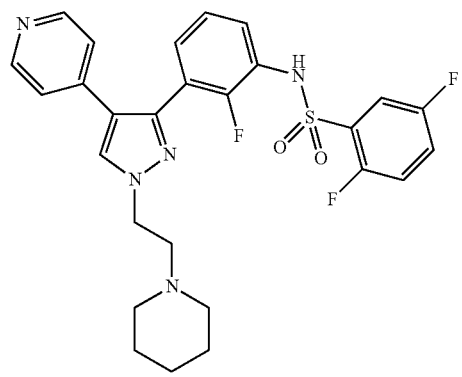 [SMILES: O=S(=O)(Nc1cccc(-c2nn(CCN3CCCCC3)cc2-c2ccncc2)c1F)c1cc(F)ccc1F]

HPLC (254 nm): $R_t$: 4.96 min; $^1$H NMR (DMSO-d6) Shift (selected signals): 10.42 (br. s., 1H), 8.35-8.40 (m, 2H), 8.34 (s, 1H), 7.47-7.55 (m, 1H), 7.38-7.46 (m, 2H), 7.29-7.37 (m, 1H), 7.15-7.22 (m, 2H), 6.99-7.05 (m, 2H), 4.31 (t, J=6.7 Hz, 2H), 2.85 (t, J=5.7 Hz, 2H), 1.51 (quin, J=5.6 Hz, 4H), 1.34-1.44 (m, 2H); HRMS (ESI) calcd for C27H27F3N5O2S [M+H]$^+$ 542.1832. found 542.1828.

Example 13

2,5-Difluoro-N-{2-fluoro-3-[1-(1-methyl-piperidin-4-yl)-4-(1H-pyrrolo[2,3-b]pyridin-4-yl)-1H-pyrazol-3-yl]-phenyl}-benzenesulfonamide (Compound 8)

Formula I, where m=2; $R_1$=1-methyl-piperidin-4-yl; R2, R3=F; R4=1 H-pyrrolo[2,3-b]pyridin-4-yl Method A, Step b

4-[3-{3-[(2,5-Difluoro-benzenesulfonyl)-methoxymethyl-amino]-2-fluoro-phenyl}-4-(4,4,5,5-tetramethyl-[1,3,2]dioxaborolan-2-yl)-pyrazol-1-yl]-piperidine-1-carboxylic acid tert-butyl ester Formula 3, where M'=4,4,5,5-tetramethyl-[1,3,2]dioxaborolan-2-yl, $PG_1$=methoxymethyl, R29=1-tert-butoxycarbonyl, R30=2,5-difluoro-benzene-sulfonyl

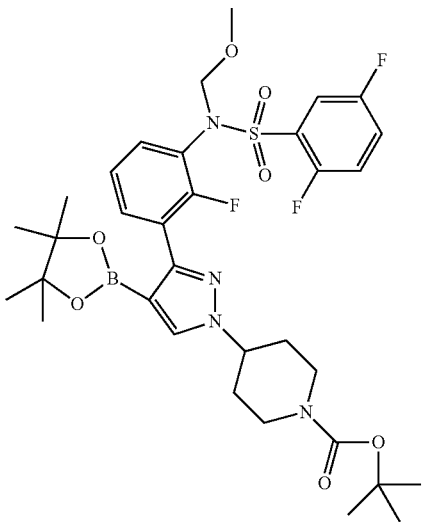 [SMILES: COCN(c1cccc(-c2nn(C3CCN(C(=O)OC(C)(C)C)CC3)cc2B2OC(C)(C)C(C)(C)O2)c1F)S(=O)(=O)c1cc(F)ccc1F]

To an argon degassed solution of 4-(4-bromo-3-{3-[(2,5-difluoro-benzenesulfonyl)-methoxymethyl-amino]-2-fluoro-phenyl}-pyrazol-1-yl)-piperidine-1-carboxylic acid tert-butyl ester (see Example 2 Method C, Step k) (730 mg, 1.1073 mmol) in toluene (11 mL) in a microwave vial, 4,4,5,5-tetramethyl-[1,3,2]dioxaborolane (1.411 g, 11.07 mmol), TEA (0.385 mL, 2.77 mmol), 2-dicyclohexylphosphino-2',6'-dimethoxy-1,1'-biphenyl (46 mg, 0.111 mmol) and bis(acetonitrile)dichloropalladium(II) (14 mg, 0.056 mmol) were added, under argon atmosphere. The mixture was heated in the microwave oven at 90° C. for 30 minutes, then it was filtered through a Celite pad. The solution was concentrated to dryness and the residue was purified by flash chromatography on silica gel (Hex/AcOEt 8:2) affording 354 mg of the title compound (45% yield). [M+H]$^+$ 707.

Method A, Step c

4-[3-{3-[(2,5-Difluoro-benzenesulfonyl)-methoxymethyl-amino]-2-fluoro-phenyl}-4-(1H-pyrrolo[2,3-b]pyridin-4-yl)-pyrazol-1-yl]-piperidine-1-carboxylic acid tert-butyl ester Formula 2, where R4=1H-pyrrolo[2,3-b]pyridin-4-yl, $PG_1$=methoxymethyl, R29=2-(4-methyl-piperazin-1-yl)-ethyl, R30=2,5-difluoro-benzene-sulfonyl

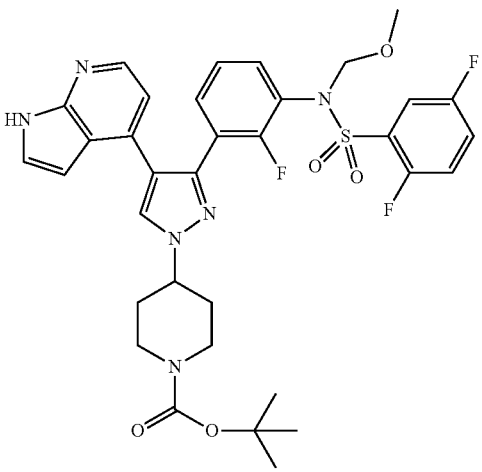 [SMILES: COCN(c1cccc(-c2nn(C3CCN(C(=O)OC(C)(C)C)CC3)cc2-c2ccnc3[nH]ccc23)c1F)S(=O)(=O)c1cc(F)ccc1F]

In a microwave tube a solution of 4-[3-{3-[(2,5-difluoro-benzenesulfonyl)-methoxymethyl-amino]-2-fluoro-phenyl}-4-(4,4,5,5-tetramethyl-[1,3,2]dioxaborolan-2-yl)-pyrazol-1-yl]-piperidine-1-carboxylic acid tert-butyl ester (354 mg, 0.501 mmol) in DME/H$_2$O 9:1 (5 mL) was degassed by bubbling argon for 5 minutes. 4-Iodo-7-azaindole (134 mg, 0.501 mmol, 1 eq) was then added, followed by cesium carbonate (325 mg, 1.0 mmol, 2 eq) and Pd(dppf)Cl$_2$.CH$_2$Cl$_2$ (82 mg, 0.050 mmol, 0.2 eq). The mixture was irradiated in the microwave oven at 90° C. for 1 hr and then filtered through a Celite pad, and was washed with saturated aqueous NaHCO$_3$ and brine. The organic layer was dried over Na$_2$SO$_4$ and evaporated to dryness. The crude product was purified by chromatography on silica gel (DCM/MeOH 98:2) affording 270 mg of the title compound (35% yield) as a white solid. [M+H]$^+$ 697.

2,5-Difluoro-N-{2-fluoro-3-[1-piperidin-4-yl-4-(1H-pyrrolo[2,3-b]pyridin-4-yl-1H-pyrazol-3-yl]-phenyl}-benzenesulfonamide Formula I, where m=2; $R_1$=piperidin-4-yl; R2, R3=F; R4=H-pyrrolo[2,3-b]pyridin-4-yl

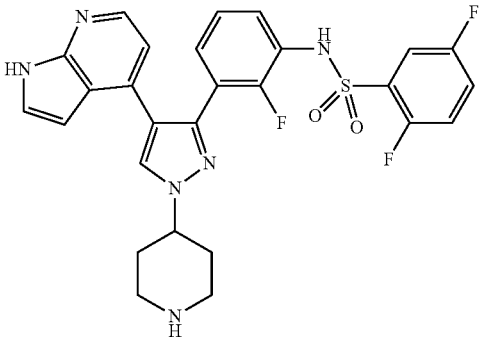 [SMILES: O=S(=O)(Nc1cccc(-c2nn(C3CCNCC3)cc2-c2ccnc3[nH]ccc23)c1F)c1cc(F)ccc1F]

4-[3-{3-[(2,5-Difluoro-benzenesulfonyl)-methoxym-ethyl-amino]-2-fluoro-phenyl}-4-(1H-pyrrolo[2,3-b]pyridin-4-yl)-pyrazol-1-yl]-piperidine-1-carboxylic acid tert-butyl ester (130 mg, 0.187 mmol) was dissolved in a 9:1 TFA/water mixture (1 mL) and stirred at 60° C. for 1 hour. The reaction mixture was concentrated under reduced pressure, then taken up with toluene and concentrated to dryness for three times. The crude was used without further purification for the following step. [M+H]$^+$ 553.

2,5-Difluoro-N-{2-fluoro-3-[1-(1-methyl-piperidin-4-yl)-4-(1H-pyrrolo[2,3-b]pyridin-4-yl)-1H-pyrazol-3-yl]-phenyl}-benzenesulfonamide Formula I, where m=2; $R_1$=1-methyl-piperidin-4-yl; R2, R3=F; R4=1H-pyrrolo[2,3-b]pyridin-4-yl

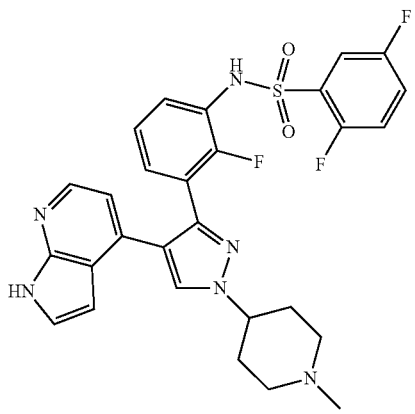 [SMILES: CN1CCC(n2cc(-c3ccnc4[nH]ccc34)c(-c3cccc(NS(=O)(=O)c4cc(F)ccc4F)c3F)n2)CC1]

To a solution of 2,5-difluoro-N-{2-fluoro-3-[1-piperidin-4-yl-4-(1H-pyrrolo[2,3-b]pyridin-4-yl)-1H-pyrazol-3-yl]-phenyl}-benzenesulfonamide (103 mg, 0.187 mmol) in MeOH (2 mL) 37% aqueous formaldehyde (0.021 mL, 0.281 mmol, 1.5 eq) was added, followed by acetic acid (0.032 mL, 0.56 mmol, 3 eq) and sodium cyanoborohydride (19 mg, 0.299 mmol, 1.6 eq) and the mixture was stirred at r.t. for 2 h. The solvent was then evaporated under reduced pressure and the residue was taken up with AcOEt and washed with aqueous NaHCO$_3$ and brine. The organic layer was dried over Na$_2$SO$_4$ and evaporated to dryness. The crude product was purified by chromatography on silica gel (DCM/MeOH/aq.NH$_3$ 90:10:1). The material so obtained was taken up with diethyl ether and filtered affording 16 mg of the title compound (15% yield over two steps) as a white solid, HPLC (254 nm): R$_t$: 4.66 min; $^1$H NMR (DMSO-d6) Shift: 11.60 (br. s., 1H), 10.57 (s, 1H), 8.34 (s, 1H), 7.97 (d, J=5.00 Hz, 1H), 7.51-7.59 (m, 1H), 7.38-7.48 (m, 2H), 7.36 (dd, J=2.69, 3.30 Hz, 1H), 7.30 (td, J=1.77, 7.60 Hz, 1H), 720-7.27 (m, 1H), 7.10-7.20 (m, 1H), 6.49 (d, J=5.00 Hz, 1H), 6.24 (dd, J=1.89, 3.31 Hz, 1H), 4.94 (t, J=4.70 Hz, 1H), 4.82 (t, J=4.70 Hz, 1H), 4.60 (t, J=4.82 Hz, 1H), 4.53 (t, J=4.82 Hz, 1H); HRMS (ESI) calcd for C28H26F3N6O2S [M+H]$^+$ 567.1785. found 567.1788.

Example 14

N-[3-(1-Ethyl-4-pyridin-4-yl-1H-pyrazol-3-yl)-2-fluoro-phenyl]-3-fluoro-benzenesulfonamide Formula I, where m=1; $R_1$=CH$_3$; R2=H; R3=F; R4=4-pyridinyl Method C, Step a {2-Fluoro-3-[2-(tetrahydro-pyran-2-yl)-2H-pyrazol-3-yl]-phenyl}-carbamic acid tert-butyl ester Formula 9, where PG$_1$=tert-butoxycarbonyl, R30=H, R29=tetrahydro-pyran-2-yl

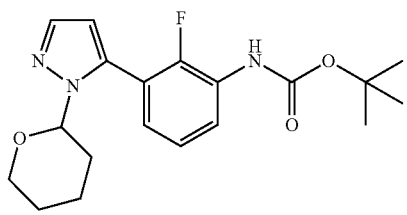 [SMILES: CC(C)(C)OC(=O)Nc1cccc(-c2ccnn2C2CCCCO2)c1F]

In a microwave tube N-Boc-3-bromo-2-fluoro-aniline (300 mg, 1.034 mmol) was dissolved in a 9:1 DME/H$_2$O mixture (12 mL) and argon was bubbled through the solution for 10 minutes. 1-(tetrahydro-2H-pyran-2-yl)-5-(4,4,5,5-tetramethyl-1,3,2-dioxaborolan-2-yl)-1H-pyrazole (prepared as described in WO2010/010154) (576 mg, 2.071 mmol, 2 eq) was then added, followed by cesium carbonate (1.0 g, 3 eq) and Pd(dppf)Cl$_2$.CH$_2$Cl$_2$ (84 mg, 14.6 mmol, 0.1 eq) and the reaction mixture was irradiated at 100° C. for 30 minutes. A further addition of 1-(tetrahydro-2H-pyran-2-yl)-5-(4,4,5,5-tetramethyl-1,3,2-dioxaborolan-2-yl)-1H-pyrazole (1 eq) was made and a second microwave cycle was performed at 100° C. for 30 min. The mixture was then filtered over a Celite pad, which was washed with AcOEt. The filtrate was washed with water and brine, dried over Na$_2$SO$_4$ and evaporated to dryness. The crude was purified by chromatography on silica gel (Hex/AcOEt 8:2) to give 570 mg of {2-Fluoro-3-[2-(tetrahydro-pyran-2-yl)-2H-pyrazol-3-yl]-phenyl}-carbamic acid tert-butyl ester contaminated by N-tetrahydropyranyl-pyrazole (NMR title about 57%). HPLC (254 nm): R$_t$: 6.82 min; $^1$H NMR (DMSO-d6) Shift: 9.09 (s, 1H), 7.72 (t, J=7.6 Hz, 1H), 7.62 (d, J=1.8 Hz, 1H), 7.22-7.29 (m, 1H), 7.16-7.22 (m, 1H), 6.42-6.45 (m, 1H), 5.09-5.15 (m, 1H), 3.86-3.95 (m, 1H), 3.35-3.46 (m, 1H), 1.51-1.73 (many m, 6H), 1.48 (s, 9H); HRMS (ESI) calcd for C19H25FN3O3 [M+H]$^+$ 362.1875. found 362.1874.

Method C, Step e

[2-Fluoro-3-(2H-pyrazol-3-yl)-phenyl]-carbamic acid tert-butyl ester

Formula 17, where PG$_1$=tert-butoxycarbonyl, R30=H

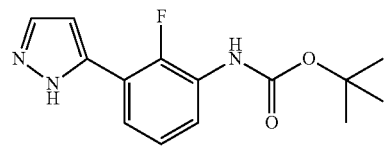 [SMILES: CC(C)(C)OC(=O)Nc1cccc(-c2ccn[nH]2)c1F]

To a solution of crude {2-fluoro-3-[2-(tetrahydro-pyran-2-yl)-2H-pyrazol-3-yl]-phenyl}-carbamic acid tert-butyl ester (570 mg containing a maximum theorical amount of 1.034 mmol) in MeOH (10 mL), p-toluensulfonic acid (48 mg) was added and the solution was stirred at r.t. for 2 h. The reaction mixture was then concentrated under reduced pressure, taken up with AcOEt (100 mL) and washed with sat, aq. NaHCO$_3$ (2×50 mL) and brine (50 mL). The organic phase was dried over Na$_2$SO$_4$ and evaporated to dryness, affording 400 mg of crude product. [M+H]$^+$ 278.

Method C, Step g

[3-(4-Bromo-2H-pyrazol-3-yl)-2-fluoro-phenyl]-carbamic acid tert-butyl ester

Formula 18, where Hal=Br, PG$_1$=tert-butoxycarbonyl, R30=H

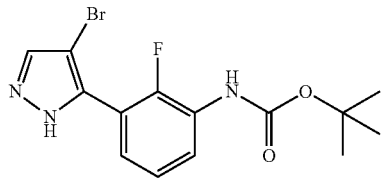 [SMILES: CC(C)(C)OC(=O)Nc1cccc(-c2[nH]ncc2Br)c1F]

To a stirred solution of [2-fluoro-3-(2H-pyrazol-3-yl)-phenyl]-carbamic acid tert-butyl ester (400 mg, containing a maximum theorical amount of 1,034 mmol) in DCM (5 mL) N-bromosuccinimide (160 mg, 0.9 mmol) was added and the solution was stirred at r.t. for 16 hrs. After a further addition of NBS (16 mg) and 1 more hour of stirring, the mixture was then diluted with DCM (50 mL) and washed with 10% aqueous NaHSO$_3$ (2×10 mL) and brine. The organic layer was dried over Na$_2$SO$_4$ and evaporated to dryness. The crude product was purified by flash chromatography on silica gel (cyclohexane/AcOEt 8:2 to 7:3) affording 310 mg of the title compound (84% yield over 3 steps). HPLC (254 nm): R$_t$: 6.28 min; $^1$H NMR (DMSO-d6) Shift (mixture of tautomers): 13.43, 13.48 (2 br. s., 1H), 9.00, 9.14 (2 br. s., 1H), 8.10 (br. s., 1H), 7.69 (br. s., 1H), 7.18 (br. s., 2H), 1.47 (s, 9H); [M+H]$^+$ 357.

Method C, Step k

[3-(4-Bromo-1-ethyl-1H-pyrazol-3-yl)-2-fluoro-phenyl]-carbamic acid tert-butyl ester Formula 1, where Hal=Br, PG$_1$=tert-butoxycarbonyl, R30=H, R29=ethyl

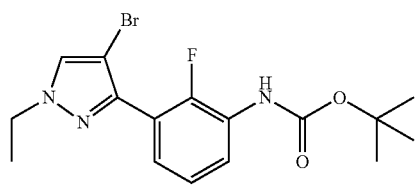 [SMILES: CCn1cc(Br)c(-c2cccc(NC(=O)OC(C)(C)C)c2F)n1]

[3-(4-Bromo-2H-pyrazol-3-yl)-2-fluoro-phenyl]-carbamic acid tert-butyl ester (305 mg, 0.856 mmol) was dissolved in DCM (4.5 mL) and aqueous 32% NaOH (4.5 mL) was added, followed by ethyl iodide (0.076 mL, 0.942 mmol, 1.1 eq) and tetrabutylammonium bromide (28 mg, 0.086 mmol, 0.1 eq) and the biphasic mixture was vigorously stirred at r.t. for 1 h. A further addition of 26 mg of tetrabutylammonium bromide and 0.030 mL of ethyl iodide were then added and the reaction mixture was stirred for 3 more h. The mixture was then diluted with DCM and water and the two phases were separated. The aqueous phase was extracted with DCM. The combined organic layers were washed with water and brine, dried over Na$_2$SO$_4$ and evaporated to dryness. The two regioisomers were separated by flash chromatography on silica gel (cyclohexane/AcOEt 9:1) to give 153 mg of the N1-alkylated product (46%) (N-[3-(4-Bromo-1-ethyl-1H-pyrazol-3-yl)-2-fluoro-phenyl]-2,5-difluoro-N-methoxymethyl-benzenesulfonamide and 78 mg of the N2-alkylated product. HPLC (254 nm): R$_t$: 7.03 min; $^1$H NMR (DMSO-d6) Shift: 9.00 (s, 1H), 8.11 (s, 1H), 7.62-7:70 (m, 1H), 710-7.22 (m, 2H), 4.18 (q, J=7.2 Hz, 2H), 1.47 (s, 9H), 1.40 (t, J=7.3 Hz, 3H); HRMS (ESI) calcd for C16H20BrFN3O2 [M+H]$^+$ 384.0718. found 384.0704.

Method A, Step a

[3-(1-Ethyl-4-pyridin-4-yl-1H-pyrazol-3-yl)-2-fluoro-phenyl]-carbamic acid tert-butyl ester Formula 2, where R4=4-pyridinyl, PG$_1$=tert-butoxycarbonyl, R30=H, R29=ethyl

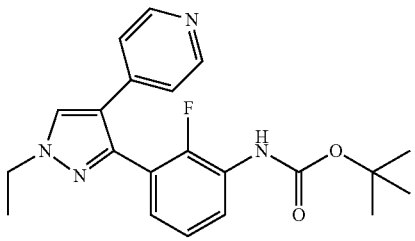 [SMILES: CCn1cc(-c2ccncc2)c(-c2cccc(NC(=O)OC(C)(C)C)c2F)n1]

To an argon degassed solution of (N-[3-(4-Bromo-1-ethyl-1H-pyrazol-3-yl)-2-fluoro-phenyl]-2,5-difluoro-N-methoxymethyl-benzenesulfonamide (153 mg, 0.398 mmol) in 1,2-dimethoxyethane:water 9:1 (4 mL) in a microwave vial, 4-(4,4,5,5-tetramethyl-[1,3,2]dioxaborolan-2-yl)-pyridine (122 mg, 0.597 mmol, 1.5 eq), cesium carbonate (260 mg, 0.798 mmol, 2 eq) and Pd(dppf)Cl$_2$.CH$_2$Cl$_2$ (33 mg, 0.040 mmol, 0.1 eq) were added, under argon atmosphere. The mixture was heated in the microwave oven at 100° C. for 30 minutes, then it was filtered through a Celite pad. The solution was taken up with AcOEt and washed with saturated aqueous NaHCO$_3$ and brine. The organic layer was dried over Na$_2$SO$_4$ and concentrated to dryness. The crude product was used in the following step without any further purification. [M+H]$^+$ 383.

Method A, Step g 3-(1-Ethyl-4-pyridin-4-yl-1H-pyrazol-3-yl)-2-fluoro-phenylamine Formula 5A, where m=1; R$_1$=methyl; R4=4-pyridinyl

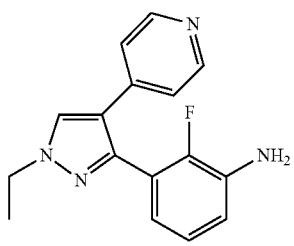 [SMILES: CCn1cc(-c2ccncc2)c(-c2cccc(N)c2F)n1]

To a solution of [3-(1-Ethyl-4-pyridin-4-yl-1H-pyrazol-3-yl)-2-fluoro-phenyl]-carbamic acid tert-butyl ester (200 mg, 0.523 mmol) in DCM (3 mL) 2 mL of trifluoacetic acid were added and the mixture was stirred at r.t. for 2 h. The mixture was then evaporated to dryness and the residue was taken up with DCM and washed with saturated aqueous NaHCO$_3$ and brine. The organic layer was dried over Na$_2$SO$_4$ and concentrated to dryness. The crude product was purified by flash chromatography on silica gel (DCM/MeOH 98:2) affording 86 mg of the title compound (77% yield over 2 steps). HPLC (254 nm): R$_t$: 4.54 min; $^1$H NMR (DMSO-d6) Shift: 8.37-8.41 (m, 2H), 8.34 (s, 1H), 7.13-7.20 (m, 2H), 6.90-6.96 (m, 1H), 6.82 (td, J=1.7, 8.2 Hz, 1H), 6.55 (ddd, J=1.8, 6.1, 7.6 Hz, 1H), 5.13 (s, 2H), 4.21 (q, J=7.3 Hz, 2H), 1.46 (t, J=7.3 Hz, 3H); HRMS (ESI) calcd for C16H16FN4 [M+H]$^+$ 283.1354. found 283.1350.

Method A, Step h

N-[3-(1-Ethyl-4-pyridin-4-yl-1H-pyrazol-3-yl)-2-fluoro-phenyl]-3-fluoro-benzenesulfonamide Formula 1, where m=2; R$_1$, R2=H; R3=F; R4=4-pyridinyl

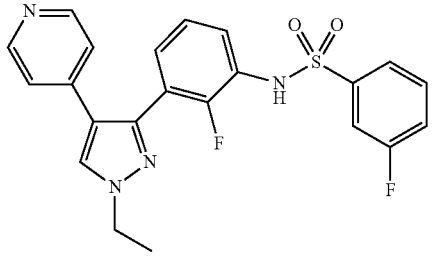 [SMILES: CCn1cc(-c2ccncc2)c(-c2cccc(NS(=O)(=O)c3cccc(F)c3)c2F)n1]

To a solution of 3-(1-Ethyl-4-pyridin-4-yl-1H-pyrazol-3-yl)-2-fluoro-phenylamine (40 mg, 0.142 mmol) in anhydrous pyridine (2 mL) at 0° C., 3-fluorobenzenesulfonylchloride was added (0.018 mL, 1 eq) and the mixture was stirred at 0° C. for 1 h. It was then diluted with DCM and washed with aqueous 0.5 N HCl (3×80 mL) and brine. The organic layer was dried over Na$_2$SO$_4$ and evaporated to dryness. The crude product was purified by flash chromatography on silica gel (DCM/MeOH 98:2), affording 30 mg of the title compound as a white powder. HPLC (254 nm): R$_t$: 5.71 min; $^1$H NMR (DMSO-d6) Shift: 10.36 (s, 1H), 8.34-8.37 (m, 2H), 8.35 (s, 1H), 7.46-7.64 (m, 4H), 7.35 (td, J=2.2, 7.4 Hz, 1H), 7.18-7.28 (m, 2H), 6.99-7.03 (m, 2H), 4.20 (q, J=7.3 Hz, 2H), 1.44 (t, J=7.3 Hz, 3H); HRMS (ESI) calcd for C22H19F2N4O2S [M+H]$^+$ 441.1192. found 441.1175.

According to this same methodology by employing the suitable solfonyl chloride, the following compound was also prepared:

N-[3-(1-Ethyl-4-pyridin-4-yl-1H-pyrazol-3-yl)-2-fluoro-phenyl]-2-fluoro-benzene-sulfonamide Formula I, where m=2; R$_1$, R3=H; R2=F; R4=4-pyridinyl

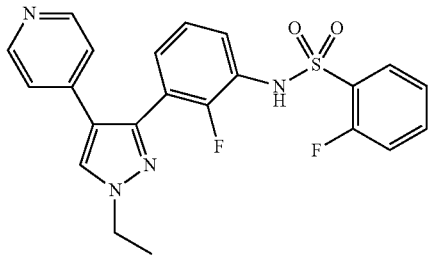 [SMILES: CCn1cc(-c2ccncc2)c(-c2cccc(NS(=O)(=O)c3ccccc3F)c2F)n1]

HPLC (254 nm): R$_t$: 5.55 min; $^1$H NMR (DMSO-d6) Shift: 10.47 (s, 1H), 8.09-8.51 (m, 3H), 7.59-7.75 (m, 2H), 7.28-7.41 (m, 3H), 7.16-7.28 (m, 2H), 6.88-7.07 (m, 2H), 4.20 (q, J=7.4 Hz, 2H), 1.44 (t, J=7.3 Hz, 3H); HRMS (ESI) calcd for C22H19F2N4O2S [M+H]$^+$ 441.1192. found 441.1174.

Example 15

2,5-Difluoro-N-[2-fluoro-3-(4-pyridin-4-yl-1H-pyrazol-3-yl)-phenyl]-benzenesulfonamide Formula I, where m=0; R$_1$=H; R2,R3=F; R4=4-pyridinyl Method A, Step f 2,5-Difluoro-N-{2-fluoro-3-[4-pyridin-4-yl-1-(tetrahydro-pyran-2-yl)-1H-pyrazol-3-yl]-phenyl}-N-methoxymethyl-benzenesulfonamide (2.86 g, 5.102 mmol) (see Example 8, Method A, Step a) was dissolved in a 9:1 TFA/water mixture (15 mL) and stirred at 60° C. for 2 h. The reaction mixture was concentrated under reduced pressure, then taken up with AcOEt and washed with a saturated solution of NaHCO$_3$ and brine. The organic layer was dried over Na$_2$SO$_4$ and concentrated to dryness. The residue was purified by flash chromatography on silica gel (DCM/MeOH 95:5) affording 936 mg of the title compound as a white solid (43% yield). HPLC (254 nm): R$_t$: 5.00 min; $^1$H NMR (DMSO-d6) Shift: 13.44 (br. s., 1H), 10.65 (br. s., 1H), 8.37 (m, 3H), 7.52-7.61 (m, 1H), 7.40-7.52 (m, 2H), 7.31 (m, 3H), 7.08 (m, 2H); HRMS (ESI) calcd for C20H14F3N4O2S [M+H]$^+$ 431.0784. found 431.0782.

Example 16

2,5-Difluoro-N-[2-fluoro-3-(1-oxetan-3-yl-4-pyridin-4-yl-1H-pyrazol-3-yl)-phenyl]-benzenesulfonamide (Compound 21)

Formula I, where m=0; R1=oxetan-3-yl; R2, R3=F; R4=4-pyridinyl

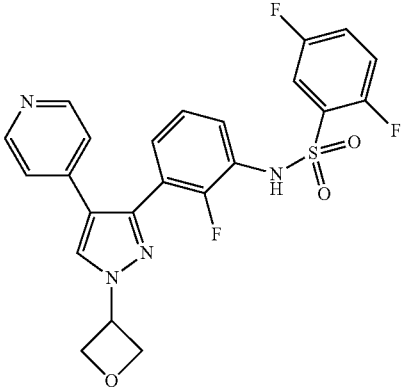 [SMILES: O=S(=O)(Nc1cccc(-c2nn(C3COC3)cc2-c2ccncc2)c1F)c1cc(F)ccc1F]

Method C, Step k

A solution of 2,5-Difluoro-N-[2-fluoro-3-(4-pyridin-4-yl-1H-pyrazol-3-yl)-phenyl]-benzenesulfonamide (200 mg, 0,465 mmol)(prepared as described in Example 15) in anhydrous DMF (4 mL) was added to sodium hydride (60% in mineral oil)(46 mg, 1.162 mmol, 2.5 eq) previously washed with n-hexane under argon atmosphere and cooled to 0° C. After stirring at 0° C. for 40 minutes, freshly prepared 3-oxetanol trifluoromethanesulfonyl ester (144 mg, 0.689 mmol, 1.5 eq) dissolved in dry DMF (1 mL) was added and the mixture was stirred at 0° C. for 1 h. A further addition of sodium hydride (40 mg) and 3-oxetanol trifluoro-methanesulfonyl ester (40 mg) was then made and the reaction mixture was then allowed to warm to room temperature during a night. The reaction mixture was then diluted with water and ethyl acetate. The aqueous phase was brought to pH 4-5 with HCl 2 N and extracted with ethyl acetate. The organic phase was dried over $Na_2SO_4$ and evaporated to dryness. The crude product was purified by flash chromatography on silica gel (ethyl acetate/n-hexane 7:3) affording 24 mg of the title product as a white solid. HPLC (254 nm): $R_t$: 6.99 min; $^1$H NMR (DMSO-d6) Shift: 10.68 (br. s., 1H), 8.52 (s, 1H), 8.36-8.40 (m, 2H), 7.51-7.59 (m, 1H), 7.31-7.49 (m, 4H), 721-7.29 (m, 1H), 7.02-7.08 (m, 2H), 5.64 (quip, J=6.9 Hz, 1H), 4.90-5.00 (m, 4H); HRMS (ESI) calcd for C23H18F3N4O3S [M+H]$^+$ 487.1046. found 487.1043.

During this synthesis the following side-product was also isolated.

2,5-difluoro-N-{2-fluoro-3-[1-(oxetan-2-yl)-4-(pyridin-4-yl)-1H-pyrazol-3-yl]phenyl}benzenesulfonamide Formula I, where m=0; R1=oxetan-2-yl; R2, R3=F; R4=4-pyridinyl

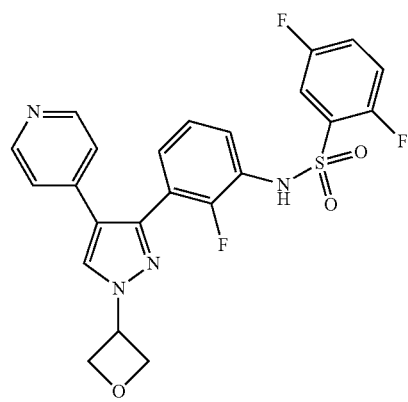 [SMILES: O=S(=O)(Nc1cccc(-c2nn(C3COC3)cc2-c2ccncc2)c1F)c1cc(F)ccc1F]

HPLC (254 nm): $R_t$: 5.44 min; $^1$H NMR (DMSO-d6) Shift: 10.82 (br. s., 1H), 8.39-8.36 (m, 2H), 8.26 (s, 1H), 7.64-7.54 (m, 1H), 7.54-7.41 (m, 3H), 7.33 (t, J=7.9 Hz, 1H), 7.26-7.16 (m, 1H), 7.05-6.99 (m, 2H), 5.10-4.93 (m, 2H), 4.82-4.69 (m, 2H), 4.69-4.58 (m, 1H). HRMS (ESI) calcd for C23H18F3N4O3S [M+H]$^+$487.1046. found 487.1033.

According to this same methodology, but employing the suitable alkylating agent, the following compounds were prepared:

2,5-Difluoro-N-{2-fluoro-3-[1-(3-methyl-oxetan-3-ylmethyl)-4-pyridin-4-yl-1H-pyrazol-3-yl]-phenyl}-benzenesulfonamide Formula I, where m=1; R1=3-methyl-oxetan-3-yl; R2, R3=F; R4=4-pyridinyl

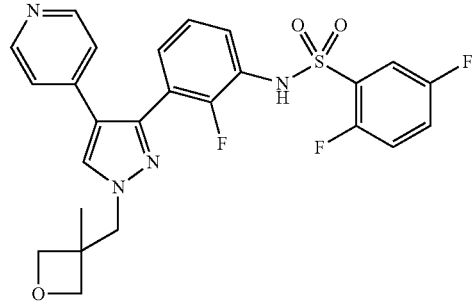 [SMILES: CC1(Cn2cc(-c3ccncc3)c(-c3cccc(NS(=O)(=O)c4cc(F)ccc4F)c3F)n2)COC1]

HPLC (254 nm): $R_t$: 5.70 min; $^1$H NMR (DMSO-d6) Shift: 10.65 (br. s., 1H), 8.38 (s, 1H), 8.39-8.35 (m, 2H), 7.59-7.51 (m, 1H), 7.51-7.40 (m, 2H), 7.36 (dt, J=2.4, 7.4 Hz, 1H), 7.31-7.16 (m, 2H), 7.03 (d, J=6.1 Hz, 2H), 4.61 (d, J=6.1 Hz, 2H), 4.41 (s, 2H), 4.25 (d, J=6.1 Hz, 2H), 1.19 (s, 3H); HRMS (ESI) calcd for C25H22F3N4O3S [M+H]$^+$ 515.1359. found 515.1382.

2,5-difluoro-N-{2-fluoro-3-[4-(pyridin-4-yl)-1-(tetrahydro-2H-pyran-4-ylmethyl)-1H-pyrazol-3-yl]-phenyl}benzenesulfonamide Formula I, where m=1; R1=tetrahydro-2H-pyran-4-yl; R2, R3=F; R4=4-pyridinyl

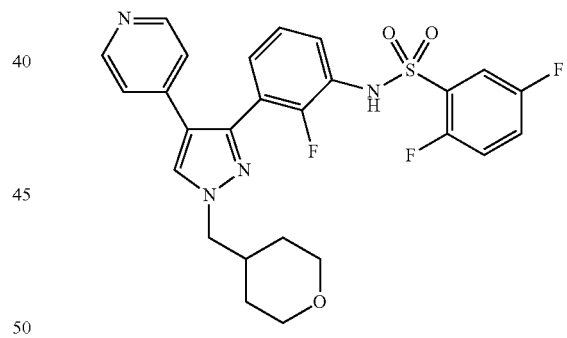

HPLC (254 nm): $R_t$: 5.70 min; $^1$H NMR (DMSO-d6) Shift: 10.81 (br. s., 1H), 8.37-8.33 (m, 2H), 8.11 (s, 1H), 7.62-7.39 (m, 4H), 7.38-7.18 (m, 2H), 7.03-6.98 (m, 2H), 3.77-3.65 (m, 3H), 3.64-3.54 (m, 1H), 3.24-3.06 (m, 2H), 1.94 (ddd, J=4.0, 7.4, 11.1 Hz, 1H), 1.31-1.15 (m, J=13.2 Hz, 2H), 1.05-0.80 (m, 2H); HRMS (ESI) calcd for C26H24F3N4O3S [M+H]$^+$ 529.1516. found 529.1537.

Example 17

N-[3-(1-Cyclopropyl-4-pyridin-4-yl-1H-pyrazol-3-yl)-2-fluoro-phenyl]-2,5-difluoro-benzenesulfonamide Formula I, where m=0; R1=cyclopropyl; R2, R3=F; R4=4-pyridinyl Method A, Step e

N-[3-(1-Cyclopropyl-4-pyridin-4-yl-1H-pyrazol-3-yl)-2-fluoro-phenyl]-2,5-difluoro-N-methoxymethyl-benzenesulfonamide Formula 2, where R4=4-pyridinyl, PG$_1$=methoxymethyl, R29=cyclopropyl, R30=2,5-difluoro-benzene-sulfonyl

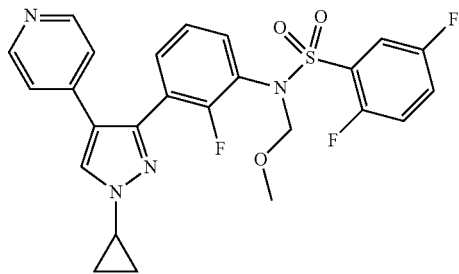 [SMILES: COCN(c1cccc(-c2nn(C3CC3)cc2-c2ccncc2)c1F)S(=O)(=O)c1cc(F)ccc1F]

2,5-Difluoro-N-[2-fluoro-3-(4-pyridin-4-yl-2H-pyrazol-3-yl)-phenyl]-N-methoxymethyl-benzenesulfonamide (300 mg, 0.632 mmol) (see Example 11, Method A, Step d), cyclopropyl boronic acid (131 mg, 1.32 mmol, 2.5 eq) and sodium carbonate (162 mg, 1.32 mmol, 2.5 eq) were suspended and stirred at r.t. in dichloroethane (6 mL). To this suspension a solution of copper(II) acetate (138 mg, 0.758 mmol, 1.2 eq) and [2,2]bipyridinyl (115 mg, 0,758 mmol, 1.2 eq) in dichloroethane (8.5 mL) warmed to 70° C. was added in a dropwise manner. The mixture was stirred at 70° C. for 3 h. After cooling, the reaction mixture was diluted with DCM and washed with a saturated solution of NH$_4$Cl and brine. The organic layer was dried over Na$_2$SO$_4$ and concentrated to dryness. The residue was purified by flash chromatography on silica gel (DCM/MeOH 98:1.5) affording 290 mg of the title compound (89% yield). HPLC (254 nm): R$_t$: 6.25 min; $^1$H NMR (DMSO-d6) Shift: 8.43 (s, 1H), 8.36-8.39 (m, 2H), 7.58-7.65 (m, 1H), 7.43-7.56 (m, 3H), 7.34 (m, 2H), 7.04-7.10 (m, 2H), 5.00 (s, 2H), 3.78-3.87 (m, 1H), 3.27 (s, 3H), 1.12-1.19 (m, 2H), 1.00-1.06 (m, 2H); HRMS (ESI) calcd for C25H22F3N4O3S [M+H]$^+$ 515.1359. found 515.1352.

Method A, Step f

N-[3-(1-Cyclopropyl-4-pyridin-4-yl-1H-pyrazol-3-yl)-2-fluoro-phenyl]-2,5-difluoro-benzenesulfonamide Formula 1, where m=0; R$_1$=cyclopropyl; R2, R3=F; R4=4-pyridinyl

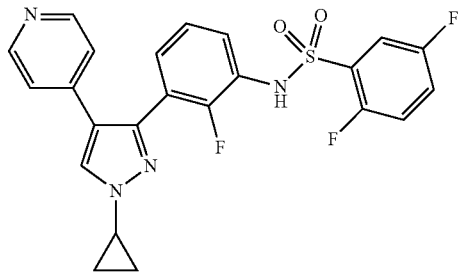 [SMILES: O=S(=O)(Nc1cccc(-c2nn(C3CC3)cc2-c2ccncc2)c1F)c1cc(F)ccc1F]

N-[3-(1-Cyclopropyl-4-pyridin-4-yl-1H-pyrazol-3-yl)-2-fluoro-phenyl]-2,5-difluoro-N-methoxymethyl-benzenesulfonamide (71 mg, 0.138 mmol) was dissolved in a mixture of TFA:water 9:1 (1 mL) and stirred for 2 h at 60° C. The reaction mixture was concentrated under reduced pressure, then taken up with a saturated solution of NaHCO$_3$ and extracted with DCM. The organic layer was dried over Na$_2$SO$_4$ and concentrated to dryness. The residue taken up with diethyl ether and filtered affording 64 mg of the title compound (99% yield), HPLC (254 nm): R$_t$: 5.85 min; $^1$H NMR (DMSO-d6) Shift: 10.66 (br. s., 1H), 8.44 (s, 1H), 8.39 (d, J=6.10 Hz, 2H), 7.51-7.59 (m, 1H), 7.40-7.50 (m, 2H), 7.36 (td, J=1.95, 7.57 Hz, 1H), 7.28-7.33 (m, 1H), 7.21-7.27 (m, 1H), 7.09 (d, J=6.10 Hz, 2H), 3.82 (tt, J=3.77, 7.34 Hz, 1H), 1.10-1.17 (m, 2H), 0.99-1.05 (m, 2H); HRMS (ESI) calcd for C20H18F3N4O2S [M+H]$^+$ 471.1097. found 471.1109.

Example 18

N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}acetamide Formula I, where m=0; R$_1$=tetrahydro-2H-pyran-4-yl; R2, R3=F; R4=2-acetylamino-pyridin-4-yl

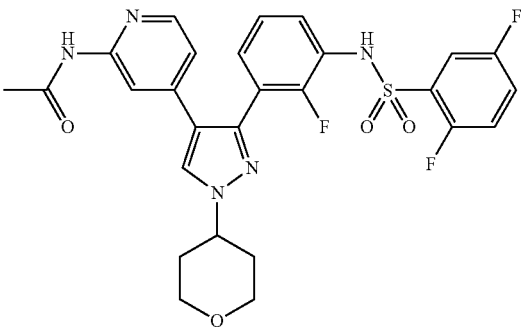 [SMILES: CC(=O)Nc1cc(-c2cn(C3CCOCC3)nc2-c2cccc(NS(=O)(=O)c3cc(F)ccc3F)c2F)ccn1]

To a solution of N-{3-[4-(2-Amino-pyridin-4-yl)-1-(tetrahydro-pyran-4-yl)-1H-pyrazol-3-yl]-2-fluoro-phenyl}-2,5-difluoro-benzenesulfonamide (65 mg, 0.123 mmol) (prepared as described in Example 8) in DCM (1 mL) at 0° C., acetyl chloride (0.030 mL, 0.369 mmol) and triethylamine (0.068 mL, 0.492 mmol, 4 eq) were added and the reaction was stirred at r.t. for 2 h. The reaction mixture was diluted with DCM and washed once with water, then with brine. The reaction mixture was concentrated under reduced pressure and the crude peracetylated product was dissolved with MeOH (1 mL) and treated with NaOH 1N (0.5 mL) to hydrolyze the two undesired acetyl groups. After 1 h at r.t. the reaction mixture was concentrated under reduced pressure and taken up with AcOEt and washed with saturated aqueous NaHCO$_3$ and brine. The residue was purified by flash chromatography on silica gel (DCM:MeOH:NH$_3$ 7N in MeOH 98:1:1) affording 49 mg of the title compound (61% yield). HPLC (254 nm): R$_t$: 5.65 min; $^1$H NMR (DMSO-d6) Shift: 10.59 (s, 1H), 10.33 (s, 1H), 8.31 (s, 1H), 8.05 (d, J=5.4 Hz, 1H), 7.94 (s, 1H), 7.58-7.50 (m, 1H), 7.48-7.38 (m, 2H), 7.34-7.25 (m, 2H), 7.23-7.14 (m, 1H), 6.64 (dd, J=1.2, 5.2 Hz, 1H), 4.61-4.32 (m, 1H), 4.05-3.90 (m, 2H), 3.47 (dt, J=2.6, 11.4 Hz, 2H), 2.17-1.93 (m, 4H), 2.04 (s, 3H); HRMS (ESI) calcd for C27H25F3N5O4S [M+H]$^+$ 572.1574. found 572.1548.

According to this same methodology, but employing the suitable acylating agent, the following compound was prepared:

N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}-2-methyl-propanamide Formula I, where m=0; R₁=tetrahydro-2H-pyran-4-yl; R2, R3=F; R4=2-methylpropanamido-pyridin-4-yl

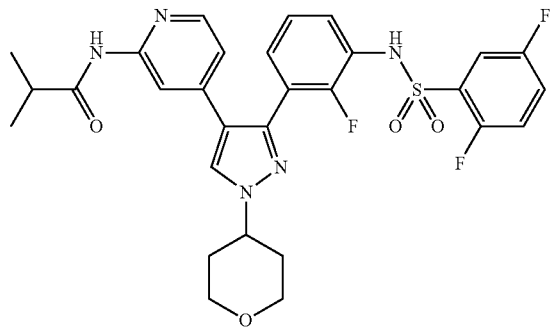 [SMILES: CC(C)C(=O)Nc1cc(-c2cn(C3CCOCC3)nc2-c2cccc(NS(=O)(=O)c3cc(F)ccc3F)c2F)ccn1]

HPLC (254 nm): R$_t$: 6.32 min; ¹H NMR (DMSO-d6) Shift: 10.59 (s, 1H), 10.30 (s, 1H), 8.32 (s, 1H), 8.06 (s, 1H), 8.03 (d, J=5.2 Hz, 1H), 7.59-7.50 (m, 1H), 7.49-7.38 (m, 2H), 7.36-7.26 (m, 2H), 7.26-7.16 (m, 1H), 6.53 (dd, J=1.3, 5.3 Hz, 1H), 4.56-4.40 (m, 1H), 4.07-3.83 (m, 2H), 3.47 (dt, J=2.7, 11.3 Hz, 2H), 2.73 (quin, J=6.8 Hz, 1H), 2.15-1.85 (m, 4H), 1.07 (d, J=6.8 Hz, 6H); HRMS (ESI) calcd for C29H29F3N5O4S [M+H]⁺ 600.1887. found 600.1888.

According to this same methodology, but starting from N-{3-[4-(2-Amino-pyridin-4-yl)-1-(1-methyl-piperidin-4-yl)-1H-pyrazol-3-yl]-2-fluoro-phenyl}-2,5-difluoro-benzenesulfonamide (prepared as described in Example 9), the following compound was prepared:

N-{4-[3-(3-{[(2,5-difluorophenyl)sulfonyl]amino}-2-fluorophenyl)-1-(1-methyl-piperidin-4-yl)-1H-pyrazol-4-yl]pyridin-2-yl}acetamide Formula 1, where m=0; R₁=1-methyl-piperidin-4-yl; R2, R3=F; R4=2-acetylamino-pyridin-4-yl

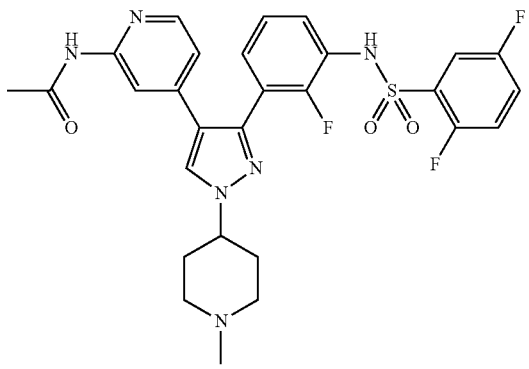 [SMILES: CC(=O)Nc1cc(-c2cn(C3CCN(C)CC3)nc2-c2cccc(NS(=O)(=O)c3cc(F)ccc3F)c2F)ccn1]

HPLC (254 nm): R$_t$: 4.41 min; ¹H NMR (DMSO-d6) Shift: 10.34 (s, 1H), 8.27 (s, 1H), 8.05 (d, J=5.4 Hz, 1H), 7.97 (s, 1H), 7.52-7.32 (m, 3H), 7.31-7.22 (m, 1H), 7.16-7.04 (m, 2H), 6.64 (dd, J=1.5, 5.2 Hz, 1H), 4.34-4.22 (m, 1H), 3.03 (d, J=11.8 Hz, 2H), 2.41-2.25 (m, 2H), 2.37 (s, 3H), 2.19-1.96 (m, 4H), 2.05 (s, 3H); HRMS (ESI) calcd for C28H28F3N6O3S [M+H]⁺ 585.1890. found 585.1916.

Example 19

N-{3-[4-(2-Cyano-pyridin-4-yl)-1-(tetrahydro-pyran-4-yl)-1H-pyrazol-3-yl]-2-fluoro-phenyl}-2,5-difluoro-benzenesulfonamide Formula I, where m=0; R₁=tetrahydro-2H-pyran-4-yl; R2, R3=F; R4=2-cyano-pyridin-4-yl Method A, Step b 2,5-Difluoro-N-{2-fluoro-3-[1-(tetrahydro-pyran-4-yl)-4-(4,4,5,5-tetramethyl-[1,3,2]dioxaborolan-2-yl)-1H-pyrazol-3-yl]-phenyl}-N-methoxymethyl-benzenesulfonamide Formula 3, where M'=4,4,5,5-tetramethyl-[1,3,2]dioxaborolan-2-yl; PG₁=methoxymethyl; R29=tetrahydropyran-4-yl; R30=2,5-difluoro-benzene-sulfonyl

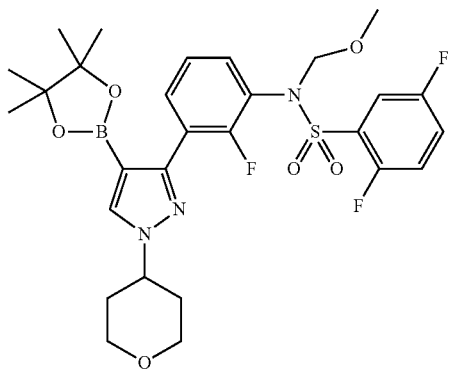 [SMILES: COCN(c1cccc(-c2nn(C3CCOCC3)cc2B2OC(C)(C)C(C)(C)O2)c1F)S(=O)(=O)c1cc(F)ccc1F]

In a microwave vial, N-{3-[4-bromo-1-(tetrahydro-pyran-4-yl)-1H-pyrazol-3-yl]-2-fluoro-phenyl}-2,5-difluoro-N-methoxymethyl-benzenesulfonamide (590 mg, 1.053 mmol) (prepared as described in Example 1) was dissolved in dry toluene (10 mL) and argon was bubbled through the solution for 5 minutes in order to degas it. Triethylamine (0.367 mL, 2.633 mmol, 2.5 eq) was then added, followed by S-Phos (43 mg, 0.105 mmol, 0.1 eq), PdCl₂(CH₃CN)₂ (14 mg, 0,053 mmol, 0.05 eq) and pinacol borane (1.5 mL, 10.53 mmol, 10 eq). The vial was then sealed and the mixture was irradiated in the microwave oven for 30 minutes at 90° C. A further amount of S-Phos (43 mg) and PdCl₂(CH₃CN)₂ (14 mg) was then added and the mixture was submitted to a second microwave cycle. It was then filtered through a Celite pad, which was washed thoroughly with ethyl acetate. The filtrate was washed with water and brine, dried over sodium sulfate and evaporated to dryness. The residue was purified by flash chromatography on silica gel (n-hexane/AcOEt 7:3) affording 890 mg of the title product impure of de-brominated side product. The product was used without further purification in the following step.

Method A, Step c

N-{3-[4-(2-Cyano-pyridin-4-yl)-1-(tetrahydro-pyran-4-yl)-1H-pyrazol-3-yl]-2-fluoro-phenyl}-2,5-difluoro-N-methoxymethyl-benzenesulfonamide Formula 2, where R4=2-cyanopyridin-4-yl; PG$_1$=methoxymethyl; R29=tetrahydro-pyran-4-yl; R30=2,5-difluoro-benzene-sulfonyl

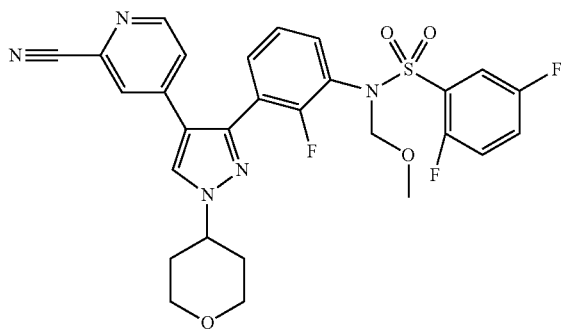 [SMILES: COCN(c1cccc(-c2nn(C3CCOCC3)cc2-c2ccnc(C#N)c2)c1F)S(=O)(=O)c1cc(F)ccc1F]

In a microwave tube a solution of 2,5-difluoro-N-{2-fluoro-3-[1-(tetrahydro-pyran-4-yl)-4-(4,4,5,5-tetramethyl-[1,3,2]dioxaborolan-2-yl)-1H-pyrazol-3-yl]-phenyl}-N-methoxymethyl-benzenesulfonamide (420 mg, 0.691 mmol) in DME/H$_2$O 9:1 (10 mL) was degassed by bubbling argon for 5 minutes. 4-Bromo-2-cyano-pyridine (252 mg, 1.383 mmol, 2 eq) was then added, followed by cesium carbonate (563 mg, 1.728 mmol, 2.5 eq) and Pd(dppf)Cl$_2$.CH$_2$Cl$_2$ (56 mg, 0.069 mmol, 0.1 eq). The mixture was irradiated in the microwave oven at 100° C. for 30 minutes and then partitioned between ethyl acetate and saturated aqueous NaHCO$_3$ the two phases were separated and the organic layer was washed again with saturated aqueous NaHCO$_3$ and then with brine. The combined organic layers were dried over Na$_2$SO$_4$ and evaporated to dryness. The crude product was purified by chromatography on silica gel (gradient cyclohexane/ethyl acetate 1:1 to 1:2) affording 210 mg of the title compound (52% yield) as a white solid, HPLC (254 nm): R$_t$: 6.69 min; $^1$H NMR (DMSO-d6) Shift: 8.63 (s, 1H), 8.56 (d, J=5.4 Hz, 1H), 7.76 (d, J=1.1 Hz, 1H), 7.70-7.45 (m, 4H), 7.42-7.25 (m, 3H), 5.03 (s, 2H), 4.61-4.35 (m, 1H), 4.04-3.96 (m, 2H), 3.59-3.45 (m, 2H), 3.26 (s, 3H), 2.18-2.06 (m, 2H), 2.05-1.93 (m, 2H); HRMS (ESI) calcd for C28H25F3N5O4S [M+H]$^+$ 584.1574. found 584.1555.

Method A, Step f

N-{3-[4-(2-Cyano-pyridin-4-yl)-1-(tetrahydro-pyran-4-yl)-1H-pyrazol-3-yl]-2-fluoro-phenyl}-2,5-difluoro-benzenesulfonamide Formula I, where m=0; R$_1$=tetrahydro-2H-pyran-4-yl; R2, R3=F; R4=2-cyano-pyridin-4-yl

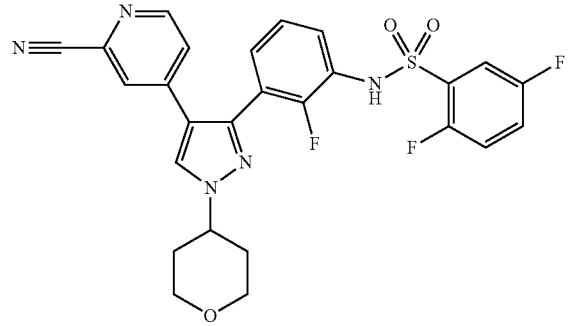 [SMILES: N#Cc1cc(-c2cn(C3CCOCC3)nc2-c2cccc(NS(=O)(=O)c3cc(F)ccc3F)c2F)ccn1]

To a solution of N-{3-[4-(2-cyano-pyridin-4-yl)-1-(tetrahydro-pyran-4-yl)-1H-pyrazol-3-yl]-2-fluoro-phenyl}-2,5-difluoro-N-methoxymethyl-benzenesulfonamide (60 mg, 0.103 mmol) in dioxane (2 mL) concentrated HCl was added (0.5 mL) and the mixture was stirred at room temperature overnight. After two more additions of concentrated HCl (0.5 mL each) and 5 more hours of stirring, the reaction mixture was diluted with water and neutralized with 32% NaOH. It was then extracted with ethyl acetate. The combined organic layers were washed with brine, dried over Na$_2$SO$_4$ and concentrated under reduced pressure, A 1.1 mixture of the title product and 4-[3-(3-{[(2,5-difluorophenyl)sulfonyl]amino}-2-fluorophenyl)-1-(tetrahydro-2H-pyran-4-yl)-1H-pyrazol-4-yl]pyridine-2-carboxamide was obtained. The two products were separated by flash chromatography on silica gel (gradient cyclohexane/AcOEt 2:8 to pure AcOEt), giving 21 mg of the title compound and 15 mg of 4-[3-(3-{[(2,5-difluorophenyl)sulfonyl]amino}-2-fluorophenyl)-1-(tetrahydro-2H-pyran-4-yl)-1H-pyrazol-4-yl]pyridine-2-carboxamide as white solids. HPLC (254 nm): R$_t$: 6.26 min; $^1$H NMR (DMSO-d6) Shift: 10.67 (s, 1H), 8.59 (s, 1H), 8.52 (d, J=5.2 Hz, 1H), 7.80 (s, 1H), 7.62-7.51 (m, 1H), 7.51-7.43 (m, 1H), 7.43-7.31 (m, 3H), 7.31-7.22 (m, 2H), 4.58-4.36 (m, 1H), 3.98 (dd, J=3.0, 11.7 Hz, 2H), 3.58-3.41 (m, 2H), 2.16-2.04 (m, 2H), 2.04-1.84 (m, 2H); HRMS (ESI) calcd for C26H21F3N5O3S [M+H]$^+$ 540.1312. found 540.1332.

4-[3-(3-{[(2,5-difluorophenyl)sulfonyl]amino}-2-fluorophenyl)-1-(tetrahydro-2H-pyran-4-yl)-1H-pyrazol-4-yl]pyridine-2-carboxamide Formula I, where m=0; R$_1$=tetrahydro-2H-pyran-4-yl; R2, R3=F; R4=2-carboxamido-pyridin-4-yl

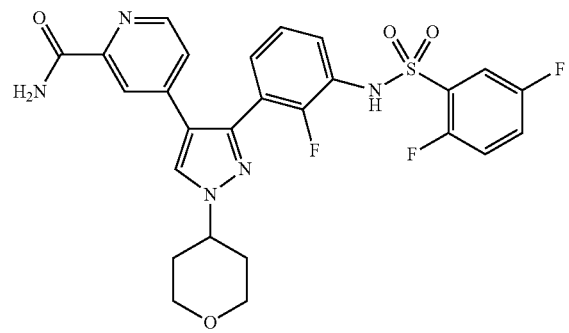 [SMILES: NC(=O)c1cc(-c2cn(C3CCOCC3)nc2-c2cccc(NS(=O)(=O)c3cc(F)ccc3F)c2F)ccn1]

HPLC (254 nm): R$_t$: 5.61 min; $^1$H NMR (DMSO-d6) Shift: 10.63 (s, 1H), 8.55 (s, 1H), 8.37 (d, J=5.1 Hz, 1H), 8.05 (br. s., 1H), 7.91 (d, J=1.1 Hz, 1H), 7.57 (d, J=2.1 Hz, 1H), 7.56-7.50 (m, 1H), 7.48-7.39 (m, 2H), 7.37-7.29 (m, 2H), 7.29-7.19 (m, 1H), 7.06 (dd, J=1.6, 5.1 Hz, 1H), 4.54-4.40 (m, 1H), 3.98 (dd, J=3.0, 11.0 Hz, 2H), 3.49 (dt, J=2.4, 11.6 Hz, 2H), 2.13-1.92 (m, 4H); HRMS (ESI) calcd for C26H23F3N5O4S [M+H]$^+$ 558.1417. found 558.1437.

Example 20

Methyl 4-[3-(3-{[(2,5-difluorophenyl)sulfonyl]amino}-2-fluorophenyl)-1-(tetrahydro-2H-pyran-4-yl)-1H-pyrazol-4-yl]pyridine-2-carboxylate Formula I, m=0; R$_1$=tetrahydro-2H-pyran-4-yl; R2, R3=F; R4=2-methoxycarbonyl-pyridin-4-yl

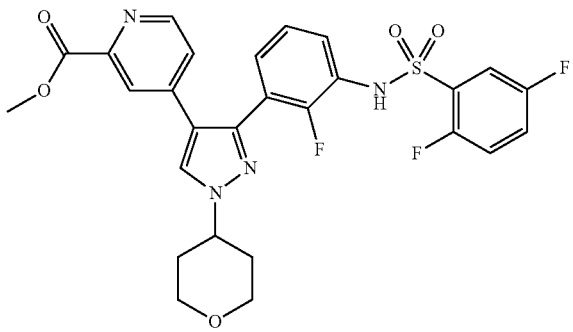 [SMILES: COC(=O)c1cc(-c2cn(C3CCOCC3)nc2-c2cccc(NS(=O)(=O)c3cc(F)ccc3F)c2F)ccn1]

In a Pirex screw cap tube N-{3-[4-(2-cyano-pyridin-4-yl)-1-(tetrahydro-pyran-4-yl)-1H-pyrazol-3-yl]-2-fluoro-phenyl}-2,5-difluoro-N-methoxymethyl-benzene-sulfonamide (140 mg, 0.240 mmol) (prepared as described in Example 19) was dissolved in methanol (2.5 mL) and 4N hydrochloric acid in dioxane was added (2 mL) The sealed tube was heated to 80° C. for 30 hours. The solvent was then evaporated under reduced pressure and after chromatography on silica gel (gradient DCM/MeOH 98:2 to 90:10), 130 mg of a mixture of MOM-protected and deprotected methylester were obtained. 40 mg of this mixture were treated with a 9'1 mixture of trifluoroacetic acid and water (1 mL) and heated to 70° C. for 50 minutes to achieve complete deprotection. The solvent was evaporated to dryness and the residue taken up with ethyl acetate and washed with saturated aqueous NaHCO$_3$ and brine. The crude was purified by chromatography on silica gel (DCM/MeOH 97:3) and triturated with ethylether, giving 25 mg of the title compound as a white solid. HPLC (254 nm): R$_t$: 5.87 min; $^1$H NMR (DMSO-d6) Shift: 10.65 (s, 1H), 8.57 (s, 1H), 8.49 (d, J=5.2 Hz, 1H), 7.80 (d, J=1.2 Hz, 1H), 7.57-7.47 (m, 1H), 7.47-7.40 (m, 1H), 7.40-7.31 (m, 3H), 7.29-7.21 (m, 2H), 4.57-4.41 (m, 1H), 3.98 (td, J=2.2, 10.1 Hz, 2H), 3.83 (s, 3H), 3.49 (dt, J=2.0, 11.6 Hz, 2H), 2.14-1.89 (m, 4H); HRMS (ESI) calcd for C27H24F3N4O5S [M+H]$^+$ 573.1414. found 573.1432.

Example 21

4-[3-(3-{[(2,5-difluorophenyl)sulfonyl]amino}-2-fluorophenyl)-1-(1-methyl-piperidin-4-yl)-1H-pyrazol-4-yl]pyridine-2-carboxamide Formula I, where m=0; R$_1$=tetrahydro-2H-pyran-4-yl; R2, R3=F; R4=2-carboxamido-pyridin-4-yl]

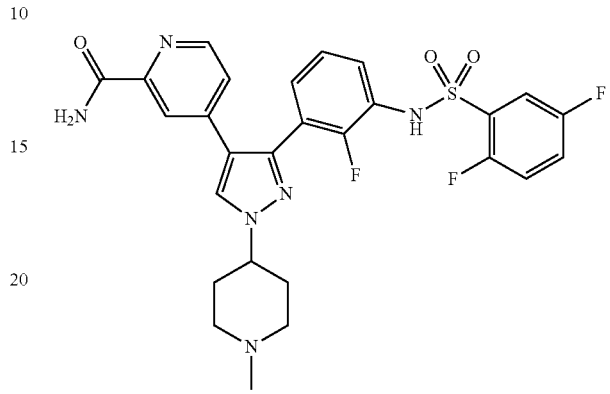

Method A, Step c 4-(4-(2-Cyano-pyridin-4-yl)-3-{3-[(2,5-difluoro-benzenesulfonyl)-methoxymethyl-amino]-2-fluoro-phenyl}-pyrazol-1-yl)-piperidine-1-carboxylic acid tert-butyl ester Formula 2, where R4=2-cyanopyridin-4-yl; PG$_1$=methoxymethyl; R29=N-tert-butoxycarbonyl-piperidin-4-yl; R30=2,5-difluoro-benzene-sulfonyl

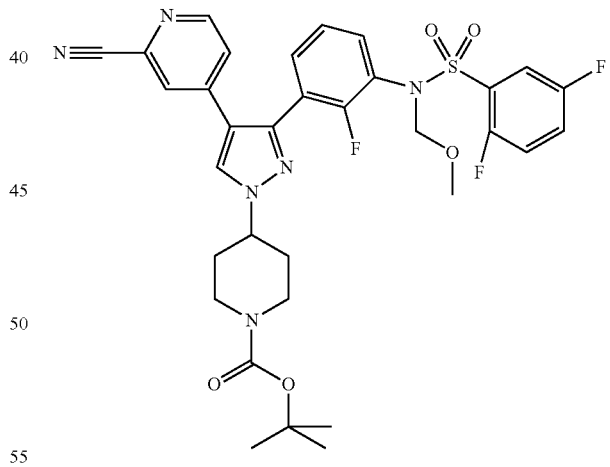

In a microwave tube a solution of 4-[3-{3-[(2,5-difluoro-benzenesulfonyl)-methoxymethyl-amino]-2-fluoro-phenyl}-4-(4,4,5,5-tetramethyl-[1,3,2]dioxaborolan-2-yl)-pyrazol-1-yl]-piperidine-1-carboxylic acid tert-butyl ester (0.708 mmol) (prepared as described in Example 13) in DME/H$_2$O 9:1 (10 mL) was degassed by bubbling argon for 5 minutes. 4-1.5 Bromo-2-cyano-pyridine (259 mg, 1.416 mmol, 2 eq) was then added, followed by cesium carbonate (577 mg, 1.770 mmol, 2.5 eq) and Pd(dppf)Cl$_2$.CH$_2$Cl$_2$ (58 mg, 0.071 mmol, 0.1 eq). The mixture was irradiated in the microwave oven at 100° C. for 30 minutes and then partitioned between ethyl acetate and saturated aqueous NaHCO₃. The two phases were separated and the organic layer was washed again with saturated aqueous NaHCO₃ and then with brine. The combined organic layers were dried over Na₂SO₄ and evaporated to dryness. The crude product was purified by chromatography on silica gel (cyclohexane/ethylacetate 1:1) affording 425 mg of the title compound. HPLC (254 nm): R$_t$: 7.62 min; ¹H NMR (DMSO-d6) Shift: 8.63 (s, 1H), 8.56 (d, J=4.9 Hz, 1H), 7.76 (d, J=1.1 Hz, 1H), 7.68-7.44 (m, 4H), 7.38-7.29 (m, 3H), 5.03 (s, 2H), 4.56-4.37 (m, 1H), 4.15-4.04 (m, 2H), 3.29 (s, 3H), 3.05-2.88 (m, 2H), 2.20-2.08 (m, J=9.6 Hz, 2H), 1.83 (dq, J=4.2, 12.2 Hz, 2H), 1.43 (s, 9H); HRMS (ESI) calcd for C33H34F3N6O5S [M+H]⁺ 683.2258. found 683.2242.

N-{3-[4-(2-Cyano-pyridin-4-yl)-1-(1-methyl-piperidin-4-yl)-1H-pyrazol-3-yl]-2-fluoro-phenyl}-2,5-difluoro-N-methoxymethyl-benzenesulfonamide Formula 2, where R4=2-cyanopyridin-4-yl; PG₁=methoxymethyl; R29=1-methyl-piperidin-4-yl; R30=2,5-difluoro-benzene-sulfonyl

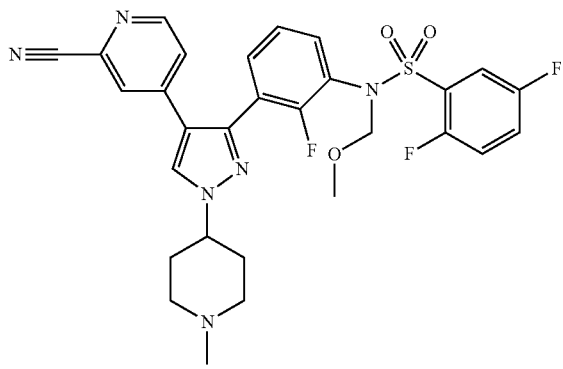 [SMILES: COCN(c1cccc(-c2nn(C3CCN(C)CC3)cc2-c2ccnc(C#N)c2)c1F)S(=O)(=O)c1cc(F)ccc1F]

To 4-(4-(2-cyano-pyridin-4-yl)-3-{3-[(2,5-difluoro-benzenesulfonyl)-methoxy-methyl-amino]-2-fluoro-phenyl}-pyrazol-1-yl)-piperidine-1-carboxylic acid tert-butyl ester (420 mg, 0.615 mmol) a 4 N solution of HCl in dioxane (3 mL, 12 mmol) was added dropwise and the mixture was stirred at r.t. for 45 minutes. The solvent was concentrated under reduced pressure and the residue was taken up with DCM and evaporated to dryness for 3 times. The residue was dissolved in MeOH (6 mL), 37% aqueous formaldehyde (0.070 mL, 0.923 mmol, 1.5 eq) was added, followed by acetic acid (0.106 mL, 1.845 mmol, 3 eq) and sodiumcyanoboro-hydride (73 mg, 0.984 mmol, 1.6 eq) and the mixture was stirred at r.t. for 1 h. The solvent was then evaporated under reduced pressure and the residue was taken up with AcOEt and saturated aqueous NaHCO₃ and the two phases were separated. The organic phase was washed with saturated aqueous NaHCO₃ and brine, dried over Na₂SO₄ and evaporated to dryness. The crude product was purified by chromatography on silica gel (DCM/MeOH/NH₃ 7N in MeOH 95:4:1 to 93:6:1) to give 140 mg of the title product, HPLC (254 nm): R$_t$: 5.25 min; ¹H NMR (DMSO-d6) Shift: 8.62 (s, 1H), 8.55 (dd, J=0.7, 5.2 Hz, 1H), 7.76 (d, J=1.1 Hz, 1H), 7.66-7.45 (m, 4H), 7.40-7.23 (m, 3H), 5.02 (s, 2H), 4.26-4.16 (m, 1H), 3.26 (s, 3H), 2.97-2.78 (m, 2H), 2.22 (s, 3H), 2.16-1.89 (m, 6H). HRMS (ESI) calcd for C29H28F3N6O3S [MA-H]⁺ 597.1890. found 597.1879.

Method E, Steps f and g

4-[3-(3-{[(2,5-difluorophenyl)sulfonyl]amino}-2-fluorophenyl)-1-(1-methyl-piperidin-4-yl)-1H-pyrazol-4-yl]pyridine-2-carboxamide Formula I, where m=0; R₁=tetrahydro-2H-pyran-4-yl; R2, R3=F; R4=2-carboxamido-pyridin-4-yl

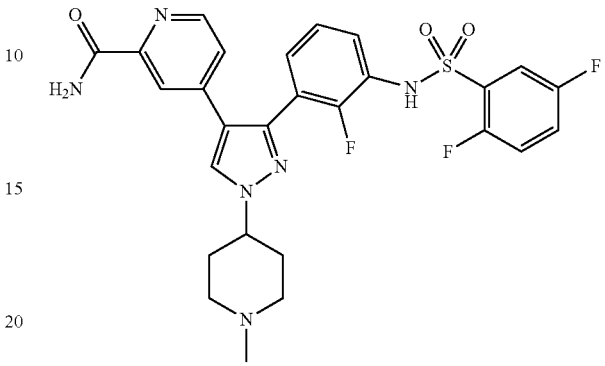

N-{3-[4-(2-cyano-pyridin-4-yl)-1-(1-methyl-piperidin-4-yl)-1H-pyrazol-3-yl]-2-fluoro-phenyl}-2,5-difluoro-N-methoxymethyl-benzenesulfonamide (68 mg, 0.114 mmol) were dissolved in a 9:1 trifluoroacetic acid/water mixture (2 mL, and stirred at 70° C. for 7 hours. The solvent was evaporated to dryness and the residue was taken up with toluene and evaporated to dryness twice. The crude product was dissolved in dry DMF (2 mL) ander argon, DIPEA was added (0.060 mL, 0.342 mmol, 3 eq), followed by ammonium acetate (93 mg, 1.206 mmol, 10 eq) and TBTU (60 mg, 0.187 mmol, 1.6 eq) and the mixture was stirred at r.t. overnight. It was then diluted with water and ethyl acetate and the phases were separated. The aqueous phase was diluted with saturated aqueous NaHCO₃ and extracted three times with ethyl acetate. The combined organic layers were washed with brine, dried over Na₂SO₄ and concentrated to dryness. The crude product was purified by chromatography on silica gel (DCM/MeOH/NH₃ 7N in MeOH 90:10:1 to 85:15:1) affording 18 mg of the title compound as a white solid. HPLC (254 nm): R$_t$: 4.41 min; ¹H NMR (DMSO-d6) Shift (selected signals)=8.53 (s, 1H), 8.37 (dd, J=0.6, 5.1 Hz, 1H), 8.05 (d, J=2.1 Hz, 1H), 7:94 (d, J=1.2 Hz, 1H), 7.57 (d, J=2.4 Hz, 1H), 7.48-7.34 (m, 3H), 7.34-7.26 (m, 1H), 7.14 (d, J=5.6 Hz, 2H), 7.08 (dd, J=1.8, 5.1 Hz, 1H), 4.35-4.23 (m, 1H), 3:12-3.01 (m, 2H), 2.47-2.38 (m, 2H), 2.40 (s, 3H), 2.22-2.01 (m, 4H); HRMS (ESI) calcd for C27H26F3N6O3S [M+H]⁺ 571.734. found 571.1735.

Example 22

4-[3-(3-{[(2,5-difluorophenyl)sulfonyl]amino}-2-fluorophenyl)-1-(tetrahydro-2H-pyran-4-yl)-1H-pyrazol-4-yl]-N-methylpyridine-2-carboxamide Formula I, where m=0; R₁=tetrahydro-2H-pyran-4-yl; R2, R3=F; R4=2-(N-methylcarboxamido)-pyridin-4-yl

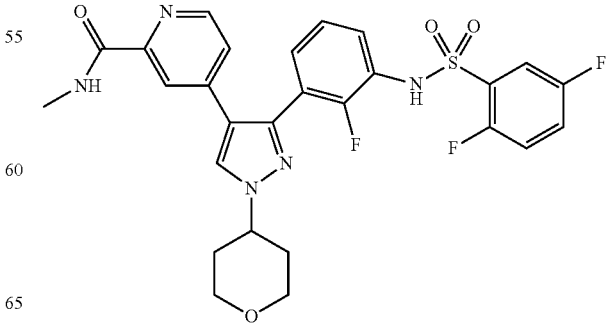

In a Pirex screw cap tube N-{3-[4-(2-cyano-pyridin-4-yl)-1-(tetrahydro-pyran-4-yl)-1H-pyrazol-3-yl]-2-fluoro-phenyl}-2,5-difluoro-N-methoxymethyl-benzene-sulfonamide (140 mg, 0.240 mmol) (prepared as described in Example 19) was dissolved in methanol (2.5 mL) and 4N hydrochloric acid in dioxane was added (2 mL). The sealed tube was heated to 80° C. for 30 hours. The solvent was then evaporated under reduced pressure and after chromatography on silica gel (gradient DCM/MeOH 98:2 to 90:10), 130 mg of a mixture of MOM-protected and deprotected methylester were obtained 85 mg of this mixture were dissolved in ethanol (1 mL) and treated with a 33% methylamine solution in ethanol (1.5 mL) at 70° C. for 5 minutes. The solvent was evaporated to dryness and the residue was treated with a 9:1 mixture of trifluoroacetic acid and water (1 mL) and heated to 60° C. for 40 minutes. The solvent was evaporated to dryness and the residue taken up with ethyl acetate and washed with saturated aqueous NaHCO$_3$ and brine. The crude was purified by chromatography on silica gel (DCM/MeOH 97:3) and triturated with ethylether, giving 56 mg of the title compound as a white solid HPLC (254 nm): R$_t$: 5.92 min; $^1$H NMR (DMSO-d6) Shift: 10.79-10.26 (br. s., 1H), 8.68 (q, J=4.6 Hz, 1H), 8.53 (s, 1H), 8.37 (d, J=5.0 Hz, 1H), 7.93 (br. s., 1H), 7.61-7.45 (m, 1H), 7.41 (ddd, J=3.2, 5.3, 8.0 Hz, 1H), 7.36-7.19 (m, 3H), 7.13 (dd, J=1.5, 5.1 Hz, 1H), 7.04 (br. s., 1H), 4.59-4.34 (m, 1H), 3.98 (dd, J=2.8, 11.1 Hz, 2H), 3.49 (dt, J=2.4, 11.6 Hz, 2H), 2.81 (d, J=4.8 Hz, 3H), 2.18-1.78 (m, 4H); HRMS (ESI) calcd for C27H25F3N5O4S [M+H]$^+$ 572.1574. found 572.1590.

According to this same methodology, but starting from N-{3-[4-(2-cyano-pyridin-4-yl)-1-(1-methyl-piperidin-4-yl)-1H-pyrazol-3-yl]-2-fluoro-phenyl}-2,5-difluoro-N-methoxymethyl-benzenesulfonamide (prepared as described in Example 21), the following compound was prepared:

4-[3-(3-{[(2,5-Difluorophenyl)sulfonyl]amino}-2-fluorophenyl)-1-(1-methyl piperidin-4-yl)-1H-pyrazol-4-yl]-N-methylpyridine-2-carboxamide Formula I, where m=0; R$_1$=1-methylpiperidin-4-yl; R2, R3=F; R4=2-(N-methyl-carboxamido)-pyridin-4-yl

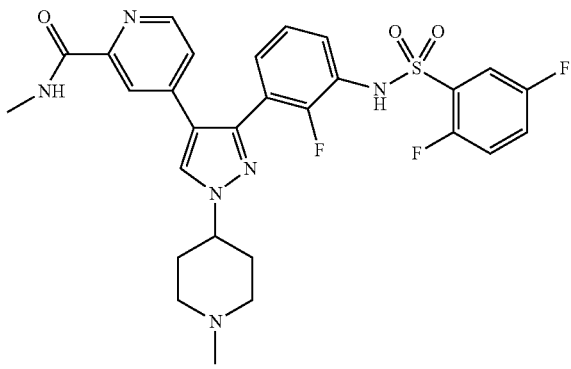 [SMILES: CNC(=O)c1cc(-c2cn(C3CCN(C)CC3)nc2-c2cccc(NS(=O)(=O)c3cc(F)ccc3F)c2F)ccn1]

HPLC (254 nm): R$_t$: 4.69 min; $^1$H NMR (DMSO-d6) Shift: 8.69 (q, J=4.8 Hz, 1H), 8.53 (s, 1H), 8.38 (d, J=5.1 Hz, 1H), 7.90 (d, J=1.1 Hz, 1H), 7.47-7.24 (m, 4H), 7.18-7.02 (m, 3H), 4.40-4.11 (m, 1H), 3.05 (d, J=11.7 Hz, 2H), 2.81 (d, J=4.9 Hz, 3H), 2.38 (s, 3H), 2.45-2.28 (m, 2H), 2.21-1.98 (m, 4H); HRMS (ESI) calcd for C28H28F3N6O3S [M+H]$^+$585.1890. found 585.1895.

Example 23

2,5-difluoro-N-(2-fluoro-3-{4-[2-(methylamino)pyridin-4-yl]-1-(tetrahydro-2H-pyran-4-yl)-1H-pyrazol-3-yl}phenyl)benzenesulfonamide Formula I, where m=0; R$_1$=tetrahydro-2H-pyran-4-yl; R2, R3=F; R4=2-methylamino-pyridin-4-yl

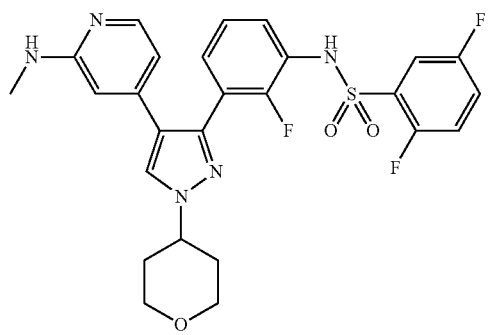 [SMILES: CNc1cc(-c2cn(C3CCOCC3)nc2-c2cccc(NS(=O)(=O)c3cc(F)ccc3F)c2F)ccn1]

To a solution of N-{3-[4-(2-amino-pyridin-4-yl)-1-(tetrahydro-pyran-4-yl)-1H-pyrazol-3-yl]-2-fluoro-phenyl}-2,5-difluoro-N-methoxymethyl-benzenesulfonamide (55 mg, 0.095 mmol) (prepared as described in Example 4) in MeOH (1 mL) at r.t. absolute acetic acid (0.011 mL, 0.2 mmol), formaldehyde (37% aq., 0.008 mL, 0.1 mmol) and sodium cyanoborohydride (7 mg, 0.11 mmol) were added and the reaction was stirred at r.t. for 1 h. All the reagents were added a second time in the same quantity and the reaction mixture was left stirring for an hour more. The reaction mixture was concentrated under reduced pressure and the crude was dissolved in a mixture of TFA:water 9:1 (1.5 mL) and stirred for 2 h at 70° C. The reaction mixture was concentrated under reduced pressure, then taken up with NaOH 1N and extracted with AcOEt. The organic layer was washed with brine, dried over Na$_2$SO$_4$ and concentrated to dryness. The residue was purified by flash chromatography on silica gel (DCM/MeOH/NH$_3$ 7N in MeOH 96:3:1) affording 3 mg of 2,5-difluoro-N-(2-fluoro-3-{4-[2-(methylamino)pyridin-4-yl]-1-(tetrahydro-2H-pyran-4-yl)-1H-pyrazol-3-yl}phenyl) benzenesulfonamide (6% yield) and 29 mg of N-(3-{4-[2-(dimethylamino)pyridin-4-yl]-1-(tetrahydro-2H-pyran-4-yl)-1H-pyrazol-3-yl}-2-fluorophenyl)-2,5-difluorobenzenesulfonamide (54% yield). HPLC (254 nm): R$_t$: 4.44 min; $^1$H NMR (DMSO-d6) Shift: 10.71 (br. s., 1H), 8.25 (s, 1H), 7.76 (d, J=5.4 Hz, 1H), 7.60-7.51 (m, 1H), 7.51-7.40 (m, 2H), 7.32 (dt, J=2.1, 7.5 Hz, 1H), 727-7.09 (m, 2H), 6.34-6.22 (m, 1H), 6.17 (s, 1H), 6.16-6.12 (m, 1H), 4.51-4.35 (m, 1H), 4.01-3.92 (m, 2H), 3.47 (dt, J=2.6, 11.6 Hz, 2H), 2.63 (d, J=4.8 Hz, 3H), 2.10-1.88 (m, 4H); HRMS (ESI) calcd for C26H25F3N5O3S [M+H]$^+$ 544.1625. found 544.1622.

N-(3-{4-[2-(dimethylamino)pyridin-4-yl]-1-(tetrahydro-2H-pyran-4-yl)-1M-pyrazol-3-yl}-2-fluorophenyl)-2,5-difluorobenzenesulfonamide Formula 1, where m=0; $R_1$=tetrahydro-2H-pyran-4-yl; R2, R3=F; R4=2-dimethylamino-pyridin-4-yl

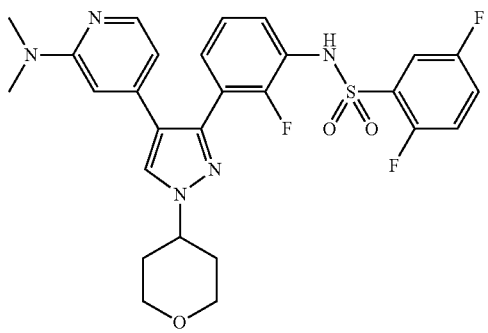 [SMILES: CN(C)c1cc(-c2cn(C3CCOCC3)nc2-c2cccc(NS(=O)(=O)c3cc(F)ccc3F)c2F)ccn1]

HPLC (254 nm): $R_t$: 5.16 min; $^1$H NMR (DMSO-d6) Shift: 10.68 (br. s., 1H), 8.35 (s, 1H), 7.87 (dd, J=0.7, 5.1 Hz, 1H), 7.60-7.51 (m, 1H), 7.50-7.41 (m, 2H), 7.34 (dt, J=2.1, 7.5 Hz, 1H), 7.28-7.16 (m, 2H), 6.32-6.21 (m, 2H), 4.52-4.36 (m, 1H), 4.06-3.90 (m, 2H), 3.48 (dt, J=2.4, 11.6 Hz, 2H), 2.85 (s, 6H), 2.10-1.89 (m, 4H); HRMS (ESI) calcd for C27H27F3N5O3S [M+H]$^+$ 558.1781. found 558.1783.

The invention claimed is:
1. Compounds of formula (I)

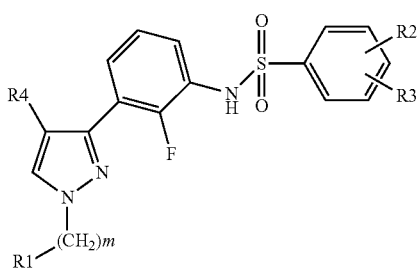

wherein:
m is 0, 1, or 2;
R1 is trifluoromethyl, halogen, cyano, OR5, COOR10, CONR11R12, ($C_3$-$C_8$) cycloalkyl, or heterocyclyl the ($C_3$-$C_8$) cycloalkyl and heterocyclyl being optionally substituted with one to two groups independently selected from $C_1$-$C_8$alkyl, $C_3$-$C_8$cycloalkyl, halogen, alkylcarbonyl, and $C_1$-$C_8$alkyl substituted with COOR', wherein R' is H or $C_1$-$C_4$alkyl;
wherein:
R5 and R10 are straight or branched ($C_1$-$C_8$) alkyl;
R11 and R12 are the same or different and are each independently hydrogen or straight or branched ($C_1$-$C_8$) alkyl;
R2 and R3 are each fluoro, wherein one of R2 and R3 is a 2-fluoro and the other is a 5-fluoro;

R4 is a heteroaryl group selected from

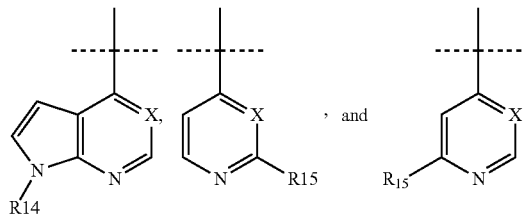

wherein
R14 is hydrogen or a group selected from straight or branched ($C_1$-$C_8$) alkyl and ($C_3$-$C_8$) cycloalkyl;
X is CH or N;
R15 is hydrogen, straight or branched ($C_1$-$C_8$) alkyl, ($C_3$-$C_8$) cycloalkyl, halogen, cyano, NR16R17, CONR18R19, COOR20, or OR20, wherein:
R16 and R17 are independently hydrogen, straight or branched ($C_1$-$C_8$) alkyl, or pyrimidinyl optionally substituted with amino or R16 is hydrogen and R17 is COR21,
wherein:
R21 is straight or branched ($C_1$-$C_8$) alkyl;
R18 and R19 are independently hydrogen or straight or branched ($C_1$-$C_8$) alkyl;
R20 is straight or branched ($C_1$-$C_8$)alkyl;
or a pharmaceutically acceptable salt thereof.
2. Compounds of formula (I)

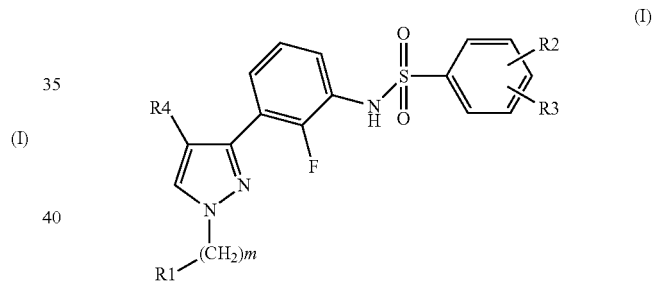

wherein:
m is 0;
R1 is isopropyl;
R2 and R3 are each fluoro wherein one of R2 and R3 is a 2-fluoro and the other is a 5-fluoro;
R4 is a heteroaryl group selected from

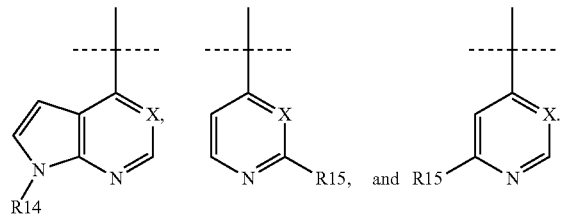

wherein
R14 is hydrogen or a group selected from straight or branched ($C_1$-$C_8$) alkyl and ($C_3$-$C_8$) cycloalkyl;
X is CH or N;
R15 is hydrogen, straight or branched ($C_1$-$C_8$) alkyl, ($C_3$-$C_8$) cycloalkyl, halogen, cyano, NR16R17, CONR18R19, COOR20, or OR20, wherein:

R16 and R17 are independently hydrogen, straight or branched ($C_1$-$C_8$) alkyl, or pyrimidinyl optionally substituted with amino; or R16 is hydrogen and R17 is COR21,
wherein:
R21 is straight or branched ($C_1$-$C_8$) alkyl
R18 and R19 are independently hydrogen or straight or branched ($C_1$-$C_8$) alkyl;
R20 is straight or branched ($C_1$-$C_8$);
or a pharmaceutically acceptable salt thereof.

3. A compound according to claim 1, wherein R4 is a heteroaryl group selected from

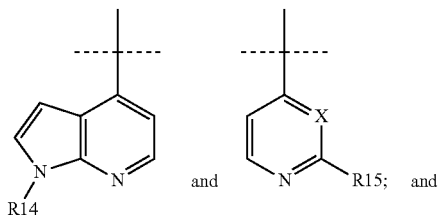

R15 is hydrogen, straight or branched ($C_1$-$C_8$) alkyl, ($C_3$-$C_8$) cycloalkyl, halogen, cyano, NR16R17, CONR18R19, or OR20.

4. A compound according to claim 2, wherein R4 is a heteroaryl group selected from

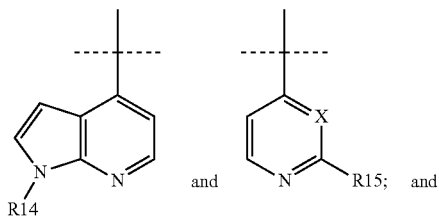

R15 is hydrogen, straight or branched ($C_1$-$C_8$) alkyl, ($C_3$-$C_8$) cycloalkyl, halogen, cyano, NR16R17, CONR18R19, or OR20.

5. A compound according to claim 1, wherein m is 2 and R1 is fluoro.

6. A compound according to claim 1, wherein R1 is selected from ($C_3$-$C_8$) cycloalkyl or heterocyclyl, the ($C_3$-$C_8$) cycloalkyl and heterocyclyl being optionally substituted with one to two groups independently selected from $C_1$-$C_8$alkyl, $C_3$-$C_8$cycloalkyl, and halogen.

7. A compound according to claim 1, wherein R4 is

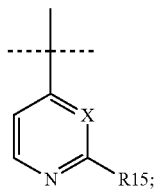

R15 is hydrogen or NR16R17;
R16 and R17 are hydrogen, or R16 is hydrogen and R17 is COR21; and
R21 is straight or branched ($C_1$-$C_8$) alkyl.

8. A compound according to claim 4, wherein R4 is

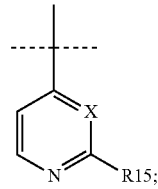

R15 is hydrogen or NR16R17;
R16 and R17 are hydrogen, or R16 is hydrogen and R17 is COR21; and
R21 is straight or branched ($C_1$-$C_8$) alkyl.

9. A compound according to claim 2, wherein R14 is hydrogen and R15 is selected from the group consisting of: hydrogen, halogen and $NH_2$.

10. A compound according to claim 1, wherein R14 is hydrogen and R15 is selected from the group consisting of hydrogen, halogen and $NH_2$.

11. A compound selected from:
1) 2,5-difluoro-N-{2-fluoro-3-[1-(1-isopropyl-piperidin-4-yl)-4-pyridin-4-yl-1H-pyrazol-3-yl]-phenyl}-benzenesulfonamide;
2) N-{3-[1-(1-cyclopropyl-piperidin-4-yl)-4-pyridin-4-yl-1H-pyrazol-3-yl]-2-fluoro-phenyl}-2,5-difluoro-benzenesulfonamide;
3) N-{3-[4-(2-amino-pyrimidin-4-yl)-1-ethyl-1H-pyrazol-3-yl]-2-fluoro-phenyl}-2,5-difluoro-benzenesulfonamide;
4) N-{3-[4-(2-amino-pyridin-4-yl)-1-ethyl-1H-pyrazol-3-yl]-2-fluoro-phenyl}-2,5-difluoro-benzenesulfonamide;
5) 2,5-difluoro-N-{2-fluoro-3-[1-(1-methyl-piperidin-4-yl)-4-pyridin-4-yl-1H-pyrazol-3-yl]-phenyl}-benzenesulfonamide;
6) N-{3-[4-(2-amino-pyrimidin-4-yl)-1-(1-methyl-piperidin-4-yl)-1H-pyrazol-3-yl]-2-fluoro-phenyl}-2,5-difluoro-benzenesulfonamide;
7) 2,5-difluoro-N-{2-fluoro-3-[1-(2-fluoro-ethyl)-4-pyridin-4-yl-1H-pyrazol-3-yl]-phenyl}-benzenesulfonamide;
8) 2,5-difluoro-N-{2-fluoro-3-[1-(1-methyl-piperidin-4-yl)-4-(1H-pyrrolo[2,3-b]pyridin-4-yl)-1H-pyrazol-3-yl]-phenyl}-benzenesulfonamide;
9) 2,5-difluoro-N-[2-fluoro-3-(1-isopropyl-4-pyridin-4-yl-1H-pyrazol-3-yl)-phenyl]-benzenesulfonamide;
10) N-{3-[4-(2-amino-pyrimidin-4-yl)-1-isopropyl-1H-pyrazol-3-yl]-2-fluoro-phenyl}-2,5-difluoro-benzenesulfonamide,
11) N-{3-[4-(2-amino-pyrimidin-4-yl)-1-(2-fluoro-ethyl)-1H-pyrazol-3-yl]-2-fluoro-phenyl}-2,5-difluoro-benzenesulfonamide;
12) N-{3-[4-(2-amino-pyridin-4-yl)-1-isopropyl-1H-pyrazol-3-yl]-2-fluoro-phenyl}-2,5-difluoro-benzenesulfonamide;
13) N-{3-[4-(2-amino-pyridin-4-yl)-1-(2-fluoro-ethyl)-1H-pyrazol-3-yl]-2-fluoro-phenyl}-2,5-difluoro-benzenesulfonamide;
14) N-{3-[4-(2-amino-pyridin-4-yl)-1-(tetrahydro-pyran-4-yl)-1H-pyrazol-3-yl]-2-fluoro-phenyl}-2,5-difluoro-benzenesulfonamide;

15) N-{3-[4-(2-amino-pyrimidin-4-yl)-1-(tetrahydro-pyran-4-yl)-1H-pyrazol-3-yl]-2-fluoro-phenyl}-2,5-difluoro-benzenesulfonamide;
16) 2,5-difluoro-N-{2-fluoro-3-[4-pyridin-4-yl-1-(tetrahydro-pyran-4-yl)-1H-pyrazol-3-yl]-phenyl}-benzenesulfonamide;
17) N-{3-[4-(2-amino-pyridin-4-yl)-1-cyclopentyl-1H-pyrazol-3-yl]-2-fluoro-phenyl}-2,5-difluoro-benzenesulfonamide;
18) N-{3-[4-(2-amino-pyrimidin-4-yl)-1-(1-isopropyl-piperidin-4-yl)-1H-pyrazol-3-yl]-2-fluoro-phenyl}-2,5-difluoro-benzenesulfonamide;
19) 2,5-difluoro-N-[2-fluoro-3-(1-oxetan-3-yl-4-pyridin-4-yl-1H-pyrazol-3-yl)-phenyl]-benzenesulfonamide;
20) N-(3-{4-[2-(2-amino-pyrimidin-4-ylamino)-pyrimidin-4-yl]-1-ethyl-1H-pyrazol-3-yl}-2-fluoro-phenyl)-2,5-difluoro-benzenesulfonamide;
21) N-{3-[4-(2-amino-pyridin-4-yl)-1-(1-cyclopropyl-piperidin-4-yl)-1H-pyrazol-3-yl]-2-fluoro-phenyl}-2,5-difluoro-benzenesulfonamide;
22) 2,5-difluoro-N-{2-fluoro-3-[4-(2-fluoropyridin-4-yl)-1-(1-methylpiperidin-4-yl)-1H-pyrazol-3-yl]phenyl}benzenesulfonamide
23) N-{3-[1-(4,4-difluorocyclohexyl)-4-(pyridin-4-yl)-1H-pyrazol-3-yl]-2-fluorophenyl}-2,5-difluorobenzenesulfonamide
24) N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}acetamide;
25) 2,5-difluoro-N-{2-fluoro-3-[4-(2-fluoropyridin-4-yl)-1-(tetrahydro-2H-pyran-4-yl)-1H-pyrazol-3-yl]phenyl}benzenesulfonamide
26) 2,5-difluoro-N-{2-fluoro-3-[1-(1-methylpiperidin-4-yl)-4-(2-methylpyridin-4-yl)-1H-pyrazol-3-yl]phenyl}benzenesulfonamide
27) 2,5-difluoro-N-{2-fluoro-3-[4-(2-methylpyridin-4-yl)-1-(tetrahydro-2H-pyran-4-yl)-1H-pyrazol-3-yl]phenyl}benzenesulfonamide
28) N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}-2-methylpropanamide
29) N-{4-[3-(3-{[(2,5-difluorophenyl)sulfonyl]amino}-2-fluorophenyl)-1-(1-methylpiperidin-4-yl)-1H-pyrazol-4-yl]pyridin-2-yl}acetamide;
30) 2,5-difluoro-N-{2-fluoro-3-[4-pyridin-4-yl-1-(2,2,2-trifluoroethyl)-1H-pyrazol-3-yl]-phenyl}-benzenesulfonamide;
31) 2,5-Difluoro-N-{2-fluoro-3-[1-(2-methoxy-ethyl)-4-pyridin-4-yl-1H-pyrazol-3-yl]-phenyl}-benzenesulfonamide;
32) N-[3-(1-Cyanomethyl-4-pyridin-4-yl-1H-pyrazol-3-yl)-2-fluoro-phenyl]-2,5-difluoro-benzenesulfonamide;
33) 2-{3-[3-(2,5-Difluoro-benzenesulfonylamino)-2-fluoro-phenyl]-4-pyridin-4-yl-pyrazol-1-yl}-acetamide;
34) 2-{3-[3-(2,5-Difluoro-benzenesulfonylamino)-2-fluoro-phenyl]-4-pyridin-4-yl-pyrazol-1-yl}-N-methyl-acetamide;
35) 2-{3-[3-(2,5-Difluoro-benzenesulfonylamino)-2-fluoro-phenyl]-4-pyridin-4-yl-pyrazol-1-yl}-N,N-dimethyl-acetamide;
36) 2,5-Difluoro-N-{2-fluoro-3-[4-(2-fluoro-pyridin-4-yl)-1-isopropyl-1H-pyrazol-3-yl]-phenyl}-benzenesulfonamide;
37) N-{3-[1-(1-cyclopropylpiperidin-4-yl)-4-(2-fluoropyridin-4-yl)-1H-pyrazol-3-yl]-2-fluorophenyl}-2,5-difluorobenzenesulfonamide;
38) N-{3-[4-(2-chloropyridin-4-yl)-1-(1-methylpiperidin-4-yl)-1H-pyrazol-3-yl]-2-fluorophenyl}-2,5-difluorobenzenesulfonamide;
39) 2,5-difluoro-N-{2-fluoro-3-[4-(2-methoxypyridin-4-yl)-1-(1-methylpiperidin-4-yl)-1H-pyrazol-3-yl]phenyl}benzenesulfonamide;
40) 2,5-difluoro-N-{2-fluoro-3-[1-(8-methyl-8-azabicyclo[3.2.1]oct-3-yl)-4-(pyridin-4-yl)-1H-pyrazol-3-yl]phenyl}benzenesulfonamide;
41) 2,5-Difluoro-N-{2-fluoro-3-[4-(2-fluoro-pyridin-4-yl)-1-(1-isopropyl-piperidin-4-yl)-1H-pyrazol-3-yl]-phenyl}-benzenesulfonamide;
42) 3-(4-{3-[3-(2,5-Difluoro-benzenesulfonylamino)-2-fluoro-phenyl]-4-pyridin-4-yl-pyrazol-1-yl}-piperidin-1-yl)-propionic acid ethyl ester;
43) 3-(4-{3-[3-(2,5-Difluoro-benzenesulfonylamino)-2-fluoro-phenyl]-4-pyridin-4-yl-pyrazol-1-yl}-piperidin-1-yl)-propionic acid methyl ester;
44) 2,5-Difluoro-N-[2-fluoro-3-(1-piperidin-4-yl-4-pyridin-4-yl-1H-pyrazol-3-yl)-phenyl]-benzenesulfonamide;
45) N-{3-[1-(1-Acetyl-piperidin-4-yl)-4-pyridin-4-yl-1H-pyrazol-3-yl]-2-fluoro-phenyl}-2,5-difluoro-benzenesulfonamide;
46) N-{3-[4-(2-chloropyridin-4-yl)-1-(tetrahydro-2H-pyran-4-yl)-1H-pyrazol-3-yl]-2-fluorophenyl}-2,5-difluorobenzenesulfonamide;
47) N-{3-[4-(6-aminopyrimidin-4-yl)-1-(tetrahydro-2H-pyran-4-yl)-1H-pyrazol-3-yl]-2-fluorophenyl}-2,5-difluorobenzenesulfonamide;
48) 2,5-difluoro-N-{2-fluoro-3-[4-(7H-pyrrolo[2,3-d]pyrimidin-4-yl)-1-(tetrahydro-2H-pyran-4-yl)-1H-pyrazol-3-yl]phenyl}benzenesulfonamide;
49) N-{3-[4-(2-Amino-pyrimidin-4-yl)-1-piperidin-4-yl-1H-pyrazol-3-yl]-2-fluoro-phenyl}-2,5-difluoro-benzenesulfonamide;
50) 2,5-Difluoro-N-{2-fluoro-3-[1-(2-fluoro-ethyl)-4-(1H-pyrrolo[2,3-b]pyridin-4-yl)-1H-pyrazol-3-yl]-phenyl}-benzenesulfonamide;
51) N-{3-[1-Ethyl-4-(1H-pyrrolo[2,3-b]pyridin-4-yl)-1H-pyrazol-3-yl]-2-fluoro-phenyl}-2,5-difluoro-benzenesulfonamide;
52) N-{3-[4-(2-Butylamino-pyridin-4-yl)-1-isopropyl-1H-pyrazol-3-yl]-2-fluoro-phenyl}-2,5-difluoro-benzenesulfonamide;
53) N-{3-[4-(2-Amino-pyridin-4-yl)-1-cyclopropyl-1H-pyrazol-3-yl]-2-fluoro-phenyl}-2,5-difluoro-benzenesulfonamide;
54) N-{3-[4-(2-Amino-pyridin-4-yl)-1-cyclohexyl-1H-pyrazol-3-yl]-2-fluoro-phenyl}-2,5-difluoro-benzenesulfonamide;
55) N-{3-[4-(2-Amino-pyridin-4-yl)-1-(1-methyl-piperidin-4-yl)-1H-pyrazol-3-yl]-2-fluoro-phenyl}-2,5-difluoro-benzenesulfonamide;
56) N-{3-[4-(2-Amino-pyridin-4-yl)-1-(1-isopropyl-piperidin-4-yl)-1H-pyrazol-3-yl]-2-fluoro-phenyl}-2,5-difluoro-benzenesulfonamide;
57) N-{3-[4-(2-Amino-pyridin-4-yl)-1-(1-ethyl-piperidin-4-yl)-1H-pyrazol-3-yl]-2-fluoro-phenyl}-2,5-difluoro-benzenesulfonamide;
58) N-{3-[4-(2-tert-Butylamino-pyridin-4-yl)-1-piperidin-4-yl-1H-pyrazol-3-yl]-2-fluoro-phenyl}-2,5-difluoro-benzenesulfonamide;
59) N-{3-[4-(2-tert-Butylamino-pyridin-4-yl)-1-(1-methyl-piperidin-4-yl)-1H-pyrazol-3-yl]-2-fluoro-phenyl}-2,5-difluoro-benzenesulfonamide;

60) N-{3-[1-(1-Acetyl-piperidin-4-yl)-4-(2-amino-pyridin-4-yl)-1H-pyrazol-3-yl]-2-fluoro-phenyl}-2,5-difluoro-benzenesulfonamide;
61) 2,5-Difluoro-N-(2-fluoro-3-{1[2-(4-methyl-piperazin-1-yl)-ethyl]-4-pyridin-4-yl-1H-pyrazol-3-yl}-phenyl)-benzenesulfonamide;
62) 2,5-Difluoro-N-{2-fluoro-3-[1-(2-piperidin-1-yl-ethyl)-4-pyridin-4-yl-1H-pyrazol-3-yl]-phenyl}-benzenesulfonamide;
63) 2,5-Difluoro-N-{2-fluoro-3-[1-piperidin-4-yl-4-(1H-pyrrolo[2,3-b]pyridin-4-yl)-1H-pyrazol-3-yl]-phenyl}-benzenesulfonamide;
64) 2,5-difluoro-N-{2-fluoro-3-[1-(oxetan-2-yl)-4-(pyridin-4-yl)-1H-pyrazol-3-yl]phenyl}benzenesulfonamide;
65) 2,5-Difluoro-N-{2-fluoro-3-[1-(3-methyl-oxetan-3-ylmethyl)-4-pyridin-4-yl-1H-pyrazol-3-yl]-phenyl}-benzenesulfonamide;
66) 2,5-difluoro-N-{2-fluoro-3-[4-(pyridin-4-yl)-1-(tetrahydro-2H-pyran-4-ylmethyl)-1H-pyrazol-3-yl]phenyl}benzenesulfonamide;
67) N-[3-(1-Cyclopropyl-4-pyridin-4-yl-1H-pyrazol-3-yl)-2-fluoro-phenyl]-2,5-difluoro-benzenesulfonamide;
68) N-{3-[4-(2-Cyano-pyridin-4-yl)-1-(tetrahydro-pyran-4-yl)-1H-pyrazol-3-yl]-2-fluoro-phenyl}-2,5-difluoro-benzenesulfonamide;
69) 4-[3-(3-{[(2,5-difluorophenyl)sulfonyl]amino}-2-fluorophenyl)-1-(tetrahydro-2H-pyran-4-yl)-1H-pyrazol-4-yl]pyridine-2-carboxamide;
70) Methyl 4-[3-(3-{[(2,5-difluorophenyl)sulfonyl]amino}-2-fluorophenyl)-1-(tetrahydro-2H-pyran-4-yl)-1H-pyrazol-4-yl]pyridine-2-carboxylate;
71) 4-[3-(3-{[(2,5-difluorophenyl)sulfonyl]amino}-2-fluorophenyl)-1-(1-methyl-piperidin-4-yl)-1H-pyrazol-4-yl]pyridine-2-carboxamide;
72) 4-[3-(3-{[(2,5-difluorophenyl)sulfonyl]amino}-2-fluorophenyl)-1-(tetrahydro-2H-pyran-4-yl)-1H-pyrazol-4-yl]-N-methylpyridine-2-carboxamide;
73) 4-[3-(3-{[(2,5-Difluorophenyl)sulfonyl]amino}-2-fluorophenyl)-1-(1-methylpiperidin-4-yl)-1H-pyrazol-4-yl]-N-methylpyridine-2-carboxamide;
74) 2,5-difluoro-N-(2-fluoro-3-{4-[2-(methylamino)pyridin-4-yl]-1-(tetrahydro-2H-Pyran-4-yl)-1H-pyrazol-3-yl}phenyl)benzenesulfonamide;
75) N-(3-{4-[2-(dimethylamino)pyridin-4-yl]-1-(tetrahydro-2H-pyran-4-yl)-1H-pyrazol-3-yl}-2-fluorophenyl)-2,5-difluorobenzenesulfonamide; or a pharmaceutically acceptable salt thereof.

12. A compound according to claim 11, selected from:
1) 2,5-difluoro-N-{2-fluoro-3-[1-(1-isopropyl-piperidin-4-yl)-4-pyridin-4-yl-1H-pyrazol-3-yl]-phenyl}-benzenesulfonamide;
2) N-{3-[1-(1-cyclopropyl-piperidin-4-yl)-4-pyridin-4-yl-1H-pyrazol-3-yl]-2-fluoro-phenyl}-2,5-difluoro-benzenesulfonamide;
3) N-{3-[4-(2-amino-pyrimidin-4-yl)-1-ethyl-1H-pyrazol-3-yl]-2-fluoro-phenyl}-2,5-difluoro-benzenesulfonamide;
4) N-{3-[4-(2-amino-pyridin-4-yl)-1-ethyl-1H-pyrazol-3-yl]-2-fluoro-phenyl}-2,5-difluoro-benzenesulfonamide;
5) 2,5-difluoro-N-{2-fluoro-3-[1-(1-methyl-piperidin-4-yl)-4-pyridin-4-yl-1H-pyrazol-3-yl]-phenyl}-benzenesulfonamide;
6) N-{3-[4-(2-amino-pyrimidin-4-yl)-1-(1-methyl-piperidin-4-yl)-1H-pyrazol-3-yl]-2-fluoro-phenyl}-2,5-difluoro-benzenesulfonamide;
7) 2,5-difluoro-N-{2-fluoro-3-[1-(2-fluoro-ethyl)-4-pyridin-4-yl-1H-pyrazol-3-yl]-phenyl}-benzenesulfonamide;
8) 2,5-difluoro-N-{2-fluoro-3-[1-(1-methyl-piperidin-4-yl)-4-(1H-pyrrolo[2,3-b]pyridin-4-yl)-1H-pyrazol-3-yl]-phenyl}-benzenesulfonamide;
9) 2,5-difluoro-N-[2-fluoro-3-(1-isopropyl-4-pyridin-4-yl-1H-pyrazol-3-yl)-phenyl]-benzenesulfonamide;
10) N-{3-[4-(2-amino-pyrimidin-4-yl)-1-isopropyl-1H-pyrazol-3-yl]-2-fluoro-phenyl}-2,5-difluoro-benzenesulfonamide;
11) N-{3-[4-(2-amino-pyrimidin-4-yl)-1-(2-fluoro-ethyl)-1H-pyrazol-3-yl]-2-fluoro-phenyl}-2,5-difluoro-benzenesulfonamide;
12) N-{3-[4-(2-amino-pyridin-4-yl)-1-isopropyl-1H-pyrazol-3-yl]-2-fluoro-phenyl}-2,5-difluoro-benzenesulfonamide;
13) N-{3-[4-(2-amino-pyridin-4-yl)-1-(2-fluoro-ethyl)-1H-pyrazol-3-yl]-2-fluoro-phenyl}-2,5-difluoro-benzenesulfonamide;
14) N-{3-[4-(2-amino-pyridin-4-yl)-1-(tetrahydro-pyran-4-yl)-1H-pyrazol-3-yl]-2-fluoro-phenyl}-2,5-difluoro-benzenesulfonamide;
15) N-{3-[4-(2-amino-pyrimidin-4-yl)-1-(tetrahydro-pyran-4-yl)-1H-pyrazol-3-yl]-2-fluoro-phenyl}-2,5-difluoro-benzenesulfonamide;
16) 2,5-difluoro-N-{2-fluoro-3-[4-pyridin-4-yl-1-(tetrahydro-pyran-4-yl)-1H-pyrazol-3-yl]-phenyl}-benzenesulfonamide;
17) N-{3-[4-(2-amino-pyridin-4-yl)-1-cyclopentyl-1H-pyrazol-3-yl]-2-fluoro-phenyl}-2,5-difluoro-benzenesulfonamide;
18) N-{3-[4-(2-amino-pyrimidin-4-yl)-1-(1-isopropyl-piperidin-4-yl)-1H-pyrazol-3-yl]-2-fluoro-phenyl}-2,5-difluoro-benzenesulfonamide;
19) 2,5-difluoro-N-[2-fluoro-3-(1-oxetan-3-yl-4-pyridin-4-yl-1H-pyrazol-3-yl)-phenyl]-benzenesulfonamide;
20) N-(3-{4-[2-(2-amino-pyrimidin-4-ylamino)-pyrimidin-4-yl]-1-ethyl-1H-pyrazol-3-yl}-2-fluoro-phenyl)-2,5-difluoro-benzenesulfonamide; and
21) N-{3-[4-(2-amino-pyridin-4-yl)-1-(1-cyclopropyl-piperidin-4-yl)-1H-pyrazol-3-yl]-2-fluoro-phenyl}-2,5-difluoro-benzenesulfonamide;
22) 2,5-difluoro-N-{2-fluoro-3-[4-(2-fluoropyridin-4-yl)-1-(1-methylpiperidin-4-yl)-1H-pyrazol-3-yl]phenyl}benzenesulfonamide
23) 2,5-difluoro-N-{2-fluoro-3-[4-pyridin-4-yl-1-(2,2,2-trifluoroethyl)-1H-pyrazol-3-yl]-phenyl}-benzenesulfonamide;
24) 2,5-Difluoro-N-{2-fluoro-3-[1-(2-methoxy-ethyl)-4-pyridin-4-yl-1H-pyrazol-3-yl]-phenyl}-benzenesulfonamide;
25) N-[3-(1-Cyanomethyl-4-pyridin-4-yl-1H-pyrazol-3-yl)-2-fluoro-phenyl]-2,5-difluoro-benzenesulfonamide;
26) 2-{3-[3-(2,5-Difluoro-benzenesulfonylamino)-2-fluoro-phenyl]-4-pyridin-4-yl-pyrazol-1-yl}-acetamide;
27) 2-{3-[3-(2,5-Difluoro-benzenesulfonylamino)-2-fluoro-phenyl]-4-pyridin-4-yl-pyrazol-1-yl}-N-methyl-acetamide;
28) 2-{3-[3-(2,5-Difluoro-benzenesulfonylamino)-2-fluoro-phenyl]-4-pyridin-4-yl-pyrazol-1-yl}-N,N-dimethyl-acetamide;
29) 2,5-Difluoro-N-{2-fluoro-3-[4-(2-fluoro-pyridin-4-yl)-1-isopropyl-1H-pyrazol-3-yl]-phenyl}-benzenesulfonamide;

30) 2,5-Difluoro-N-{2-fluoro-3-[4-(2-fluoro-pyridin-4-yl)-1-(1-isopropyl-piperidin-4-yl)-1H-pyrazol-3-yl]-phenyl}-benzenesulfonamide;
31) 3-(4-{3-[3-(2,5-Difluoro-benzenesulfonylamino)-2-fluoro-phenyl]-4-pyridin-4-yl-pyrazol-1-yl}-piperidin-1-yl)-propionic acid ethyl ester;
32) 3-(4-{3-[3-(2,5-Difluoro-benzenesulfonylamino)-2-fluoro-phenyl]-4-pyridin-4-yl-pyrazol-1-yl}-piperidin-1-yl)-propionic acid methyl ester;
33) 2,5-Difluoro-N-[2-fluoro-3-(1-piperidin-4-yl-4-pyridin-4-yl-1H-pyrazol-3-yl)-phenyl]-benzenesulfonamide;
34) N-{3-[1-(1-Acetyl-piperidin-4-yl)-4-pyridin-4-yl-1H-pyrazol-3-yl]-2-fluoro-phenyl}-2,5-difluoro-benzenesulfonamide;
35) N-{3-[4-(2-Amino-pyrimidin-4-yl)-1-piperidin-4-yl-1H-pyrazol-3-yl]-2-fluoro-phenyl}-2,5-difluoro-benzenesulfonamide;
36) 2,5-Difluoro-N-{2-fluoro-3-[1-(2-fluoro-ethyl)-4-(1H-pyrrolo[2,3-b]pyridin-4-yl)-1H-pyrazol-3-yl]-phenyl}-benzenesulfonamide;
37) N-{3-[1-Ethyl-4-(1H-pyrrolo[2,3-b]pyridin-4-yl)-1H-pyrazol-3-yl]-2-fluoro-phenyl}-2,5-difluoro-benzenesulfonamide;
38) N-{3-[4-(2-Butylamino-pyridin-4-yl)-1-isopropyl-1H-pyrazol-3-yl]-2-fluoro-phenyl}-2,5-difluoro-benzenesulfonamide;
39) N-{3-[4-(2-Amino-pyridin-4-yl)-1-cyclopropyl-1H-pyrazol-3-yl]-2-fluoro-phenyl}-2,5-difluoro-benzenesulfonamide;
40) N-{3-[4-(2-Amino-pyridin-4-yl)-1-cyclohexyl-1H-pyrazol-3-yl]-2-fluoro-phenyl}-2,5-difluoro-benzenesulfonamide;
41) N-{3-[4-(2-Amino-pyridin-4-yl)-1-(1-methyl-piperidin-4-yl)-1H-pyrazol-3-yl]-2-fluoro-phenyl}-2,5-difluoro-benzenesulfonamide;
42) N-{3-[4-(2-Amino-pyridin-4-yl)-1-(1-isopropyl-piperidin-4-yl)-1H-pyrazol-3-yl]-2-fluoro-phenyl}-2,5-difluoro-benzenesulfonamide;
43) N-{3-[4-(2-Amino-pyridin-4-yl)-1-(1-ethyl-piperidin-4-yl)-1H-pyrazol-3-yl]-2-fluoro-phenyl}-2,5-difluoro-benzenesulfonamide;
44) N-{3-[4-(2-tert-Butylamino-pyridin-4-yl)-1-piperidin-4-yl-1H-pyrazol-3-yl]-2-fluoro-phenyl}-2,5-difluoro-benzenesulfonamide;
45) N-{3-[4-(2-tert-Butylamino-pyridin-4-yl)-1-(1-methyl-piperidin-4-yl)-1H-pyrazol-3-yl]-2-fluoro-phenyl}-2,5-difluoro-benzenesulfonamide;
46) N-{3-[1-(1-Acetyl-piperidin-4-yl)-4-(2-amino-pyridin-4-yl)-1H-pyrazol-3-yl]-2-fluoro-phenyl}-2,5-difluoro-benzenesulfonamide;
47) 2,5-Difluoro-N-(2-fluoro-3-{1-[2-(4-methyl-piperazin-1-yl)-ethyl]-4-pyridin-4-yl-1H-pyrazol-3-yl}-phenyl)-benzenesulfonamide;
48) 2,5-Difluoro-N-{2-fluoro-3-[1-(2-piperidin-1-yl-ethyl)-4-pyridin-4-yl-1H-pyrazol-3-yl]-phenyl}-benzenesulfonamide;
49) 2,5-Difluoro-N-{2-fluoro-3-[1-piperidin-4-yl-4-(1H-pyrrolo[2,3-b]pyridin-4-yl)-1H-pyrazol-3-yl]-phenyl}-benzenesulfonamide;
50) N-[3-(1-Cyclopropyl-4-pyridin-4-yl-1H-pyrazol-3-yl)-2-fluoro-phenyl]-2,5-difluoro-benzenesulfonamide; or a pharmaceutically acceptable salt thereof.

13. A compound according to claim 11, selected from:
1) N-{3-[1-(1-cyclopropyl-piperidin-4-yl)-4-pyridin-4-yl-1H-pyrazol-3-yl]-2-fluoro-phenyl}-2,5-difluoro-benzenesulfonamide;
2) 2,5-difluoro-N-{2-fluoro-3-[1-(1-methyl-piperidin-4-yl)-4-pyridin-4-yl-1H-pyrazol-3-yl]-phenyl}-benzenesulfonamide;
3) 2,5-difluoro-N-{2-fluoro-3-[1-(2-fluoro-ethyl)-4-pyridin-4-yl-1H-pyrazol-3-yl]-phenyl}-benzenesulfonamide;
4) 2,5-difluoro-N-[2-fluoro-3-(1-isopropyl-4-pyridin-4-yl-1H-pyrazol-3-yl)-phenyl]-benzenesulfonamide;
5) N-{3-[4-(2-amino-pyrimidin-4-yl)-1-isopropyl-1H-pyrazol-3-yl]-2-fluoro-phenyl}-2,5-difluoro-benzenesulfonamide;
6) N-{3-[4-(2-amino-pyrimidin-4-yl)-1-(2-fluoro-ethyl)-1H-pyrazol-3-yl]-2-fluoro-phenyl}-2,5-difluoro-benzenesulfonamide;
7) N-{3-[4-(2-amino-pyridin-4-yl)-1-isopropyl-1H-pyrazol-3-yl]-2-fluoro-phenyl}-2,5-difluoro-benzenesulfonamide;
8) N-{3-[4-(2-amino-pyridin-4-yl)-1-(2-fluoro-ethyl)-1H-pyrazol-3-yl]-2-fluoro-phenyl}-2,5-difluoro-benzenesulfonamide;
9) N-{3-[4-(2-amino-pyrimidin-4-yl)-1-(tetrahydro-pyran-4-yl)-1H-pyrazol-3-yl]-2-fluoro-phenyl}-2,5-difluoro-benzenesulfonamide;
10) N-{3-[1-(4,4-difluorocyclohexyl)-4-(pyridin-4-yl)-1H-pyrazol-3-yl]-2-fluorophenyl}-2,5-difluorobenzenesulfonamide;
11) N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}acetamide;
12) N-{4-[3-(3-{[(2,5-difluorophenyl)sulfonyl]amino}-2-fluorophenyl)-1-(tetrahydro-2H-pyran-4-yl)-1H-pyrazol-4-yl]pyridin-2-yl}-2-methylpropanamide;
13) N-{4-[3-(3-{[(2,5-difluorophenyl)sulfonyl]amino}-2-fluorophenyl)-1-(1-methylpiperidin-4-yl)-1H-pyrazol-4-yl]pyridin-2-yl}acetamide;
14) 2,5-difluoro-N-{2-fluoro-3-[4-pyridin-4-yl-1-(2,2,2-trifluoroethyl)-1H-pyrazol-3-yl]-phenyl}-benzenesulfonamide; or a pharmaceutically acceptable salt thereof.

14. A process for preparing a compound of claim 1 characterized in that the process comprises the following steps:
a) coupling a compound of formula 1:

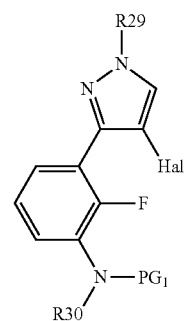

1 wherein
Hal is a halogen atom, R29 is —(CH$_2$)$_m$R1 or PG$_2$, wherein m and R1 are as defined in claim 1 and PG$_2$ is a suitable protective group of the pyrazole ring,
PG$_1$ is a suitable protective group of the aniline or the sulfonamide, and
R30 is either hydrogen or a group SO$_2$Ph(R2)(R3), wherein R2 and R3 are as defined in claim 1 with an organometallic compound of formula R4M, wherein R4 is as defined in claim 1 and M is $B(OH)_2$, $B(OAlk)_2$, $Sn(Alk)_3$, $Al(Alk)_2$, ZnHal, MgHal or $ZrCp_2Hal$;

or b) reacting a compound of formula 1 as defined above with an organo metallic compound such as an alkylboron compound or an alkyl tin compound;

c) cross-coupling the resultant compound of formula 3:

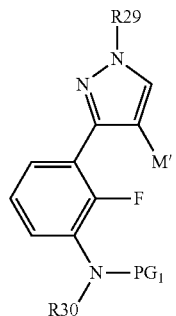

3 wherein M' is $B(OAlk)_2$ or $Sn(Alk)_3$, and R29, $PG_1$ and R30 are as defined above, with a suitable electrophile of formula R4L', wherein R4 is as defined above and L' is a group that may work as a leaving group, such as a halogen atom, a tosylate, mesylate or triflate;

optionally, d) removing the group R29 from the resultant compound 2 obtained in step a or c:

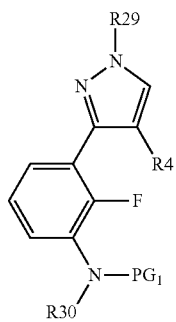

2 wherein R29 is $PG_2$, wherein $PG_2$, $PG_S$, and R30 are as defined above;

e) alkylating the resultant compound of formula 4A:

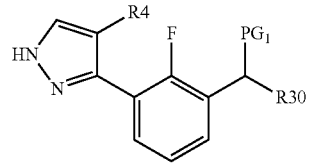

4A wherein R4 is as defined in claim 1 and $PG_1$ and R30 are as defined above, by reaction with a suitable alkylating agent of formula L-$(CH_2)_m$R1, wherein L is OH, a leaving group or —$B(OH)_2$, if necessary separating the resultant regioisomers, to obtain a compound of formula 2 wherein R29 is —$(CH_2)_m$R1;

f) removing the $PG_1$ group from the resultant compound of formula 2 wherein R29 is —$(CH_2)_m$R1, wherein m and R1 are as defined above, and R30 is SO2Ph(R2)(R3), wherein R2 and R3 are as defined in claim 1;

or g) removing the $PG_1$ group from the resultant compound of formula 2 wherein R29 is —$(CH_2)_m$R1, wherein m and R1 are as defined above, and R30 is hydrogen;

h) reacting the resultant compound of formula 5A:

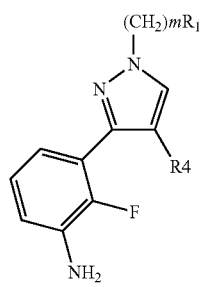

5A wherein R4, m and R1 are defined above, with a sulfonyl chloride of formula Cl—SO2Ph(R2)(R3), to obtain a compound of formula (I), optionally converting it into a pharmaceutical salt.

15. A pharmaceutical composition comprising one or more compounds of claim 1, or a pharmaceutically acceptable salt thereof, and a pharmaceutically acceptable excipient.

16. A pharmaceutical composition according to claim 15, further comprising one or more chemotherapeutic agents.

17. A product or kit comprising a compound according to claim 1, or a pharmaceutically acceptable salt thereof, and one or more chemotherapeutic agents, as a combined preparation for simultaneous, separate or sequential use in anticancer therapy.

* * * * *

UNITED STATES PATENT AND TRADEMARK OFFICE
CERTIFICATE OF CORRECTION

PATENT NO. : 9,114,137 B2  
APPLICATION NO. : 13/752807  
DATED : August 25, 2015  
INVENTOR(S) : Maurizio Pulici et al.

It is certified that error appears in the above-identified patent and that said Letters Patent is hereby corrected as shown below:

In the Specification

Column 1, Line 9 (Approx.), delete "Aug. 3, 2011," and insert -- Aug. 2, 2011, --, therefor.

In the Claims

Column 141, Line 53 (Approx.), in Claim 1, delete "heterocyclyl the" and insert -- heterocyclyl, the --, therefor.

Column 141, Lines 56-58, in Claim 1, delete "$C_1$-$C_8$alkyl, $C_3$-$C_8$cycloalkyl, halogen, alkylcarbonyl, and $C_1$-$C_8$alkyl substituted with COOR', wherein R' is H or $C_1$-$C_4$alkyl;" and insert -- ($C_1$-$C_8$) alkyl, ($C_3$-$C_8$) cycloalkyl, halogen, alkylcarbonyl, and ($C_1$-$C_8$) alkyl substituted with COOR', wherein R' is H or ($C_1$-$C_4$) alkyl; --, therefor.

Column 142, Line 27, in Claim 1, delete "($C_1$-$C_8$)alkyl" and insert -- ($C_1$-$C_8$) alkyl --, therefor.

Column 142, Lines 52-58, in Claim 2, delete " 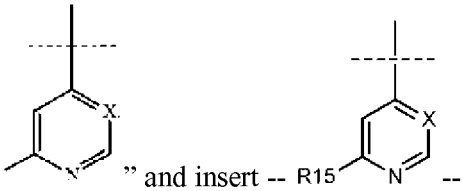 " and insert -- , therefor.

Column 143, Line 6 (Approx.), in Claim 2, delete "alkyl" and insert -- alkyl; --, therefor.

Column 143, Line 9 (Approx.), in Claim 2, delete "($C_1$-$C_8$);" and insert -- ($C_1$-$C_8$) alkyl; --, therefor.

Signed and Sealed this  
Sixteenth Day of February, 2016

Michelle K. Lee  
*Director of the United States Patent and Trademark Office*

CERTIFICATE OF CORRECTION (continued)
U.S. Pat. No. 9,114,137 B2

In the Claims

Column 143, Lines 49-50, in Claim 6, delete "$C_1$-$C_8$alkyl, $C_3$-$C_8$cycloalkyl, and halogen." and insert -- ($C_1$-$C_8$) alkyl, ($C_3$-$C_8$) cycloalkyl, and halogen. --, therefor.

Column 144, Line 54, in Claim 11, delete "sulfonamide," and insert -- sulfonamide; --, therefor.

Column 145, Line 23, in Claim 11, delete "benzenesulfonamide" and insert -- benzenesulfonamide; --, therefor.

Column 145, Lines 25-26, in Claim 11, delete "difluorobenzenesulfonamide" and insert -- difluorobenzenesulfonamide; --, therefor.

Column 145, Line 32, in Claim 11, delete "benzenesulfonamide" and insert -- benzenesulfonamide; --, therefor.

Column 145, Line 35, in Claim 11, delete "benzenesulfonamide" and insert -- benzenesulfonamide; --, therefor.

Column 145, Line 38, in Claim 11, delete "benzenesulfonamide" and insert -- benzenesulfonamide; --, therefor.

Column 145, Line 41, in Claim 11, delete "methylpropanamide" and insert -- methylpropanamide; --, therefor.

Column 147, Line 4, in Claim 11, delete "2,5-Difluoro-N-(2-fluoro-3-{1[2-(4-methyl-piperazin-1-yl)-ethyl]-4-pyridin-4-yl-lH-pyrazol-3-yl}-phenyl)-benzenesulfonamide;" and insert -- 2,5-Difluoro-N-(2-fluoro-3-{1-[2-(4-methyl-piperazin-1-yl)-ethyl]-4-pyridin-4-yl-lH-pyrazol-3-yl}-phenyl)-benzenesulfonamide; --, therefor.

Column 150, Line 67, in Claim 14, delete "claim 1" and insert -- claim 1, --, therefor.

Column 151, Line 8 (Approx.), in Claim 14, delete "organo metallic" and insert -- organometallic --, therefor.

Column 151, Line 9, in Claim 14, delete "alkyl tin" and insert -- alkyltin --, therefor.

Column 151, Line 54, in Claim 14, delete "$PG_S$" and insert -- $PG_1$ --, therefor.